United States Patent
Eichenseher

(10) Patent No.: US 11,690,899 B2
(45) Date of Patent: Jul. 4, 2023

(54) COMBINATION OF BACTERICIDAL AGENT WITH A LYSOSOMOTROPIC ALKALINISING AGENT FOR THE TREATMENT OF A BACTERIAL INFECTION

(71) Applicant: Micreos Human Health B.V., The Hague (NL)

(72) Inventor: Fritz Eichenseher, Zürich (CH)

(73) Assignee: Micreos Human Health B.V., The Hague (NL)

( * ) Notice: Subject to any disclaimer, the term of this patent is extended or adjusted under 35 U.S.C. 154(b) by 0 days.

(21) Appl. No.: 15/557,296

(22) PCT Filed: Mar. 10, 2016

(86) PCT No.: PCT/EP2016/055076
§ 371 (c)(1),
(2) Date: Sep. 11, 2017

(87) PCT Pub. No.: WO2016/142445
PCT Pub. Date: Sep. 15, 2016

(65) Prior Publication Data
US 2018/0271952 A1    Sep. 27, 2018

(30) Foreign Application Priority Data

Mar. 12, 2015   (EP) .................................... 15158880

(51) Int. Cl.
| A61K 38/43 | (2006.01) |
| A61K 38/16 | (2006.01) |
| A61K 31/5383 | (2006.01) |
| A61K 31/545 | (2006.01) |
| A61K 31/43 | (2006.01) |
| A61K 31/7042 | (2006.01) |
| A61K 31/431 | (2006.01) |
| A61K 31/4164 | (2006.01) |
| A61P 31/04 | (2006.01) |

(52) U.S. Cl.
CPC .......... *A61K 38/43* (2013.01); *A61K 31/4164* (2013.01); *A61K 31/43* (2013.01); *A61K 31/431* (2013.01); *A61K 31/5383* (2013.01); *A61K 31/545* (2013.01); *A61K 31/7042* (2013.01); *A61K 38/16* (2013.01); *A61P 31/04* (2018.01)

(58) Field of Classification Search
CPC ................................ A61K 38/43; A61P 31/04
See application file for complete search history.

(56) References Cited

U.S. PATENT DOCUMENTS

| 8,232,370 | B2 * | 7/2012 | Yoon | A61K 38/162 |
| | | | | 530/350 |
| 9,603,909 | B2 * | 3/2017 | Yoon | A61K 38/162 |
| 9,889,181 | B2 * | 2/2018 | Schuch | C12N 9/503 |
| 2002/0187136 | A1 * | 12/2002 | Loomis | A61K 38/46 |
| | | | | 424/94.1 |
| 2004/0023897 | A1 * | 2/2004 | Caplan | A61K 31/496 |
| | | | | 514/29 |
| 2010/0028334 | A1 * | 2/2010 | Cottarel | A61K 31/16 |
| | | | | 514/1.1 |
| 2011/0027249 | A1 | 2/2011 | Donovan | |
| 2013/0302306 | A1 * | 11/2013 | Schuch | A61K 38/46 |
| | | | | 424/94.6 |
| 2013/0336954 | A1 | 12/2013 | Donovan et al. | |
| 2016/0097044 | A1 | 4/2016 | Donovan | |

FOREIGN PATENT DOCUMENTS

| EP | 2338916 A1 | 6/2011 |
| WO | WO 2012/150858 A1 * | 11/2012 |
| WO | 2013/169104 A1 | 11/2013 |
| WO | 2014/001572 A1 | 1/2014 |

OTHER PUBLICATIONS

Jitta et al., Health Policy, 2003; 65: 167-178 (Year: 2003).*
Loessner et al., FEMS Microbiology Letters, 1998; 162: 265-274 (Year: 1998).*
Gu et al., Journal of Clinical Microbiology, 2011; 49(1): 111-117 (Year: 2011).*
Dey et al., Journal of Inflammation Research, Jan. 2015; 8:29-47. (Year: 2015).*
Gilliams et al., Journal of Infectious Diseases, 2014; 210:585-92. (Year: 2014).*
Leimer et al., The Journal of Infectious Diseases, 2016 (published online Jul. 17, 2015 and presented in part at the 24th European Congress of Clinical Microbiology and Infectious Diseases on May 10-13, 2014); 213:305-13 (Year: 2014).*
Fischetti, Curr Opin Microbiol., 2008; 11(5):393-400 (Year: 2008).*
Healthline (https://www.healthline.com/health/infections#6; accessed on Dec. 14, 2021 (Year: 2021).*
Bowie et al., Science, 1990, 257:1306-1310 (Year: 1990).*
MedlinePlus, https://medlineplus.gov/staphylococcalinfections.html, accessed Jun. 16, 2022 (Year: 2022).*
Jofre et al., Encyclopedia of Food Microbiology, 1999, Lysin, accessed from (https://www.sciencedirect.com/topics/biochemistry-genetics-and-molecular-biology/lysin) (Year: 1999).*
Borysowski et al., Fusion to cell-penetrating peptides will enable lytic enzymes to kill intracellular bacteria, Medical Hypotheses, Eden Press, Penrith, vol. 74, No. 1, Jan. 1, 2010, pp. 164-166 (3 pages).
Charpot-Chartier, Bacterial Autolysins, Prokaryotic Cell Wall Compounds, Springer-Verlag Berlin Heidelberg, Jan. 1, 2010, pp. 383-406 (24 pages).
Craven et al., pH-Dependent Penicillin Tolerance May Protect Intraleukocytic *Staphylococcus aureus* from Killing by Cloxacillin, Antimicrobial Agents and Chemotherapy, vol. 21, No. 4, Apr. 1, 1982, pp. 618-621 (4 pages).

(Continued)

*Primary Examiner* — Brian Gangle
*Assistant Examiner* — Lakia J Jackson-Tongue
(74) *Attorney, Agent, or Firm* — McDonnell Boehnen Hulbert & Berghoff LLP

(57) ABSTRACT

The present invention relates to the field of medicine, specifically the field of bacterial infection and treatment thereof.

10 Claims, 13 Drawing Sheets

Figure 1A:
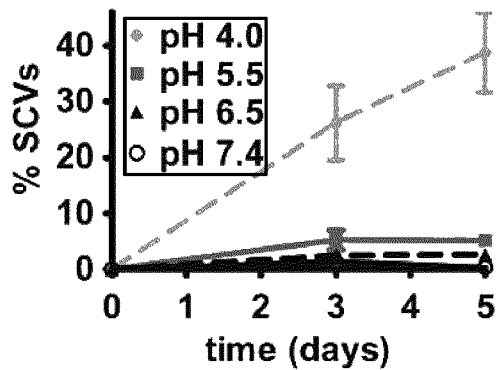

Specification includes a Sequence Listing.

(56) References Cited

OTHER PUBLICATIONS

Dey and Bishayi, Killing of *Staphylococcus aureus* in murine macrophages by chloroquine used alone and in combination with ciprofloxacin or azithromycin, Journal of Inflammation Research, vol. 8, Jan. 22, 2015, pp. 29-47 (19 pages).

Kåhrström, Bacterial Physiology: Tracking persisters in vivo, Nature Reviews Microbiology, vol. 12, No. 3, published online Jan. 27, 2014, p. 152 (1 page).

Maurin et al., Use of Aminoglycosides in Treatment of Infections Due to Intracellular Bacteria, Antimicrobial Agents and Chemotherapy, vol. 45, No. 11, Nov. 1, 2001, p. 2977-2986 (10 pages).

Nelson et al., Endolysins as Antimicrobials, Advances in Virus Research, Jan. 1, 2012, Academic Press, vol. 83, pp. 299-365 (67 pages).

Nguyen et al., Factors influencing the intracellular activity of fluoroquinolones: a study using levofloxacin in a *Staphylococcus aureus* THP-1 monocyte model, Journal of Antimicrobial Chemotherapy, vol. 57, No. 5, Mar. 20, 2006, pp. 883-890 (8 pages).

Schindler et al., Lysostaphin: A New Bacteriolytic Agent for the *Staphylococcus*, Proceedings of the National Academy of Sciences, vol. 51, No. 3, Mar. 1, 1964, pp. 414-421 (8 pages).

Schmelcher et al., Chimeric Phage Lysins Act Synergistically with Lysostaphin to Kill Mastitis-Causing *Staphylococcus aureus* in Murine Mammary Glands, Applied and Environmental, Microbiology, American Society for Microbiology, vol. 78, No. 7, Apr. 1, 2012, pp. 2297-2305 (9 pages).

Vesga et al., *Staphylococcus aureus* Small Colony Variants Are Induced by the Endothelial Cell Intracellular Milieu, The Journal of Infectious Diseases, vol. 173, Jan. 1, 1996, pp. 739-742 (4 pages).

International Search Report, Intl. Appl. No. PCT/EP2016/055076, dated Oct. 6, 2016 (8 pages).

Written Opinion of the International Searching Authority, Intl. Appl. No. PCT/EP2016/055076, dated Oct. 10, 2016 (26 pages).

Elizabeth A. Gilliams, et al., "Chloroquine-Azithromycin Combination Antimalarial Treatment Decreases Risk of Respiratory- and Gastrointestinal-Tract Infections in Malawian Children," CQ-Azithromycin Prevents Infections, JID 2014:210 (Aug. 15) pp. 585-592.

* cited by examiner

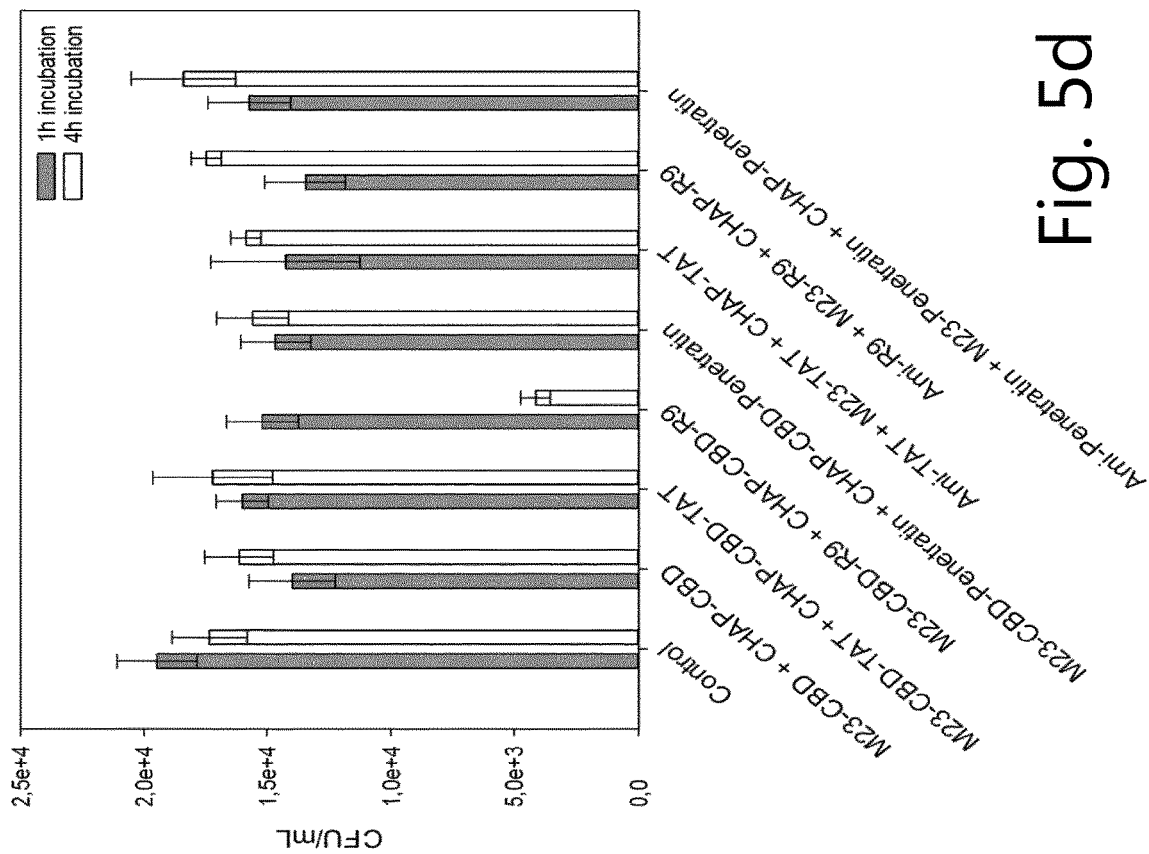
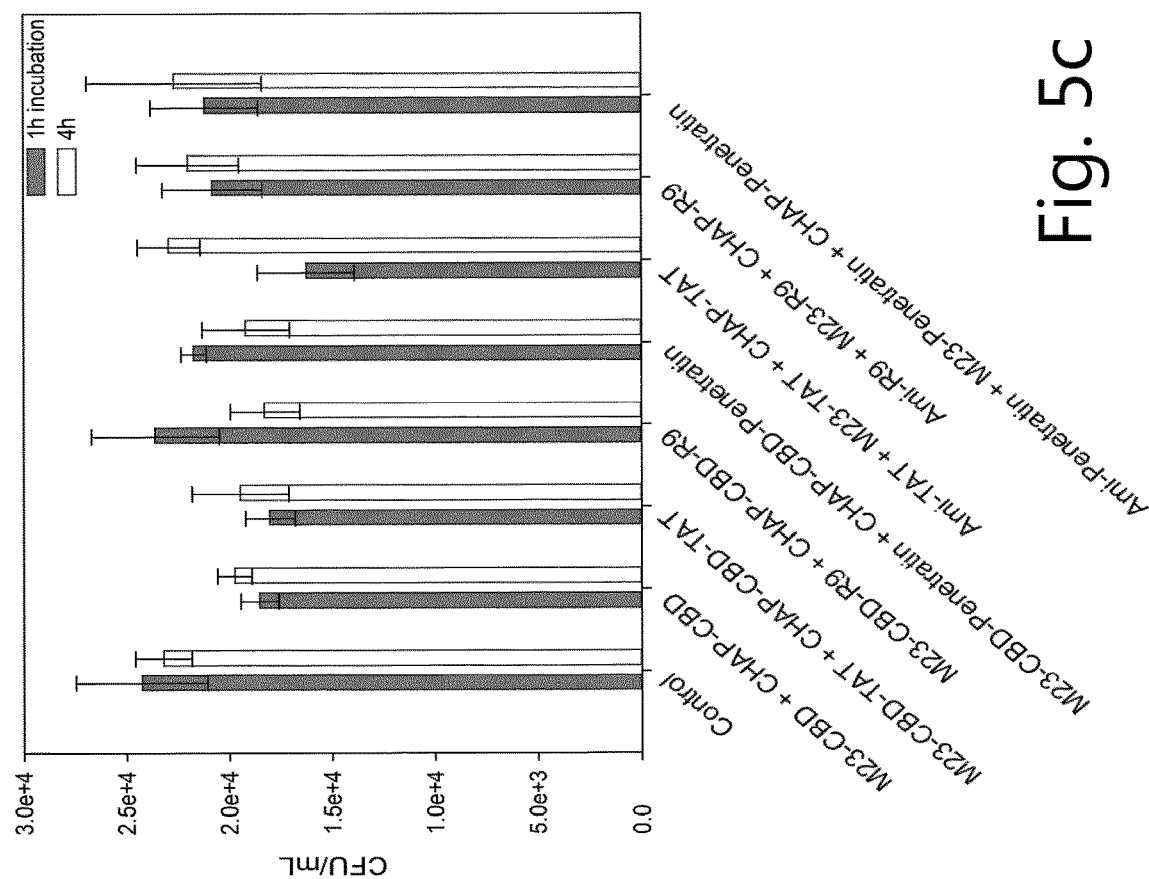

SEQUENCE LISTING

```
<160> NUMBER OF SEQ ID NOS: 108

<210> SEQ ID NO 1
<211> LENGTH: 180
<212> TYPE: PRT
<213> ORGANISM: Artificial
<220> FEATURE:
<223> OTHER INFORMATION: Polypeptide fragment

<400> SEQUENCE: 1

Met Leu Lys His Ile Tyr Ser Asn His Ile Lys Gly Asn Lys Ile Thr
1               5                   10                  15

Ala Pro Lys Pro Ser Ile Gln Gly Val Val Ile His Asn Asp Tyr Gly
            20                  25                  30
```

```
Ser Met Thr Pro Ser Gln Tyr Leu Pro Trp Leu Tyr Ala Arg Glu Asn
        35                  40                  45

Asn Gly Thr His Val Asn Gly Trp Ala Ser Val Tyr Ala Asn Arg Asn
 50                  55                  60

Glu Val Leu Trp Tyr His Pro Thr Asp Tyr Val Glu Trp His Cys Gly
 65                  70                  75                  80

Asn Gln Trp Ala Asn Ala Asn Leu Ile Gly Phe Glu Val Cys Glu Ser
                 85                  90                  95

Tyr Pro Gly Arg Ile Ser Asp Lys Leu Phe Leu Glu Asn Glu Ala
                100                 105                 110

Thr Leu Lys Val Ala Ala Asp Val Met Lys Ser Tyr Gly Leu Pro Val
            115                 120                 125

Asn Arg Asn Thr Val Arg Leu His Asn Glu Phe Phe Gly Thr Ser Cys
130                 135                 140

Pro His Arg Ser Trp Asp Leu His Val Gly Lys Gly Glu Pro Tyr Thr
145                 150                 155                 160

Thr Thr Asn Ile Asn Lys Met Lys Asp Tyr Phe Ile Lys Arg Ile Lys
                165                 170                 175

His Tyr Tyr Asp
            180

<210> SEQ ID NO 2
<211> LENGTH: 141
<212> TYPE: PRT
<213> ORGANISM: Artificial
<220> FEATURE:
<223> OTHER INFORMATION: Polypeptide fragment

<400> SEQUENCE: 2

Ala Ala Thr His Glu His Ser Ala Gln Trp Leu Asn Asn Tyr Lys Lys
 1               5                  10                  15

Gly Tyr Gly Tyr Gly Pro Tyr Pro Leu Gly Ile Asn Gly Gly Met His
                 20                  25                  30

Tyr Gly Val Asp Phe Phe Met Asn Ile Gly Thr Pro Val Lys Ala Ile
            35                  40                  45

Ser Ser Gly Lys Ile Val Glu Ala Gly Trp Ser Asn Tyr Gly Gly Gly
 50                  55                  60

Asn Gln Ile Gly Leu Ile Glu Asn Asp Gly Val His Arg Gln Trp Tyr
 65                  70                  75                  80

Met His Leu Ser Lys Tyr Asn Val Lys Val Gly Asp Tyr Val Lys Ala
                 85                  90                  95

Gly Gln Ile Ile Gly Trp Ser Gly Ser Thr Gly Tyr Ser Thr Ala Pro
                100                 105                 110

His Leu His Phe Gln Arg Met Val Asn Ser Phe Ser Asn Ser Thr Ala
            115                 120                 125

Gln Asp Pro Met Pro Phe Leu Lys Ser Ala Gly Tyr Gly
130                 135                 140

<210> SEQ ID NO 3
<211> LENGTH: 161
<212> TYPE: PRT
<213> ORGANISM: Artificial
<220> FEATURE:
<223> OTHER INFORMATION: Polypeptide fragment

<400> SEQUENCE: 3

Met Ser Ile Ile Met Glu Val Ala Thr Met Gln Ala Lys Leu Thr Lys
 1               5                  10                  15
```

```
Asn Glu Phe Ile Glu Trp Leu Lys Thr Ser Glu Gly Lys Gln Phe Asn
             20                  25                  30

Val Asp Leu Trp Tyr Gly Phe Gln Cys Phe Asp Tyr Ala Asn Ala Gly
         35                  40                  45

Trp Lys Val Leu Phe Gly Leu Leu Lys Gly Leu Gly Ala Lys Asp
 50                  55                  60

Ile Pro Phe Ala Asn Asn Phe Asp Gly Leu Ala Thr Val Tyr Gln Asn
 65                  70                  75                  80

Thr Pro Asp Phe Leu Ala Gln Pro Gly Asp Met Val Val Phe Gly Ser
                 85                  90                  95

Asn Tyr Gly Ala Gly Tyr Gly His Val Ala Trp Val Ile Glu Ala Thr
                100                 105                 110

Leu Asp Tyr Ile Ile Val Tyr Glu Gln Asn Trp Leu Gly Gly Gly Trp
                115                 120                 125

Thr Asp Gly Ile Glu Gln Pro Gly Trp Gly Trp Glu Lys Val Thr Arg
130                 135                 140

Arg Gln His Ala Tyr Asp Phe Pro Met Trp Phe Ile Arg Pro Asn Phe
145                 150                 155                 160

Lys

<210> SEQ ID NO 4
<211> LENGTH: 145
<212> TYPE: PRT
<213> ORGANISM: Artificial
<220> FEATURE:
<223> OTHER INFORMATION: Polypeptide fragment

<400> SEQUENCE: 4

Met Lys Thr Leu Lys Gln Ala Glu Ser Tyr Ile Lys Ser Lys Val Asn
 1               5                  10                  15

Thr Gly Thr Asp Phe Asp Gly Leu Tyr Gly Tyr Gln Cys Met Asp Leu
             20                  25                  30

Ala Val Asp Tyr Ile Tyr His Val Thr Asp Gly Lys Ile Arg Met Trp
         35                  40                  45

Gly Asn Ala Lys Asp Ala Ile Asn Asn Ser Phe Gly Gly Thr Ala Thr
 50                  55                  60

Val Tyr Lys Asn Tyr Pro Ala Phe Arg Pro Lys Tyr Gly Asp Val Val
 65                  70                  75                  80

Val Trp Thr Thr Gly Asn Phe Ala Thr Tyr Gly His Ile Ala Ile Val
                 85                  90                  95

Thr Asn Pro Asp Pro Tyr Gly Asp Leu Gln Tyr Val Thr Val Leu Glu
                100                 105                 110

Gln Asn Trp Asn Gly Asn Gly Ile Tyr Lys Thr Glu Leu Ala Thr Ile
                115                 120                 125

Arg Thr His Asp Tyr Thr Gly Ile Thr His Phe Ile Arg Pro Asn Phe
130                 135                 140

Ala
145

<210> SEQ ID NO 5
<211> LENGTH: 151
<212> TYPE: PRT
<213> ORGANISM: Artificial
<220> FEATURE:
<223> OTHER INFORMATION: Polypeptide fragement

<400> SEQUENCE: 5
```

Met Gly Leu Pro Ser Pro Lys Arg Lys Pro Thr Ala Ser Glu Val
1               5                   10                  15

Ala Ala Trp Ala Lys Arg Met Ile Gly Arg Arg Val Asp Val Asp Gly
                20                  25                  30

Tyr His Gly Ala Gln Cys Trp Asp Leu Pro Asn Tyr Ile Phe Asn Arg
            35                  40                  45

Tyr Trp His Phe Lys Thr Thr Gly Asn Ala Ile Ala Met Ala Trp Tyr
        50                  55                  60

Arg Tyr Pro Lys Gly Phe Lys Phe Tyr Arg Asn Thr Arg Asn Phe Val
65                  70                  75                  80

Pro Lys Pro Gly Asp Met Ala Val Trp Gly Lys Gly Ser Phe Asn Asn
                85                  90                  95

Gly Val Gly His Thr Ala Val Val Ile Gly Pro Ser Thr Lys Ser Tyr
            100                 105                 110

Phe Thr Ser Val Asp Gln Asn Trp Ile Gly Ala Asn Ser Tyr Thr Gly
        115                 120                 125

Ser Pro Gly Ala Lys Ile Lys His Ser Tyr Asn Gly Ile Ser Gly Phe
130                 135                 140

Val Arg Pro Pro Tyr His Ala
145                 150

<210> SEQ ID NO 6
<211> LENGTH: 147
<212> TYPE: PRT
<213> ORGANISM: Artificial
<220> FEATURE:
<223> OTHER INFORMATION: Polyppetide fragment

<400> SEQUENCE: 6

Met Ala Leu Pro Lys Thr Gly Lys Pro Thr Ala Lys Gln Val Val Asp
1               5                   10                  15

Trp Ala Ile Asn Leu Ile Gly Ser Gly Val Asp Val Asp Gly Tyr Tyr
                20                  25                  30

Gly Arg Gln Cys Trp Asp Leu Pro Asn Tyr Ile Phe Asn Arg Tyr Trp
            35                  40                  45

Asn Phe Lys Thr Pro Gly Asn Ala Arg Asp Met Ala Trp Tyr Arg Tyr
        50                  55                  60

Pro Glu Gly Phe Lys Val Phe Arg Asn Thr Ser Asp Phe Val Pro Lys
65                  70                  75                  80

Pro Gly Asp Ile Ala Val Trp Thr Gly Asn Tyr Asn Trp Asn Thr
                85                  90                  95

Trp Gly His Thr Gly Ile Val Val Gly Pro Ser Thr Lys Ser Tyr Phe
            100                 105                 110

Tyr Ser Val Asp Gln Asn Trp Asn Ser Asn Ser Tyr Val Gly Ser
        115                 120                 125

Pro Ala Ala Lys Ile Lys His Ser Tyr Phe Gly Val Thr His Phe Val
130                 135                 140

Arg Pro Ala
145

<210> SEQ ID NO 7
<211> LENGTH: 165
<212> TYPE: PRT
<213> ORGANISM: Artificial
<220> FEATURE:
<223> OTHER INFORMATION: Polypeptide fragment

<400> SEQUENCE: 7

Met Ala Lys Thr Gln Ala Glu Ile Asn Lys Arg Leu Asp Ala Tyr Ala
1               5                   10                  15

Lys Gly Thr Val Asp Ser Pro Tyr Arg Ile Lys Lys Ala Thr Ser Tyr
            20                  25                  30

Asp Pro Ser Phe Gly Val Met Glu Ala Gly Ala Ile Asp Ala Asp Gly
        35                  40                  45

Tyr Tyr His Ala Gln Cys Gln Asp Leu Ile Thr Asp Tyr Val Leu Trp
    50                  55                  60

Leu Thr Asp Asn Lys Val Arg Thr Trp Gly Asn Ala Lys Asp Gln Ile
65                  70                  75                  80

Lys Gln Ser Tyr Gly Thr Gly Phe Lys Ile His Glu Asn Lys Pro Ser
                85                  90                  95

Thr Val Pro Lys Lys Gly Trp Ile Ala Val Phe Thr Ser Gly Ser Tyr
            100                 105                 110

Gln Gln Trp Gly His Ile Gly Ile Val Tyr Asp Gly Gly Asn Thr Ser
                115                 120                 125

Thr Phe Thr Ile Leu Glu Gln Asn Trp Asn Gly Tyr Ala Asn Lys Lys
            130                 135                 140

Pro Thr Lys Arg Val Asp Asn Tyr Tyr Gly Leu Thr His Phe Ile Glu
145                 150                 155                 160

Ile Pro Val Lys Ala
            165

<210> SEQ ID NO 8
<211> LENGTH: 128
<212> TYPE: PRT
<213> ORGANISM: Artificial
<220> FEATURE:
<223> OTHER INFORMATION: Polypeptide fragment

<400> SEQUENCE: 8

Gly Gly Lys Leu Glu Val Ser Lys Ala Ala Thr Ile Lys Gln Ser Asp
1               5                   10                  15

Val Lys Gln Glu Val Lys Lys Gln Glu Ala Lys Gln Ile Val Lys Ala
            20                  25                  30

Thr Asp Trp Lys Gln Asn Lys Asp Gly Ile Trp Tyr Lys Ala Glu His
            35                  40                  45

Ala Ser Phe Thr Val Thr Ala Pro Glu Gly Ile Ile Thr Arg Tyr Lys
    50                  55                  60

Gly Pro Trp Thr Gly His Pro Gln Ala Gly Val Leu Gln Lys Gly Gln
65                  70                  75                  80

Thr Ile Lys Tyr Asp Glu Val Gln Lys Phe Asp Gly His Val Trp Val
                85                  90                  95

Ser Trp Glu Thr Phe Glu Gly Glu Thr Val Tyr Met Pro Val Arg Thr
            100                 105                 110

Trp Asp Ala Lys Thr Gly Lys Val Gly Lys Leu Trp Gly Glu Ile Lys
                115                 120                 125

<210> SEQ ID NO 9
<211> LENGTH: 78
<212> TYPE: PRT
<213> ORGANISM: Artificial
<220> FEATURE:
<223> OTHER INFORMATION: Polypeptide fragment

<400> SEQUENCE: 9

```
Ala Pro Lys Ser Lys Pro Ser Lys Ile Lys Thr Thr Trp Asn Trp Gly
1               5                   10                  15

Gly Lys Phe Thr Ala Asn Ser Thr Ile Lys Val Arg Lys Ser Pro Gly
            20                  25                  30

Leu Lys Gly Ile Val Val Glu Ser Gly Ser Trp Leu Tyr Lys Gly Asn
        35                  40                  45

Tyr Val Pro Phe Asp Gln Val Ile Lys Lys Asp Gly Tyr Trp Trp Ile
    50                  55                  60

Arg Phe Lys Tyr Val Gln Pro Gly Ser Ser Asn Lys His Phe
65                  70                  75
```

<210> SEQ ID NO 10
<211> LENGTH: 92
<212> TYPE: PRT
<213> ORGANISM: Artificial
<220> FEATURE:
<223> OTHER INFORMATION: Polypeptide fragment

<400> SEQUENCE: 10

```
Trp Lys Thr Asn Lys Tyr Gly Thr Leu Tyr Lys Ser Glu Ser Ala Ser
1               5                   10                  15

Phe Thr Pro Asn Thr Asp Ile Ile Thr Arg Thr Thr Gly Pro Phe Arg
            20                  25                  30

Ser Met Pro Gln Ser Gly Val Leu Lys Ala Gly Gln Thr Ile His Tyr
        35                  40                  45

Asp Glu Val Met Lys Gln Asp Gly His Val Trp Val Gly Tyr Thr Gly
    50                  55                  60

Asn Ser Gly Gln Arg Ile Tyr Leu Pro Val Arg Thr Asn Lys Ser
65                  70                  75                  80

Thr Asn Thr Leu Gly Val Leu Trp Gly Thr Ile Lys
                85                  90
```

<210> SEQ ID NO 11
<211> LENGTH: 92
<212> TYPE: PRT
<213> ORGANISM: Artificial
<220> FEATURE:
<223> OTHER INFORMATION: Polypeptide fragment

<400> SEQUENCE: 11

```
Tyr Lys Thr Asn Lys Tyr Gly Thr Leu Tyr Lys Ser Glu Ser Ala Ser
1               5                   10                  15

Phe Thr Ala Asn Thr Asp Ile Ile Thr Arg Leu Thr Gly Pro Phe Arg
            20                  25                  30

Ser Met Pro Gln Ser Gly Val Leu Arg Lys Gly Leu Thr Ile Lys Tyr
        35                  40                  45

Asp Glu Val Met Lys Gln Asp Gly His Val Trp Val Gly Tyr Asn Thr
    50                  55                  60

Asn Ser Gly Lys Arg Val Tyr Leu Pro Val Arg Thr Trp Asn Glu Ser
65                  70                  75                  80

Thr Gly Glu Leu Gly Pro Leu Trp Gly Thr Ile Lys
                85                  90
```

<210> SEQ ID NO 12
<211> LENGTH: 30
<212> TYPE: PRT
<213> ORGANISM: Artificial
<220> FEATURE:
<223> OTHER INFORMATION: Polypeptide fragment

```
<400> SEQUENCE: 12

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
            20                  25                  30

<210> SEQ ID NO 13
<211> LENGTH: 22
<212> TYPE: PRT
<213> ORGANISM: Artificial
<220> FEATURE:
<223> OTHER INFORMATION: Polypeptide fragment

<400> SEQUENCE: 13

Met Val Thr Val Leu Phe Arg Arg Leu Arg Ile Arg Arg Ala Ser Gly
1               5                   10                  15

Pro Pro Arg Val Arg Val
            20

<210> SEQ ID NO 14
<211> LENGTH: 18
<212> TYPE: PRT
<213> ORGANISM: Artificial
<220> FEATURE:
<223> OTHER INFORMATION: Polypeptide fragment

<400> SEQUENCE: 14

Lys Leu Ala Leu Lys Leu Ala Leu Lys Ala Leu Lys Ala Ala Leu Lys
1               5                   10                  15

Leu Ala

<210> SEQ ID NO 15
<211> LENGTH: 27
<212> TYPE: PRT
<213> ORGANISM: Artificial
<220> FEATURE:
<223> OTHER INFORMATION: GALFLGFLGAAGSTMGAWSQPKKKRKV

<400> SEQUENCE: 15

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 16
<211> LENGTH: 16
<212> TYPE: PRT
<213> ORGANISM: Artificial
<220> FEATURE:
<223> OTHER INFORMATION: Polypeptide fragment

<400> SEQUENCE: 16

Arg Gln Ile Lys Ile Trp Phe Gln Asn Arg Arg Met Lys Trp Lys Lys
1               5                   10                  15

<210> SEQ ID NO 17
<211> LENGTH: 21
<212> TYPE: PRT
<213> ORGANISM: Artificial
<220> FEATURE:
<223> OTHER INFORMATION: Polypeptide fragment

<400> SEQUENCE: 17

Lys Glu Thr Trp Trp Glu Thr Trp Trp Thr Glu Trp Ser Gln Pro Lys
```

```
1               5                   10                  15
Lys Lys Arg Lys Val
            20

<210> SEQ ID NO 18
<211> LENGTH: 12
<212> TYPE: PRT
<213> ORGANISM: Artificial
<220> FEATURE:
<223> OTHER INFORMATION: Polypeptide fragment

<400> SEQUENCE: 18

Arg Arg Gln Arg Arg Thr Ser Lys Leu Met Lys Arg
1               5                   10

<210> SEQ ID NO 19
<211> LENGTH: 18
<212> TYPE: PRT
<213> ORGANISM: Artificial
<220> FEATURE:
<223> OTHER INFORMATION: Polypeptide fragment

<400> SEQUENCE: 19

Leu Leu Ile Ile Leu Arg Arg Arg Ile Arg Lys Gln Ala His Ala His
1               5                   10                  15

Ser Lys

<210> SEQ ID NO 20
<211> LENGTH: 9
<212> TYPE: PRT
<213> ORGANISM: Artificial
<220> FEATURE:
<223> OTHER INFORMATION: Polypeptide fragment

<400> SEQUENCE: 20

Arg Arg Trp Trp Arg Arg Trp Arg Arg
1               5

<210> SEQ ID NO 21
<211> LENGTH: 16
<212> TYPE: PRT
<213> ORGANISM: Artificial
<220> FEATURE:
<223> OTHER INFORMATION: Polypeptide fragment comprises 6 to 15 R
      residues

<400> SEQUENCE: 21

Arg Arg Arg Arg Arg Arg Arg Arg Arg Arg Arg Arg Arg Arg Arg Arg
1               5                   10                  15

<210> SEQ ID NO 22
<211> LENGTH: 13
<212> TYPE: PRT
<213> ORGANISM: Artificial
<220> FEATURE:
<223> OTHER INFORMATION: Polypeptide fragment

<400> SEQUENCE: 22

Gly Arg Lys Lys Arg Arg Gln Arg Arg Arg Pro Pro Gln
1               5                   10

<210> SEQ ID NO 23
<211> LENGTH: 9
<212> TYPE: PRT
<213> ORGANISM: Artificial
<220> FEATURE:
```

<223> OTHER INFORMATION: Polypeptide fragment

<400> SEQUENCE: 23

Arg Lys Lys Arg Arg Gln Arg Arg Arg
1               5

<210> SEQ ID NO 24
<211> LENGTH: 27
<212> TYPE: PRT
<213> ORGANISM: Artificial
<220> FEATURE:
<223> OTHER INFORMATION: Polypeptide fragment

<400> SEQUENCE: 24

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 25
<211> LENGTH: 21
<212> TYPE: PRT
<213> ORGANISM: Artificial
<220> FEATURE:
<223> OTHER INFORMATION: Polypeptide fragment

<400> SEQUENCE: 25

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 26

<400> SEQUENCE: 26

000

<210> SEQ ID NO 27
<211> LENGTH: 269
<212> TYPE: PRT
<213> ORGANISM: Artificial Sequence
<220> FEATURE:
<223> OTHER INFORMATION: Polypeptide fragment

<400> SEQUENCE: 27

Met Ala Ala Thr His Glu His Ser Ala Gln Trp Leu Asn Asn Tyr Lys
1               5                   10                  15

Lys Gly Tyr Gly Tyr Gly Pro Tyr Pro Leu Gly Ile Asn Gly Gly Met
            20                  25                  30

His Tyr Gly Val Asp Phe Phe Met Asn Ile Gly Thr Pro Val Lys Ala
        35                  40                  45

Ile Ser Ser Gly Lys Ile Val Glu Ala Gly Trp Ser Asn Tyr Gly Gly
    50                  55                  60

Gly Asn Gln Ile Gly Leu Ile Glu Asn Asp Gly Val His Arg Gln Trp
65                  70                  75                  80

Tyr Met His Leu Ser Lys Tyr Asn Val Lys Val Gly Asp Tyr Val Lys
                85                  90                  95

Ala Gly Gln Ile Ile Gly Trp Ser Gly Ser Thr Gly Tyr Ser Thr Ala
            100                 105                 110

Pro His Leu His Phe Gln Arg Met Val Asn Ser Phe Ser Asn Ser Thr
        115                 120                 125

Ala Gln Asp Pro Met Pro Phe Leu Lys Ser Ala Gly Tyr Gly Gly Lys
        130                 135                 140

Leu Glu Val Ser Lys Ala Ala Thr Ile Lys Gln Ser Asp Val Lys Gln
145                 150                 155                 160

Glu Val Lys Lys Gln Glu Ala Lys Gln Ile Val Lys Ala Thr Asp Trp
                165                 170                 175

Lys Gln Asn Lys Asp Gly Ile Trp Tyr Lys Ala Glu His Ala Ser Phe
            180                 185                 190

Thr Val Thr Ala Pro Glu Gly Ile Ile Thr Arg Tyr Lys Gly Pro Trp
        195                 200                 205

Thr Gly His Pro Gln Ala Gly Val Leu Gln Lys Gly Gln Thr Ile Lys
    210                 215                 220

Tyr Asp Glu Val Gln Lys Phe Asp Gly His Val Trp Val Ser Trp Glu
225                 230                 235                 240

Thr Phe Glu Gly Glu Thr Val Tyr Met Pro Val Arg Thr Trp Asp Ala
                245                 250                 255

Lys Thr Gly Lys Val Gly Lys Leu Trp Gly Glu Ile Lys
            260                 265

<210> SEQ ID NO 28
<211> LENGTH: 289
<212> TYPE: PRT
<213> ORGANISM: Artificial Sequence
<220> FEATURE:
<223> OTHER INFORMATION: Polypeptide fragment

<400> SEQUENCE: 28

Met Ser Ile Ile Met Glu Val Ala Thr Met Gln Ala Lys Leu Thr Lys
1               5                   10                  15

Asn Glu Phe Ile Glu Trp Leu Lys Thr Ser Gly Lys Gln Phe Asn
                20                  25                  30

Val Asp Leu Trp Tyr Gly Phe Gln Cys Phe Asp Tyr Ala Asn Ala Gly
            35                  40                  45

Trp Lys Val Leu Phe Gly Leu Leu Lys Gly Leu Gly Ala Lys Asp
    50                  55                  60

Ile Pro Phe Ala Asn Asn Phe Asp Gly Leu Ala Thr Val Tyr Gln Asn
65                  70                  75                  80

Thr Pro Asp Phe Leu Ala Gln Pro Gly Asp Met Val Val Phe Gly Ser
                85                  90                  95

Asn Tyr Gly Ala Gly Tyr Gly His Val Ala Trp Val Ile Glu Ala Thr
            100                 105                 110

Leu Asp Tyr Ile Ile Val Tyr Glu Gln Asn Trp Leu Gly Gly Gly Trp
        115                 120                 125

Thr Asp Gly Ile Glu Gln Pro Gly Trp Gly Trp Glu Lys Val Thr Arg
    130                 135                 140

Arg Gln His Ala Tyr Asp Phe Pro Met Trp Phe Ile Arg Pro Asn Phe
145                 150                 155                 160

Lys Gly Gly Lys Leu Glu Val Ser Lys Ala Ala Thr Ile Lys Gln Ser
                165                 170                 175

Asp Val Lys Gln Glu Val Lys Lys Gln Glu Ala Lys Gln Ile Val Lys
            180                 185                 190

Ala Thr Asp Trp Lys Gln Asn Lys Asp Gly Ile Trp Tyr Lys Ala Glu
        195                 200                 205

His Ala Ser Phe Thr Val Thr Ala Pro Glu Gly Ile Ile Thr Arg Tyr
    210                 215                 220

```
Lys Gly Pro Trp Thr Gly His Pro Gln Ala Gly Val Leu Gln Lys Gly
225                 230                 235                 240

Gln Thr Ile Lys Tyr Asp Glu Val Gln Lys Phe Asp Gly His Val Trp
            245                 250                 255

Val Ser Trp Glu Thr Phe Glu Gly Glu Thr Val Tyr Met Pro Val Arg
        260                 265                 270

Thr Trp Asp Ala Lys Thr Gly Lys Val Gly Lys Leu Trp Gly Glu Ile
        275                 280                 285

Lys
```

<210> SEQ ID NO 29
<211> LENGTH: 308
<212> TYPE: PRT
<213> ORGANISM: Artificial Sequence
<220> FEATURE:
<223> OTHER INFORMATION: Polypeptide fragment

<400> SEQUENCE: 29

```
Met Leu Lys His Ile Tyr Ser Asn His Ile Lys Gly Asn Lys Ile Thr
1               5                   10                  15

Ala Pro Lys Pro Ser Ile Gln Gly Val Val Ile His Asn Asp Tyr Gly
            20                  25                  30

Ser Met Thr Pro Ser Gln Tyr Leu Pro Trp Leu Tyr Ala Arg Glu Asn
        35                  40                  45

Asn Gly Thr His Val Asn Gly Trp Ala Ser Val Tyr Ala Asn Arg Asn
    50                  55                  60

Glu Val Leu Trp Tyr His Pro Thr Asp Tyr Glu Trp His Cys Gly
65                  70                  75                  80

Asn Gln Trp Ala Asn Ala Asn Leu Ile Gly Phe Glu Val Cys Glu Ser
                85                  90                  95

Tyr Pro Gly Arg Ile Ser Asp Lys Leu Phe Leu Glu Asn Glu Glu Ala
            100                 105                 110

Thr Leu Lys Val Ala Ala Asp Val Met Lys Ser Tyr Gly Leu Pro Val
        115                 120                 125

Asn Arg Asn Thr Val Arg Leu His Asn Glu Phe Phe Gly Thr Ser Cys
    130                 135                 140

Pro His Arg Ser Trp Asp Leu His Val Gly Lys Gly Glu Pro Tyr Thr
145                 150                 155                 160

Thr Thr Asn Ile Asn Lys Met Lys Asp Tyr Phe Ile Lys Arg Ile Lys
                165                 170                 175

His Tyr Tyr Asp Gly Gly Lys Leu Glu Val Ser Lys Ala Ala Thr Ile
            180                 185                 190

Lys Gln Ser Asp Val Lys Gln Glu Val Lys Gln Glu Ala Lys Gln
        195                 200                 205

Ile Val Lys Ala Thr Asp Trp Lys Gln Asn Lys Asp Gly Ile Trp Tyr
    210                 215                 220

Lys Ala Glu His Ala Ser Phe Thr Val Thr Ala Pro Glu Gly Ile Ile
225                 230                 235                 240

Thr Arg Tyr Lys Gly Pro Trp Thr Gly His Pro Gln Ala Gly Val Leu
                245                 250                 255

Gln Lys Gly Gln Thr Ile Lys Tyr Asp Glu Val Gln Lys Phe Asp Gly
            260                 265                 270

His Val Trp Val Ser Trp Glu Thr Phe Glu Gly Glu Thr Val Tyr Met
        275                 280                 285
```

Pro Val Arg Thr Trp Asp Ala Lys Thr Gly Lys Val Gly Lys Leu Trp
290                 295                 300

Gly Glu Ile Lys
305

<210> SEQ ID NO 30
<211> LENGTH: 326
<212> TYPE: PRT
<213> ORGANISM: Artificial
<220> FEATURE:
<223> OTHER INFORMATION: Polypeptide construct

<400> SEQUENCE: 30

Met Leu Lys His Ile Tyr Ser Asn His Ile Lys Gly Asn Lys Ile Thr
1               5                   10                  15

Ala Pro Lys Pro Ser Ile Gln Gly Val Val Ile His Asn Asp Tyr Gly
            20                  25                  30

Ser Met Thr Pro Ser Gln Tyr Leu Pro Trp Leu Tyr Ala Arg Glu Asn
        35                  40                  45

Asn Gly Thr His Val Asn Gly Trp Ala Ser Val Tyr Ala Asn Arg Asn
    50                  55                  60

Glu Val Leu Trp Tyr His Pro Thr Asp Tyr Val Glu Trp His Cys Gly
65                  70                  75                  80

Asn Gln Trp Ala Asn Ala Asn Leu Ile Gly Phe Glu Val Cys Glu Ser
                85                  90                  95

Tyr Pro Gly Arg Ile Ser Asp Lys Leu Phe Leu Glu Asn Glu Glu Ala
            100                 105                 110

Thr Leu Lys Val Ala Ala Asp Val Met Lys Ser Tyr Gly Leu Pro Val
        115                 120                 125

Asn Arg Asn Thr Val Arg Leu His Asn Glu Phe Phe Gly Thr Ser Cys
130                 135                 140

Pro His Arg Ser Trp Asp Leu His Val Gly Lys Gly Glu Pro Tyr Thr
145                 150                 155                 160

Thr Thr Asn Ile Asn Lys Met Lys Asp Tyr Phe Ile Lys Arg Ile Lys
                165                 170                 175

His Tyr Tyr Asp Gly Gly Lys Leu Glu Val Ser Lys Ala Ala Thr Ile
            180                 185                 190

Lys Gln Ser Asp Val Lys Gln Glu Val Lys Gln Glu Ala Lys Gln
        195                 200                 205

Ile Val Lys Ala Thr Asp Trp Lys Gln Asn Lys Asp Gly Ile Trp Tyr
210                 215                 220

Lys Ala Glu His Ala Ser Phe Thr Val Thr Ala Pro Glu Gly Ile Ile
225                 230                 235                 240

Thr Arg Tyr Lys Gly Pro Trp Thr Gly His Pro Gln Ala Gly Val Leu
            245                 250                 255

Gln Lys Gly Gln Thr Ile Lys Tyr Asp Glu Val Gln Lys Phe Asp Gly
        260                 265                 270

His Val Trp Val Ser Trp Glu Thr Phe Glu Gly Glu Thr Val Tyr Met
    275                 280                 285

Pro Val Arg Thr Trp Asp Ala Lys Thr Gly Lys Val Gly Lys Leu Trp
290                 295                 300

Gly Glu Ile Lys Glu Leu Arg Gln Ile Lys Ile Trp Phe Gln Asn Arg
305                 310                 315                 320

Arg Met Lys Trp Lys Lys
                325

```
<210> SEQ ID NO 31
<211> LENGTH: 319
<212> TYPE: PRT
<213> ORGANISM: Artificial
<220> FEATURE:
<223> OTHER INFORMATION: Polypeptide construct

<400> SEQUENCE: 31

Met Leu Lys His Ile Tyr Ser Asn His Ile Lys Gly Asn Lys Ile Thr
1               5                   10                  15

Ala Pro Lys Pro Ser Ile Gln Gly Val Val Ile His Asn Asp Tyr Gly
                20                  25                  30

Ser Met Thr Pro Ser Gln Tyr Leu Pro Trp Leu Tyr Ala Arg Glu Asn
            35                  40                  45

Asn Gly Thr His Val Asn Gly Trp Ala Ser Val Tyr Ala Asn Arg Asn
        50                  55                  60

Glu Val Leu Trp Tyr His Pro Thr Asp Tyr Val Glu Trp His Cys Gly
65                  70                  75                  80

Asn Gln Trp Ala Asn Ala Asn Leu Ile Gly Phe Val Cys Glu Ser
                85                  90                  95

Tyr Pro Gly Arg Ile Ser Asp Lys Leu Phe Leu Glu Asn Glu Glu Ala
                100                 105                 110

Thr Leu Lys Val Ala Ala Asp Val Met Lys Ser Tyr Gly Leu Pro Val
            115                 120                 125

Asn Arg Asn Thr Val Arg Leu His Asn Glu Phe Phe Gly Thr Ser Cys
        130                 135                 140

Pro His Arg Ser Trp Asp Leu His Val Gly Lys Gly Glu Pro Tyr Thr
145                 150                 155                 160

Thr Thr Asn Ile Asn Lys Met Lys Asp Tyr Phe Ile Lys Arg Ile Lys
                165                 170                 175

His Tyr Tyr Asp Gly Gly Lys Leu Glu Val Ser Lys Ala Ala Thr Ile
            180                 185                 190

Lys Gln Ser Asp Val Lys Gln Glu Val Lys Gln Glu Ala Lys Gln
        195                 200                 205

Ile Val Lys Ala Thr Asp Trp Lys Gln Asn Lys Asp Gly Ile Trp Tyr
210                 215                 220

Lys Ala Glu His Ala Ser Phe Thr Val Thr Ala Pro Glu Gly Ile Ile
225                 230                 235                 240

Thr Arg Tyr Lys Gly Pro Trp Thr Gly His Pro Gln Ala Gly Val Leu
                245                 250                 255

Gln Lys Gly Gln Thr Ile Lys Tyr Asp Glu Val Gln Lys Phe Asp Gly
            260                 265                 270

His Val Trp Val Ser Trp Glu Thr Phe Glu Gly Glu Thr Val Tyr Met
        275                 280                 285

Pro Val Arg Thr Trp Asp Ala Lys Thr Gly Lys Val Gly Lys Leu Trp
        290                 295                 300

Gly Glu Ile Lys Glu Leu Arg Arg Arg Arg Arg Arg Arg
305                 310                 315

<210> SEQ ID NO 32
<211> LENGTH: 323
<212> TYPE: PRT
<213> ORGANISM: Artificial
<220> FEATURE:
<223> OTHER INFORMATION: Polypeptide construct

<400> SEQUENCE: 32
```

-continued

Met Leu Lys His Ile Tyr Ser Asn His Ile Lys Gly Asn Lys Ile Thr
1               5                   10                  15

Ala Pro Lys Pro Ser Ile Gln Gly Val Val Ile His Asn Asp Tyr Gly
            20                  25                  30

Ser Met Thr Pro Ser Gln Tyr Leu Pro Trp Leu Tyr Ala Arg Glu Asn
        35                  40                  45

Asn Gly Thr His Val Asn Gly Trp Ala Ser Val Tyr Ala Asn Arg Asn
    50                  55                  60

Glu Val Leu Trp Tyr His Pro Thr Asp Tyr Val Glu Trp His Cys Gly
65                  70                  75                  80

Asn Gln Trp Ala Asn Ala Asn Leu Ile Gly Phe Glu Val Cys Glu Ser
                85                  90                  95

Tyr Pro Gly Arg Ile Ser Asp Lys Leu Phe Leu Glu Asn Glu Glu Ala
            100                 105                 110

Thr Leu Lys Val Ala Ala Asp Val Met Lys Ser Tyr Gly Leu Pro Val
        115                 120                 125

Asn Arg Asn Thr Val Arg Leu His Asn Glu Phe Phe Gly Thr Ser Cys
130                 135                 140

Pro His Arg Ser Trp Asp Leu His Val Gly Lys Gly Glu Pro Tyr Thr
145                 150                 155                 160

Thr Thr Asn Ile Asn Lys Met Lys Asp Tyr Phe Ile Lys Arg Ile Lys
                165                 170                 175

His Tyr Tyr Asp Gly Gly Lys Leu Glu Val Ser Lys Ala Ala Thr Ile
            180                 185                 190

Lys Gln Ser Asp Val Lys Gln Glu Val Lys Gln Glu Ala Lys Gln
        195                 200                 205

Ile Val Lys Ala Thr Asp Trp Lys Gln Asn Lys Asp Gly Ile Trp Tyr
210                 215                 220

Lys Ala Glu His Ala Ser Phe Thr Val Thr Ala Pro Glu Gly Ile Ile
225                 230                 235                 240

Thr Arg Tyr Lys Gly Pro Trp Thr Gly His Pro Gln Ala Gly Val Leu
            245                 250                 255

Gln Lys Gly Gln Thr Ile Lys Tyr Asp Glu Val Gln Lys Phe Asp Gly
        260                 265                 270

His Val Trp Val Ser Trp Glu Thr Phe Glu Gly Glu Thr Val Tyr Met
    275                 280                 285

Pro Val Arg Thr Trp Asp Ala Lys Thr Gly Val Gly Lys Leu Trp
290                 295                 300

Gly Glu Ile Lys Glu Leu Gly Arg Lys Lys Arg Arg Gln Arg Arg Arg
305                 310                 315                 320

Pro Pro Gln

<210> SEQ ID NO 33
<211> LENGTH: 199
<212> TYPE: PRT
<213> ORGANISM: Artificial
<220> FEATURE:
<223> OTHER INFORMATION: Polypeptide construct

<400> SEQUENCE: 33

Met Leu Lys His Ile Tyr Ser Asn His Ile Lys Gly Asn Lys Ile Thr
1               5                   10                  15

Ala Pro Lys Pro Ser Ile Gln Gly Val Val Ile His Asn Asp Tyr Gly
            20                  25                  30

```
Ser Met Thr Pro Ser Gln Tyr Leu Pro Trp Leu Tyr Ala Arg Glu Asn
        35                  40                  45

Asn Gly Thr His Val Asn Gly Trp Ala Ser Val Tyr Ala Asn Arg Asn
 50                  55                  60

Glu Val Leu Trp Tyr His Pro Thr Asp Tyr Val Glu Trp His Cys Gly
 65                  70                  75                  80

Asn Gln Trp Ala Asn Ala Asn Leu Ile Gly Phe Glu Val Cys Glu Ser
                 85                  90                  95

Tyr Pro Gly Arg Ile Ser Asp Lys Leu Phe Leu Glu Asn Glu Glu Ala
            100                 105                 110

Thr Leu Lys Val Ala Ala Asp Val Met Lys Ser Tyr Gly Leu Pro Val
        115                 120                 125

Asn Arg Asn Thr Val Arg Leu His Asn Glu Phe Phe Gly Thr Ser Cys
130                 135                 140

Pro His Arg Ser Trp Asp Leu His Val Gly Lys Gly Glu Pro Tyr Thr
145                 150                 155                 160

Thr Thr Asn Ile Asn Lys Met Lys Asp Tyr Phe Ile Lys Arg Ile Lys
                165                 170                 175

His Tyr Tyr Asp Gly Glu Leu Arg Gln Ile Lys Ile Trp Phe Gln Asn
            180                 185                 190

Arg Arg Met Lys Trp Lys Lys
            195
```

<210> SEQ ID NO 34
<211> LENGTH: 192
<212> TYPE: PRT
<213> ORGANISM: Artificial
<220> FEATURE:
<223> OTHER INFORMATION: Polypeptide construct

<400> SEQUENCE: 34

```
Met Leu Lys His Ile Tyr Ser Asn His Ile Lys Gly Asn Lys Ile Thr
 1               5                  10                  15

Ala Pro Lys Pro Ser Ile Gln Gly Val Val Ile His Asn Asp Tyr Gly
            20                  25                  30

Ser Met Thr Pro Ser Gln Tyr Leu Pro Trp Leu Tyr Ala Arg Glu Asn
        35                  40                  45

Asn Gly Thr His Val Asn Gly Trp Ala Ser Val Tyr Ala Asn Arg Asn
 50                  55                  60

Glu Val Leu Trp Tyr His Pro Thr Asp Tyr Val Glu Trp His Cys Gly
 65                  70                  75                  80

Asn Gln Trp Ala Asn Ala Asn Leu Ile Gly Phe Glu Val Cys Glu Ser
                 85                  90                  95

Tyr Pro Gly Arg Ile Ser Asp Lys Leu Phe Leu Glu Asn Glu Glu Ala
            100                 105                 110

Thr Leu Lys Val Ala Ala Asp Val Met Lys Ser Tyr Gly Leu Pro Val
        115                 120                 125

Asn Arg Asn Thr Val Arg Leu His Asn Glu Phe Phe Gly Thr Ser Cys
130                 135                 140

Pro His Arg Ser Trp Asp Leu His Val Gly Lys Gly Glu Pro Tyr Thr
145                 150                 155                 160

Thr Thr Asn Ile Asn Lys Met Lys Asp Tyr Phe Ile Lys Arg Ile Lys
                165                 170                 175

His Tyr Tyr Asp Gly Glu Leu Arg Arg Arg Arg Arg Arg Arg Arg Arg
            180                 185                 190
```

<210> SEQ ID NO 35
<211> LENGTH: 196
<212> TYPE: PRT
<213> ORGANISM: Artificial
<220> FEATURE:
<223> OTHER INFORMATION: Polypeptide construct

<400> SEQUENCE: 35

```
Met Leu Lys His Ile Tyr Ser Asn His Ile Lys Gly Asn Lys Ile Thr
1               5                   10                  15

Ala Pro Lys Pro Ser Ile Gln Gly Val Val Ile His Asn Asp Tyr Gly
            20                  25                  30

Ser Met Thr Pro Ser Gln Tyr Leu Pro Trp Leu Tyr Ala Arg Glu Asn
        35                  40                  45

Asn Gly Thr His Val Asn Gly Trp Ala Ser Val Tyr Ala Asn Arg Asn
    50                  55                  60

Glu Val Leu Trp Tyr His Pro Thr Asp Tyr Val Glu Trp His Cys Gly
65                  70                  75                  80

Asn Gln Trp Ala Asn Ala Asn Leu Ile Gly Phe Val Cys Glu Ser
                85                  90                  95

Tyr Pro Gly Arg Ile Ser Asp Lys Leu Phe Leu Glu Asn Glu Glu Ala
            100                 105                 110

Thr Leu Lys Val Ala Ala Asp Val Met Lys Ser Tyr Gly Leu Pro Val
        115                 120                 125

Asn Arg Asn Thr Val Arg Leu His Asn Glu Phe Phe Gly Thr Ser Cys
    130                 135                 140

Pro His Arg Ser Trp Asp Leu His Val Gly Lys Gly Pro Tyr Thr
145                 150                 155                 160

Thr Thr Asn Ile Asn Lys Met Lys Asp Tyr Phe Ile Lys Arg Ile Lys
                165                 170                 175

His Tyr Tyr Asp Gly Glu Leu Gly Arg Lys Lys Arg Gln Arg Arg
            180                 185                 190

Arg Pro Pro Gln
        195
```

<210> SEQ ID NO 36
<211> LENGTH: 307
<212> TYPE: PRT
<213> ORGANISM: Artificial
<220> FEATURE:
<223> OTHER INFORMATION: Polypeptide construct

<400> SEQUENCE: 36

```
Met Ser Ile Ile Met Glu Val Ala Thr Met Gln Ala Lys Leu Thr Lys
1               5                   10                  15

Asn Glu Phe Ile Glu Trp Leu Lys Thr Ser Gly Lys Gln Phe Asn
            20                  25                  30

Val Asp Leu Trp Tyr Gly Phe Gln Cys Phe Asp Tyr Ala Asn Ala Gly
        35                  40                  45

Trp Lys Val Leu Phe Gly Leu Leu Lys Gly Leu Gly Ala Lys Asp
    50                  55                  60

Ile Pro Phe Ala Asn Asn Phe Asp Gly Leu Ala Thr Val Tyr Gln Asn
65                  70                  75                  80

Thr Pro Asp Phe Leu Ala Gln Pro Gly Asp Met Val Val Phe Gly Ser
                85                  90                  95

Asn Tyr Gly Ala Gly Tyr Gly His Val Ala Trp Val Ile Glu Ala Thr
            100                 105                 110
```

```
Leu Asp Tyr Ile Ile Val Tyr Glu Gln Asn Trp Leu Gly Gly Gly Trp
            115                 120                 125

Thr Asp Gly Ile Glu Gln Pro Gly Trp Gly Trp Glu Lys Val Thr Arg
        130                 135                 140

Arg Gln His Ala Tyr Asp Phe Pro Met Trp Phe Ile Arg Pro Asn Phe
145                 150                 155                 160

Lys Gly Gly Lys Leu Glu Val Ser Lys Ala Ala Thr Ile Lys Gln Ser
                165                 170                 175

Asp Val Lys Gln Glu Val Lys Lys Gln Glu Ala Lys Gln Ile Val Lys
            180                 185                 190

Ala Thr Asp Trp Lys Gln Asn Lys Asp Gly Ile Trp Tyr Lys Ala Glu
        195                 200                 205

His Ala Ser Phe Thr Val Thr Ala Pro Glu Gly Ile Ile Thr Arg Tyr
210                 215                 220

Lys Gly Pro Trp Thr Gly His Pro Gln Ala Gly Val Leu Gln Lys Gly
225                 230                 235                 240

Gln Thr Ile Lys Tyr Asp Glu Val Gln Lys Phe Asp Gly His Val Trp
                245                 250                 255

Val Ser Trp Glu Thr Phe Glu Gly Glu Thr Val Tyr Met Pro Val Arg
            260                 265                 270

Thr Trp Asp Ala Lys Thr Gly Lys Val Gly Lys Leu Trp Gly Glu Ile
        275                 280                 285

Lys Glu Leu Arg Gln Ile Lys Ile Trp Phe Gln Asn Arg Arg Met Lys
290                 295                 300

Trp Lys Lys
305

<210> SEQ ID NO 37
<211> LENGTH: 300
<212> TYPE: PRT
<213> ORGANISM: Artificial
<220> FEATURE:
<223> OTHER INFORMATION: Polypeptide construct

<400> SEQUENCE: 37

Met Ser Ile Ile Met Glu Val Ala Thr Met Gln Ala Lys Leu Thr Lys
1               5                   10                  15

Asn Glu Phe Ile Glu Trp Leu Lys Thr Ser Glu Gly Lys Gln Phe Asn
                20                  25                  30

Val Asp Leu Trp Tyr Gly Phe Gln Cys Phe Asp Tyr Ala Asn Ala Gly
            35                  40                  45

Trp Lys Val Leu Phe Gly Leu Leu Lys Gly Leu Ala Lys Asp
50                  55                  60

Ile Pro Phe Ala Asn Asn Phe Asp Gly Leu Ala Thr Val Tyr Gln Asn
65                  70                  75                  80

Thr Pro Asp Phe Leu Ala Gln Pro Gly Asp Met Val Val Phe Gly Ser
                85                  90                  95

Asn Tyr Gly Ala Gly Tyr Gly His Val Ala Trp Val Ile Glu Ala Thr
            100                 105                 110

Leu Asp Tyr Ile Ile Val Tyr Glu Gln Asn Trp Leu Gly Gly Gly Trp
        115                 120                 125

Thr Asp Gly Ile Glu Gln Pro Gly Trp Gly Trp Glu Lys Val Thr Arg
    130                 135                 140

Arg Gln His Ala Tyr Asp Phe Pro Met Trp Phe Ile Arg Pro Asn Phe
145                 150                 155                 160
```

Lys Gly Gly Lys Leu Glu Val Ser Lys Ala Ala Thr Ile Lys Gln Ser
                165                 170                 175

Asp Val Lys Gln Glu Val Lys Lys Gln Glu Ala Lys Gln Ile Val Lys
            180                 185                 190

Ala Thr Asp Trp Lys Gln Asn Lys Asp Gly Ile Trp Tyr Lys Ala Glu
        195                 200                 205

His Ala Ser Phe Thr Val Thr Ala Pro Glu Gly Ile Ile Thr Arg Tyr
    210                 215                 220

Lys Gly Pro Trp Thr Gly His Pro Gln Ala Gly Val Leu Gln Lys Gly
225                 230                 235                 240

Gln Thr Ile Lys Tyr Asp Glu Val Gln Lys Phe Asp Gly His Val Trp
                245                 250                 255

Val Ser Trp Glu Thr Phe Glu Gly Glu Thr Val Tyr Met Pro Val Arg
            260                 265                 270

Thr Trp Asp Ala Lys Thr Gly Lys Val Gly Lys Leu Trp Gly Glu Ile
        275                 280                 285

Lys Glu Leu Arg Arg Arg Arg Arg Arg Arg
    290                 295                 300

<210> SEQ ID NO 38
<211> LENGTH: 304
<212> TYPE: PRT
<213> ORGANISM: Artificial
<220> FEATURE:
<223> OTHER INFORMATION: Polypeptide construct

<400> SEQUENCE: 38

Met Ser Ile Ile Met Glu Val Ala Thr Met Gln Ala Lys Leu Thr Lys
1               5                   10                  15

Asn Glu Phe Ile Glu Trp Leu Lys Thr Ser Gly Lys Gln Phe Asn
            20                  25                  30

Val Asp Leu Trp Tyr Gly Phe Gln Cys Phe Asp Tyr Ala Asn Ala Gly
            35                  40                  45

Trp Lys Val Leu Phe Gly Leu Leu Lys Gly Leu Gly Ala Lys Asp
    50                  55                  60

Ile Pro Phe Ala Asn Asn Phe Asp Gly Leu Ala Thr Val Tyr Gln Asn
65              70                  75                  80

Thr Pro Asp Phe Leu Ala Gln Pro Gly Asp Met Val Val Phe Gly Ser
            85                  90                  95

Asn Tyr Gly Ala Gly Tyr Gly His Val Ala Trp Val Ile Glu Ala Thr
        100                 105                 110

Leu Asp Tyr Ile Ile Val Tyr Glu Gln Asn Trp Leu Gly Gly Gly Trp
    115                 120                 125

Thr Asp Gly Ile Glu Gln Pro Gly Trp Gly Trp Glu Lys Val Thr Arg
    130                 135                 140

Arg Gln His Ala Tyr Asp Phe Pro Met Trp Phe Ile Arg Pro Asn Phe
145                 150                 155                 160

Lys Gly Gly Lys Leu Glu Val Ser Lys Ala Ala Thr Ile Lys Gln Ser
                165                 170                 175

Asp Val Lys Gln Glu Val Lys Lys Gln Glu Ala Lys Gln Ile Val Lys
            180                 185                 190

Ala Thr Asp Trp Lys Gln Asn Lys Asp Gly Ile Trp Tyr Lys Ala Glu
        195                 200                 205

His Ala Ser Phe Thr Val Thr Ala Pro Glu Gly Ile Ile Thr Arg Tyr
    210                 215                 220

```
Lys Gly Pro Trp Thr Gly His Pro Gln Ala Gly Val Leu Gln Lys Gly
225                 230                 235                 240

Gln Thr Ile Lys Tyr Asp Glu Val Gln Lys Phe Asp Gly His Val Trp
            245                 250                 255

Val Ser Trp Glu Thr Phe Glu Gly Glu Thr Val Tyr Met Pro Val Arg
        260                 265                 270

Thr Trp Asp Ala Lys Thr Gly Lys Val Gly Lys Leu Trp Gly Glu Ile
    275                 280                 285

Lys Glu Leu Gly Arg Lys Lys Arg Gln Arg Arg Pro Pro Gln
290                 295                 300

<210> SEQ ID NO 39
<211> LENGTH: 179
<212> TYPE: PRT
<213> ORGANISM: Artificial
<220> FEATURE:
<223> OTHER INFORMATION: Polypeptide construct

<400> SEQUENCE: 39

Met Ser Ile Ile Met Glu Val Ala Thr Met Gln Ala Lys Leu Thr Lys
1               5                   10                  15

Asn Glu Phe Ile Glu Trp Leu Lys Thr Ser Glu Gly Lys Gln Phe Asn
            20                  25                  30

Val Asp Leu Trp Tyr Gly Phe Gln Cys Phe Asp Tyr Ala Asn Ala Gly
        35                  40                  45

Trp Lys Val Leu Phe Gly Leu Leu Leu Lys Gly Leu Gly Ala Lys Asp
    50                  55                  60

Ile Pro Phe Ala Asn Asn Phe Asp Gly Leu Ala Thr Val Tyr Gln Asn
65              70                  75                  80

Thr Pro Asp Phe Leu Ala Gln Pro Gly Asp Met Val Val Phe Gly Ser
            85                  90                  95

Asn Tyr Gly Ala Gly Tyr Gly His Val Ala Trp Val Ile Glu Ala Thr
        100                 105                 110

Leu Asp Tyr Ile Ile Val Tyr Glu Gln Asn Trp Leu Gly Gly Gly Trp
    115                 120                 125

Thr Asp Gly Ile Glu Gln Pro Gly Trp Gly Trp Glu Lys Val Thr Arg
130                 135                 140

Arg Gln His Ala Tyr Asp Phe Pro Met Trp Phe Ile Arg Pro Asn Phe
145                 150                 155                 160

Lys Glu Leu Arg Gln Ile Lys Ile Trp Phe Gln Asn Arg Arg Met Lys
            165                 170                 175

Trp Lys Lys

<210> SEQ ID NO 40
<211> LENGTH: 172
<212> TYPE: PRT
<213> ORGANISM: Artificial
<220> FEATURE:
<223> OTHER INFORMATION: Polypeptide construct

<400> SEQUENCE: 40

Met Ser Ile Ile Met Glu Val Ala Thr Met Gln Ala Lys Leu Thr Lys
1               5                   10                  15

Asn Glu Phe Ile Glu Trp Leu Lys Thr Ser Glu Gly Lys Gln Phe Asn
            20                  25                  30

Val Asp Leu Trp Tyr Gly Phe Gln Cys Phe Asp Tyr Ala Asn Ala Gly
        35                  40                  45
```

```
Trp Lys Val Leu Phe Gly Leu Leu Lys Gly Leu Gly Ala Lys Asp
        50                  55                  60

Ile Pro Phe Ala Asn Asn Phe Asp Gly Leu Ala Thr Val Tyr Gln Asn
65                  70                  75                  80

Thr Pro Asp Phe Leu Ala Gln Pro Gly Asp Met Val Val Phe Gly Ser
                85                  90                  95

Asn Tyr Gly Ala Gly Tyr Gly His Val Ala Trp Val Ile Glu Ala Thr
                100                 105                 110

Leu Asp Tyr Ile Ile Val Tyr Glu Gln Asn Trp Leu Gly Gly Gly Trp
                115                 120                 125

Thr Asp Gly Ile Glu Gln Pro Gly Trp Gly Trp Glu Lys Val Thr Arg
            130                 135                 140

Arg Gln His Ala Tyr Asp Phe Pro Met Trp Phe Ile Arg Pro Asn Phe
145                 150                 155                 160

Lys Glu Leu Arg Arg Arg Arg Arg Arg Arg
                165                 170

<210> SEQ ID NO 41
<211> LENGTH: 176
<212> TYPE: PRT
<213> ORGANISM: Artificial
<220> FEATURE:
<223> OTHER INFORMATION: Polypeptide construct

<400> SEQUENCE: 41

Met Ser Ile Ile Met Glu Val Ala Thr Met Gln Ala Lys Leu Thr Lys
1               5                   10                  15

Asn Glu Phe Ile Glu Trp Leu Lys Thr Ser Glu Gly Lys Gln Phe Asn
                20                  25                  30

Val Asp Leu Trp Tyr Gly Phe Gln Cys Phe Asp Tyr Ala Asn Ala Gly
                35                  40                  45

Trp Lys Val Leu Phe Gly Leu Leu Lys Gly Leu Gly Ala Lys Asp
        50                  55                  60

Ile Pro Phe Ala Asn Asn Phe Asp Gly Leu Ala Thr Val Tyr Gln Asn
65                  70                  75                  80

Thr Pro Asp Phe Leu Ala Gln Pro Gly Asp Met Val Val Phe Gly Ser
                85                  90                  95

Asn Tyr Gly Ala Gly Tyr Gly His Val Ala Trp Val Ile Glu Ala Thr
                100                 105                 110

Leu Asp Tyr Ile Ile Val Tyr Glu Gln Asn Trp Leu Gly Gly Gly Trp
                115                 120                 125

Thr Asp Gly Ile Glu Gln Pro Gly Trp Gly Trp Glu Lys Val Thr Arg
            130                 135                 140

Arg Gln His Ala Tyr Asp Phe Pro Met Trp Phe Ile Arg Pro Asn Phe
145                 150                 155                 160

Lys Glu Leu Gly Arg Lys Lys Arg Arg Gln Arg Arg Arg Pro Pro Gln
                165                 170                 175

<210> SEQ ID NO 42
<211> LENGTH: 287
<212> TYPE: PRT
<213> ORGANISM: Artificial
<220> FEATURE:
<223> OTHER INFORMATION: Polypeptide construct

<400> SEQUENCE: 42

Met Ala Ala Thr His Glu His Ser Ala Gln Trp Leu Asn Asn Tyr Lys
```

```
   1               5                  10                 15
Lys Gly Tyr Gly Tyr Gly Pro Tyr Pro Leu Gly Ile Asn Gly Met
                20                 25                 30

His Tyr Gly Val Asp Phe Phe Met Asn Ile Gly Thr Pro Val Lys Ala
            35                 40                 45

Ile Ser Ser Gly Lys Ile Val Glu Ala Gly Trp Ser Asn Tyr Gly Gly
     50                 55                 60

Gly Asn Gln Ile Gly Leu Ile Glu Asn Asp Gly Val His Arg Gln Trp
 65                 70                 75                 80

Tyr Met His Leu Ser Lys Tyr Asn Val Lys Val Gly Asp Tyr Val Lys
                85                 90                 95

Ala Gly Gln Ile Ile Gly Trp Ser Gly Ser Thr Gly Tyr Ser Thr Ala
             100                105                110

Pro His Leu His Phe Gln Arg Met Val Asn Ser Phe Ser Asn Ser Thr
             115                120                125

Ala Gln Asp Pro Met Pro Phe Leu Lys Ser Ala Gly Tyr Gly Gly Lys
         130                135                140

Leu Glu Val Ser Lys Ala Ala Thr Ile Lys Gln Ser Asp Val Lys Gln
145                150                155                160

Glu Val Lys Lys Gln Glu Ala Lys Gln Ile Val Lys Ala Thr Asp Trp
                 165                170                175

Lys Gln Asn Lys Asp Gly Ile Trp Tyr Lys Ala Glu His Ala Ser Phe
             180                185                190

Thr Val Thr Ala Pro Glu Gly Ile Ile Thr Arg Tyr Lys Gly Pro Trp
         195                200                205

Thr Gly His Pro Gln Ala Gly Val Leu Gln Lys Gly Gln Thr Ile Lys
     210                215                220

Tyr Asp Glu Val Gln Lys Phe Asp Gly His Val Trp Val Ser Trp Glu
225                230                235                240

Thr Phe Glu Gly Glu Thr Val Tyr Met Pro Val Arg Thr Trp Asp Ala
                 245                250                255

Lys Thr Gly Lys Val Gly Lys Leu Trp Gly Glu Ile Lys Glu Leu Arg
             260                265                270

Gln Ile Lys Ile Trp Phe Gln Asn Arg Arg Met Lys Trp Lys Lys
         275                280                285

<210> SEQ ID NO 43
<211> LENGTH: 280
<212> TYPE: PRT
<213> ORGANISM: Artificial
<220> FEATURE:
<223> OTHER INFORMATION: Polypeptide construct

<400> SEQUENCE: 43

Met Ala Ala Thr His Glu His Ser Ala Gln Trp Leu Asn Asn Tyr Lys
 1               5                  10                 15

Lys Gly Tyr Gly Tyr Gly Pro Tyr Pro Leu Gly Ile Asn Gly Met
                20                 25                 30

His Tyr Gly Val Asp Phe Phe Met Asn Ile Gly Thr Pro Val Lys Ala
            35                 40                 45

Ile Ser Ser Gly Lys Ile Val Glu Ala Gly Trp Ser Asn Tyr Gly Gly
     50                 55                 60

Gly Asn Gln Ile Gly Leu Ile Glu Asn Asp Gly Val His Arg Gln Trp
 65                 70                 75                 80

Tyr Met His Leu Ser Lys Tyr Asn Val Lys Val Gly Asp Tyr Val Lys
```

-continued

```
                85                  90                  95
Ala Gly Gln Ile Ile Gly Trp Ser Gly Ser Thr Gly Tyr Ser Thr Ala
            100                 105                 110

Pro His Leu His Phe Gln Arg Met Val Asn Ser Phe Ser Asn Ser Thr
            115                 120                 125

Ala Gln Asp Pro Met Pro Phe Leu Lys Ser Ala Gly Tyr Gly Gly Lys
            130                 135                 140

Leu Glu Val Ser Lys Ala Ala Thr Ile Lys Gln Ser Asp Val Lys Gln
145                 150                 155                 160

Glu Val Lys Lys Gln Glu Ala Lys Gln Ile Val Lys Ala Thr Asp Trp
                165                 170                 175

Lys Gln Asn Lys Asp Gly Ile Trp Tyr Lys Ala Glu His Ala Ser Phe
            180                 185                 190

Thr Val Thr Ala Pro Glu Gly Ile Ile Thr Arg Tyr Lys Gly Pro Trp
            195                 200                 205

Thr Gly His Pro Gln Ala Gly Val Leu Gln Lys Gly Gln Thr Ile Lys
            210                 215                 220

Tyr Asp Glu Val Gln Lys Phe Asp Gly His Val Trp Val Ser Trp Glu
225                 230                 235                 240

Thr Phe Glu Gly Glu Thr Val Tyr Met Pro Val Arg Thr Trp Asp Ala
                245                 250                 255

Lys Thr Gly Lys Val Gly Lys Leu Trp Gly Glu Ile Lys Glu Leu Arg
            260                 265                 270

Arg Arg Arg Arg Arg Arg Arg Arg
            275                 280
```

<210> SEQ ID NO 44
<211> LENGTH: 284
<212> TYPE: PRT
<213> ORGANISM: Artificial
<220> FEATURE:
<223> OTHER INFORMATION: Polypeptide construct

<400> SEQUENCE: 44

```
Met Ala Ala Thr His Glu His Ser Ala Gln Trp Leu Asn Asn Tyr Lys
1               5                   10                  15

Lys Gly Tyr Gly Tyr Gly Pro Tyr Pro Leu Gly Ile Asn Gly Gly Met
            20                  25                  30

His Tyr Gly Val Asp Phe Phe Met Asn Ile Gly Thr Pro Val Lys Ala
            35                  40                  45

Ile Ser Ser Gly Lys Ile Val Glu Ala Gly Trp Ser Asn Tyr Gly Gly
        50                  55                  60

Gly Asn Gln Ile Gly Leu Ile Glu Asn Asp Gly Val His Arg Gln Trp
65                  70                  75                  80

Tyr Met His Leu Ser Lys Tyr Asn Val Lys Val Gly Asp Tyr Val Lys
                85                  90                  95

Ala Gly Gln Ile Ile Gly Trp Ser Gly Ser Thr Gly Tyr Ser Thr Ala
            100                 105                 110

Pro His Leu His Phe Gln Arg Met Val Asn Ser Phe Ser Asn Ser Thr
            115                 120                 125

Ala Gln Asp Pro Met Pro Phe Leu Lys Ser Ala Gly Tyr Gly Gly Lys
            130                 135                 140

Leu Glu Val Ser Lys Ala Ala Thr Ile Lys Gln Ser Asp Val Lys Gln
145                 150                 155                 160

Glu Val Lys Lys Gln Glu Ala Lys Gln Ile Val Lys Ala Thr Asp Trp
```

```
            165                 170                 175
Lys Gln Asn Lys Asp Gly Ile Trp Tyr Lys Ala Glu His Ala Ser Phe
            180                 185                 190

Thr Val Thr Ala Pro Glu Gly Ile Ile Thr Arg Tyr Lys Gly Pro Trp
            195                 200                 205

Thr Gly His Pro Gln Ala Gly Val Leu Gln Lys Gly Gln Thr Ile Lys
            210                 215                 220

Tyr Asp Glu Val Gln Lys Phe Asp Gly His Val Trp Val Ser Trp Glu
225                 230                 235                 240

Thr Phe Glu Gly Glu Thr Val Tyr Met Pro Val Arg Thr Trp Asp Ala
                245                 250                 255

Lys Thr Gly Lys Val Gly Lys Leu Trp Gly Glu Ile Lys Glu Leu Gly
            260                 265                 270

Arg Lys Lys Arg Arg Gln Arg Arg Pro Pro Gln
            275                 280
```

<210> SEQ ID NO 45
<211> LENGTH: 160
<212> TYPE: PRT
<213> ORGANISM: Artificial
<220> FEATURE:
<223> OTHER INFORMATION: Polypeptide construct

<400> SEQUENCE: 45

```
Met Ala Ala Thr His Glu His Ser Ala Gln Trp Leu Asn Asn Tyr Lys
1               5                   10                  15

Lys Gly Tyr Gly Tyr Gly Pro Tyr Pro Leu Gly Ile Asn Gly Gly Met
            20                  25                  30

His Tyr Gly Val Asp Phe Phe Met Asn Ile Gly Thr Pro Val Lys Ala
        35                  40                  45

Ile Ser Ser Gly Lys Ile Val Glu Ala Gly Trp Ser Asn Tyr Gly Gly
    50                  55                  60

Gly Asn Gln Ile Gly Leu Ile Glu Asn Asp Gly Val His Arg Gln Trp
65                  70                  75                  80

Tyr Met His Leu Ser Lys Tyr Asn Val Lys Val Gly Asp Tyr Val Lys
                85                  90                  95

Ala Gly Gln Ile Ile Gly Trp Ser Gly Ser Thr Gly Tyr Ser Thr Ala
            100                 105                 110

Pro His Leu His Phe Gln Arg Met Val Asn Ser Phe Ser Asn Ser Thr
        115                 120                 125

Ala Gln Asp Pro Met Pro Phe Leu Lys Ser Ala Gly Tyr Gly Glu Leu
    130                 135                 140

Arg Gln Ile Lys Ile Trp Phe Gln Asn Arg Arg Met Lys Trp Lys Lys
145                 150                 155                 160
```

<210> SEQ ID NO 46
<211> LENGTH: 153
<212> TYPE: PRT
<213> ORGANISM: Artificial
<220> FEATURE:
<223> OTHER INFORMATION: Polypeptide construct

<400> SEQUENCE: 46

```
Met Ala Ala Thr His Glu His Ser Ala Gln Trp Leu Asn Asn Tyr Lys
1               5                   10                  15

Lys Gly Tyr Gly Tyr Gly Pro Tyr Pro Leu Gly Ile Asn Gly Gly Met
            20                  25                  30
```

His Tyr Gly Val Asp Phe Phe Met Asn Ile Gly Thr Pro Val Lys Ala
            35                  40                  45

Ile Ser Ser Gly Lys Ile Val Glu Ala Gly Trp Ser Asn Tyr Gly Gly
 50                  55                  60

Gly Asn Gln Ile Gly Leu Ile Glu Asn Asp Gly Val His Arg Gln Trp
 65                  70                  75                  80

Tyr Met His Leu Ser Lys Tyr Asn Val Lys Val Gly Asp Tyr Val Lys
                 85                  90                  95

Ala Gly Gln Ile Ile Gly Trp Ser Gly Ser Thr Gly Tyr Ser Thr Ala
            100                 105                 110

Pro His Leu His Phe Gln Arg Met Val Asn Ser Phe Ser Asn Ser Thr
            115                 120                 125

Ala Gln Asp Pro Met Pro Phe Leu Lys Ser Ala Gly Tyr Gly Glu Leu
    130                 135                 140

Arg Arg Arg Arg Arg Arg Arg Arg
145                 150

<210> SEQ ID NO 47
<211> LENGTH: 157
<212> TYPE: PRT
<213> ORGANISM: Artificial
<220> FEATURE:
<223> OTHER INFORMATION: Polypeptide construct

<400> SEQUENCE: 47

Met Ala Ala Thr His Glu His Ser Ala Gln Trp Leu Asn Asn Tyr Lys
 1               5                   10                  15

Lys Gly Tyr Gly Tyr Gly Pro Tyr Pro Leu Gly Ile Asn Gly Gly Met
            20                  25                  30

His Tyr Gly Val Asp Phe Phe Met Asn Ile Gly Thr Pro Val Lys Ala
            35                  40                  45

Ile Ser Ser Gly Lys Ile Val Glu Ala Gly Trp Ser Asn Tyr Gly Gly
 50                  55                  60

Gly Asn Gln Ile Gly Leu Ile Glu Asn Asp Gly Val His Arg Gln Trp
 65                  70                  75                  80

Tyr Met His Leu Ser Lys Tyr Asn Val Lys Val Gly Asp Tyr Val Lys
                 85                  90                  95

Ala Gly Gln Ile Ile Gly Trp Ser Gly Ser Thr Gly Tyr Ser Thr Ala
            100                 105                 110

Pro His Leu His Phe Gln Arg Met Val Asn Ser Phe Ser Asn Ser Thr
            115                 120                 125

Ala Gln Asp Pro Met Pro Phe Leu Lys Ser Ala Gly Tyr Gly Glu Leu
    130                 135                 140

Gly Arg Lys Lys Arg Arg Gln Arg Arg Arg Pro Pro Gln
145                 150                 155

<210> SEQ ID NO 48

<400> SEQUENCE: 48

000

<210> SEQ ID NO 49

<400> SEQUENCE: 49

000

<210> SEQ ID NO 50
<211> LENGTH: 981
<212> TYPE: DNA
<213> ORGANISM: Artificial
<220> FEATURE:
<223> OTHER INFORMATION: Polynucleotide

<400> SEQUENCE: 50

```
atgctgaaac atatttactc caaccacatt aaaggtaaca aaatcacagc ccctaaaccg      60
tcaattcagg gcgtggtgat ccacaacgat tatggctcaa tgacccctte acagtacctg     120
ccttggctgt acgctcgcga aaacaacggt acacatgtga atggctgggc ctcagtgtat     180
gccaatcgca acgaggtgct gtggtatcat cctacagact acgtggaatg gcactgcggc     240
aaccaatggg ccaacgccaa cctgatcggc tttgaagttt gcgaatcata tcctggtcgc     300
atctcagaca aactgtttct ggaaaacgag gaagccacac tgaaagtagc tgccgacgtg     360
atgaaatcgt atggcctgcc tgtgaatcgc aacacagtgc gcctgcacaa cgaattttc      420
ggtacatcat gccctcatcg ttcatgggac ctgcacgtgg gcaaaggcga gccttatacc     480
acaacaaata tcaataaaat gaaagattat ttcattaaac ggattaaaca ctactatgac     540
ggtggcaaac tggaagttag caaagcagcc accattaaac agagtgatgt taaacaagaa     600
gtgaaaaaac aagaggccaa acaaattgtg aaagccaccg attggaaaca gaacaaagat     660
ggcatctggt ataaagcaga acatgccagc tttaccgtga ccgcaccgga aggcattatt     720
acccgttata aggtccgtg gaccggtcat ccgcaggcag gcgtgctgca gaaaggtcag     780
accatcaaat atgatgaagt gcagaaattt gatggccatg tttgggttag ctgggaaacc     840
tttgaaggtg aaaccgttta tatgccggtt cgtacctggg atgcaaaaac cggtaaagtt     900
ggtaaactgt ggggtgagat taagagctc cgccagatca aaatttggtt tcagaatcgt     960
cgcatgaaat ggaaaaaata a                                                981
```

<210> SEQ ID NO 51
<211> LENGTH: 960
<212> TYPE: DNA
<213> ORGANISM: Artificial
<220> FEATURE:
<223> OTHER INFORMATION: Polynucleotide

<400> SEQUENCE: 51

```
atgctgaaac atatttactc caaccacatt aaaggtaaca aaatcacagc ccctaaaccg      60
tcaattcagg gcgtggtgat ccacaacgat tatggctcaa tgacccctte acagtacctg     120
ccttggctgt acgctcgcga aaacaacggt acacatgtga atggctgggc ctcagtgtat     180
gccaatcgca acgaggtgct gtggtatcat cctacagact acgtggaatg gcactgcggc     240
aaccaatggg ccaacgccaa cctgatcggc tttgaagttt gcgaatcata tcctggtcgc     300
atctcagaca aactgtttct ggaaaacgag gaagccacac tgaaagtagc tgccgacgtg     360
atgaaatcgt atggcctgcc tgtgaatcgc aacacagtgc gcctgcacaa cgaattttc      420
ggtacatcat gccctcatcg ttcatgggac ctgcacgtgg gcaaaggcga gccttatacc     480
acaacaaata tcaataaaat gaaagattat ttcattaaac ggattaaaca ctactatgac     540
ggtggcaaac tggaagttag caaagcagcc accattaaac agagtgatgt taaacaagaa     600
gtgaaaaaac aagaggccaa acaaattgtg aaagccaccg attggaaaca gaacaaagat     660
ggcatctggt ataaagcaga acatgccagc tttaccgtga ccgcaccgga aggcattatt     720
acccgttata aggtccgtg gaccggtcat ccgcaggcag gcgtgctgca gaaaggtcag     780
```

| accatcaaat atgatgaagt gcagaaattt gatggccatg tttgggttag ctgggaaacc | 840 |
| tttgaaggtg aaaccgttta tatgccggtt cgtacctggg atgcaaaaac cggtaaagtt | 900 |
| ggtaaactgt ggggtgagat taaagagctc cgtcgtcgtc gccgtcggcg tcgtcgttaa | 960 |

<210> SEQ ID NO 52
<211> LENGTH: 972
<212> TYPE: DNA
<213> ORGANISM: Artificial
<220> FEATURE:
<223> OTHER INFORMATION: Polynucleotide

<400> SEQUENCE: 52

| atgctgaaac atatttactc caaccacatt aaaggtaaca aaatcacagc ccctaaaccg | 60 |
| tcaattcagg gcgtggtgat ccacaacgat tatggctcaa tgacccctc acagtacctg | 120 |
| ccttggctgt acgctcgcga aaacaacggt acacatgtga atggctgggc ctcagtgtat | 180 |
| gccaatcgca acgaggtgct gtggtatcat cctacagact acgtggaatg cactgcggc | 240 |
| aaccaatggg ccaacgccaa cctgatcggc tttgaagttt gcgaatcata tcctggtcgc | 300 |
| atctcagaca aactgtttct ggaaaacgag gaagccacac tgaaagtagc tgccgacgtg | 360 |
| atgaaatcgt atggcctgcc tgtgaatcgc aacacagtgc gcctgcacaa cgaattttc | 420 |
| ggtacatcat gccctcatcg ttcatgggac ctgcacgtgg gcaaaggcga gccttatacc | 480 |
| acaacaaata tcaataaaat gaaagattat ttcattaaac ggattaaaca ctactatgac | 540 |
| ggtggcaaac tggaagttag caaagcagcc accattaaac agagtgatgt aaacaagaa | 600 |
| gtgaaaaaac aagaggccaa acaaattgtg aaagccaccg attggaaaca gaacaaagat | 660 |
| ggcatctggt ataaagcaga acatgccagc tttaccgtga ccgcaccgga aggcattatt | 720 |
| acccgttata aaggtccgtg gaccggtcat ccgcaggcag gcgtgctgca gaaaggtcag | 780 |
| accatcaaat atgatgaagt gcagaaattt gatggccatg tttgggttag ctgggaaacc | 840 |
| tttgaaggtg aaaccgttta tatgccggtt cgtacctggg atgcaaaaac cggtaaagtt | 900 |
| ggtaaactgt ggggtgagat taaagagctc ggtcgtaaaa acgtcgtca gcgtcgtcgt | 960 |
| ccgcctcagt aa | 972 |

<210> SEQ ID NO 53
<211> LENGTH: 600
<212> TYPE: DNA
<213> ORGANISM: Artificial
<220> FEATURE:
<223> OTHER INFORMATION: Polynucleotide

<400> SEQUENCE: 53

| atgctgaaac atatttactc caaccacatt aaaggtaaca aaatcacagc ccctaaaccg | 60 |
| tcaattcagg gcgtggtgat ccacaacgat tatggctcaa tgacccctc acagtacctg | 120 |
| ccttggctgt acgctcgcga aaacaacggt acacatgtga atggctgggc ctcagtgtat | 180 |
| gccaatcgca acgaggtgct gtggtatcat cctacagact acgtggaatg cactgcggc | 240 |
| aaccaatggg ccaacgccaa cctgatcggc tttgaagttt gcgaatcata tcctggtcgc | 300 |
| atctcagaca aactgtttct ggaaaacgag gaagccacac tgaaagtagc tgccgacgtg | 360 |
| atgaaatcgt atggcctgcc tgtgaatcgc aacacagtgc gcctgcacaa cgaattttc | 420 |
| ggtacatcat gccctcatcg ttcatgggac ctgcacgtgg gcaaaggcga gccttatacc | 480 |
| acaacaaata tcaataaaat gaaagattat ttcattaaac ggattaaaca ctactatgac | 540 |
| ggtgagctcc gccagatcaa atttggttt cagaatcgtc gcatgaaatg gaaaaaataa | 600 |

<210> SEQ ID NO 54
<211> LENGTH: 579
<212> TYPE: DNA
<213> ORGANISM: Artificial
<220> FEATURE:
<223> OTHER INFORMATION: Polynucleotide

<400> SEQUENCE: 54

| | |
|---|---|
| atgctgaaac atatttactc caaccacatt aaaggtaaca aaatcacagc ccctaaaccg | 60 |
| tcaattcagg gcgtggtgat ccacaacgat tatggctcaa tgacccccttc acagtacctg | 120 |
| ccttggctgt acgctcgcga aaacaacggt acacatgtga atggctgggc ctcagtgtat | 180 |
| gccaatcgca acgaggtgct gtggtatcat cctacagact acgtggaatg cactgcggc | 240 |
| aaccaatggg ccaacgccaa cctgatcggc tttgaagttt gcgaatcata tcctggtcgc | 300 |
| atctcagaca aactgtttct ggaaaacgag gaagccacac tgaaagtagc tgccgacgtg | 360 |
| atgaaatcgt atggcctgcc tgtgaatcgc aacacagtgc gcctgcacaa cgaattttc | 420 |
| ggtacatcat gccctcatcg ttcatgggac ctgcacgtgg gcaaaggcga gccttatacc | 480 |
| acaacaaata tcaataaaat gaaagattat ttcattaaac ggattaaaca ctactatgac | 540 |
| ggtgagctcc gtcgtcgtcg ccgtcggcgt cgtcgttaa | 579 |

<210> SEQ ID NO 55
<211> LENGTH: 591
<212> TYPE: DNA
<213> ORGANISM: Artificial
<220> FEATURE:
<223> OTHER INFORMATION: Polynculeotide

<400> SEQUENCE: 55

| | |
|---|---|
| atgctgaaac atatttactc caaccacatt aaaggtaaca aaatcacagc ccctaaaccg | 60 |
| tcaattcagg gcgtggtgat ccacaacgat tatggctcaa tgacccccttc acagtacctg | 120 |
| ccttggctgt acgctcgcga aaacaacggt acacatgtga atggctgggc ctcagtgtat | 180 |
| gccaatcgca acgaggtgct gtggtatcat cctacagact acgtggaatg cactgcggc | 240 |
| aaccaatggg ccaacgccaa cctgatcggc tttgaagttt gcgaatcata tcctggtcgc | 300 |
| atctcagaca aactgtttct ggaaaacgag gaagccacac tgaaagtagc tgccgacgtg | 360 |
| atgaaatcgt atggcctgcc tgtgaatcgc aacacagtgc gcctgcacaa cgaattttc | 420 |
| ggtacatcat gccctcatcg ttcatgggac ctgcacgtgg gcaaaggcga gccttatacc | 480 |
| acaacaaata tcaataaaat gaaagattat ttcattaaac ggattaaaca ctactatgac | 540 |
| ggtgagctcg gtcgtaaaaa acgtcgtcag cgtcgtcgtc cgcctcagta a | 591 |

<210> SEQ ID NO 56
<211> LENGTH: 924
<212> TYPE: DNA
<213> ORGANISM: Artificial
<220> FEATURE:
<223> OTHER INFORMATION: Polynucleotide

<400> SEQUENCE: 56

| | |
|---|---|
| atgtccatta tcatggaagt ggccacaatg caagccaaac tgacaaaaaa tgagttcatt | 60 |
| gagtggctga aaacgtccga gggtaaacag ttcaacgtgg acctgtggta cggttttcag | 120 |
| tgtttcgact acgccaacgc tggctggaaa gtgctgttcg gcctgctgct gaaaggcctg | 180 |
| ggagccaaag acatcccttt tgcaaacaat ttcgatggcc tggccacagt ttatcaaaac | 240 |

| | |
|---|---|
| accccctgact ttctggccca accaggcgac atggtggtgt ttggttctaa ttatggcgca | 300 |
| ggctatggcc acgtagcctg ggtgatcgaa gccacactgg actacattat tgtttatgag | 360 |
| caaaactggc tgggaggcgg atggacagac ggcatcgaac agcctggctg gggctgggag | 420 |
| aaagtgacac gccgtcaaca tgcctatgac ttccctatgt ggttcatccg tcctaatttc | 480 |
| aaaggtggta aactggaagt tagcaaagca gcaaccatta acagtccga tgttaaacaa | 540 |
| gaagtgaaaa acaagaggc caaacaaatt gtgaaagcca ccgattggaa acagaacaaa | 600 |
| gatggcattt ggtataaagc agaacatgcc agctttaccg ttaccgcacc ggaaggcatt | 660 |
| attacccgtt ataaaggtcc gtgaccggt catccgcagg caggcgtact gcagaaaggt | 720 |
| cagaccatta aatacgatga agtgcagaaa tttgatggcc atgtttgggt tagctgggaa | 780 |
| acctttgaag gtgaaaccgt ttatatgccg gttcgtacct gggatgcaaa aaccggtaaa | 840 |
| gtgggcaaac tgtggggtga aatcaaagag ctccgccaga tcaaaatttg gtttcagaat | 900 |
| cgtcgcatga aatggaaaaa ataa | 924 |

<210> SEQ ID NO 57
<211> LENGTH: 903
<212> TYPE: DNA
<213> ORGANISM: Artificial
<220> FEATURE:
<223> OTHER INFORMATION: Polynucleotide

<400> SEQUENCE: 57

| | |
|---|---|
| atgtccatta tcatggaagt ggccacaatg caagccaaac tgacaaaaaa tgagttcatt | 60 |
| gagtggctga aaacgtccga gggtaaacag ttcaacgtgg acctgtggta cggttttcag | 120 |
| tgtttcgact acgccaacgc tggctggaaa gtgctgttcg gcctgctgct gaaaggcctg | 180 |
| ggagccaaag acatcccttt tgcaaacaat ttcgatggcc tggccacagt ttatcaaaac | 240 |
| accccctgact ttctggccca accaggcgac atggtggtgt ttggttctaa ttatggcgca | 300 |
| ggctatggcc acgtagcctg ggtgatcgaa gccacactgg actacattat tgtttatgag | 360 |
| caaaactggc tgggaggcgg atggacagac ggcatcgaac agcctggctg gggctgggag | 420 |
| aaagtgacac gccgtcaaca tgcctatgac ttccctatgt ggttcatccg tcctaatttc | 480 |
| aaaggtggta aactggaagt tagcaaagca gcaaccatta acagtccga tgttaaacaa | 540 |
| gaagtgaaaa acaagaggc caaacaaatt gtgaaagcca ccgattggaa acagaacaaa | 600 |
| gatggcattt ggtataaagc agaacatgcc agctttaccg ttaccgcacc ggaaggcatt | 660 |
| attacccgtt ataaaggtcc gtgaccggt catccgcagg caggcgtact gcagaaaggt | 720 |
| cagaccatta aatacgatga agtgcagaaa tttgatggcc atgtttgggt tagctgggaa | 780 |
| acctttgaag gtgaaaccgt ttatatgccg gttcgtacct gggatgcaaa aaccggtaaa | 840 |
| gtgggcaaac tgtggggtga aatcaaagag ctccgtcgtc gtcgccgtcg gcgtcgtcgt | 900 |
| taa | 903 |

<210> SEQ ID NO 58
<211> LENGTH: 915
<212> TYPE: DNA
<213> ORGANISM: Artificial
<220> FEATURE:
<223> OTHER INFORMATION: Polynucleotide

<400> SEQUENCE: 58

| | |
|---|---|
| atgtccatta tcatggaagt ggccacaatg caagccaaac tgacaaaaaa tgagttcatt | 60 |
| gagtggctga aaacgtccga gggtaaacag ttcaacgtgg acctgtggta cggttttcag | 120 |

| | |
|---|---|
| tgtttcgact acgccaacgc tggctggaaa gtgctgttcg gcctgctgct gaaaggcctg | 180 |
| ggagccaaag acatcccttt tgcaaacaat ttcgatggcc tggccacagt ttatcaaaac | 240 |
| accccctgact ttctggccca accaggcgac atggtggtgt ttggttctaa ttatggcgca | 300 |
| ggctatggcc acgtagcctg ggtgatcgaa gccacactgg actacattat tgtttatgag | 360 |
| caaaactggc tgggaggcgg atggacagac ggcatcgaac agcctggctg gggctgggag | 420 |
| aaagtgacac gccgtcaaca tgcctatgac ttccctatgt ggttcatccg tcctaatttc | 480 |
| aaaggtggta aactggaagt tagcaaagca gcaaccatta acagtccga tgttaaacaa | 540 |
| gaagtgaaaa acaagaggc caaacaaatt gtgaaagcca ccgattggaa acagaacaaa | 600 |
| gatggcattt ggtataaagc agaacatgcc agctttaccg ttaccgcacc ggaaggcatt | 660 |
| attacccgtt ataaaggtcc gtggaccggt catccgcagg caggcgtact gcagaaaggt | 720 |
| cagaccatta atacgatga agtgcagaaa tttgatggcc atgtttgggt tagctgggaa | 780 |
| acctttgaag gtgaaaccgt ttatatgccg gttcgtacct gggatgcaaa aaccggtaaa | 840 |
| gtgggcaaac tgtggggtga aatcaaagag ctcggtcgta aaaaacgtcg tcagcgtcgt | 900 |
| cgtccgcctc agtaa | 915 |

<210> SEQ ID NO 59
<211> LENGTH: 540
<212> TYPE: DNA
<213> ORGANISM: Artificial
<220> FEATURE:
<223> OTHER INFORMATION: Polynucleotide

<400> SEQUENCE: 59

| | |
|---|---|
| atgtccatta tcatggaagt ggccacaatg caagccaaac tgacaaaaaa tgagttcatt | 60 |
| gagtggctga aaacgtccga gggtaaacag ttcaacgtgg acctgtggta cggttttcag | 120 |
| tgtttcgact acgccaacgc tggctggaaa gtgctgttcg gcctgctgct gaaaggcctg | 180 |
| ggagccaaag acatcccttt tgcaaacaat ttcgatggcc tggccacagt ttatcaaaac | 240 |
| accccctgact ttctggccca accaggcgac atggtggtgt ttggttctaa ttatggcgca | 300 |
| ggctatggcc acgtagcctg ggtgatcgaa gccacactgg actacattat tgtttatgag | 360 |
| caaaactggc tgggaggcgg atggacagac ggcatcgaac agcctggctg gggctgggag | 420 |
| aaagtgacac gccgtcaaca tgcctatgac ttccctatgt ggttcatccg tcctaatttc | 480 |
| aaagagctcc gccagatcaa aatttggttt cagaatcgtc gcatgaaatg gaaaaaataa | 540 |

<210> SEQ ID NO 60
<211> LENGTH: 519
<212> TYPE: DNA
<213> ORGANISM: Artificial
<220> FEATURE:
<223> OTHER INFORMATION: Polynucleotide

<400> SEQUENCE: 60

| | |
|---|---|
| atgtccatta tcatggaagt ggccacaatg caagccaaac tgacaaaaaa tgagttcatt | 60 |
| gagtggctga aaacgtccga gggtaaacag ttcaacgtgg acctgtggta cggttttcag | 120 |
| tgtttcgact acgccaacgc tggctggaaa gtgctgttcg gcctgctgct gaaaggcctg | 180 |
| ggagccaaag acatcccttt tgcaaacaat ttcgatggcc tggccacagt ttatcaaaac | 240 |
| accccctgact ttctggccca accaggcgac atggtggtgt ttggttctaa ttatggcgca | 300 |
| ggctatggcc acgtagcctg ggtgatcgaa gccacactgg actacattat tgtttatgag | 360 |

```
caaaactggc tgggaggcgg atggacagac ggcatcgaac agcctggctg gggctgggag      420
aaagtgacac gccgtcaaca tgcctatgac ttccctatgt ggttcatccg tcctaatttc      480
aaagagctcc gtcgtcgtcg ccgtcggcgt cgtcgttaa                             519

<210> SEQ ID NO 61
<211> LENGTH: 531
<212> TYPE: DNA
<213> ORGANISM: Artificial
<220> FEATURE:
<223> OTHER INFORMATION: Polynucleotide

<400> SEQUENCE: 61
atgtccatta tcatggaagt ggccacaatg caagccaaac tgacaaaaaa tgagttcatt       60
gagtggctga aaacgtccga gggtaaacag ttcaacgtgg acctgtggta cggttttcag      120
tgtttcgact acgccaacgc tggctggaaa gtgctgttcg gcctgctgct gaaaggcctg      180
ggagccaaag acatcccttt tgcaaacaat ttcgatggcc tggccacagt ttatcaaaac      240 accctgact ttctggccca accaggcgac atggtggtgt tggttctaa ttatggcgca        300 ggctatggcc acgtagcctg ggtgatcgaa gccacactgg actacattat tgtttatgag      360
caaaactggc tgggaggcgg atggacagac ggcatcgaac agcctggctg gggctgggag      420
aaagtgacac gccgtcaaca tgcctatgac ttccctatgt ggttcatccg tcctaatttc      480
aaagagctcg gtcgtaaaaa acgtcgtcag cgtcgtcgtc gcctcagta a                531

<210> SEQ ID NO 62
<211> LENGTH: 864
<212> TYPE: DNA
<213> ORGANISM: Artificial
<220> FEATURE:
<223> OTHER INFORMATION: Polynculeotide

<400> SEQUENCE: 62
atggcagcca cacatgaaca ctctgcccaa tggctgaaca actacaaaaa aggctacggt       60
tatggccctt accctctggg cattaacggt ggcatgcact acggcgttga cttttttatg      120
aacatcggca cccctgtgaa agccattagc tcaggcaaaa tcgtggaagc cggttggtca      180
aactatggcg gtggcaacca gatcggtctg atcgagaacg atggtgtgca ccgccaatgg      240
tacatgcacc tgtccaaata caacgttaaa gttggtgact acgtgaaagc aggccagatt      300
atcggctggt caggttcaac cggttattca acagcccctc atctgcactt ccaacgcatg      360
gtgaatagtt ttagtaattc taccgctcaa gatccgatgc cattcctgaa atctgccggt      420
tatggtggca aactggaagt tagcaaagca gcaaccatta acagtccga tgttaaacaa       480 gaagtgaaaa acaagaggc caaacaaatt gtgaaagcga ccgattggaa acagaacaaa       540
gatggcattt ggtataaagc agaacatgcc agctttaccg tgaccgcacc ggaaggcatt      600
attacccgtt ataaaggtcc gtggaccggt catccgcagg caggcgtgct gcagaaaggt      660
cagaccatca aatatgatga ggtgcagaaa tttgatggcc atgtttgggt tagctgggaa      720 accttttgaag gtgaaaccgt ttatatgccg gttcgtacct gggatgcaaa aaccggtaaa     780
gtgggtaaac tgtgggtga aatcaaagag ctccgccaga tcaaaatttg gtttcagaat      840
cgtcgcatga aatggaaaaa ataa                                             864

<210> SEQ ID NO 63
<211> LENGTH: 843
<212> TYPE: DNA
<213> ORGANISM: Artificial
```

<220> FEATURE:
<223> OTHER INFORMATION: Polynucleotide

<400> SEQUENCE: 63

| | |
|---|---|
| atggcagcca cacatgaaca ctctgcccaa tggctgaaca actacaaaaa aggctacggt | 60 |
| tatggcccct tacccctctggg cattaacggt ggcatgcact acggcgttga cttttttatg | 120 |
| aacatcggca ccccctgtgaa agccattagc tcaggcaaaa tcgtggaagc cggttggtca | 180 |
| aactatggcg gtggcaacca gatcggtctg atcgagaacg atggtgtgca ccgccaatgg | 240 |
| tacatgcacc tgtccaaata caacgttaaa gttggtgact acgtgaaagc aggccagatt | 300 |
| atcggctggt caggttcaac cggttattca acagcccctc atctgcactt ccaacgcatg | 360 |
| gtgaatagtt ttagtaattc taccgctcaa gatccgatgc cattcctgaa atctgccggt | 420 |
| tatggtggca aactggaagt tagcaaagca gcaaccatta acagtccga tgttaaacaa | 480 |
| gaagtgaaaa acaagaggc caaacaaatt gtgaaagcga ccgattggaa acagaacaaa | 540 |
| gatggcattt ggtataaagc agaacatgcc agctttaccg tgaccgcacc ggaaggcatt | 600 |
| attacccgtt ataaaggtcc gtggaccggt catccgcagg caggcgtgct gcagaaaggt | 660 |
| cagaccatca aatatgatga ggtgcagaaa tttgatggcc atgtttgggt tagctgggaa | 720 |
| accttttgaag gtgaaaccgt ttatatgccg gttcgtacct gggatgcaaa aaccggtaaa | 780 |
| gtgggtaaac tgtgggggtga aatcaaagag ctccgtcgtc gtcgccgtcg gcgtcgtcgt | 840 |
| taa | 843 |

<210> SEQ ID NO 64
<211> LENGTH: 855
<212> TYPE: DNA
<213> ORGANISM: Artificial
<220> FEATURE:
<223> OTHER INFORMATION: Polynucleotide

<400> SEQUENCE: 64

| | |
|---|---|
| atggcagcca cacatgaaca ctctgcccaa tggctgaaca actacaaaaa aggctacggt | 60 |
| tatggcccct tacccctctggg cattaacggt ggcatgcact acggcgttga cttttttatg | 120 |
| aacatcggca ccccctgtgaa agccattagc tcaggcaaaa tcgtggaagc cggttggtca | 180 |
| aactatggcg gtggcaacca gatcggtctg atcgagaacg atggtgtgca ccgccaatgg | 240 |
| tacatgcacc tgtccaaata caacgttaaa gttggtgact acgtgaaagc aggccagatt | 300 |
| atcggctggt caggttcaac cggttattca acagcccctc atctgcactt ccaacgcatg | 360 |
| gtgaatagtt ttagtaattc taccgctcaa gatccgatgc cattcctgaa atctgccggt | 420 |
| tatggtggca aactggaagt tagcaaagca gcaaccatta acagtccga tgttaaacaa | 480 |
| gaagtgaaaa acaagaggc caaacaaatt gtgaaagcga ccgattggaa acagaacaaa | 540 |
| gatggcattt ggtataaagc agaacatgcc agctttaccg tgaccgcacc ggaaggcatt | 600 |
| attacccgtt ataaaggtcc gtggaccggt catccgcagg caggcgtgct gcagaaaggt | 660 |
| cagaccatca aatatgatga ggtgcagaaa tttgatggcc atgtttgggt tagctgggaa | 720 |
| accttttgaag gtgaaaccgt ttatatgccg gttcgtacct gggatgcaaa aaccggtaaa | 780 |
| gtgggtaaac tgtgggggtga aatcaaagag ctcggtcgta aaaaacgtcg tcagcgtcgt | 840 |
| cgtccgcctc agtaa | 855 |

<210> SEQ ID NO 65
<211> LENGTH: 483
<212> TYPE: DNA

<213> ORGANISM: Artificial
<220> FEATURE:
<223> OTHER INFORMATION: Polynucleotide

<400> SEQUENCE: 65

```
atggcagcca cacatgaaca ctctgcccaa tggctgaaca actacaaaaa aggctacggt    60
tatggccctt accctctggg cattaacggt ggcatgcact acggcgttga cttttttatg   120
aacatcggca cccctgtgaa agccattagc tcaggcaaaa tcgtggaagc cggttggtca   180
aactatggcg gtggcaacca gatcggtctg atcgagaacg atggtgtgca ccgccaatgg   240
tacatgcacc tgtccaaata caacgttaaa gttggtgact acgtgaaagc aggccagatt   300
atcggctggt caggttcaac cggttattca acagcccctc atctgcactt ccaacgcatg   360
gtgaatagtt ttagtaattc taccgctcaa gatccgatgc cattcctgaa atctgccggt   420
tatggtgagc tccgccagat caaaatttgg tttcagaatc gtcgcatgaa atggaaaaaa   480
taa                                                                  483
```

<210> SEQ ID NO 66
<211> LENGTH: 462
<212> TYPE: DNA
<213> ORGANISM: Artificial
<220> FEATURE:
<223> OTHER INFORMATION: Polynucleotide

<400> SEQUENCE: 66

```
atggcagcca cacatgaaca ctctgcccaa tggctgaaca actacaaaaa aggctacggt    60
tatggccctt accctctggg cattaacggt ggcatgcact acggcgttga cttttttatg   120
aacatcggca cccctgtgaa agccattagc tcaggcaaaa tcgtggaagc cggttggtca   180
aactatggcg gtggcaacca gatcggtctg atcgagaacg atggtgtgca ccgccaatgg   240
tacatgcacc tgtccaaata caacgttaaa gttggtgact acgtgaaagc aggccagatt   300
atcggctggt caggttcaac cggttattca acagcccctc atctgcactt ccaacgcatg   360
gtgaatagtt ttagtaattc taccgctcaa gatccgatgc cattcctgaa atctgccggt   420
tatggtgagc tccgtcgtcg tcgccgtcgg cgtcgtcgtt aa                       462
```

<210> SEQ ID NO 67
<211> LENGTH: 474
<212> TYPE: DNA
<213> ORGANISM: Artificial
<220> FEATURE:
<223> OTHER INFORMATION: Polynucleotide

<400> SEQUENCE: 67

```
atggcagcca cacatgaaca ctctgcccaa tggctgaaca actacaaaaa aggctacggt    60
tatggccctt accctctggg cattaacggt ggcatgcact acggcgttga cttttttatg   120
aacatcggca cccctgtgaa agccattagc tcaggcaaaa tcgtggaagc cggttggtca   180
aactatggcg gtggcaacca gatcggtctg atcgagaacg atggtgtgca ccgccaatgg   240
tacatgcacc tgtccaaata caacgttaaa gttggtgact acgtgaaagc aggccagatt   300
atcggctggt caggttcaac cggttattca acagcccctc atctgcactt ccaacgcatg   360
gtgaatagtt ttagtaattc taccgctcaa gatccgatgc cattcctgaa atctgccggt   420
tatggtgagc tcggtcgtaa aaaacgtcgt cagcgtcgtc gtccgcctca gtaa          474
```

<210> SEQ ID NO 68

<400> SEQUENCE: 68

000

<210> SEQ ID NO 69

<400> SEQUENCE: 69

000

<210> SEQ ID NO 70
<211> LENGTH: 37
<212> TYPE: PRT
<213> ORGANISM: Artificial
<220> FEATURE:
<223> OTHER INFORMATION: Polypeptide fragment

<400> SEQUENCE: 70

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
        35

<210> SEQ ID NO 71
<211> LENGTH: 29
<212> TYPE: PRT
<213> ORGANISM: Artificial
<220> FEATURE:
<223> OTHER INFORMATION: Polypeptide fragment

<400> SEQUENCE: 71

Arg Gly Leu Arg Arg Leu Gly Arg Lys Ile Ala His Gly Val Lys Lys
1               5                   10                  15

Tyr Gly Pro Thr Val Leu Arg Ile Ile Arg Ile Ala Gly
            20                  25

<210> SEQ ID NO 72
<211> LENGTH: 13
<212> TYPE: PRT
<213> ORGANISM: Artificial
<220> FEATURE:
<223> OTHER INFORMATION: Polypeptide fragment

<400> SEQUENCE: 72

Ile Leu Pro Trp Lys Trp Pro Trp Trp Pro Trp Arg Arg
1               5                   10

<210> SEQ ID NO 73
<211> LENGTH: 18
<212> TYPE: PRT
<213> ORGANISM: Artificial
<220> FEATURE:
<223> OTHER INFORMATION: Polypeptide fragment

<400> SEQUENCE: 73

Arg Gly Gly Arg Leu Cys Tyr Cys Arg Arg Arg Phe Cys Val Cys Val
1               5                   10                  15

Gly Arg

<210> SEQ ID NO 74
<211> LENGTH: 31
<212> TYPE: PRT
<213> ORGANISM: Artificial

```
<220> FEATURE:
<223> OTHER INFORMATION: Polypeptide fragment

<400> SEQUENCE: 74

Ser Trp Leu Ser Lys Thr Ala Lys Lys Leu Glu Asn Ser Ala Lys Lys
1               5                   10                  15
Arg Ile Ser Glu Gly Ile Ala Ile Ala Ile Gln Gly Gly Pro Arg
            20                  25                  30

<210> SEQ ID NO 75
<211> LENGTH: 23
<212> TYPE: PRT
<213> ORGANISM: Artificial
<220> FEATURE:
<223> OTHER INFORMATION: Polypeptide fragment

<400> SEQUENCE: 75

Gly Ile Gly Lys Phe Leu His Ser Ala Lys Lys Phe Gly Lys Ala Phe
1               5                   10                  15
Val Gly Glu Ile Met Asn Ser
            20

<210> SEQ ID NO 76
<211> LENGTH: 25
<212> TYPE: PRT
<213> ORGANISM: Artificial
<220> FEATURE:
<223> OTHER INFORMATION: Polypeptide fragment

<400> SEQUENCE: 76

Gly Trp Gly Ser Phe Phe Lys Lys Ala Ala His Val Gly Lys His Val
1               5                   10                  15
Gly Lys Ala Ala Leu Thr His Tyr Leu
            20                  25

<210> SEQ ID NO 77
<211> LENGTH: 36
<212> TYPE: PRT
<213> ORGANISM: Artificial
<220> FEATURE:
<223> OTHER INFORMATION: Polypeptide fragment

<400> SEQUENCE: 77

Gly Gly Leu Lys Lys Leu Gly Lys Lys Leu Glu Gly Ala Gly Lys Arg
1               5                   10                  15
Val Phe Asn Ala Ala Glu Lys Ala Leu Pro Val Val Ala Gly Ala Lys
            20                  25                  30
Ala Leu Arg Lys
        35

<210> SEQ ID NO 78
<211> LENGTH: 40
<212> TYPE: PRT
<213> ORGANISM: Artificial
<220> FEATURE:
<223> OTHER INFORMATION: Polypeptide fragment

<400> SEQUENCE: 78

Gly Trp Leu Lys Lys Ile Gly Lys Lys Ile Glu Arg Val Gly Gln His
1               5                   10                  15
Thr Arg Asp Ala Thr Ile Gln Gly Leu Gly Ile Pro Gln Gln Ala Ala
            20                  25                  30
Asn Val Ala Ala Thr Ala Arg Gly
```

```
                35                  40

<210> SEQ ID NO 79
<211> LENGTH: 21
<212> TYPE: PRT
<213> ORGANISM: Artificial
<220> FEATURE:
<223> OTHER INFORMATION: Polypeptide fragment

<400> SEQUENCE: 79

Thr Arg Ser Ser Arg Ala Gly Leu Gln Phe Pro Val Gly Arg Val His
1               5                   10                  15

Arg Leu Leu Arg Lys
            20

<210> SEQ ID NO 80
<211> LENGTH: 39
<212> TYPE: PRT
<213> ORGANISM: Artificial
<220> FEATURE:
<223> OTHER INFORMATION: Polypeptide fragment

<400> SEQUENCE: 80

Gly Trp Leu Lys Lys Ile Gly Lys Lys Ile Glu Arg Val Gly Gln His
1               5                   10                  15

Thr Arg Asp Ala Thr Ile Gln Gly Leu Gly Ile Ala Gln Gln Ala Ala
            20                  25                  30

Asn Val Ala Ala Thr Ala Arg
        35

<210> SEQ ID NO 81
<211> LENGTH: 24
<212> TYPE: PRT
<213> ORGANISM: Artificial
<220> FEATURE:
<223> OTHER INFORMATION: Polypeptide fragment

<400> SEQUENCE: 81

Gly Ile Lys Asp Trp Ile Lys Gly Ala Ala Lys Lys Leu Ile Lys Thr
1               5                   10                  15

Val Ala Ser His Ile Ala Asn Gln
            20

<210> SEQ ID NO 82
<211> LENGTH: 17
<212> TYPE: PRT
<213> ORGANISM: Artificial
<220> FEATURE:
<223> OTHER INFORMATION: Polypeptide fragement

<400> SEQUENCE: 82

Ala Asn Arg Pro Val Tyr Ile Pro Pro Pro Arg Pro Pro His Pro Arg
1               5                   10                  15

Leu

<210> SEQ ID NO 83
<211> LENGTH: 22
<212> TYPE: PRT
<213> ORGANISM: Artificial
<220> FEATURE:
<223> OTHER INFORMATION: Polypeptide fragment

<400> SEQUENCE: 83

Gly Leu Leu Ser Lys Val Leu Gly Val Gly Lys Lys Val Leu Cys Gly
```

```
                 1               5                  10                 15

Val Ser Gly Leu Val Cys
            20

<210> SEQ ID NO 84
<211> LENGTH: 24
<212> TYPE: PRT
<213> ORGANISM: Artificial
<220> FEATURE:
<223> OTHER INFORMATION: Polypeptide fragment

<400> SEQUENCE: 84

Gly Leu Asn Thr Leu Lys Lys Val Phe Gln Gly Leu His Glu Ala Ile
1               5                   10                  15

Lys Leu Ile Asn Asn His Val Gln
            20

<210> SEQ ID NO 85
<211> LENGTH: 19
<212> TYPE: PRT
<213> ORGANISM: Artificial
<220> FEATURE:
<223> OTHER INFORMATION: Polypeptide fragment

<400> SEQUENCE: 85

Lys Gly Arg Gly Lys Gln Gly Gly Lys Val Arg Ala Lys Ala Lys Thr
1               5                   10                  15

Arg Ser Ser

<210> SEQ ID NO 86
<211> LENGTH: 25
<212> TYPE: PRT
<213> ORGANISM: Artificial
<220> FEATURE:
<223> OTHER INFORMATION: Polypeptide fragment

<400> SEQUENCE: 86

Ile Trp Leu Thr Ala Leu Lys Phe Leu Gly Lys His Ala Ala Lys Lys
1               5                   10                  15

Leu Ala Lys Gln Gln Leu Ser Lys Leu
            20                  25

<210> SEQ ID NO 87
<211> LENGTH: 18
<212> TYPE: PRT
<213> ORGANISM: Artificial
<220> FEATURE:
<223> OTHER INFORMATION: Polypeptide fragment

<400> SEQUENCE: 87

Phe Leu Gly Gly Leu Ile Val Pro Ala Met Ile Cys Ala Val Thr Lys
1               5                   10                  15

Lys Cys

<210> SEQ ID NO 88
<211> LENGTH: 26
<212> TYPE: PRT
<213> ORGANISM: Artificial
<220> FEATURE:
<223> OTHER INFORMATION: Polypeptide fragment

<400> SEQUENCE: 88

Gly Ile Gly Ala Val Leu Lys Val Leu Thr Thr Gly Leu Pro Ala Leu
1               5                   10                  15
```

Ile Ser Trp Ile Lys Arg Lys Arg Gln Gln
            20                  25

<210> SEQ ID NO 89
<211> LENGTH: 54
<212> TYPE: PRT
<213> ORGANISM: Artificial
<220> FEATURE:
<223> OTHER INFORMATION: Polypeptide fragment

<400> SEQUENCE: 89

Lys Thr Tyr Tyr Gly Thr Asn Gly Val His Cys Thr Lys Asn Ser Leu
1               5                   10                  15

Trp Gly Lys Val Arg Leu Lys Asn Met Lys Tyr Asp Gln Asn Thr Thr
            20                  25                  30

Tyr Met Gly Arg Leu Gln Asp Ile Leu Leu Gly Trp Ala Thr Gly Ala
        35                  40                  45

Phe Gly Lys Thr Phe His
    50

<210> SEQ ID NO 90
<211> LENGTH: 39
<212> TYPE: PRT
<213> ORGANISM: Artificial
<220> FEATURE:
<223> OTHER INFORMATION: Polypeptide fragment

<400> SEQUENCE: 90

Ala Gly Arg Gly Lys Gln Gly Gly Lys Val Arg Ala Lys Ala Lys Thr
1               5                   10                  15

Arg Ser Ser Arg Ala Gly Leu Gln Phe Pro Val Gly Arg Val His Arg
            20                  25                  30

Leu Leu Arg Lys Gly Asn Tyr
        35

<210> SEQ ID NO 91
<211> LENGTH: 6628
<212> TYPE: DNA
<213> ORGANISM: Artificial
<220> FEATURE:
<223> OTHER INFORMATION: Vector construct

<400> SEQUENCE: 91

```
gatctcgatc ccgcgaaatt aatacgactc actatagggg aattgtgagc ggataacaat      60
tcccctctag aaataatttt gtttaaactt taagaaggag atatacatat gctgaaacat     120
atttactcca accacattaa aggtaacaaa atcacagccc ctaaaccgtc aattcagggc     180
gtggtgatcc acaacgatta tggctcaatg accccttcac agtacctgcc ttggctgtac     240
gctcgcgaaa acaacggtac acatgtgaat ggctgggcct cagtgtatgc caatcgcaac     300
gaggtgctgt ggtatcatcc tacagactac gtggaatggc actgcggcaa ccaatgggcc     360
aacgccaacc tgatcggctt tgaagtttgc gaatcatatc tggtcgcat ctcagacaaa      420 ctgtttctgg aaaacgagga agccacactg aaagtagctg ccgacgtgat gaaatcgtat     480
ggcctgcctg tgaatcgcaa cacagtgcgc ctgcacaacg aattttttcgg tacatcatgc     540 cctcatcgtt catgggacct gcacgtgggc aaaggcgagc cttataccac aacaaatatc     600
aataaaatga agattatttt cattaaacgg attaaacact actatgacgg tggcaaactg     660
gaagttagca aagcagccac cattaaacag agtgatgtta acaagaagt gaaaaaacaa      720
```

```
gaggccaaac aaattgtgaa agccaccgat tggaaacaga acaaagatgg catctggtat    780
aaagcagaac atgccagctt taccgtgacc gcaccggaag gcattattac ccgttataaa    840
ggtccgtgga ccggtcatcc gcaggcaggc gtgctgcaga aaggtcagac catcaaatat    900
gatgaagtgc agaaatttga tggccatgtt tgggttagct gggaaaccct tgaaggtgaa    960
accgttaata tgccggttcg tacctgggat gcaaaaaccg gtaaagttgg taaactgtgg   1020
ggtgagatta aagagctccg ccagatcaaa atttggttc agaatcgtcg catgaaatgg    1080
aaaaaataag gatccggctg ctaacaaagc ccgaaaggaa gctgagttgg ctgctgccac   1140
cgctgagcaa taactagcat aacccccttgg ggcctctaaa cgggtcttga ggggttttt   1200 gctgaaagga ggaactatat ccggatatcc cgcaagaggc ccggcagtac cggcataacc   1260
aagcctatgc ctacagcatc cagggtgacg gtgccgagga tgacgatgag cgcattgtta   1320
gatttcatac acggtgcctg actgcgttag caatttaact gtgataaact accgcattaa   1380
agctagctta tcgatgataa gctgtcaaac atgagaatta attcttgaag acgaaagggc   1440
ctcgtgatac gcctattttt ataggttaat gtcatgataa taatggtttc ttagacgtca   1500
ggtggcactt ttcggggaaa tgtgcgcgga acccctattt gtttattttt ctaaatacat   1560
tcaaatatgt atccgctcat gagacaataa ccctgataaa tgcttcaata atattgaaaa   1620
aggaagagta tgagtattca acatttccgt gtcgccctta ttccctttt tgcggcattt   1680 tgccttcctg ttttgctca cccagaaacg ctggtgaaag taaaagatgc tgaagatcag   1740
ttgggtgcac gagtgggtta catcgaactg gatctcaaca gcggtaagat ccttgagagt   1800
tttcgccccg aagaacgttt tccaatgatg agcacttta aagttctgct atgtggcgcg   1860
gtattatccc gtgttgacgc cgggcaagag caactcggtc gccgcataca ctattctcag   1920
aatgacttgg ttgagtactc accagtcaca gaaaagcatc ttacgatgg catgacagta   1980 agagaattat gcagtgctgc cataaccatg agtgataaca ctgcggccaa cttacttctg   2040
acaacgatcg gaggaccgaa ggagctaacc gcttttttgc acaacatggg ggatcatgta   2100
actcgccttg atcgttggga accggagctg aatgaagcca taccaaacga cgagcgtgac   2160
accacgatgc ctgcagcaat ggcaacaacg ttgcgcaaac tattaactgg cgaactactt   2220
actctagctt cccggcaaca attaatagac tggatggagg cggataaagt tgcaggacca   2280
cttctgcgct cggcccttcc ggctggctgg tttattgctg ataaatctgg agccggtgag   2340
cgtgggtctc gcggtatcat tgcagcactg gggccagatg gtaagccctc ccgtatcgta   2400
gttatctaca cgacggggag tcaggcaact atggatgaac gaaatagaca gatcgctgag   2460
ataggtgcct cactgattaa gcattggtaa ctgtcagacc aagtttactc atatatactt   2520
tagattgatt taaaacttca ttttaattt aaaaggatct aggtgaagat ccttttttgat   2580 aatctcatga ccaaaatccc ttaacgtgag ttttcgttcc actgagcgtc agaccccgta   2640
gaaaagatca aaggatcttc ttgagatcct ttttttctgc gcgtaatctg ctgcttgcaa   2700
acaaaaaaac caccgctacc agcggtggtt tgtttgccgg atcaagagct accaactctt   2760
tttccgaagg taactggctt cagcagagcg cagataccaa atactgtcct tctagtgtag   2820
ccgtagttag gccaccactt caagaactct gtagcaccgc ctacatacct cgctctgcta   2880
atcctgttac cagtggctgc tgccagtggc gataagtcgt gtcttaccgg gttggactca   2940
agacgatagt taccggataa ggcgcagcgg tcgggctgaa cggggggttc gtgcacacag   3000
cccagcttgg agcgaacgac ctacaccgaa ctgagatacc tacagcgtga gctatgagaa   3060
agcgccacgc ttcccgaagg gagaaaggcg gacaggtatc cggtaagcgg cagggtcgga   3120
```

```
acaggagagc gcacgaggga gcttccaggg ggaaacgcct ggtatcttta tagtcctgtc    3180
gggtttcgcc acctctgact tgagcgtcga tttttgtgat gctcgtcagg ggggcggagc    3240
ctatggaaaa acgccagcaa cgcggccttt ttacggttcc tggccttttg ctggcctttt    3300
gctcacatgt tctttcctgc gttatcccct gattctgtgg ataaccgtat taccgccttt    3360
gagtgagctg ataccgctcg ccgcagccga acgaccgagc gcagcgagtc agtgagcgag    3420
gaagcggaag agcgcctgat gcggtatttt ctccttacgc atctgtgcgg tatttcacac    3480
cgcaatggtg cactctcagt acaatctgct ctgatgccgc atagttaagc cagtatacac    3540
tccgctatcg ctacgtgact gggtcatggc tgcgccccga cacccgccaa cacccgctga    3600
cgcgccctga cgggcttgtc tgctcccggc atccgcttac agacaagctg tgaccgtctc    3660
cgggagctgc atgtgtcaga ggttttcacc gtcatcaccg aaacgcgcga ggcagctgcg    3720
gtaaagctca tcagcgtggt cgtgaagcga ttcacagatg tctgcctgtt catccgcgtc    3780
cagctcgttg agtttctcca gaagcgttaa tgtctggctt ctgataaagc gggccatgtt    3840
aagggcggtt ttttcctgtt tggtcactga tgcctccgtg taagggggat ttctgttcat    3900
gggggtaatg ataccgatga aacgagagag gatgctcacg atacgggtta ctgatgatga    3960
acatgcccgg ttactggaac gttgtgaggg taaacaactg gcggtatgga tgcggcggga    4020
ccagagaaaa atcactcagg gtcaatgcca gcgcttcgtt aatacagatg taggtgttcc    4080
acagggtagc cagcagcatc ctgcgatgca gatccggaac ataatggtgc agggcgctga    4140
cttccgcgtt tccagacttt acgaaacacg gaaaccgaag accattcatg ttgttgctca    4200
ggtcgcagac gttttgcagc agcagtcgct tcacgttcgc tcgcgtatcg tgattcatt    4260 ctgctaacca gtaaggcaac cccgccagcc tagccgggtc ctcaacgaca ggagcacgat    4320
catgcgcacc cgtggccagg acccaacgct gcccgagatg cgccgcgtgc ggctgctgga    4380
gatggcggac gcgatggata tgttctgcca agggttggtt tgcgcattca cagttctccg    4440
caagaattga ttggctccaa ttcttggagt ggtgaatccg ttagcgaggt gccgccggct    4500
tccattcagg tcgaggtggc ccggctccat gcaccgcgac gcaacgcggg gaggcagaca    4560
aggtataggg cggcgcctac aatccatgcc aacccgttcc atgtgctcgc cgaggcggca    4620
taaatcgccg tgacgatcag cggtccaatg atcgaagtta ggctggtaag agccgcgagc    4680
gatccttgaa gctgtccctg atggtcgtca tctacctgcc tggacagcat ggcctgcaac    4740
gcgggcatcc cgatgccgcc ggaagcgaga agaatcataa tggggaaggc catccagcct    4800
cgcgtcgcga acgccagcaa gacgtagccc agcgcgtcgg ccgccatgcc ggcgataatg    4860
gcctgcttct cgccgaaacg tttggtggcg ggaccagtga cgaaggcttg agcgagggcg    4920
tgcaagattc cgaataccgc aagcgacagg ccgatcatcg tcgcgctcca gcgaaagcgg    4980
tcctcgccga aaatgaccca gagcgctgcc ggcacctgtc ctacgagttg catgataaag    5040
aagacagtca taagtgcggc gacgatagtc atgccccgcg cccaccggaa ggagctgact    5100
gggttgaagg ctctcaaggg catcggtcga gatcccggtg cctaatgagt gagctaactt    5160
acattaattg cgttgcgctc actgcccgct ttccagtcgg gaaacctgtc gtgccagctg    5220
cattaatgaa tcggccaacg cgcggggaga ggcggtttgc gtattgggcg ccagggtggt    5280
ttttcttttc accagtgaga cgggcaacag ctgattgccc ttcaccgcct ggccctgaga    5340
gagttgcagc aagcggtcca cgctggtttg ccccagcagg cgaaaatcct gtttgatggt    5400
ggttaacggc gggatataac atgagctgtc ttcggtatcg tcgtatccca ctaccgagat    5460
```

```
atccgcacca acgcgcagcc cggactcggt aatggcgcgc attgcgccca gcgccatctg    5520
atcgttggca accagcatcg cagtgggaac gatgccctca ttcagcattt gcatggtttg    5580
ttgaaaaccg gacatggcac tccagtcgcc ttcccgttcc gctatcggct gaatttgatt    5640
gcgagtgaga tatttatgcc agccagccag acgcagacgc gccgagacag aacttaatgg    5700
gcccgctaac agcgcgattt gctggtgacc caatgcgacc agatgctcca cgcccagtcg    5760
cgtaccgtct tcatgggaga aaataatact gttgatgggt gtctggtcag agacatcaag    5820
aaataacgcc ggaacattag tgcaggcagc ttccacagca atggcatcct ggtcatccag    5880
cggatagtta atgatcagcc cactgacgcg ttgcgcgaga agattgtgca ccgccgcttt    5940
acaggcttcg acgccgcttc gttctaccat cgacaccacc acgctggcac ccagttgatc    6000
ggcgcgagat ttaatcgccg cgacaatttg cgacggcgcg tgcagggcca gactggaggt    6060
ggcaacgcca atcagcaacg actgtttgcc cgccagttgt tgtgccacgc ggttgggaat    6120
gtaattcagc tccgccatcg ccgcttccac ttttccccgc gttttcgcag aaacgtggct    6180
ggcctggttc accacgcggg aaacggtctg ataagagaca ccggcatact ctgcgacatc    6240
gtataacgtt actggtttca cattcaccac cctgaattga ctctcttccg ggcgctatca    6300
tgccataccg cgaaaggttt tgcgccattc gatggtgtcc gggatctcga cgctctccct    6360
tatgcgactc ctgcattagg aagcagccca gtagtaggtt gaggccgttg agcaccgccg    6420
ccgcaaggaa tggtgcatgc aaggagatgg cgcccaacag tcccccggcc acggggcctg    6480
ccaccatacc cacgccgaaa caagcgctca tgagcccgaa gtggcgagcc cgatcttccc    6540
catcggtgat gtcggcgata taggcgccag caaccgcacc tgtggcgccg gtgatgccgg    6600
ccacgatgcg tccggcgtag aggatcga                                       6628
```

<210> SEQ ID NO 92
<211> LENGTH: 6607
<212> TYPE: DNA
<213> ORGANISM: Artificial
<220> FEATURE:
<223> OTHER INFORMATION: Vector construct

<400> SEQUENCE: 92

```
gatctcgatc ccgcgaaatt aatacgactc actatagggg aattgtgagc ggataacaat      60
tcccctctag aaataatttt gtttaaactt taagaaggag atatacatat gctgaaacat     120
atttactcca accacattaa aggtaacaaa atcacagccc ctaaaccgtc aattcagggc     180
gtggtgatcc acaacgatta tggctcaatg acccccttcac agtacctgcc ttggctgtac     240
gctcgcgaaa acaacggtac acatgtgaat ggctgggcct cagtgtatgc caatcgcaac     300
gaggtgctgt ggtatcatcc tacagactac gtggaatggc actgcggcaa ccaatgggcc     360
aacgccaacc tgatcggctt tgaagtttgc gaatcatatc ctggtcgcat ctcagacaaa     420
ctgtttctgg aaaacgagga agccacactg aaagtagctg ccgacgtgat gaaatcgtat     480
ggcctgcctg tgaatcgcaa cacagtgcgc ctgcacaacg aattttttcgg tacatcatgc     540 cctcatcgtt catgggacct gcacgtgggc aaaggcgagc cttataccac aacaaatatc     600
aataaaatga agattatttt cattaaacgg attaaacact actatgacgg tggcaaactg     660
gaagttagca agcagccac cattaaacag agtgatgtta acaagaagt gaaaaaacaa     720 gaggccaaac aaattgtgaa agccaccgat tggaaacaga acaaagatgg catctggtat     780
aaagcagaac atgccagctt taccgtgacc gcaccggaag gcattattac ccgttataaa     840
ggtccgtgga ccggtcatcc gcaggcaggc gtgctgcaga aaggtcagac catcaaatat     900
```

```
gatgaagtgc agaaatttga tggccatgtt tgggttagct gggaaacctt tgaaggtgaa      960
accgtttata tgccggttcg tacctgggat gcaaaaaccg gtaaagttgg taaactgtgg     1020
ggtgagatta aagagctccg tcgtcgtcgc cgtcggcgtc gtcgttaagg atccggctgc     1080
taacaaagcc cgaaaggaag ctgagttggc tgctgccacc gctgagcaat aactagcata     1140
accccttggg gcctctaaac gggtcttgag gggttttttg ctgaaaggag gaactatatc     1200
cggatatccc gcaagaggcc cggcagtacc ggcataacca agcctatgcc tacagcatcc     1260
agggtgacgg tgccgaggat gacgatgagc gcattgttag atttcataca cggtgcctga     1320
ctgcgttagc aatttaactg tgataaacta ccgcattaaa gctagcttat cgatgataag     1380
ctgtcaaaca tgagaattaa ttcttgaaga cgaaagggcc tcgtgatacg cctatttta      1440 taggttaatg tcatgataat aatggtttct tagacgtcag gtggcacttt tcggggaaat     1500
gtgcgcggaa cccctatttg tttattttc taaatacatt caaatatgta tccgctcatg      1560
agacaataac cctgataaat gcttcaataa tattgaaaaa ggaagagtat gagtattcaa     1620
catttccgtg tcgcccttat tccctttttt gcggcatttt gccttcctgt ttttgctcac     1680
ccagaaacgc tggtgaaagt aaaagatgct gaagatcagt tgggtgcacg agtgggttac     1740
atcgaactgg atctcaacag cggtaagatc cttgagagtt ttcgccccga agaacgtttt     1800
ccaatgatga gcacttttaa agttctgcta tgtggcgcgg tattatcccg tgttgacgcc     1860
gggcaagagc aactcggtcg ccgcatacac tattctcaga atgacttggt tgagtactca     1920
ccagtcacag aaaagcatct tacgatggca tgacagtaa gagaattatg cagtgctgcc      1980
ataaccatga gtgataacac tgcggccaac ttacttctga caacgatcgg aggaccgaag     2040
gagctaaccg cttttttgca acatgggga tcatgtaa ctcgccttga tcgttgggaa        2100
ccggagctga atgaagccat accaaacgac gagcgtgaca ccacgatgcc tgcagcaatg     2160
gcaacaacgt tgcgcaaact attaactggc gaactactta ctctagcttc ccggcaacaa     2220
ttaatagact ggatggaggc ggataaagtt gcaggaccac ttctgcgctc ggcccttccg     2280
gctggctggt ttattgctga taaatctgga gccggtgagc gtgggtctcg cggtatcatt     2340
gcagcactgg ggccagatgg taagccctcc cgtatcgtag ttatctacac gacggggagt     2400
caggcaacta tggatgaacg aaatagacag atcgctgaga taggtgcctc actgattaag     2460
cattggtaac tgtcagacca agtttactca tatatacttt agattgattt aaaacttcat     2520
ttttaattta aaaggatcta ggtgaagatc ctttttgata atctcatgac caaaatccct     2580
taacgtgagt tttcgttcca ctgagcgtca gaccccgtag aaaagatcaa aggatcttct     2640
tgagatcctt ttttctgcg cgtaatctgc tgcttgcaaa caaaaaaacc accgctacca      2700
gcggtggttt gtttgccgga tcaagagcta ccaactcttt ttccgaaggt aactggcttc     2760
agcagagcgc agataccaaa tactgtcctt ctagtgtagc cgtagttagg ccaccacttc     2820
aagaactctg tagcaccgcc tacatacctc gctctgctaa tcctgttacc agtggctgct     2880
gccagtggcg ataagtcgtg tcttaccggg ttggactcaa gacgatagtt accggataag     2940
gcgcagcggt cgggctgaac ggggggttcg tgcacacagc ccagcttgga gcgaacgacc     3000
tacaccgaac tgagatacct acagcgtgag ctatgagaaa gcgccacgct tcccgaaggg     3060
agaaaggcgg acaggtatcc ggtaagcggc agggtcggaa caggagagcg cacgagggag     3120
cttccagggg gaaacgcctg gtatctttat agtcctgtcg ggtttcgcca cctctgactt     3180
gagcgtcgat ttttgtgatg ctcgtcaggg gggcggagcc tatggaaaaa cgccagcaac     3240
```

```
gcggccttttt tacggttcct ggcctttttgc tggccttttg ctcacatgtt ctttcctgcg    3300
ttatcccctg attctgtgga taaccgtatt accgcctttg agtgagctga taccgctcgc    3360
cgcagccgaa cgaccgagcg cagcgagtca gtgagcgagg aagcggaaga gcgcctgatg    3420
cggtattttc tccttacgca tctgtgcggt atttcacacc gcaatggtgc actctcagta    3480
caatctgctc tgatgccgca tagttaagcc agtatacact ccgctatcgc tacgtgactg    3540
ggtcatggct gcgccccgac acccgccaac acccgctgac gcgccctgac gggcttgtct    3600
gctcccggca tccgcttaca gacaagctgt gaccgtctcc gggagctgca tgtgtcagag    3660
gttttcaccg tcatcaccga aacgcgcgag gcagctgcgg taaagctcat cagcgtggtc    3720
gtgaagcgat tcacagatgt ctgcctgttc atccgcgtcc agctcgttga gtttctccag    3780
aagcgttaat gtctggcttc tgataaagcg ggccatgtta agggcggttt tttcctgttt    3840
ggtcactgat gcctccgtgt aagggggatt tctgttcatg ggggtaatga taccgatgaa    3900
acgagagagg atgctcacga tacgggttac tgatgatgaa catgcccggt tactggaacg    3960
ttgtgagggt aaacaactgg cggtatggat gcggcgggac cagagaaaaa tcactcaggg    4020
tcaatgccag cgcttcgtta atacagatgt aggtgttcca cagggtagcc agcagcatcc    4080
tgcgatgcag atccggaaca taatggtgca gggcgctgac ttccgcgttt ccagactttta    4140
cgaaacacgg aaaccgaaga ccattcatgt tgttgctcag gtcgcagacg ttttgcagca    4200
gcagtcgctt cacgttcgct cgcgtatcgg tgattcattc tgctaaccag taaggcaacc    4260
ccgccagcct agccgggtcc tcaacgacag gagcacgatc atgcgcaccc gtggccagga    4320
cccaacgctg cccgagatgc gccgcgtgcg gctgctggag atggcggacg cgatggatat    4380
gttctgccaa gggttggttt gcgcattcac agttctccgc aagaattgat tggctccaat    4440
tcttggagtg tgaatccgt tagcgaggtg ccgccggctt ccattcaggt cgaggtggcc    4500
cggctccatg caccgcgacg caacgcgggg aggcagacaa ggtatagggc ggcgcctaca    4560
atccatgcca acccgttcca tgtgctcgcc gaggcggcat aaatcgccgt gacgatcagc    4620
ggtccaatga tcgaagttag gctggtaaga gccgcgagcg atccttgaag ctgtccctga    4680
tggtcgtcat ctacctgcct ggacagcatg gcctgcaacg cgggcatccc gatgccgccg    4740
gaagcgagaa gaatcataat ggggaaggcc atccagcctc gcgtcgcgaa cgccagcaag    4800
acgtagccca gcgcgtcggc cgccatgccg gcgataatgg cctgcttctc gccgaaacgt    4860
ttggtggcgg gaccagtgac gaaggcttga gcgagggcgt gcaagattcc gaataccgca    4920
agcgacaggc cgatcatcgt cgcgctccag cgaaagcggt cctcgccgaa aatgacccag    4980
agcgctgccg gcacctgtcc tacgagttgc atgataaaga agacagtcat aagtgcggcg    5040
acgatagtca tgccccgcgc ccaccggaag gagctgactg ggttgaaggc tctcaagggc    5100
atcggtcgag atcccggtgc ctaatgagtg agctaactta cattaattgc gttgcgctca    5160
ctgcccgctt tccagtcggg aaacctgtcg tgccagctgc attaatgaat cggccaacgc    5220
gcggggagag gcggtttgcg tattgggcgc cagggtggtt tttcttttca ccagtgagac    5280
gggcaacagc tgattgccct tcaccgcctg gccctgagag agttgcagca agcggtccac    5340
gctggtttgc cccagcaggc gaaaatcctg tttgatggtg gttaacggcg ggatataaca    5400
tgagctgtct tcggtatcgt cgtatcccac taccgagata tccgcaccaa cgcgcagccc    5460
ggactcggta atggcgcgca ttgcgcccag cgccatctga tcgttggcaa ccagcatcgc    5520
agtgggaacg atgccctcat tcagcatttg catggtttgt tgaaaaccgg acatggcact    5580
ccagtcgcct tcccgttccg ctatcggctg aatttgattg cgagtgagat atttatgcca    5640
```

```
gccagccaga cgcagacgcg ccgagacaga acttaatggg cccgctaaca gcgcgatttg    5700
ctggtgaccc aatgcgacca gatgctccac gcccagtcgc gtaccgtctt catgggagaa    5760
aataatactg ttgatgggtg tctggtcaga gacatcaaga aataacgccg gaacattagt    5820
gcaggcagct tccacagcaa tggcatcctg gtcatccagc ggatagttaa tgatcagccc    5880
actgacgcgt tgcgcgagaa gattgtgcac cgccgcttta caggcttcga cgccgcttcg    5940
ttctaccatc gacaccacca cgctggcacc cagttgatcg gcgcgagatt taatcgccgc    6000
gacaatttgc gacggcgcgt gcagggccag actggaggtg gcaacgccaa tcagcaacga    6060
ctgtttgccc gccagttgtt gtgccacgcg gttgggaatg taattcagct ccgccatcgc    6120
cgcttccact ttttcccgcg ttttcgcaga acgtggctg gcctggttca ccacgcggga    6180
aacggtctga taagagacac cggcatactc tgcgacatcg tataacgtta ctggtttcac    6240
attcaccacc ctgaattgac tctcttccgg gcgctatcat gccataccgc gaaaggtttt    6300
gcgccattcg atggtgtccg ggatctcgac gctctccctt atgcgactcc tgcattagga    6360
agcagcccag tagtaggttg aggccgttga gcaccgccgc cgcaaggaat ggtgcatgca    6420
aggagatggc gcccaacagt cccccggcca cggggcctgc caccatacccc acgccgaaac    6480 aagcgctcat gagcccgaag tggcgagccc gatcttcccc atcggtgatg tcggcgatat    6540
aggcgccagc aaccgcacct gtggcgccgg tgatgccggc cacgatgcgt ccggcgtaga    6600
ggatcga                                                              6607

<210> SEQ ID NO 93
<211> LENGTH: 6619
<212> TYPE: DNA
<213> ORGANISM: Artificial
<220> FEATURE:
<223> OTHER INFORMATION: Vector construct

<400> SEQUENCE: 93
gatctcgatc ccgcgaaatt aatacgactc actatagggg aattgtgagc ggataacaat      60
tcccctctag aaataatttt gtttaaactt taagaaggag atatacatat gctgaaacat     120
atttactcca accacattaa aggtaacaaa atcacagccc ctaaaccgtc aattcagggc     180
gtggtgatcc acaacgatta tggctcaatg acccccttcac agtacctgcc ttggctgtac     240
gctcgcgaaa caacggtac acatgtgaat ggctgggcct cagtgtatgc caatcgcaac      300
gaggtgctgt ggtatcatcc tacagactac gtggaatggc actgcggcaa ccaatgggcc     360
aacgccaacc tgatcggctt tgaagtttgc gaatcatatc ctggtcgcat ctcagacaaa     420
ctgtttctgg aaaacgagga agccacactg aaagtagctg ccgacgtgat gaaatcgtat     480
ggcctgcctg tgaatcgcaa cacagtgcgc ctgcacaacg aattttttcgg tacatcatgc     540 cctcatcgtt catgggacct gcacgtgggc aaaggcgagc cttataccac aacaaatatc     600
aataaaatga aagattattt cattaaacgg attaaacact actatgacgg tggcaaactg     660
gaagttagca aagcagccac cattaaacag agtgatgtta acaagaagt gaaaaaacaa     720 gaggccaaac aaattgtgaa agccaccgat tggaaacaga acaagatgg catctggtat     780 aaagcagaac atgccagctt taccgtgacc gcaccggaag gcattattac ccgttataaa     840
ggtccgtgga ccggtcatcc gcaggcaggc gtgctgcaga aaggtcagac catcaaatat     900
gatgaagtgc agaaatttga tggccatgtt tgggttagct gggaaacctt gaaggtgaa     960 accgttatat gccggttcg tacctgggat gcaaaaaccg gtaaagttgg taaactgtgg     1020
```

```
ggtgagatta aagagctcgg tcgtaaaaaa cgtcgtcagc gtcgtcgtcc gcctcagtaa    1080
ggatccggct gctaacaaag cccgaaagga agctgagttg gctgctgcca ccgctgagca    1140
ataactagca taaccccttg gggcctctaa acgggtcttg aggggttttt tgctgaaagg    1200
aggaactata tccggatatc ccgcaagagg cccggcagta ccggcataac caagcctatg    1260
cctacagcat ccagggtgac ggtgccgagg atgacgatga gcgcattgtt agatttcata    1320
cacggtgcct gactgcgtta gcaatttaac tgtgataaac taccgcatta aagctagctt    1380
atcgatgata agctgtcaaa catgagaatt aattcttgaa gacgaaaggg cctcgtgata    1440
cgcctatttt tataggttaa tgtcatgata ataatggttt cttagacgtc aggtggcact    1500
tttcggggaa atgtgcgcgg aaccccctatt tgtttatttt tctaaataca ttcaaatatg    1560
tatccgctca tgagacaata accctgataa atgcttcaat aatattgaaa aggaagagt    1620 atgagtattc aacatttccg tgtcgccctt attcccttttt ttgcggcatt ttgccttcct    1680
gtttttgctc acccagaaac gctggtgaaa gtaaaagatg ctgaagatca gttgggtgca    1740
cgagtgggtt acatcgaact ggatctcaac agcggtaaga tccttgagag ttttcgcccc    1800
gaagaacgtt ttccaatgat gagcactttt aaagttctgc tatgtggcgc ggtattatcc    1860
cgtgttgacg ccgggcaaga gcaactcggt cgccgcatac actattctca gaatgacttg    1920
gttgagtact caccagtcac agaaaagcat cttacggatg gcatgacagt aagagaatta    1980
tgcagtgctg ccataaccat gagtgataac actgcggcca acttacttct gacaacgatc    2040
ggaggaccga aggagctaac cgcttttttg cacaacatgg gggatcatgt aactcgcctt    2100
gatcgttggg aaccggagct gaatgaagcc ataccaaacg acgagcgtga caccacgatg    2160
cctgcagcaa tggcaacaac gttgcgcaaa ctattaactg gcgaactact tactctagct    2220
tcccggcaac aattaataga ctggatggag gcggataaag ttgcaggacc acttctgcgc    2280
tcggcccttc cggctggctg gtttattgct gataaatctg gagccggtga gcgtgggtct    2340
cgcggtatca ttgcagcact ggggccagat ggtaagccct cccgtatcgt agttatctac    2400
acgacgggga gtcaggcaac tatggatgaa cgaaatagac agatcgctga gataggtgcc    2460
tcactgatta gcattggta actgtcagac caagtttact catatatact ttagattgat    2520
ttaaaacttc atttttaatt taaaaggatc taggtgaaga tccttttga taatctcatg    2580 accaaaatcc cttaacgtga gttttcgttc cactgagcgt cagacccccgt agaaaagatc    2640 aaaggatctt cttgagatcc ttttttttctg cgcgtaatct gctgcttgca acaaaaaaa    2700 ccaccgctac cagcggtggt ttgtttgccg gatcaagagc taccaactct ttttccgaag    2760
gtaactggct tcagcagagc gcagatacca aatactgtcc ttctagtgta gccgtagtta    2820
ggccaccact tcaagaactc tgtagcaccg cctacatacc tcgctctgct aatcctgtta    2880
ccagtggctg ctgccagtgg cgataagtcg tgtcttaccg ggttggactc aagacgatag    2940
ttaccggata aggcgcagcg gtcgggctga acggggggtt cgtgcacaca gcccagcttg    3000
gagcgaacga cctacaccga actgagatac ctacagcgtg agctatgaga aagcgccacg    3060
cttcccgaag ggagaaaggc ggacaggtat ccggtaagcg gcagggtcgg aacaggagag    3120
cgcacgaggg agcttccagg gggaaacgcc tggtatcttt atagtcctgt cgggtttcgc    3180
cacctctgac ttgagcgtcg atttttgtga tgctcgtcag ggggcggag cctatggaaa    3240 aacgccagca acgcggcctt tttacggttc ctggccttt gctggccttt tgctcacatg    3300
ttctttcctg cgttatcccc tgattctgtg ataaccgta ttaccgcctt tgagtgagct    3360
gataccgctc gccgcagccg aacgaccgag cgcagcgagt cagtgagcga ggaagcggaa    3420
```

```
gagcgcctga tgcggtattt tctccttacg catctgtgcg gtatttcaca ccgcaatggt    3480
gcactctcag tacaatctgc tctgatgccg catagttaag ccagtataca ctccgctatc    3540
gctacgtgac tgggtcatgg ctgcgccccg acacccgcca acacccgctg acgcgccctg    3600
acgggcttgt ctgctcccgg catccgctta cagacaagct gtgaccgtct ccgggagctg    3660
catgtgtcag aggttttcac cgtcatcacc gaaacgcgcg aggcagctgc ggtaaagctc    3720
atcagcgtgg tcgtgaagcg attcacagat gtctgcctgt tcatccgcgt ccagctcgtt    3780
gagtttctcc agaagcgtta atgtctggct tctgataaag cgggccatgt taagggcggt    3840
tttttcctgt ttggtcactg atgcctccgt gtaaggggga tttctgttca tgggggtaat    3900
gataccgatg aaacgagaga ggatgctcac gatacgggtt actgatgatg aacatgcccg    3960
gttactggaa cgttgtgagg gtaaacaact ggcggtatgg atgcggcggg accagagaaa    4020
aatcactcag ggtcaatgcc agcgcttcgt taatacagat gtaggtgttc cacagggtag    4080
ccagcagcat cctgcgatgc agatccggaa cataatggtg cagggcgctg acttccgcgt    4140
ttccagactt tacgaaacac ggaaaccgaa gaccattcat gttgttgctc aggtcgcaga    4200
cgttttgcag cagcagtcgc ttcacgttcg ctcgcgtatc ggtgattcat tctgctaacc    4260
agtaaggcaa ccccgccagc ctagccgggt cctcaacgac aggagcacga tcatgcgcac    4320
ccgtggccag gacccaacgc tgcccgagat gcgccgcgtg cggctgctgg agatggcgga    4380
cgcgatggat atgttctgcc aagggttggt ttgcgcattc acagttctcc gcaagaattg    4440
attggctcca attcttggag tggtgaatcc gttagcgagg tgccgccggc ttccattcag    4500
gtcgaggtgg cccggctcca tgcaccgcga cgcaacgcgg ggaggcagac aaggtatagg    4560
gcggcgccta caatccatgc caacccgttc catgtgctcg ccgaggcggc ataaatcgcc    4620
gtgacgatca gcggtccaat gatcgaagtt aggctggtaa gagccgcgag cgatccttga    4680
agctgtccct gatggtcgtc atctacctgc ctggacagca tggcctgcaa cgcgggcatc    4740
ccgatgccgc cggaagcgag aagaatcata atggggaagg ccatccagcc tcgcgtcgcg    4800
aacgccagca agacgtagcc cagcgcgtcg gccgccatgc cggcgataat ggcctgcttc    4860
tcgccgaaac gtttggtggc gggaccagtg acgaaggctt gagcgagggc gtgcaagatt    4920
ccgaataccg caagcgacag gccgatcatc gtcgcgctcc agcgaaagcg gtcctcgccg    4980
aaaatgaccc agagcgctgc cggcacctgt cctacgagtt gcatgataaa gaagacagtc    5040
ataagtgcgg cgacgatagt catgccccgc gcccaccgga aggagctgac tgggttgaag    5100
gctctcaagg gcatcggtcg agatcccggt gcctaatgag tgagctaact tacattaatt    5160
gcgttgcgct cactgcccgc tttccagtcg ggaaacctgt cgtgccagct gcattaatga    5220
atcggccaac gcgcggggag aggcggtttg cgtattgggc gccagggtgg tttttctttt    5280
caccagtgag acgggcaaca gctgattgcc cttcaccgcc tggccctgag agagttgcag    5340
caagcggtcc acgctggttt gccccagcag gcgaaaatcc tgtttgatgg tggttaacgg    5400
cgggatataa catgagctgt cttcggtatc gtcgtatccc actaccgaga tatccgcacc    5460
aacgcgcagc ccggactcgg taatggcgcg cattgcgccc agcgccatct gatcgttggc    5520
aaccagcatc gcagtgggaa cgatgccctc attcagcatt tgcatggttt gttgaaaacc    5580
ggacatggca ctccagtcgc cttcccgttc cgctatcggc tgaatttgat tgcgagtgag    5640
atatttatgc cagccagcca gacgcagacg cgccgagaca gaacttaatg ggcccgctaa    5700
cagcgcgatt tgctggtgac ccaatgcgac cagatgctcc acgcccagtc gcgtaccgtc    5760
```

```
ttcatgggag aaaataatac tgttgatggg tgtctggtca gagacatcaa gaaataacgc    5820
cggaacatta gtgcaggcag cttccacagc aatggcatcc tggtcatcca gcggatagtt    5880
aatgatcagc ccactgacgc gttgcgcgag aagattgtgc accgccgctt tacaggcttc    5940
gacgccgctt cgttctacca tcgacaccac cacgctggca cccagttgat cggcgcgaga    6000
tttaatcgcc gcgacaattt gcgacggcgc gtgcagggcc agactggagg tggcaacgcc    6060
aatcagcaac gactgtttgc ccgccagttg ttgtgccacg cggttgggaa tgtaattcag    6120
ctccgccatc gccgcttcca cttttccccg cgttttcgca gaaacgtggc tggcctggtt    6180
caccacgcgg gaaacggtct gataagagac accggcatac tctgcgacat cgtataacgt    6240
tactggtttc acattcacca ccctgaattg actctcttcc gggcgctatc atgccatacc    6300
gcgaaaggtt ttgcgccatt cgatggtgtc cgggatctcg acgctctccc ttatgcgact    6360
cctgcattag gaagcagccc agtagtaggt tgaggccgtt gagcaccgcc gccgcaagga    6420
atggtgcatg caaggagatg cgcccaaca gtcccccggc cacggggcct gccaccatac    6480
ccacgccgaa acaagcgctc atgagcccga agtggcgagc cgatcttcc ccatcggtga    6540 tgtcggcgat ataggcgcca gcaaccgcac ctgtggcgcc ggtgatgccg gccacgatgc    6600
gtccggcgta gaggatcga                                                  6619
```

<210> SEQ ID NO 94
<211> LENGTH: 6247
<212> TYPE: DNA
<213> ORGANISM: Artificial
<220> FEATURE:
<223> OTHER INFORMATION: Vector construct

<400> SEQUENCE: 94

```
gatctcgatc ccgcgaaatt aatacgactc actatagggg aattgtgagc ggataacaat      60
tcccctctag aaataatttt gtttaaactt taagaaggag atatacatat gctgaaacat     120
atttactcca accacattaa aggtaacaaa atcacagccc ctaaaccgtc aattcagggc     180
gtggtgatcc acaacgatta tggctcaatg acccccttcac agtacctgcc ttggctgtac     240
gctcgcgaaa caacggtac acatgtgaat ggctgggcct cagtgtatgc caatcgcaac     300
gaggtgctgt ggtatcatcc tacagactac gtggaatggc actgcggcaa ccaatgggcc     360
aacgccaacc tgatcggctt tgaagtttgc gaatcatatc ctggtcgcat ctcagacaaa     420
ctgtttctgg aaaacgagga agccacactg aaagtagctg ccgacgtgat gaaatcgtat     480
ggcctgcctg tgaatcgcaa cacagtgcgc ctgcacaacg aatttttcgg tacatcatgc     540
cctcatcgtt catgggacct gcacgtgggc aaaggcgagc cttataccac aacaaatatc     600
aataaaatga agattattt cattaaacgg attaaacact actatgacgg tgagctccgc     660
cagatcaaaa tttggtttca gaatcgtcgc atgaaatgga aaaataagg atccggctgc     720 taacaaagcc cgaaaggaag ctgagttggc tgctgccacc gctgagcaat aactagcata     780
accccttggg gcctctaaac gggtcttgag ggttttttg ctgaaaggag aactatatc      840 cggatatccc gcaagaggcc cggcagtacc ggcataacca agcctatgcc tacagcatcc     900
agggtgacgt gccgaggat gacgatgagc gcattgttag atttcataca cggtgcctga     960
ctgcgttagc aatttaactg tgataaacta ccgcattaaa gctagcttat cgatgataag    1020
ctgtcaaaca tgagaattaa ttcttgaaga cgaaagggcc tcgtgatacg cctatttta    1080 taggttaatg tcatgataat aatggtttct tagacgtcag gtggcacttt tcggggaaat    1140
gtgcgcggaa cccctatttg tttatttttc taaatacatt caaatatgta tccgctcatg    1200
```

```
agacaataac cctgataaat gcttcaataa tattgaaaaa ggaagagtat gagtattcaa    1260
catttccgtg tcgcccttat tcccttttt gcggcatttt gccttcctgt ttttgctcac    1320
ccagaaacgc tggtgaaagt aaaagatgct gaagatcagt tgggtgcacg agtgggttac    1380
atcgaactgg atctcaacag cggtaagatc cttgagagtt ttcgcccga agaacgtttt    1440 ccaatgatga gcacttttaa agttctgcta tgtggcgcgg tattatcccg tgttgacgcc    1500
gggcaagagc aactcggtcg ccgcatacac tattctcaga atgacttggt tgagtactca    1560
ccagtcacag aaaagcatct tacggatggc atgacagtaa gagaattatg cagtgctgcc    1620
ataaccatga gtgataacac tgcggccaac ttacttctga caacgatcgg aggaccgaag    1680
gagctaaccg cttttttgca acatggggg atcatgtaa ctcgccttga tcgttgggaa    1740
ccggagctga atgaagccat accaaacgac gagcgtgaca ccacgatgcc tgcagcaatg    1800
gcaacaacgt tgcgcaaact attaactggc gaactactta ctctagcttc ccggcaacaa    1860
ttaatagact ggatggaggc ggataaagtt gcaggaccac ttctgcgctc ggcccttccg    1920
gctggctggt ttattgctga taaatctgga gccggtgagc gtgggtctcg cggtatcatt    1980
gcagcactgg ggccagatgg taagccctcc cgtatcgtag ttatctacac gacggggagt    2040
caggcaacta tggatgaacg aaatagacag atcgctgaga taggtgcctc actgattaag    2100
cattggtaac tgtcagacca agtttactca tatatacttt agattgattt aaaacttcat    2160
ttttaattta aaaggatcta ggtgaagatc ctttttgata atctcatgac caaaatccct    2220
taacgtgagt tttcgttcca ctgagcgtca gaccccgtag aaaagatcaa aggatcttct    2280
tgagatcctt ttttctgcg cgtaatctgc tgcttgcaaa caaaaaaacc accgctacca    2340
gcggtggttt gtttgccgga tcaagagcta ccaactcttt ttccgaaggt aactggcttc    2400
agcagagcgc agataccaaa tactgtcctt ctagtgtagc cgtagttagg ccaccacttc    2460
aagaactctg tagcaccgcc tacatacctc gctctgctaa tcctgttacc agtggctgct    2520
gccagtggcg ataagtcgtg tcttaccggg ttggactcaa gacgatagtt accggataag    2580
gcgcagcggt cgggctgaac ggggggttcg tgcacacagc ccagcttgga gcgaacgacc    2640
tacaccgaac tgagatacct acagcgtgag ctatgagaaa gcgccacgct cccgaaggg    2700 agaaaggcgg acaggtatcc ggtaagcggc agggtcggaa caggagagcg cacgagggag    2760
cttccagggg gaaacgcctg gtatctttat agtcctgtcg ggtttcgcca cctctgactt    2820
gagcgtcgat ttttgtgatg ctcgtcaggg gggcggagcc tatggaaaaa cgccagcaac    2880
gcggcctttt tacggttcct ggccttttgc tggccttttg ctcacatgtt ctttcctgcg    2940
ttatcccctg attctgtgga taaccgtatt accgcctttg agtgagctga taccgctcgc    3000
cgcagccgaa cgaccgagcg cagcgagtca gtgagcgagg aagcggaaga gcgcctgatg    3060
cggtattttc tccttacgca tctgtgcggt atttcacacc gcaatggtgc actctcagta    3120
caatctgctc tgatgccgca tagttaagcc agtatacact ccgctatcgc tacgtgactg    3180
ggtcatggct gcgccccgac acccgccaac acccgctgac gcgccctgac gggcttgtct    3240
gctcccggca tccgcttaca gacaagctgt gaccgtctcc gggagctgca tgtgtcagag    3300
gttttcaccg tcatcaccga aacgcgcgag gcagctgcgg taaagctcat cagcgtggtc    3360
gtgaagcgat tcacagatgt ctgcctgttc atccgcgtcc agctcgttga gtttctccag    3420
aagcgttaat gtctggcttc tgataaagcg gccatgttca agggcggttt ttcctgtttt    3480
ggtcactgat gcctccgtgt aagggggatt tctgttcatg ggggtaatga taccgatgaa    3540
```

-continued

```
acgagagagg atgctcacga tacgggttac tgatgatgaa catgcccggt tactggaacg    3600
ttgtgagggt aaacaactgg cggtatggat gcggcgggac cagagaaaaa tcactcaggg    3660
tcaatgccag cgcttcgtta atacagatgt aggtgttcca cagggtagcc agcagcatcc    3720
tgcgatgcaa atccggaaca taatggtgca gggcgctgac ttccgcgttt ccagacttta    3780
cgaaacacgg aaaccgaaga ccattcatgt tgttgctcag gtcgcagacg ttttgcagca    3840
gcagtcgctt cacgttcgct cgcgtatcgg tgattcattc tgctaaccag taaggcaacc    3900
ccgccagcct agccgggtcc tcaacgacag gagcacgatc atgcgcaccc gtggccagga    3960
cccaacgctg cccgagatgc gccgcgtgcg gctgctggag atggcggacg cgatggatat    4020
gttctgccaa gggttggttt gcgcattcac agttctccgc aagaattgat tggctccaat    4080
tcttggagtg gtgaatccgt tagcgaggtg ccgccggctt ccattcaggt cgaggtggcc    4140
cggctccatg caccgcgacg caacgcgggg aggcagacaa ggtatagggc ggcgcctaca    4200
atccatgcca acccgttcca tgtgctcgcc gaggcggcat aaatcgccgt gacgatcagc    4260
ggtccaatga tcgaagttag gctggtaaga gccgcgagcg atccttgaag ctgtccctga    4320
tggtcgtcat ctacctgcct ggacagcatg gcctgcaacg cgggcatccc gatgccgccg    4380
gaagcgagaa gaatcataat ggggaaggcc atccagcctc gcgtcgcgaa cgccagcaag    4440
acgtagccca gcgcgtcggc cgccatgccg gcgataatgg cctgcttctc gccgaaacgt    4500
ttggtggcgg gaccagtgac gaaggcttga gcgagggcgt gcaagattcc gaataccgca    4560
agcgacaggc cgatcatcgt cgcgctccag cgaaagcggt cctcgccgaa aatgacccag    4620
agcgctgccg gcacctgtcc tacgagttgc atgataaaga agacagtcat aagtgcggcg    4680
acgatagtca tgccccgcgc ccaccggaag gagctgactg ggttgaaggc tctcaagggc    4740
atcggtcgag atcccggtgc ctaatgagtg agctaactta cattaattgc gttgcgctca    4800
ctgcccgctt tccagtcggg aaacctgtcg tgccagctgc attaatgaat cggccaacgc    4860
gcggggagag gcggtttgcg tattgggcgc caggtggtt tttcttttca ccagtgagac    4920
gggcaacagc tgattgccct tcaccgcctg gccctgagag agttgcagca agcggtccac    4980
gctggtttgc cccagcaggc gaaaatcctg tttgatggtg gttaacggcg ggatataaca    5040
tgagctgtct tcggtatcgt cgtatcccac taccgagata tccgcaccaa cgcgcagccc    5100
ggactcggta atggcgcgca ttgcgcccag cgccatctga tcgttggcaa ccagcatcgc    5160
agtgggaacg atgccctcat tcagcatttg catggtttgt tgaaaaccgg acatggcact    5220
ccagtcgcct tcccgttccg ctatcggctg aatttgattg cgagtgagat atttatgcca    5280
gccagccaga cgcagacgcg ccgagacaga acttaatggg cccgctaaca gcgcgatttg    5340
ctggtgaccc aatgcgacca gatgctccac gcccagtcgc gtaccgtctt catgggagaa    5400
aataatactg ttgatgggtg tctggtcaga gacatcaaga aataacgccg gaacattagt    5460
gcaggcagct tccacagcaa tggcatcctg gtcatccagc ggatagttaa tgatcagccc    5520
actgacgcgt tgcgcgagaa gattgtgcac cgccgcttta caggcttcga cgccgcttcg    5580
ttctaccatc gacaccacca cgctggcacc cagttgatcg gcgcgagatt taatcgccgc    5640
gacaatttgc gacggcgcgt gcagggccag actgaggtg gcaacgccaa tcagcaacga    5700
ctgtttgccc gccagttgtt gtgccacgcg gttgggaatg taattcagct ccgccatcgc    5760
cgcttccact ttttcccgcg ttttcgcaga acgtggctg gcctggttca ccacgcggga    5820
aacggtctga taagagacac cggcatactc tgcgacatcg tataacgtta ctggtttcac    5880
attcaccacc ctgaattgac tctcttccgg gcgctatcat gccataccgc gaaaggtttt    5940
```

```
gcgccattcg atggtgtccg ggatctcgac gctctcccct atgcgactcc tgcattagga      6000
agcagcccag tagtaggttg aggccgttga gcaccgccgc cgcaaggaat ggtgcatgca      6060
aggagatggc gcccaacagt cccccggcca cggggcctgc caccatacc  acgccgaaac      6120 aagcgctcat gagcccgaag tggcgagccc gatcttcccc atcggtgatg tcggcgatat      6180
aggcgccagc aaccgcacct gtggcgccgg tgatgccggc cacgatgcgt ccggcgtaga      6240
ggatcga                                                                6247

<210> SEQ ID NO 95
<211> LENGTH: 6226
<212> TYPE: DNA
<213> ORGANISM: Artificial
<220> FEATURE:
<223> OTHER INFORMATION: Vector construct

<400> SEQUENCE: 95
gatctcgatc ccgcgaaatt aatacgactc actatagggg aattgtgagc ggataacaat        60
tcccctctag aaataatttt gtttaaactt taagaaggag atatacatat gctgaaacat       120
atttactcca accacattaa aggtaacaaa atcacagccc ctaaaccgtc aattcagggc       180
gtggtgatcc acaacgatta tggctcaatg accccttcac agtacctgcc ttggctgtac       240
gctcgcgaaa acaacggtac acatgtgaat ggctgggcct cagtgtatgc caatcgcaac       300
gaggtgctgt ggtatcatcc tacagactac gtggaatggc actgcggcaa ccaatgggcc       360
aacgccaacc tgatcggctt tgaagtttgc gaatcatatc ctggtcgcat ctcagacaaa       420
ctgtttctgg aaaacgagga agccacactg aaagtagctg ccgacgtgat gaaatcgtat       480
ggcctgcctg tgaatcgcaa cacagtgcgc ctgcacaacg aatttttcgg tacatcatgc       540
cctcatcgtt catgggacct gcacgtgggc aaaggcgagc cttataccac aacaaatatc       600
aataaaatga agattatttt cattaaacga attaaacact actatgacgg tgagctccgt       660
cgtcgtcgcc gtcggcgtcg tcgttaagga tccggctgct aacaaagccc gaaaggaagc       720
tgagttggct gctgccaccg ctgagcaata actagcataa ccccttgggg cctctaaacg       780
ggtcttgagg ggttttttgc tgaaaggagg aactatatcc ggatatcccg caagaggccc       840
ggcagtaccg gcataaccaa gcctatgcct acagcatcca gggtgacggt gccgaggatg       900
acgatgagcg cattgttaga tttcatacac ggtgcctgac tgcgttagca atttaactgt       960
gataaactac cgcattaaag ctagcttatc gatgataagc tgtcaaacat gagaattaat      1020
tcttgaagac gaaagggcct cgtgatacgc ctatttttat aggttaatgt catgataata      1080
atggtttctt agacgtcagg tggcactttt cggggaaatg tgcgcggaac ccctatttgt      1140
ttatttttct aaatacattc aaatatgtat ccgctcatga caataaacc  ctgataaatg      1200 cttcaataat attgaaaaag gaagagtatg agtattcaac atttccgtgt cgcccttatt      1260 ccctttttg  cggcattttg ccttcctgtt tttgctcacc cagaaacgct ggtgaaagta      1320
aaagatgctg aagatcagtt gggtgcacga gtgggttaca tcgaactgga tctcaacagc      1380
ggtaagatcc ttgagagttt tcgccccgaa gaacgttttc caatgatgag cacttttaaa      1440
gttctgctat gtggcgcggt attatcccgt gttgacgccg ggcaagagca actcggtcgc      1500
cgcatacact attctcagaa tgacttggtt gagtactcac cagtcacaga aaagcatctt      1560
acggatggca tgacagtaag agaattatgc agtgctgcca taaccatgag tgataacact      1620
gcggccaact tacttctgac aacgatcgga ggaccgaagg agctaaccgc ttttttgcac      1680
```

```
aacatggggg atcatgtaac tcgccttgat cgttgggaac cggagctgaa tgaagccata    1740
ccaaacgacg agcgtgacac cacgatgcct gcagcaatgg caacaacgtt gcgcaaacta    1800
ttaactggcg aactacttac tctagcttcc cggcaacaat taatagactg gatggaggcg    1860
gataaagttg caggaccact tctgcgctcg gcccttccgg ctggctggtt tattgctgat    1920
aaatctggag ccggtgagcg tgggtctcgc ggtatcattg cagcactggg gccagatggt    1980
aagccctccc gtatcgtagt tatctacacg acggggagtc aggcaactat ggatgaacga    2040
aatagacaga tcgctgagat aggtgcctca ctgattaagc attggtaact gtcagaccaa    2100
gtttactcat atatacttta gattgattta aaacttcatt tttaatttaa aaggatctag    2160
gtgaagatcc ttttttgataa tctcatgacc aaaatccctt aacgtgagtt tcgttccac    2220 tgagcgtcag accccgtaga aaagatcaaa ggatcttctt gagatccttt ttttctgcgc    2280
gtaatctgct gcttgcaaac aaaaaaacca ccgctaccag cggtggtttg tttgccggat    2340
caagagctac caactctttt tccgaaggta actggcttca gcagagcgca gataccaaat    2400
actgtccttc tagtgtagcc gtagttaggc caccacttca agaactctgt agcaccgcct    2460
acatacctcg ctctgctaat cctgttacca gtggctgctg ccagtggcga taagtcgtgt    2520
cttaccgggt tggactcaag acgatagtta ccggataagg cgcagcggtc gggctgaacg    2580
gggggttcgt gcacacagcc cagcttggag cgaacgacct acaccgaact gagatacccta   2640 cagcgtgagc tatgagaaag cgccacgctt cccgaaggga gaaaggcgga caggtatccg    2700
gtaagcggca gggtcggaac aggagagcgc acgagggagc ttccaggggg aaacgcctgg    2760
tatctttata gtcctgtcgg gtttcgccac ctctgacttg agcgtcgatt tttgtgatgc    2820
tcgtcagggg ggcggagcct atggaaaaac gccagcaacg cggccttttt acggttcctg    2880
gccttttgct ggccttttgc tcacatgttc tttcctgcgt tatccctga ttctgtggat    2940 aaccgtatta ccgcctttga gtgagctgat accgctcgcc gcagccgaac gaccgagcgc    3000
agcgagtcag tgagcgagga agcggaagag cgcctgatgc ggtattttct ccttacgcat    3060
ctgtgcggta tttcacaccg caatggtgca ctctcagtac aatctgctct gatgccgcat    3120
agttaagcca gtatacactc cgctatcgct acgtgactgg gtcatggctg cgccccgaca    3180
cccgccaaca cccgctgacg cgccctgacg ggcttgtctg ctcccggcat ccgcttacag    3240
acaagctgtg accgtctccg ggagctgcat gtgtcagagg ttttcaccgt catcaccgaa    3300
acgcgcgagg cagctgcggt aaagctcatc agcgtggtcg tgaagcgatt cacagatgtc    3360
tgcctgttca tccgcgtcca gctcgttgag tttctccaga agcgttaatg tctggcttct    3420
gataaagcgg ccatgttaa gggcggtttt ttcctgtttg gtcactgatg cctccgtgta    3480
agggggattt ctgttcatgg gggtaatgat accgatgaaa cgagagagga tgctcacgat    3540
acgggttact gatgatgaac atgcccggtt actggaacgt tgtgagggta aacaactggc    3600 ggtatgatg cggcgggacc agagaaaaat cactcagggt caatgccagc gcttcgttaa    3660
tacagatgta ggtgttccac agggtagcca gcagcatcct gcgatgcaga tccggaacat    3720
aatggtgcag gcgctgact tccgcgtttc cagactttac gaaacacgga aaccgaagac    3780
cattcatgtt gttgctcagg tcgcagacgt tttgcagcag cagtcgcttc acgttcgctc    3840
gcgtatcggt gattcattct gctaaccagt aaggcaaccc cgccagccta gccgggtcct    3900
caacgacagg agcacgatca tgcgcacccg tggccaggac ccaacgctgc ccgagatgcg    3960
ccgcgtgcgg ctgctggaga tggcggacgc gatggatatg ttctgccaag ggttggtttg    4020
cgcattcaca gttctccgca agaattgatt ggctccaatt cttggagtgg tgaatccgtt    4080
```

```
agcgaggtgc cgccggcttc cattcaggtc gaggtggccc ggctccatgc accgcgacgc    4140
aacgcgggga ggcagacaag gtatagggcg gcgcctacaa tccatgccaa cccgttccat    4200
gtgctcgccg aggcggcata atcgccgtg acgatcagcg gtccaatgat cgaagttagg     4260
ctggtaagag ccgcgagcga tccttgaagc tgtccctgat ggtcgtcatc tacctgcctg    4320
gacagcatgg cctgcaacgc gggcatcccg atgccgccgg aagcgagaag aatcataatg    4380
gggaaggcca tccagcctcg cgtcgcgaac gccagcaaga cgtagcccag cgcgtcggcc    4440
gccatgccgg cgataatggc ctgcttctcg ccgaaacgtt tggtggcggg accagtgacg    4500
aaggcttgag cgagggcgtg caagattccg aataccgcaa cgacaggcc gatcatcgtc     4560
gcgctccagc gaaagcggtc ctcgccgaaa atgacccaga gcgctgccgg cacctgtcct    4620
acgagttgca tgataaagaa gacagtcata agtgcggcga cgatagtcat gccccgcgcc    4680
caccggaagg agctgactgg gttgaaggct ctcaagggca tcggtcgaga tcccggtgcc    4740
taatgagtga gctaacttac attaattgcg ttgcgctcac tgcccgcttt ccagtcggga    4800
aacctgtcgt gccagctgca ttaatgaatc ggccaacgcg cggggagagg cggtttgcgt    4860
attgggcgcc agggtggttt ttcttttcac cagtgagacg ggcaacagct gattgccctt    4920
caccgcctgg ccctgagaga gttgcagcaa gcggtccacg ctggtttgcc ccagcaggcg    4980
aaaatcctgt ttgatggtgg ttaacggcgg gatataacat gagctgtctt cggtatcgtc    5040
gtatcccact accgagatat ccgcaccaac gcgcagcccg gactcggtaa tggcgcgcat    5100
tgcgcccagc gccatctgat cgttggcaac cagcatcgca gtgggaacga tgccctcatt    5160
cagcatttgc atggtttgtt gaaaaccgga catggcactc cagtcgcctt cccgttccgc    5220
tatcggctga atttgattgc gagtgagata tttatgccag ccagccagac gcagacgcgc    5280
cgagacagaa cttaatgggc ccgctaacag cgcgatttgc tggtgaccca atgcgaccag    5340
atgctccacg cccagtcgcg taccgtcttc atgggagaaa ataatactgt tgatgggtgt    5400
ctggtcgaga acatcaagaa ataacgccgg aacattagtg caggcagctt ccacagcaat    5460
ggcatcctgg tcatccagcg gatagttaat gatcagccca ctgacgcgtt gcgcgagaag    5520
attgtgcacc gccgctttac aggcttcgac gccgcttcgt tctaccatcg acaccaccac    5580
gctggcaccc agttgatcgg cgcgagattt aatcgccgcg acaatttgcg acggcgcgtg    5640
cagggccaga ctggaggtgg caacgccaat cagcaacgca tgtttgcccg ccagttgttg    5700
tgccacgcgg ttgggaatgt aattcagctc cgccatcgcc gcttccactt tttcccgcgt    5760
tttcgcagaa acgtggctgg cctggttcac cacgcggaa acggtctgat aagagacacc    5820
ggcatactct gcgacatcgt ataacgttac tggtttcaca ttcaccaccc tgaattgact    5880
ctcttccggg cgctatcatg ccataccgcg aaaggttttg cgccattcga tggtgtccgg    5940
gatctcgacg ctctccctta tgcgactcct gcattaggaa gcagcccagt agtaggttga    6000
ggccgttgag caccgccgcc gcaaggaatg gtgcatgcaa ggagatggcg cccaacagtc    6060
ccccggccac ggggcctgcc accatacccca cgccgaaaca agcgctcatg agcccgaagt    6120
ggcgagcccg atcttcccca tcggtgatgt cggcgatata ggcgccagca accgcacctg    6180
tggcgccggt gatgccggcc acgatgcgtc cggcgtagag gatcga                   6226
```

<210> SEQ ID NO 96
<211> LENGTH: 6238
<212> TYPE: DNA
<213> ORGANISM: Artificial
<220> FEATURE:

<223> OTHER INFORMATION: Vector construct

<400> SEQUENCE: 96

```
gatctcgatc cgcgaaatt aatacgactc actatagggg aattgtgagc ggataacaat    60
tcccctctag aaataatttt gtttaaactt taagaaggag atatacatat gctgaaacat   120
atttactcca accacattaa aggtaacaaa atcacagccc ctaaaccgtc aattcagggc   180
gtggtgatcc acaacgatta tggctcaatg accccttcac agtacctgcc ttggctgtac   240
gctcgcgaaa acaacggtac acatgtgaat ggctgggcct cagtgtatgc caatcgcaac   300
gaggtgctgt ggtatcatcc tacagactac gtggaatggc actgcggcaa ccaatgggcc   360
aacgccaacc tgatcggctt tgaagtttgc gaatcatatc ctggtcgcat ctcagacaaa   420
ctgtttctgg aaaacgagga agccacactg aaagtagctg ccgacgtgat gaaatcgtat   480
ggcctgcctg tgaatcgcaa cacagtgcgc ctgcacaacg aatttttcgg tacatcatgc   540
cctcatcgtt catgggacct gcacgtgggc aaaggcgagc cttataccac aacaaatatc   600
aataaaatga agattatttt cattaaacgg attaaacact actatgacgg tgagctcggt   660
cgtaaaaaac gtcgtcagcg tcgtcgtccg cctcagtaag gatccggctg ctaacaaagc   720
ccgaaaggaa gctgagttgg ctgctgccac cgctgagcaa taactagcat aacccccttgg   780
ggcctctaaa cgggtcttga gggttttttt gctgaaagga ggaactatat ccggatatcc   840
cgcaagaggc ccggcagtac cggcataacc aagcctatgc ctacagcatc agggtgacg   900
gtgccgagga tgacgatgag cgcattgtta gatttcatac acggtgcctg actgcgttag   960
caatttaact gtgataaact accgcattaa agctagctta tcgatgataa gctgtcaaac  1020
atgagaatta attcttgaag acgaaagggc ctcgtgatac gcctattttt ataggttaat  1080
gtcatgataa taatggtttc ttagacgtca ggtggcactt ttcggggaaa tgtgcgcgga  1140
accccctattt gtttattttt ctaaatacat tcaaatatgt atccgctcat gagacaataa  1200
ccctgataaa tgcttcaata atattgaaaa aggaagagta tgagtattca acatttccgt  1260
gtcgccctta ttcccttttt tgcggcattt tgccttcctg ttttttgctca cccagaaacg  1320
ctggtgaaag taaagatgc tgaagatcag ttgggtgcac gagtgggtta catcgaactg  1380
gatctcaaca gcggtaagat ccttgagagt tttcgccccg aagaacgttt tccaatgatg  1440
agcactttta agttctgct atgtggcgcg gtattatccc gtgttgacgc cgggcaagag  1500
caactcggtc gccgcataca ctattctcag aatgacttgg ttgagtactc accagtcaca  1560
gaaaagcatc ttacggatgg catgacagta agagaattat gcagtgctgc cataaccatg  1620
agtgataaca ctgcggccaa cttacttctg acaacgatcg gaggaccgaa ggagctaacc  1680
gcttttttgc acaacatggg ggatcatgta actcgccttg atcgttggga accggagctg  1740
aatgaagcca taccaaacga cgagcgtgac accacgatgc ctgcagcaat ggcaacaacg  1800
ttgcgcaaac tattaactgg cgaactactt actctagctt cccggcaaca attaatagac  1860
tggatggagg cggataaagt tgcaggacca cttctgcgct cggcccttcc ggctggctgg  1920
tttattgctg ataaatctgg agccggtgag cgtgggtctc gcggtatcat tgcagcactg  1980
gggccagatg gtaagccctc ccgtatcgta gttatctaca cgacggggag tcaggcaact  2040
atggatgaac gaaatagaca gatcgctgag ataggtgcct cactgattaa gcattggtaa  2100
ctgtcagacc aagtttactc atatatactt tagattgatt taaaacttca ttttttaattt  2160
aaaaggatct aggtgaagat cctttttgat aatctcatga ccaaaatccc ttaacgtgag  2220
ttttcgttcc actgagcgtc agaccccgta gaaaagatca aggatcttc ttgagatcct  2280
```

```
tttttctgc gcgtaatctg ctgcttgcaa acaaaaaaac caccgctacc agcggtggtt    2340
tgtttgccgg atcaagagct accaactctt tttccgaagg taactggctt cagcagagcg    2400
cagataccaa atactgtcct tctagtgtag ccgtagttag gccaccactt caagaactct    2460
gtagcaccgc ctacatacct cgctctgcta atcctgttac cagtggctgc tgccagtggc    2520
gataagtcgt gtcttaccgg gttggactca agacgatagt taccggataa ggcgcagcgg    2580
tcgggctgaa cggggggttc gtgcacacag cccagcttgg agcgaacgac ctacaccgaa    2640
ctgagatacc tacagcgtga gctatgagaa agcgccacgc ttcccgaagg gagaaaggcg    2700
gacaggtatc cggtaagcgg cagggtcgga acaggagagc gcacgaggga gcttccaggg    2760
ggaaacgcct ggtatcttta tagtcctgtc gggtttcgcc acctctgact tgagcgtcga    2820
tttttgtgat gctcgtcagg ggggcggagc ctatggaaaa acgccagcaa cgcggccttt    2880
ttacggttcc tggccttttg ctggcctttt gctcacatgt tctttcctgc gttatcccct    2940
gattctgtgg ataaccgtat taccgccttt gagtgagctg ataccgctcg ccgcagccga    3000
acgaccgagc gcagcgagtc agtgagcgag gaagcggaag agcgcctgat gcggtatttt    3060
ctccttacgc atctgtgcgg tatttcacac cgcaatggtg cactctcagt acaatctgct    3120
ctgatgccgc atagttaagc cagtatacac tccgctatcg ctacgtgact gggtcatggc    3180
tgcgccccga cacccgccaa cacccgctga cgcgccctga cgggcttgtc tgctcccggc    3240
atccgcttac agacaagctg tgaccgtctc cgggagctgc atgtgtcaga ggttttcacc    3300
gtcatcaccg aaacgcgcga ggcagctgcg gtaaagctca tcagcgtggt cgtgaagcga    3360
ttcacagatg tctgcctgtt catccgcgtc cagctcgttg agtttctcca gaagcgttaa    3420
tgtctggctt ctgataaagc gggccatgtt aagggcggtt ttttcctgtt tggtcactga    3480
tgcctccgtg taagggggat ttctgttcat gggggtaatg ataccgatga acgagagag     3540 gatgctcacg atacgggtta ctgatgatga acatgcccgg ttactggaac gttgtgaggg    3600
taaacaactg gcggtatgga tgcggcggga ccagagaaaa atcactcagg gtcaatgcca    3660
gcgcttcgtt aatacagatg taggtgttcc acagggtagc cagcagcatc ctgcgatgca    3720
gatccggaac ataatggtgc agggcgctga cttccgcgtt tccagacttt acgaaacacg    3780
gaaaccgaag accattcatg ttgttgctca ggtcgcagac gttttgcagc agcagtcgct    3840
tcacgttcgc tcgcgtatcg gtgattcatt ctgctaacca gtaaggcaac cccgccagcc    3900
tagccgggtc ctcaacgaca ggagcacgat catgcgcacc cgtggccagg acccaacgct    3960
gcccgagatg cgccgcgtgc ggctgctgga gatggcggac gcgatggata tgttctgcca    4020
agggttggtt tgcgcattca cagttctccg caagaattga ttggctccaa ttcttggagt    4080
ggtgaatccg ttagcgaggt gccgccggct tccattcagg tcgaggtggc ccggctccat    4140
gcaccgcgac gcaacgcggg gaggcagaca aggtataggg cggcgcctac aatccatgcc    4200
aacccgttcc atgtgctcgc cgaggcggca taaatcgccg tgacgatcag cggtccaatg    4260
atcgaagtta ggctggtaag agccgcgagc gatccttgaa gctgtccctg atggtcgtca    4320
tctacctgcc tggacagcat ggcctgcaac gcgggcatcc cgatgccgcc ggaagcgaga    4380
agaatcataa tggggaaggc catccagcct cgcgtcgcga acgccagcaa gacgtagccc    4440
agcgcgtcgg ccgccatgcc ggcgataatg gcctgcttct cgccgaaacg tttggtggcg    4500
ggaccagtga cgaaggcttg agcgagggcg tgcaagattc cgaataccgc aagcgacagg    4560
ccgatcatcg tcgcgctcca gcgaaagcgg tcctcgccga aaatgaccca gagcgctgcc    4620
```

-continued

| | | | | |
|---|---|---|---|---|
| ggcacctgtc | ctacgagttg | catgataaag | aagacagtca | taagtgcggc gacgatagtc | 4680 |
| atgccccgcg | cccaccggaa | ggagctgact | gggttgaagg | ctctcaaggg catcggtcga | 4740 |
| gatcccggtg | cctaatgagt | gagctaactt | acattaattg | cgttgcgctc actgcccgct | 4800 |
| ttccagtcgg | gaaacctgtc | gtgccagctg | cattaatgaa | tcggccaacg cgcgggaga | 4860 |
| ggcggtttgc | gtattgggcg | ccagggtggt | ttttcttttc | accagtgaga cgggcaacag | 4920 |
| ctgattgccc | ttcaccgcct | ggccctgaga | gagttgcagc | aagcggtcca cgctggtttg | 4980 |
| ccccagcagg | cgaaaatcct | gtttgatggt | ggttaacggc | gggatataac atgagctgtc | 5040 |
| ttcggtatcg | tcgtatccca | ctaccgagat | atccgcacca | acgcgcagcc cggactcggt | 5100 |
| aatggcgcgc | attgcgccca | cgccatctg | atcgttggca | accagcatcg cagtgggaac | 5160 |
| gatgccctca | ttcagcattt | gcatggtttg | ttgaaaaccg | gacatggcac tccagtcgcc | 5220 |
| ttcccgttcc | gctatcggct | gaatttgatt | gcgagtgaga | tatttatgcc agccagccag | 5280 |
| acgcagacgc | gccgagacag | aacttaatgg | gcccgctaac | agcgcgattt gctggtgacc | 5340 |
| caatgcgacc | agatgctcca | cgcccagtcg | cgtaccgtct | tcatgggaga aaataatact | 5400 |
| gttgatgggt | gtctggtcag | agacatcaag | aaataacgcc | ggaacattag tgcaggcagc | 5460 |
| ttccacagca | atggcatcct | ggtcatccag | cggatagtta | atgatcagcc cactgacgcg | 5520 |
| ttgcgcgaga | agattgtgca | ccgccgcttt | acaggcttcg | acgccgcttc gttctaccat | 5580 |
| cgacaccacc | acgctggcac | ccagttgatc | ggcgcgagat | taatcgccg cgacaatttg | 5640 |
| cgacggcgcg | tgcagggcca | gactggaggt | ggcaacgcca | atcagcaacg actgtttgcc | 5700 |
| cgccagttgt | tgtgccacgc | ggttgggaat | gtaattcagc | tccgccatcg ccgcttccac | 5760 |
| ttttttcccgc | gttttcgcag | aaacgtggct | ggcctggttc | accacgcggg aaacggtctg | 5820 |
| ataagagaca | ccggcatact | ctgcgacatc | gtataacgtt | actggtttca cattcaccac | 5880 |
| cctgaattga | ctctcttccg | ggcgctatca | tgccataccg | cgaaaggttt tgcgccattc | 5940 |
| gatggtgtcc | gggatctcga | cgctctccct | tatgcgactc | ctgcattagg aagcagccca | 6000 |
| gtagtaggtt | gaggccgttg | agcaccgccg | ccgcaaggaa | tggtgcatgc aaggagatgg | 6060 |
| cgcccaacag | tcccccggcc | acggggcctg | ccaccatacc | cacgccgaaa caagcgctca | 6120 |
| tgagcccgaa | gtggcgagcc | cgatcttccc | catcggtgat | gtcggcgata taggcgccag | 6180 |
| caaccgcacc | tgtggcgccg | gtgatgccgg | ccacgatgcg | tccggcgtag aggatcga | 6238 |

<210> SEQ ID NO 97
<211> LENGTH: 6571
<212> TYPE: DNA
<213> ORGANISM: Artificial
<220> FEATURE:
<223> OTHER INFORMATION: Vector construct

<400> SEQUENCE: 97

| | | | | |
|---|---|---|---|---|
| gatctcgatc | ccgcgaaatt | aatacgactc | actatagggg | aattgtgagc ggataacaat | 60 |
| tcccctctag | aaataatttt | gtttaaactt | taagaaggag | atatacatat gtccattatc | 120 |
| atggaagtgg | ccacaatgca | agccaaactg | acaaaaaatg | agttcattga gtggctgaaa | 180 |
| acgtccgagg | gtaaacagtt | caacgtggac | ctgtggtacg | gttttcagtg tttcgactac | 240 |
| gccaacgctg | gctggaaagt | gctgttcggc | ctgctgctga | aaggcctggg agccaaagac | 300 |
| atccctttg | caaacaattt | cgatggcctg | gccacagttt | atcaaaacac ccctgacttt | 360 |
| ctggcccaac | caggcgacat | ggtggtgttt | ggttctaatt | atggcgcagg ctatggccac | 420 |
| gtagcctggg | tgatcgaagc | cacactggac | tacattattg | tttatgagca aaactggctg | 480 |

```
ggaggcggat ggacagacgg catcgaacag cctggctggg gctgggagaa agtgacacgc   540
cgtcaacatg cctatgactt ccctatgtgg ttcatccgtc ctaatttcaa aggtggtaaa   600
ctggaagtta gcaaagcagc aaccattaaa cagtccgatg ttaaacaaga agtgaaaaaa   660
caagaggcca aacaaattgt gaaagccacc gattggaaac agaacaaaga tggcatttgg   720
tataaagcag aacatgccag ctttaccgtt accgcaccgg aaggcattat tacccgttat   780
aaaggtccgt ggaccggtca tccgcaggca ggcgtactgc agaaaggtca gaccattaaa   840
tacgatgaag tgcagaaatt tgatggccat gtttgggtta gctgggaaac ctttgaaggt   900
gaaaccgttt atatgccggt tcgtacctgg gatgcaaaaa ccggtaaagt gggcaaactg   960
tggggtgaaa tcaaagagct ccgccagatc aaaatttggt ttcagaatcg tcgcatgaaa  1020
tggaaaaaat aaggatccgg ctgctaacaa agcccgaaag gaagctgagt tggctgctgc  1080
caccgctgag caataactag cataacccct tggggcctct aaacgggtct tgaggggttt  1140
tttgctgaaa ggaggaacta tatccggata tcccgcaaga ggcccggcag taccggcata  1200
accaagccta tgcctacagc atccaggg tg acggtgccga ggatgacgat gagcgcattg  1260
ttagatttca tacacggtgc ctgactgcgt tagcaattta actgtgataa actaccgcat  1320
taaagctagc ttatcgatga taagctgtca aacatgagaa ttaattcttg aagacgaaag  1380
ggcctcgtga tacgcctatt tttataggtt aatgtcatga taataatggt ttcttagacg  1440
tcaggtggca cttttcgggg aaatgtgcgc ggaaccccta tttgtttatt tttctaaata  1500
cattcaaata tgtatccgct catgagacaa taaccctgat aaatgcttca ataatattga  1560
aaaaggaaga gtatgagtat tcaacatttc cgtgtcgccc ttattccctt ttttgcggca  1620
ttttgccttc ctgttttgc tcacccagaa acgctggtga agtaaaaga tgctgaagat  1680 cagttgggtg cacgagtggg ttacatcgaa ctggatctca acagcggtaa gatccttgag  1740
agttttcgcc ccgaagaacg ttttccaatg atgagcactt ttaaagttct gctatgtggc  1800
gcggtattat cccgtgttga cgccgggcaa gagcaactcg gtcgccgcat acactattct  1860
cagaatgact tggttgagta ctcaccagtc acagaaaagc atcttacgga tggcatgaca  1920
gtaagagaat tatgcagtgc tgccataacc atgagtgata acactgcggc caacttactt  1980
ctgacaacga tcggaggacc gaaggagcta accgcttttt tgcacaacat ggggg gatcat  2040 gtaactcgcc ttgatcgttg ggaaccggag ctgaatgaag ccataccaaa cgacgagcgt  2100
gacaccacga tgcctgcagc aatggcaaca acgttgcgca aactattaac tggcgaacta  2160
cttactctag cttcccggca acaattaata gactggatgg aggcggataa agttgcagga  2220
ccacttctgc gctcggccct tccggctggc tggtttattg ctgataaatc tggagccggt  2280
gagcgtgggt ctcgcggtat cattgcagca ctggggccag atggtaagcc ctcccgtatc  2340
gtagttatct acacgacggg gagtcaggca actatggatg aacgaaatag acagatcgct  2400
gagataggtg cctcactgat taagcattgg taactgtcag accaagttta ctcatatata  2460
ctttagattg atttaaaact tcatttttaa tttaaaagga tctaggtgaa gatcctttt   2520 gataatctca tgaccaaaat cccttaacgt gagttttcgt tccactgagc gtcagacccc  2580
gtagaaaaga tcaaaggatc ttcttgagat cctttttttc tgcgcgtaat ctgctgcttg  2640
caaacaaaaa aaccaccgct accagcggtg gtttgtttgc cggatcaaga gctaccaact  2700
ctttttccga aggtaactgg cttcagcaga gcgcagatac caaatactgt ccttctagtg  2760
tagccgtagt taggccacca cttcaagaac tctgtagcac cgcctacata cctcgctctg  2820
```

```
ctaatcctgt taccagtggc tgctgccagt ggcgataagt cgtgtcttac cgggttggac    2880
tcaagacgat agttaccgga taaggcgcag cggtcgggct gaacgggggg ttcgtgcaca    2940
cagcccagct tggagcgaac gacctacacc gaactgagat acctacagcg tgagctatga    3000
gaaagcgcca cgcttcccga agggagaaag cggacaggat atccggtaag cggcagggtc    3060
ggaacaggag agcgcacgag ggagcttcca gggggaaacg cctggtatct ttatagtcct    3120
gtcgggtttc gccacctctg acttgagcgt cgattttcgt gatgctcgtc aggggggcgg    3180
agcctatgga aaaacgccag caacgcggcc ttttacggt tcctggcctt ttgctggcct    3240
tttgctcaca tgttctttcc tgcgttatcc cctgattctg tggataaccg tattaccgcc    3300
tttgagtgag ctgataccgc tcgccgcagc cgaacgaccg agcgcagcga gtcagtgagc    3360
gaggaagcgg aagagcgcct gatgcggtat tttctcctta cgcatctgtg cggtatttca    3420
caccgcaatg gtgcactctc agtacaatct gctctgatgc cgcatagtta agccagtata    3480
cactccgcta tcgctacgtg actgggtcat ggctgcgccc cgacaccgc caacacccgc    3540 tgacgcgccc tgacgggctt gtctgctccc ggcatccgct tacagacaag ctgtgaccgt    3600
ctccgggagc tgcatgtgtc agaggttttc accgtcatca ccgaaacgcg cgaggcagct    3660
gcggtaaagc tcatcagcgt ggtcgtgaag cgattcacag atgtctgcct gttcatccgc    3720
gtccagctcg ttgagtttct ccagaagcgt taatgtctgg cttctgataa agcgggccat    3780
gttaagggcg gttttttcct gtttggtcac tgatgcctcc gtgtaagggg gatttctgtt    3840
catgggggta atgataccga tgaaacgaga gaggatgctc acgatacggg ttactgatga    3900
tgaacatgcc cggttactgg aacgttgtga gggtaaacaa ctggcggtat ggatgcggcg    3960
ggaccagaga aaaatcactc agggtcaatg ccagcgcttc gttaatacag atgtaggtgt    4020
tccacagggt agccagcagc atcctgcgat gcagatccgg aacataatgg tgcagggcgc    4080
tgacttccgc gtttccagac tttacgaaac acggaaaccg aagaccattc atgttgttgc    4140
tcaggtcgca gacgttttgc agcagcagtc gcttcacgtt cgctcgcgta tcggtgattc    4200
attctgctaa ccagtaaggc aaccccgcca gcctagccgg gtcctcaacg acaggagcac    4260
gatcatgcgc acccgtggcc aggacccaac gctgcccgag atgcgccgcg tgcggctgct    4320
ggagatggcg gacgcgatgg atatgttctg ccaagggttg gtttgcgcat tcacagttct    4380
ccgcaagaat tgattggctc caattcttgg agtggtgaat ccgttagcga ggtgccgccg    4440
gcttccattc aggtcgaggt ggcccggctc catgcaccgc gacgcaacgc ggggaggcag    4500
acaaggtata gggcggcgcc tacaatccat gccaacccgt tccatgtgct cgccgaggcg    4560
gcataaatcg ccgtgacgat cagcggtcca atgatcgaag ttaggctggt aagagccgcg    4620
agcgatcctt gaagctgtcc ctgatggtcg tcatctacct gcctggacag catgccctgc    4680
aacgcgggca tcccgatgcc gccggaagcg agaagaatca taatgggaa ggccatccag    4740 cctcgcgtcg cgaacgccag caagacgtag cccagcgcgt cggccgccat gccggcgata    4800
atggcctgct tctcgccgaa acgtttggtg gcgggaccag tgacgaaggc ttgagcgagg    4860
gcgtgcaaga ttccgaatac cgcaagcgac aggccgatca tcgtcgcgct ccagcgaaag    4920
cggtcctcgc cgaaaatgac ccagagcgct gccggcacct gtcctacgag ttgcatgata    4980
aagaagacag tcataagtgc ggcgacgata gtcatgcccc gcgcccaccg gaaggagctg    5040
actgggttga aggctctcaa gggcatcggt cgagatcccg gtgcctaatg agtgagctaa    5100
cttacattaa ttgcgttgcg ctcactgccc gctttccagt cgggaaacct gtcgtgccag    5160
ctgcattaat gaatcggcca acgcgcgggg agaggcggtt tgcgtattgg gcgccagggt    5220
```

```
ggtttttctt ttcaccagtg agacgggcaa cagctgattg cccttcaccg cctggccctg    5280
agagagttgc agcaagcggt ccacgctggt ttgccccagc aggcgaaaat cctgtttgat    5340
ggtggttaac ggcgggatat aacatgagct gtcttcggta tcgtcgtatc ccactaccga    5400
gatatccgca ccaacgcgca gcccggactc ggtaatggcg cgcattgcgc ccagcgccat    5460
ctgatcgttg gcaaccagca tcgcagtggg aacgatgccc tcattcagca tttgcatggt    5520
ttgttgaaaa ccgacatgg cactccagtc gccttcccgt tccgctatcg gctgaatttg    5580
attgcgagtg agatatttat gccagccagc cagacgcaga cgcgccgaga cagaacttaa    5640
tgggcccgct aacagcgcga tttgctggtg acccaatgcg accagatgct ccacgcccag    5700
tcgcgtaccg tcttcatggg agaaaataat actgttgatg ggtgtctggt cagagacatc    5760
aagaaataac gccggaacat tagtgcaggc agcttccaca gcaatggcat cctggtcatc    5820
cagcggatag ttaatgatca gcccactgac gcgttgcgcg agaagattgt gcaccgccgc    5880
tttacaggct tcgacgccgc ttcgttctac catcgacacc accacgctgg cacccagttg    5940
atcggcgcga gatttaatcg ccgcgacaat ttgcgacggc gcgtgcaggg ccagactgga    6000
ggtggcaacg ccaatcagca acgactgttt gcccgccagt tgttgtgcca cgcggttggg    6060
aatgtaattc agctccgcca tcgccgcttc cactttttcc cgcgttttcg cagaaacgtg    6120
gctggcctgg ttcaccacgc gggaaacggt ctgataagag acaccggcat actctgcgac    6180
atcgtataac gttactggtt tcacattcac caccctgaat tgactctctt ccgggcgcta    6240
tcatgccata ccgcgaaagg ttttgcgcca ttcgatggtg tccggatct cgacgctctc    6300 ccttatgcga ctcctgcatt aggaagcagc ccagtagtag gttgaggccg ttgagcaccg    6360
ccgccgcaag gaatggtgca tgcaaggaga tggcgcccaa cagtcccccg gccacggggc    6420
ctgccaccat acccacgccg aaacaagcgc tcatgagccc gaagtggcga gcccgatctt    6480
ccccatcggt gatgtcggcg atataggcgc cagcaaccgc acctgtggcg ccggtgatgc    6540
cggccacgat gcgtccggcg tagaggatcg a                                   6571
```

<210> SEQ ID NO 98
<211> LENGTH: 6550
<212> TYPE: DNA
<213> ORGANISM: Artificial
<220> FEATURE:
<223> OTHER INFORMATION: Vector construct

<400> SEQUENCE: 98

```
gatctcgatc ccgcgaaatt aatacgactc actatagggg aattgtgagc ggataacaat      60
tcccctctag aaataatttt gtttaaactt taagaaggag atatacatat gtccattatc     120
atggaagtgg ccacaatgca agccaaactg acaaaaaatg agttcattga gtggctgaaa     180
acgtccgagg gtaaacagtt caacgtggac ctgtggtacg gttttcagtg tttcgactac     240
gccaacgctg gctggaaagt gctgttcggc ctgctgctga aaggcctggg agccaaagac     300 atccctttg caaacaattt cgatggcctg gccacagttt atcaaaacac ccctgacttt     360
ctggcccaac caggcgacat ggtggtgttt ggttctaatt atggcgcagg ctatggccac     420
gtagcctggg tgatcgaagc cacactggac tacattattg tttatgagca aaactggctg     480
ggaggcggat ggacagacgg catcgaacag cctggctggg gctgggagaa agtgacacgc     540
cgtcaacatg cctatgactt ccctatgtgg ttcatccgtc ctaatttcaa aggtggtaaa     600
ctggaagtta gcaaagcagc aaccattaaa cagtccgatg ttaaacaaga agtgaaaaaa     660
```

-continued

```
caagaggcca aacaaattgt gaaagccacc gattggaaac agaacaaaga tggcatttgg    720
tataaagcag aacatgccag ctttaccgtt accgcaccgg aaggcattat tacccgttat    780
aaaggtccgt ggaccggtca tccgcaggca ggcgtactgc agaaaggtca gaccattaaa    840
tacgatgaag tgcagaaatt tgatggccat gtttgggtta gctgggaaac ctttgaaggt    900
gaaaccgttt atatgccggt tcgtacctgg gatgcaaaaa ccggtaaagt gggcaaactg    960
tggggtgaaa tcaaagagct ccgtcgtcgt cgccgtcggc gtcgtcgtta aggatccggc   1020
tgctaacaaa gcccgaaagg aagctgagtt ggctgctgcc accgctgagc aataactagc   1080 ataaccccttt ggggcctcta aacgggtctt gaggggtttt ttgctgaaag gaggaactat   1140
atccggatat cccgcaagag gcccggcagt accggcataa ccaagcctat gcctacagca   1200
tccagggtga cggtgccgag gatgacgatg agcgcattgt tagatttcat acacggtgcc   1260
tgactgcgtt agcaatttaa ctgtgataaa ctaccgcatt aaagctagct tatcgatgat   1320
aagctgtcaa acatgagaat taattcttga agacgaaagg gcctcgtgat acgcctattt   1380
ttataggtta atgtcatgat aataatggtt tcttagacgt caggtggcac ttttcgggga   1440
aatgtgcgcg gaacccctat ttgtttattt ttctaaatac attcaaatat gtatccgctc   1500
atgagacaat aaccctgata aatgcttcaa taatattgaa aaaggaagag tatgagtatt   1560
caacatttcc gtgtcgccct tattcccttt tttgcggcat tttgccttcc tgttttgct   1620 cacccagaaa cgctggtgaa agtaaaagat gctgaagatc agttgggtgc acgagtgggt   1680
tacatcgaac tggatctcaa cagcggtaag atccttgaga gttttcgccc cgaagaacgt   1740
tttccaatga tgagcacttt taaagttctg ctatgtggcg cggtattatc ccgtgttgac   1800
gccgggcaag agcaactcgg tcgccgcata cactattctc agaatgactt ggttgagtac   1860
tcaccagtca cagaaaagca tcttacggat ggcatgacag taagagaatt atgcagtgct   1920
gccataacca tgagtgataa cactgcggcc aacttacttc tgacaacgat cggaggaccg   1980
aaggagctaa ccgcttttt gcacaacatg ggggatcatg taactcgcct tgatcgttgg   2040
gaaccggagc tgaatgaagc cataccaaac gacgagcgtg acaccacgat gcctgcagca   2100
atggcaacaa cgttgcgcaa actattaact ggcgaactac ttactctagc ttcccggcaa   2160
caattaatag actggatgga ggcggataaa gttgcaggac cacttctgcg ctcggccctt   2220
ccggctggct ggtttattgc tgataaatct ggagccggtg agcgtgggtc tcgcggtatc   2280
attgcagcac tggggccaga tggtaagccc tcccgtatcg tagttatcta cacgacgggg   2340
agtcaggcaa ctatggatga acgaaataga cagatcgctg agataggtgc ctcactgatt   2400
aagcattggt aactgtcaga ccaagtttac tcatatatac tttagattga tttaaaactt   2460
catttttaat ttaaaaggat ctaggtgaag atccttttg ataatctcat gaccaaaatc   2520
ccttaacgtg agttttcgtt ccactgagcg tcagaccccg tagaaaagat caaaggatct   2580
tcttgagatc cttttttct gcgcgtaatc tgctgcttgc aaacaaaaaa accaccgcta   2640
ccagcggtgg tttgtttgcc ggatcaagag ctaccaactc ttttccgaa ggtaactggc   2700 ttcagcagag cgcagatacc aaatactgtc cttctagtgt agccgtagtt aggccaccac   2760
ttcaagaact ctgtagcacc gcctacatac ctcgctctgc taatcctgtt accagtggct   2820
gctgccagtg gcgataagtc gtgtcttacc gggttggact caagacgata gttaccggat   2880
aaggcgcagc ggtcgggctg aacggggggt tcgtgcacac agcccagctt ggagcgaacg   2940
acctacaccg aactgagata cctacagcgt gagctatgag aaagcgccac gcttcccgaa   3000
gggagaaagg cggacaggta tccggtaagc ggcagggtcg aacaggaga gcgcacgagg   3060
```

-continued

| | | |
|---|---|---|
| gagcttccag ggggaaacgc ctggtatctt tatagtcctg tcgggtttcg ccacctctga | 3120 |
| cttgagcgtc gattttttgtg atgctcgtca gggggggcgga gcctatggaa aaacgccagc | 3180 |
| aacgcggcct ttttacggtt cctggccttt tgctggcctt ttgctcacat gttctttcct | 3240 |
| gcgttatccc ctgattctgt ggataaccgt attaccgcct ttgagtgagc tgataccgct | 3300 |
| cgccgcagcc gaacgaccga gcgcagcgag tcagtgagcg aggaagcgga agagcgcctg | 3360 |
| atgcggtatt ttctccttac gcatctgtgc ggtatttcac accgcaatgg tgcactctca | 3420 |
| gtacaatctg ctctgatgcc gcatagttaa gccagtatac actccgctat cgctacgtga | 3480 |
| ctgggtcatg gctgcgcccc gacacccgcc aacacccgct gacgcgccct gacgggcttg | 3540 |
| tctgctcccg gcatccgctt acagacaagc tgtgaccgtc tccgggagct gcatgtgtca | 3600 |
| gaggttttca ccgtcatcac cgaaacgcgc gaggcagctg cggtaaagct catcagcgtg | 3660 |
| gtcgtgaagc gattcacaga tgtctgcctg ttcatccgcg tccagctcgt tgagtttctc | 3720 |
| cagaagcgtt aatgtctggc ttctgataaa gcgggccatg ttaagggcgg ttttttcctg | 3780 |
| tttggtcact gatgcctccg tgtaaggggg atttctgttc atggggggtaa tgataccgat | 3840 |
| gaaacgagag aggatgctca cgatacgggt tactgatgat gaacatgccc ggttactgga | 3900 |
| acgttgtgag ggtaaacaac tggcggtatg gatgcggcgg gaccagagaa aaatcactca | 3960 |
| gggtcaatgc cagcgcttcg ttaatacaga tgtaggtgtt ccacagggta gccagcagca | 4020 |
| tcctgcgatg cagatccgga acataatggt gcagggcgct gacttccgcg tttccagact | 4080 |
| ttacgaaaca cggaaaccga agaccattca tgttgttgct caggtcgcag acgttttgca | 4140 |
| gcagcagtcg cttcacgttc gctcgcgtat cggtgattca ttctgctaac cagtaaggca | 4200 |
| accccgccag cctagccggg tcctcaacga caggagcacg atcatgcgca cccgtggcca | 4260 |
| ggacccaacg ctgcccgaga tgcgccgcgt gcggctgctg gagatggcgg acgcgatgga | 4320 |
| tatgttctgc caagggttgg tttgcgcatt cacagttctc cgcaagaatt gattggctcc | 4380 |
| aattcttgga gtggtgaatc cgttagcgag gtgccgccgg cttccattca ggtcgaggtg | 4440 |
| gcccggctcc atgcaccgcg acgcaacgcg gggaggcaga caaggtatag gcggcgcct | 4500 |
| acaatccatg ccaacccgtt ccatgtgctc gccgaggcgg cataaatcgc cgtgacgatc | 4560 |
| agcggtccaa tgatcgaagt taggctggta agagccgcga gcgatccttg aagctgtccc | 4620 |
| tgatggtcgt catctacctg cctggacagc atggcctgca acgcgggcat cccgatgccg | 4680 |
| ccggaagcga agaatcat aatggggaag gccatccagc ctcgcgtcgc gaacgccagc | 4740 |
| aagacgtagc ccagcgcgtc ggccgccatg ccggcgataa tggcctgctt ctcgccgaaa | 4800 |
| cgtttggtgg cgggaccagt gacgaaggct tgagcgaggg cgtgcaagat tccgaatacc | 4860 |
| gcaagcgaca ggccgatcat cgtcgcgctc agcgaaagc ggtcctcgcc gaaaatgacc | 4920 |
| cagagcgctg ccggcacctg tcctacgagt tgcatgataa agaagacagt cataagtgcg | 4980 |
| gcgacgatag tcatgccccg cgcccaccgg aaggagctga ctgggttgaa ggctctcaag | 5040 |
| ggcatcggtc gagatcccgg tgcctaatga gtgagctaac ttacattaat tgcgttgcgc | 5100 |
| tcactgcccg ctttccagtc gggaaacctg tcgtgccagc tgcattaatg aatcggccaa | 5160 |
| cgcgcgggga gaggcggttt gcgtattggg cgccagggtg ttttttcttt tcaccagtga | 5220 |
| gacgggcaac agctgattgc ccttcaccgc ctggccctga gagagttgca gcaagcggtc | 5280 |
| cacgctggtt tgccccagca ggcgaaaatc ctgtttgatg gtggttaacg gcgggatata | 5340 |
| acatgagctg tcttcggtat cgtcgtatcc cactaccgag atatccgcac caacgcgcag | 5400 |

```
cccggactcg gtaatggcgc gcattgcgcc cagcgccatc tgatcgttgg caaccagcat    5460
cgcagtggga acgatgccct cattcagcat ttgcatggtt tgttgaaaac cggacatggc    5520
actccagtcg ccttcccgtt ccgctatcgg ctgaatttga ttgcgagtga gatatttatg    5580
ccagccagcc agacgcagac gcgccgagac agaacttaat gggcccgcta acagcgcgat    5640
ttgctggtga cccaatgcga ccagatgctc cacgcccagt cgcgtaccgt cttcatggga    5700
gaaaataata ctgttgatgg gtgtctggtc agagacatca agaaataacg ccggaacatt    5760
agtgcaggca gcttccacag caatggcatc ctggtcatcc agcggatagt taatgatcag    5820
cccactgacg cgttgcgcga aagattgtg caccgccgct ttacaggctt cgacgccgct    5880
tcgttctacc atcgacacca ccacgctggc acccagttga tcggcgcgag atttaatcgc    5940
cgcgacaatt tgcgacggcg cgtgcagggc cagactggag gtggcaacgc caatcagcaa    6000
cgactgtttg cccgccagtt gttgtgccac gcggttggga atgtaattca gctccgccat    6060
cgccgcttcc acttttccc gcgttttcgc agaaacgtgg ctggcctggt tcaccacgcg    6120
ggaaacggtc tgataagaga caccggcata ctctgcgaca tcgtataacg ttactggttt    6180
cacattcacc accctgaatt gactctcttc cgggcgctat catgccatac cgcgaaaggt    6240
tttgcgccat tcgatggtgt ccgggatctc gacgctctcc cttatgcgac tcctgcatta    6300
ggaagcagcc cagtagtagg ttgaggccgt tgagcaccgc cgccgcaagg aatggtgcat    6360
gcaaggagat ggcgcccaac agtccccgg ccacgggcc tgccaccata cccacgccga    6420
aacaagcgct catgagcccg aagtggcgag cccgatcttc cccatcggtg atgtcggcga    6480
tataggcgcc agcaaccgca cctgtggcgc cggtgatgcc ggccacgatg cgtccggcgt    6540
agaggatcga                                                          6550
```

<210> SEQ ID NO 99
<211> LENGTH: 6562
<212> TYPE: DNA
<213> ORGANISM: Artificial
<220> FEATURE:
<223> OTHER INFORMATION: Vector construct

<400> SEQUENCE: 99

```
gatctcgatc ccgcgaaatt aatacgactc actatagggg aattgtgagc ggataacaat      60
tcccctctag aaataatttt gtttaaactt taagaaggag atatacatat gtccattatc     120
atggaagtgg ccacaatgca agccaaactg acaaaaaatg agttcattga gtggctgaaa     180
acgtccgagg gtaaacagtt caacgtggac ctgtggtacg gttttcagtg tttcgactac     240
gccaacgctg gctggaaagt gctgttcggc ctgctgctga aaggcctggg agccaaagac     300
atcccttttg caaacaattt cgatggcctg gccacagttt atcaaaacac ccctgacttt     360
ctggcccaac caggcgacat ggtggtgttt ggttctaatt atggcgcagg ctatggccac     420
gtagcctggg tgatcgaagc cacactggac tacattattg tttatgagca aaactggctg     480
ggaggcggat ggacagacgg catcgaacag cctggctggg gctgggagaa agtgacacgc     540
cgtcaacatg cctatgactt ccctatgtgg ttcatccgtc ctaatttcaa aggtggtaaa     600
ctggaagtta gcaaagcagc aaccattaaa cagtccgatg ttaaacaaga agtgaaaaaa     660
caagaggcca aacaaattgt gaaagccacc gattggaaac agaacaaaga tggcatttgg     720
tataaagcag aacatgccag ctttaccgtt accgcaccgg aaggcattat tacccgttat     780
aaaggtccgt ggaccggtca tccgcaggca ggcgtactgc agaaaggtca gaccattaaa     840
tacgatgaag tgcagaaatt tgatggccat gtttgggtta gctgggaaac ctttgaaggt     900
```

```
gaaaccgttt atatgccggt tcgtacctgg gatgcaaaaa ccggtaaagt gggcaaactg      960
tggggtgaaa tcaaagagct cggtcgtaaa aacgtcgtc agcgtcgtcg tccgcctcag     1020
taaggatccg gctgctaaca aagcccgaaa ggaagctgag ttggctgctg ccaccgctga     1080
gcaataacta gcataacccc ttggggcctc taaacgggtc ttgagggggtt ttttgctgaa    1140
aggaggaact atatccggat atcccgcaag aggcccggca gtaccggcat aaccaagcct     1200
atgcctacag catccagggt gacggtgccg aggatgacga tgagcgcatt gttagatttc     1260
atacacggtg cctgactgcg ttagcaattt aactgtgata aactaccgca ttaaagctag     1320
cttatcgatg ataagctgtc aaacatgaga attaattctt gaagacgaaa gggcctcgtg     1380
atacgcctat ttttataggt taatgtcatg ataataatgg tttcttagac gtcaggtggc     1440
acttttcggg gaaatgtgcg cggaacccct atttgtttat ttttctaaat acattcaaat     1500
atgtatccgc tcatgagaca ataaccctga taaatgcttc aataatattg aaaaaggaag     1560
agtatgagta ttcaacattt ccgtgtcgcc cttattccct ttttgcggc attttgcctt      1620
cctgttttg ctcacccaga aacgctggtg aaagtaaaag atgctgaaga tcagttgggt      1680
gcacgagtgg gttacatcga actggatctc aacagcggta agatccttga gagttttcgc     1740
cccgaagaac gttttccaat gatgagcact tttaaagttc tgctatgtgg cgcggtatta     1800
tcccgtgttg acgccgggca agagcaactc ggtcgccgca tacactattc tcagaatgac     1860
ttggttgagt actcaccagt cacagaaaag catcttacgg atggcatgac agtaagagaa     1920
ttatgcagtg ctgccataac catgagtgat aacactgcgg ccaacttact tctgacaacg     1980
atcggaggac cgaaggagct aaccgctttt ttgcacaaca tgggggatca tgtaactcgc     2040
cttgatcgtt gggaaccgga gctgaatgaa gccataccaa acgacgagcg tgacaccacg     2100
atgcctgcag caatggcaac aacgttgcgc aaactattaa ctggcgaact acttactcta     2160
gcttcccggc aacaattaat agactggatg gaggcggata agttgcagg accacttctg      2220
cgctcggccc ttccggctgg ctggtttatt gctgataaat ctggagccgg tgagcgtggg     2280
tctcgcggta tcattgcagc actggggcca gatggtaagc cctcccgtat cgtagttatc     2340
tacacgacgg ggagtcaggc aactatggat gaacgaaata gacagatcgc tgagataggt     2400
gcctcactga ttaagcattg gtaactgtca gaccaagttt actcatatat actttagatt     2460
gatttaaaac ttcattttta atttaaaagg atctaggtga agatccttt tgataatctc      2520
atgaccaaaa tcccttaacg tgagttttcg ttccactgag cgtcagaccc cgtagaaaag     2580
atcaaaggat cttcttgaga tcctttttt ctgcgcgtaa tctgctgctt gcaaacaaaa      2640
aaaccaccgc taccagcggt ggtttgtttg ccggatcaag agctaccaac tctttttccg     2700
aaggtaactg gcttcagcag agcgcagata ccaaatactg tccttctagt gtagccgtag     2760
ttaggccacc acttcaagaa ctctgtagca ccgcctacat acctcgctct gctaatcctg     2820
ttaccagtgg ctgctgccag tggcgataag tcgtgtctta ccgggttgga ctcaagacga     2880
tagttaccgg ataaggcgca gcggtcgggc tgaacggggg gttcgtgcac acagcccagc     2940
ttggagcgaa cgacctacac cgaactgaga tacctacagc gtgagctatg agaaagcgcc     3000
acgcttcccg aagggagaaa ggcggacagg tatccggtaa gcggcagggt cggaacagga     3060
gagcgcacga gggagcttcc agggggaaac gcctggtatc tttatagtcc tgtcgggttt     3120
cgccaccctct gacttgagcg tcgatttttg tgatgctcgt caggggggcg agcctatgg     3180
aaaaacgcca gcaacgcggc cttttacgg ttcctggcct tttgctggcc ttttgctcac      3240
```

```
atgttctttc ctgcgttatc ccctgattct gtggataacc gtattaccgc ctttgagtga    3300
gctgataccg ctcgccgcag ccgaacgacc gagcgcagcg agtcagtgag cgaggaagcg    3360
gaagagcgcc tgatgcggta ttttctcctt acgcatctgt gcggtatttc acaccgcaat    3420
ggtgcactct cagtacaatc tgctctgatg ccgcatagtt aagccagtat acactccgct    3480
atcgctacgt gactgggtca tggctgcgcc ccgacacccg ccaacacccg ctgacgcgcc    3540
ctgacgggct tgtctgctcc cggcatccgc ttacagacaa gctgtgaccg tctccgggag    3600
ctgcatgtgt cagaggtttt caccgtcatc accgaaacgc gcgaggcagc tgcggtaaag    3660
ctcatcagcg tggtcgtgaa gcgattcaca gatgtctgcc tgttcatccg cgtccagctc    3720
gttgagtttc tccagaagcg ttaatgtctg gcttctgata aagcgggcca tgttaagggc    3780
ggttttttcc tgtttggtca ctgatgcctc cgtgtaaggg ggatttctgt tcatgggggt    3840
aatgataccg atgaaacgag agaggatgct cacgatacgg gttactgatg atgaacatgc    3900
ccggttactg gaacgttgtg agggtaaaca actggcggta tggatgcggc gggaccagag    3960
aaaaatcact cagggtcaat gccagcgctt cgttaataca gatgtaggtg ttccacaggg    4020
tagccagcag catcctgcga tgcagatccg gaacataatg gtgcagggcg ctgacttccg    4080
cgtttccaga ctttacgaaa cacggaaacc gaagaccatt catgttgttg ctcaggtcgc    4140
agacgttttg cagcagcagt cgcttcacgt tcgctcgcgt atcggtgatt cattctgcta    4200
accagtaagg caacccgcc agcctagccg ggtcctcaac gacaggagca cgatcatgcg    4260
cacccgtggc caggacccaa cgctgcccga tgcggccgc gtgcggctgc tggagatggc    4320
ggacgcgatg gatatgttct gccaagggtt ggtttgcgca ttcacagttc tccgcaagaa    4380
ttgattggct ccaattcttg gagtggtgaa tccgttagcg aggtgccgcc ggcttccatt    4440
caggtcgagg tggcccggct ccatgcaccg cgacgcaacg cggggaggca gacaaggtat    4500
agggcggcgc ctacaatcca tgccaacccg ttccatgtgc tcgccgaggc ggcataaatc    4560
gccgtgacga tcagcggtcc aatgatcgaa gttaggctgg taagagccgc gagcgatcct    4620
tgaagctgtc cctgatggtc gtcatctacc tgcctggaca gcatggcctg caacgcgggc    4680
atcccgatgc cgccggaagc gagaagaatc ataatgggga aggccatcca gcctcgcgtc    4740
gcgaacgcca gcaagacgta gcccagcgcg tcggccgcca tgccggcgat aatggcctgc    4800
ttctcgccga aacgtttggt ggcgggacca gtgacgaagg cttgagcgag ggcgtgcaag    4860
attccgaata ccgcaagcga caggccgatc atcgtcgcgc tccagcgaaa gcggtcctcg    4920
ccgaaaatga cccagagcgc tgccggcacc tgtcctacga gttgcatgat aaagaagaca    4980
gtcataagtg cggcgacgat agtcatgccc cgcgcccacc ggaaggagct gactgggttg    5040
aaggctctca agggcatcgg tcgagatccc ggtgcctaat gagtgagcta acttacatta    5100
attgcgttgc gctcactgcc cgctttccag tcgggaaacc tgtcgtgcca gctgcattaa    5160
tgaatcggcc aacgcgcggg gagaggcggt ttgcgtattg ggcgccaggg tggttttcct    5220
tttcaccagt gagacgggca acagctgatt gcccttcacc gcctggccct gagagagttg    5280
cagcaagcgg tccacgctgg tttgccccag caggcgaaaa tcctgtttga tggtggttaa    5340
cggcgggata taacatgagc tgtcttcggt atcgtcgtat cccactaccg agatatccgc    5400
accaacgcgc agcccggact cggtaatggc gcgcattgcg cccagcgcca tctgatcgtt    5460
ggcaaccagc atcgcagtgg gaacgatgcc ctcattcagc atttgcatgg tttgttgaaa    5520 accgacatg gcactccagt cgccttcccg ttccgctatc ggctgaattt gattgcgagt    5580
gagatattta tgccagccag ccagacgcag acgcgccgag acagaactta atgggcccgc    5640
```

```
taacagcgcg atttgctggt gacccaatgc gaccagatgc tccacgccca gtcgcgtacc    5700
gtcttcatgg gagaaaataa tactgttgat gggtgtctgg tcagagacat caagaaataa    5760
cgccggaaca ttagtgcagg cagcttccac agcaatggca tcctggtcat ccagcggata    5820
gttaatgatc agcccactga cgcgttgcgc gagaagattg tgcaccgccg ctttacaggc    5880
ttcgacgccg cttcgttcta ccatcgacac caccacgctg cacccagtt gatcggcgcg     5940 agatttaatc gccgcgacaa tttgcgacgg cgcgtgcagg gccagactgg aggtggcaac    6000
gccaatcagc aacgactgtt tgcccgccag ttgttgtgcc acgcggttgg gaatgtaatt    6060
cagctccgcc atcgccgctt ccacttttc ccgcgttttc gcagaaacgt ggctggcctg     6120
gttcaccacg cgggaaacgg tctgataaga gacaccggca tactctgcga catcgtataa    6180
cgttactggt ttcacattca ccaccctgaa ttgactctct tccgggcgct atcatgccat    6240
accgcgaaag gttttgcgcc attcgatggt gtccgggatc tcgacgctct cccttatgcg    6300
actcctgcat taggaagcag cccagtagta ggttgaggcc gttgagcacc gccgccgcaa    6360
ggaatggtgc atgcaaggag atggcgccca acagtccccc ggccacgggg cctgccacca    6420
tacccacgcc gaaacaagcg ctcatgagcc cgaagtggcg agcccgatct tccccatcgg    6480
tgatgtcggc gatataggcg ccagcaaccg cacctgtggc gccggtgatg ccggccacga    6540
tgcgtccggc gtagaggatc ga                                             6562

<210> SEQ ID NO 100
<211> LENGTH: 6187
<212> TYPE: DNA
<213> ORGANISM: Artificial
<220> FEATURE:
<223> OTHER INFORMATION: Vector construct

<400> SEQUENCE: 100
gatctcgatc ccgcgaaatt aatacgactc actataggg aattgtgagc ggataacaat      60 tccctctag aaataatttt gtttaaactt taagaaggag atatacatat gtccattatc      120
atggaagtgg ccacaatgca agccaaactg acaaaaaatg agttcattga gtggctgaaa     180
acgtccgagg gtaaacagtt caacgtggac ctgtggtacg gttttcagtg tttcgactac     240
gccaacgctg gctggaaagt gctgttcggc ctgctgctga aaggcctggg agccaaagac     300
atcccttttg caaacaattt cgatggcctg gccacagttt atcaaaacac ccctgacttt     360
ctggcccaac caggcgacat ggtggtgttt ggttctaatt atggcgcagg ctatggccac    420
gtagcctggg tgatcgaagc cacactggac tacattattg tttatgagca aaactggctg    480
ggaggcggat ggacagacgg catcgaacag cctggctggg gctgggagaa agtgacacgc    540
cgtcaacatg cctatgactt ccctatgtgg ttcatccgtc taatttcaa agagctccgc     600 cagatcaaaa tttggtttca gaatcgtcgc atgaaatgga aaaataagg atccggctgc    660 taacaaagcc cgaaaggaag ctgagttggc tgctgccacc gctgagcaat aactagcata   720
accccttggg gcctctaaac gggtcttgag gggttttttg ctgaaaggag gaactatatc    780
cggatatccc gcaagaggcc cggcagtacc ggcataacca agcctatgcc tacagcatcc    840
agggtgacgg tgccgaggat gacgatgagc gcattgttag atttcataca cggtgcctga    900
ctgcgttagc aatttaactg tgataaacta ccgcattaaa gctagcttat cgatgataag    960
ctgtcaaaca tgagaattaa ttcttgaaga cgaaagggcc tcgtgatacg cctattttta   1020
taggttaatg tcatgataat aatggtttct tagacgtcag gtggcacttt tcggggaaat   1080
```

```
gtgcgcggaa cccctatttg tttattttc taaatacatt caaatatgta tccgctcatg     1140
agacaataac cctgataaat gcttcaataa tattgaaaaa ggaagagtat gagtattcaa     1200
catttccgtg tcgcccttat tcccttttt gcggcatttt gccttcctgt ttttgctcac     1260
ccagaaacgc tggtgaaagt aaaagatgct gaagatcagt tgggtgcacg agtgggttac     1320
atcgaactgg atctcaacag cggtaagatc cttgagagtt ttcgccccga agaacgtttt     1380
ccaatgatga gcacttttaa agttctgcta tgtggcgcgg tattatcccg tgttgacgcc     1440
gggcaagagc aactcggtcg ccgcatacac tattctcaga atgacttggt tgagtactca     1500
ccagtcacag aaaagcatct tacggatggc atgacagtaa gagaattatg cagtgctgcc     1560
ataaccatga gtgataacac tgcggccaac ttacttctga acgatcgg aggaccgaag     1620 gagctaaccg cttttttgca acatgggg atcatgtaa ctcgccttga tcgttgggaa     1680
ccggagctga atgaagccat accaaacgac gagcgtgaca ccacgatgcc tgcagcaatg     1740
gcaacaacgt tgcgcaaact attaactggc gaactactta ctctagcttc ccggcaacaa     1800
ttaatagact ggatggaggc ggataaagtt gcaggaccac ttctgcgctc ggcccttccg     1860
gctggctggt ttattgctga taaatctgga gccggtgagc gtgggtctcg cggtatcatt     1920
gcagcactgg ggccagatgg taagccctcc cgtatcgtag ttatctacac gacggggagt     1980
caggcaacta tggatgaacg aaatagacag atcgctgaga taggtgcctc actgattaag     2040
cattggtaac tgtcagacca gtttactca tatatacttt agattgattt aaaacttcat     2100
ttttaattta aaaggatcta ggtgaagatc cttttgata atctcatgac caaaatccct     2160
taacgtgagt tttcgttcca ctgagcgtca gaccccgtag aaaagatcaa aggatcttct     2220
tgagatcctt tttttctgcg cgtaatctgc tgcttgcaaa caaaaaaacc accgctacca     2280
gcggtggttt gtttgccgga tcaagagcta ccaactcttt ttccgaaggt aactggcttc     2340
agcagagcgc agataccaaa tactgtcctt ctagtgtagc cgtagttagg ccaccacttc     2400
aagaactctg tagcaccgcc tacatacctc gctctgctaa tcctgttacc agtggctgct     2460
gccagtggcg ataagtcgtg tcttaccggg ttggactcaa gacgatagtt accggataag     2520
gcgcagcggt cgggctgaac ggggggttcg tgcacacagc ccagcttgga gcgaacgacc     2580
tacaccgaac tgagatacct acagcgtgag ctatgagaaa gcgccacgct tcccgaaggg     2640
agaaaggcgg acaggtatcc ggtaagcggc agggtcggaa caggagagcg cacgagggag     2700
cttccagggg gaaacgcctg gtatctttat agtcctgtcg ggtttcgcca cctctgactt     2760
gagcgtcgat ttttgtgatg ctcgtcaggg gggcggagcc tatggaaaaa cgccagcaac     2820
gcggcctttt tacggttcct ggcctttgc tggccttttg ctcacatgtt ctttcctgcg     2880
ttatcccctg attctgtgga taaccgtatt accgcctttg agtgagctga taccgctcgc     2940
cgcagccgaa cgaccgagcg cagcgagtca gtgagcgagg aagcggaaga gcgcctgatg     3000
cggtattttc tccttacgca tctgtgcggt atttcacacc gcaatggtgc actctcagta     3060
caatctgctc tgatgccgca tagttaagcc agtatacact ccgctatcgc tacgtgactg     3120
ggtcatggct gcgccccgac acccgccaac acccgctgac gcgccctgac gggcttgtct     3180
gctcccggca tccgcttaca gacaagctgt gaccgtctcc gggagctgca tgtgtcagag     3240
gttttcaccg tcatcaccga aacgcgcgag gcagctgcgg taaagctcat cagcgtggtc     3300
gtgaagcgat tcacagatgt ctgcctgttc atccgcgtcc agctcgttga gtttctccag     3360
aagcgttaat gtctggcttc tgataaagcg ggccatgtta agggcggttt ttcctgtttt     3420
ggtcactgat gcctccgtgt aagggggatt tctgttcatg ggggtaatga taccgatgaa     3480
```

```
acgagagagg atgctcacga tacgggttac tgatgatgaa catgcccggt tactggaacg   3540
ttgtgagggt aaacaactgg cggtatggat gcggcgggac cagagaaaaa tcactcaggg   3600
tcaatgccag cgcttcgtta atacagatgt aggtgttcca cagggtagcc agcagcatcc   3660
tgcgatgcag atccggaaca taatggtgca gggcgctgac ttccgcgttt ccagacttta   3720
cgaaacacgg aaaccgaaga ccattcatgt tgttgctcag gtcgcagacg ttttgcagca   3780
gcagtcgctt cacgttcgct cgcgtatcgg tgattcattc tgctaaccag taaggcaacc   3840
ccgccagcct agccgggtcc tcaacgacag gagcacgatc atgcgcaccc gtggccagga   3900
cccaacgctg cccgagatgc gccgcgtgcg gctgctggag atggcggacg cgatggatat   3960
gttctgccaa gggttggttt gcgcattcac agttctccgc aagaattgat tggctccaat   4020
tcttggagtg gtgaatccgt tagcgaggtg ccgccggctt ccattcaggt cgaggtggcc   4080
cggctccatg caccgcgacg caacgcgggg aggcagacaa ggtatagggc ggcgcctaca   4140
atccatgcca acccgttcca tgtgctcgcc gaggcggcat aaatcgccgt gacgatcagc   4200
ggtccaatga tcgaagttag gctggtaaga gccgcgagcg atccttgaag ctgtccctga   4260
tggtcgtcat ctacctgcct ggacagcatg gcctgcaacg cgggcatccc gatgccgccg   4320
gaagcgagaa gaatcataat ggggaaggcc atccagcctc gcgtcgcgaa cgccagcaag   4380
acgtagccca gcgcgtcggc cgccatgccg gcgataatgg cctgcttctc gccgaaacgt   4440
ttggtggcgg gaccagtgac gaaggcttga gcgagggcgt gcaagattcc gaataccgca   4500
agcgacaggc cgatcatcgt cgcgctccag cgaaagcggt cctcgccgaa aatgacccag   4560
agcgctgccg gcacctgtcc tacgagttgc atgataaaga agacagtcat aagtgcggcg   4620
acgatagtca tgccccgcgc ccaccggaag gagctgactg ggttgaaggc tctcaagggc   4680
atcggtcgag atcccggtgc ctaatgagtg agctaactta cattaattgc gttgcgctca   4740
ctgcccgctt tccagtcggg aaacctgtcg tgccagctgc attaatgaat cggccaacgc   4800
gcggggagag gcggtttgcg tattgggcgc cagggtggtt tttcttttca ccagtgagac   4860
gggcaacagc tgattgccct tcaccgcctg gccctgagag agttgcagca agcggtccac   4920
gctggtttgc cccagcaggc gaaaatcctg tttgatggtg gttaacggcg ggatataaca   4980
tgagctgtct tcggtatcgt cgtatcccac taccgagata tccgcaccaa cgcgcagccc   5040
ggactcggta atggcgcgca ttgcgcccag cgccatctga tcgttggcaa ccagcatcgc   5100
agtgggaacg atgccctcat tcagcatttg catggtttgt tgaaaaccgg acatggcact   5160
ccagtcgcct tcccgttccg ctatcggctg aatttgattg cgagtgagat atttatgcca   5220
gccagccaga cgcagacgcg ccgagacaga acttaatggg cccgctaaca gcgcgatttg   5280
ctggtgaccc aatgcgacca gatgctccac gccagtcgc gtaccgtctt catgggagaa   5340
aataatactg ttgatgggtg tctggtcaga gacatcaaga aataacgccg gaacattagt   5400
gcaggcagct tccacagcaa tggcatcctg gtcatccagc ggatagttaa tgatcagccc   5460
actgacgcgt tgcgcgagaa gattgtgcac cgccgcttta caggcttcga cgccgcttcg   5520
ttctaccatc gacaccacca cgctggcacc cagttgatcg gcgcgagatt taatcgccgc   5580
gacaatttgc gacggcgcgt gcagggccag actggaggtg gcaacgccaa tcagcaacga   5640
ctgtttgccc gccagttgtt gtgccacgcg gttgggaatg taattcagct ccgccatcgc   5700
cgcttccact ttttcccgcg ttttcgcaga acgtggctg gcctggttca ccacgcggga   5760
aacggtctga taagagacac cggcatactc tgcgacatcg tataacgtta ctggtttcac   5820
```

| | |
|---|---|
| attcaccacc ctgaattgac tctcttccgg gcgctatcat gccataccgc gaaaggtttt | 5880 |
| gcgccattcg atggtgtccg ggatctcgac gctctccctt atgcgactcc tgcattagga | 5940 |
| agcagcccag tagtaggttg aggccgttga gcaccgccgc cgcaaggaat ggtgcatgca | 6000 |
| aggagatggc gcccaacagt cccccggcca cggggcctgc caccataccc acgccgaaac | 6060 |
| aagcgctcat gagcccgaag tggcgagccc gatcttcccc atcggtgatg tcggcgatat | 6120 |
| aggcgccagc aaccgcacct gtggcgccgg tgatgccggc cacgatgcgt ccggcgtaga | 6180 |
| ggatcga | 6187 |

<210> SEQ ID NO 101
<211> LENGTH: 6166
<212> TYPE: DNA
<213> ORGANISM: Artificial
<220> FEATURE:
<223> OTHER INFORMATION: Vector construct

<400> SEQUENCE: 101

| | |
|---|---|
| gatctcgatc ccgcgaaatt aatacgactc actatagggg aattgtgagc ggataacaat | 60 |
| tcccctctag aaataatttt gtttaaactt taagaaggag atatacatat gtccattatc | 120 |
| atggaagtgg ccacaatgca agccaaactg acaaaaaatg agttcattga gtggctgaaa | 180 |
| acgtccgagg gtaaacagtt caacgtggac ctgtggtacg gttttcagtg tttcgactac | 240 |
| gccaacgctg gctggaaagt gctgttcggc ctgctgctga aaggcctggg agccaaagac | 300 |
| atcccttttg caaacaattt cgatggcctg ccacagtttt atcaaaacac ccctgacttt | 360 |
| ctggcccaac caggcgacat ggtggtgttt ggttctaatt atggcgcagg ctatggccac | 420 |
| gtagcctggg tgatcgaagc cacactggac tacattattg tttatgagca aaactggctg | 480 |
| ggaggcggat ggacagacgg catcgaacag cctggctggg gctgggagaa agtgacacgc | 540 |
| cgtcaacatg cctatgactt ccctatgtgg ttcatccgtc ctaatttcaa agagctccgt | 600 |
| cgtcgtcgcc gtcggcgtcg tcgttaagga tccggctgct aacaaagccc gaaaggaagc | 660 |
| tgagttggct gctgccaccg ctgagcaata actagcataa ccccttgggg cctctaaacg | 720 |
| ggtcttgagg ggttttttgc tgaaaggagg aactatatcc ggatatcccg caagaggccc | 780 |
| ggcagtaccg gcataaccaa gcctatgcct acagcatcca gggtgacggt gccgaggatg | 840 |
| acgatgagcg cattgttaga tttcatacac ggtgcctgac tgcgttagca atttaactgt | 900 |
| gataaactac cgcattaaag ctagcttatc gatgataagc tgtcaaacat gagaattaat | 960 |
| tcttgaagac gaaagggcct cgtgatacgc ctatttttat aggttaatgt catgataata | 1020 |
| atggtttctt agacgtcagg tggcactttt cggggaaatg tgcgcggaac ccctatttgt | 1080 |
| ttatttttct aaatacattc aaatatgtat ccgctcatga caataaccct gataaatg | 1140 |
| cttcaataat attgaaaaag gaagagtatg agtattcaac atttccgtgt cgcccttatt | 1200 |
| cccttttttg cggcattttg ccttcctgtt tttgctcacc cagaaacgct ggtgaaagta | 1260 |
| aaagatgctg aagatcagtt gggtgcacga gtgggttaca tcgaactgga tctcaacagc | 1320 |
| ggtaagatcc ttgagagttt tcgccccgaa gaacgttttc caatgatgag cacttttaaa | 1380 |
| gttctgctat gtggcgcggt attatcccgt gttgacgccg gcaagagca actcggtcgc | 1440 |
| cgcatacact attctcagaa tgacttggtt gagtactcac cagtcacaga aaagcatctt | 1500 |
| acggatggca tgacagtaag agaattatgc agtgctgcca taaccatgag tgataacact | 1560 |
| gcggccaact tacttctgac aacgatcgga ggaccgaagg agctaaccgc ttttttgcac | 1620 |
| aacatggggg atcatgtaac tcgccttgat cgttgggaac cggagctgaa tgaagccata | 1680 |

-continued

```
ccaaacgacg agcgtgacac cacgatgcct gcagcaatgg caacaacgtt gcgcaaacta    1740
ttaactggcg aactacttac tctagcttcc cggcaacaat taatagactg gatggaggcg    1800
gataaagttg caggaccact tctgcgctcg gcccttccgg ctggctggtt tattgctgat    1860
aaatctggag ccggtgagcg tgggtctcgc ggtatcattg cagcactggg gccagatggt    1920
aagccctccc gtatcgtagt tatctacacg acggggagtc aggcaactat ggatgaacga    1980
aatagacaga tcgctgagat aggtgcctca ctgattaagc attggtaact gtcagaccaa    2040
gtttactcat atatacttta gattgattta aaacttcatt tttaatttaa aaggatctag    2100
gtgaagatcc ttttgataa tctcatgacc aaaatccctt aacgtgagtt ttcgttccac     2160
tgagcgtcag accccgtaga aaagatcaaa ggatcttctt gagatccttt ttttctgcgc    2220
gtaatctgct gcttgcaaac aaaaaaacca ccgctaccag cggtggtttg tttgccggat    2280
caagagctac caactctttt tccgaaggta actggcttca gcagagcgca gataccaaat    2340
actgtccttc tagtgtagcc gtagttaggc caccacttca agaactctgt agcaccgcct    2400
acatacctcg ctctgctaat cctgttacca gtggctgctg ccagtggcga taagtcgtgt    2460
cttaccgggt tggactcaag acgatagtta ccggataagg cgcagcggtc gggctgaacg    2520
gggggttcgt gcacacagcc cagcttggag cgaacgacct acaccgaact gagataccta    2580
cagcgtgagc tatgagaaag cgccacgctt cccgaaggga gaaaggcgga caggtatccg    2640
gtaagcggca gggtcggaac aggagagcgc acgagggagc ttccaggggg aaacgcctgg    2700
tatctttata gtcctgtcgg gtttcgccac ctctgacttg agcgtcgatt tttgtgatgc    2760
tcgtcagggg gcggagccta tggaaaaac gccagcaacg cggcctttt acggttcctg      2820 gccttttgct ggccttttgc tcacatgttc tttcctgcgt tatccctga ttctgtggat     2880 aaccgtatta ccgcctttga gtgagctgat accgctcgcc gcagccgaac gaccgagcgc    2940
agcgagtcag tgagcgagga gcggaagag cgcctgatgc ggtattttct ccttacgcat     3000
ctgtgcggta tttcacaccg caatggtgca ctctcagtac aatctgctct gatgccgcat    3060
agttaagcca gtatacactc cgctatcgct acgtgactgg gtcatggctg cgccccgaca    3120
cccgccaaca cccgctgacg cgccctgacg ggcttgtctg ctcccggcat ccgcttacag    3180
acaagctgtg accgtctccg ggagctgcat gtgtcagagg ttttcaccgt catcaccgaa    3240
acgcgcgagg cagctgcggt aaagctcatc agcgtggtcg tgaagcgatt cacagatgtc    3300
tgcctgttca tccgcgtcca gctcgttgag tttctccaga agcgttaatg tctggcttct    3360
gataaagcgg gccatgttaa gggcggtttt ttcctgtttg gtcactgatg cctccgtgta    3420
agggggattt ctgttcatgg ggtaatgat accgatgaaa cgagagagga tgctcacgat     3480
acgggttact gatgatgaac atgcccggtt actggaacgt tgtgagggta acaactggc     3540 ggtatggatg cggcgggacc agagaaaaat cactcagggt caatgccagc gcttcgttaa    3600
tacagatgta ggtgttccac agggtagcca gcagcatcct gcgatgcaga tccgaacat     3660 aatggtgcag ggcgctgact ccgcgtttc cagactttac gaaacacgga aaccgaagac     3720
cattcatgtt gttgctcagg tcgcagacgt tttgcagcag cagtcgcttc acgttcgctc    3780
gcgtatcggt gattcattct gctaaccagt aaggcaaccc cgccagccta gccgggtcct    3840
caacgacagg agcacgatca tgcgcacccg tggccaggac ccaacgctgc ccgagatgcg    3900
ccgcgtgcgg ctgctggaga tggcggacgc gatggatatg ttctgccaag ggttggtttg    3960
cgcattcaca gttctccgca agaattgatt ggctccaatt cttggagtgg tgaatccgtt    4020
```

```
agcgaggtgc cgccggcttc cattcaggtc gaggtggccc ggctccatgc accgcgacgc    4080
aacgcgggga ggcagacaag gtatagggcg gcgcctacaa tccatgccaa cccgttccat    4140
gtgctcgccg aggcggcata atcgccgtg acgatcagcg gtccaatgat cgaagttagg    4200
ctggtaagag ccgcgagcga tccttgaagc tgtccctgat ggtcgtcatc tacctgcctg    4260
gacagcatgg cctgcaacgc gggcatcccg atgccgccgg aagcgagaag aatcataatg    4320
gggaaggcca tccagcctcg cgtcgcgaac gccagcaaga cgtagcccag cgcgtcggcc    4380
gccatgccgg cgataatggc ctgcttctcg ccgaaacgtt tggtggcggg accagtgacg    4440
aaggcttgag cgagggcgtg caagattccg aataccgcaa gcgacaggcc gatcatcgtc    4500
gcgctccagc gaaagcggtc ctcgccgaaa atgacccaga gcgctgccgg cacctgtcct    4560
acgagttgca tgataaagaa gacagtcata agtgcggcga cgatagtcat gccccgcgcc    4620
caccggaagg agctgactgg gttgaaggct ctcaagggca tcggtcgaga tcccggtgcc    4680
taatgagtga gctaacttac attaattgcg ttgcgctcac tgcccgcttt ccagtcggga    4740
aacctgtcgt gccagctgca ttaatgaatc ggccaacgcg cggggagagg cggtttgcgt    4800
attgggcgcc agggtggttt ttcttttcac cagtgagacg ggcaacagct gattgccctt    4860
caccgcctgg ccctgagaga gttgcagcaa gcggtccacg ctggtttgcc ccagcaggcg    4920
aaaatcctgt ttgatggtgg ttaacggcgg gatataacat gagctgtctt cggtatcgtc    4980
gtatcccact accgagatat ccgcaccaac gcgcagcccg gactcggtaa tggcgcgcat    5040
tgcgcccagc gccatctgat cgttggcaac cagcatcgca gtgggaacga tgccctcatt    5100
cagcatttgc atggtttgtt gaaaaccgga catggcactc cagtcgcctt cccgttccgc    5160
tatcggctga atttgattgc gagtgagata tttatgccag ccagccagac gcagacgcgc    5220
cgagacagaa cttaatgggc ccgctaacag cgcgatttgc tggtgaccca atgcgaccag    5280
atgctccacg cccagtcgcg taccgtcttc atgggagaaa ataatactgt tgatgggtgt    5340
ctggtcagag acatcaagaa ataacgccgg aacattagtg caggcagctt ccacagcaat    5400
ggcatcctgg tcatccagcg gatagttaat gatcagccca ctgacgcgtt gcgcgagaag    5460
attgtgcacc gccgctttac aggcttcgac gccgcttcgt tctaccatcg acaccaccac    5520
gctggcaccc agttgatcgg cgcgagattt aatcgccgcg acaatttgcg acggcgcgtg    5580
cagggccaga ctggaggtgg caacgccaat cagcaacgac tgtttgcccg ccagttgttg    5640
tgccacgcgg ttgggaatgt aattcagctc cgccatcgcc gcttccactt tttcccgcgt    5700
tttcgcagaa acgtggctgg cctggttcac cacgcgggaa acgtctgat aagagacacc    5760 ggcatactct gcgacatcgt ataacgttac tggtttcaca ttcaccaccc tgaattgact    5820
ctcttccggg cgctatcatg ccataccgcg aaaggttttg cgccattcga tggtgtccgg    5880
gatctcgacg ctctccctta tgcgactcct gcattaggaa gcagcccagt agtaggttga    5940
ggccgttgag caccgccgcc gcaaggaatg gtgcatgcaa ggagatggcg cccaacagtc    6000 cccccggccac ggggcctgcc accataccca cgccgaaaca agcgctcatg agcccgaagt    6060
ggcgagcccg atcttcccca tcggtgatgt cggcgatata ggcgccagca accgcacctg    6120
tggcgccggt gatgccggcc acgatgcgtc cggcgtagag gatcga              6166

<210> SEQ ID NO 102
<211> LENGTH: 6178
<212> TYPE: DNA
<213> ORGANISM: Artificial
<220> FEATURE:
<223> OTHER INFORMATION: Vector construct
```

<400> SEQUENCE: 102

```
gatctcgatc cgcgaaatt aatacgactc actatagggg aattgtgagc ggataacaat      60
tcccctctag aaataatttt gtttaaactt taagaaggag atatacatat gtccattatc     120
atggaagtgg ccacaatgca agccaaactg acaaaaaatg agttcattga gtggctgaaa     180
acgtccgagg gtaaacagtt caacgtggac ctgtggtacg ttttcagtg tttcgactac      240
gccaacgctg gctggaaagt gctgttcggc ctgctgctga aaggcctggg agccaaagac     300
atccctttg caaacaattt cgatggcctg ccacagttt atcaaaacac ccctgacttt       360
ctggcccaac caggcgacat ggtggtgttt ggttctaatt atggcgcagg ctatggccac     420
gtagcctggg tgatcgaagc cacactggac tacattattg tttatgagca aaactggctg     480
ggaggcggat ggacagacgg catcgaacag cctggctggg gctgggagaa agtgacacgc     540
cgtcaacatg cctatgactt ccctatgtgg ttcatccgtc taatttcaa agagctcggt      600
cgtaaaaaac gtcgtcagcg tcgtcgtccg cctcagtaag gatccggctg ctaacaaagc     660
ccgaaaggaa gctgagttgg ctgctgccac cgctgagcaa taactagcat aaccccttgg     720
ggcctctaaa cgggtcttga ggggttttt gctgaaagga ggaactatat ccggatatcc      780
cgcaagaggc ccggcagtac cggcataacc aagcctatgc ctacagcatc cagggtgacg     840
gtgccgagga tgacgatgag cgcattgtta gatttcatac acggtgcctg actgcgttag     900
caatttaact gtgataaact accgcattaa agctagctta tcgatgataa gctgtcaaac     960
atgagaatta ttcttgaag acgaaagggc ctcgtgatac gcctatttt ataggttaat    1020
gtcatgataa taatggtttc ttagacgtca ggtggcactt ttcggggaaa tgtgcgcgga    1080
acccctattt gtttattttt ctaaatacat tcaaatatgt atccgctcat gagacaataa    1140
ccctgataaa tgcttcaata atattgaaaa aggaagagta tgagtattca acatttccgt    1200
gtcgccctta ttcccttttt tgcggcattt gccttcctg ttttgctca cccagaaacg     1260
ctggtgaaag taaaagatgc tgaagatcag ttgggtgcac gagtgggtta catcgaactg    1320
gatctcaaca gcggtaagat ccttgagagt tttcgccccg aagaacgttt tccaatgatg    1380
agcactttta aagttctgct atgtggcgcg gtattatccc gtgttgacgc cgggcaagag    1440
caactcggtc gccgcataca ctattctcag aatgacttgg ttgagtactc accagtcaca    1500
gaaaagcatc ttacgatgg catgacagta agagaattat gcagtgctgc cataaccatg    1560
agtgataaca ctgcggccaa cttacttctg acaacgatcg gaggaccgaa ggagctaacc    1620
gcttttttgc acaacatggg ggatcatgta actcgccttg atcgttggga accggagctg    1680
aatgaagcca taccaaacga cgagcgtgac accacgatgc ctgcagcaat ggcaacaacg    1740
ttgcgcaaac tattaactgg cgaactactt actctagctt cccggcaaca attaatagac    1800
tggatggagg cggataaagt tgcaggacca cttctgcgct cggcccttcc ggctggctgg    1860
tttattgctg ataaatctgg agccggtgag cgtgggtctc gcggtatcat tgcagcactg    1920
gggccagatg gtaagccctc ccgtatcgta gttatctaca cgacggggag tcaggcaact    1980
atggatgaac gaaatagaca gatcgctgag ataggtgcct cactgattaa gcattggtaa    2040
ctgtcagacc aagtttactc atatatactt tagattgatt taaaacttca ttttaatttt    2100
aaaaggatct aggtgaagat cctttttgat aatctcatga ccaaaatccc ttaacgtgag    2160
ttttcgttcc actgagcgtc agaccccgta gaaaagatca aggatcttc ttgagatcct     2220
tttttctgc gcgtaatctg ctgcttgcaa acaaaaaaac caccgctacc agcggtggtt    2280
```

```
tgtttgccgg atcaagagct accaactctt tttccgaagg taactggctt cagcagagcg    2340
cagataccaa atactgtcct tctagtgtag ccgtagttag gccaccactt caagaactct    2400
gtagcaccgc ctacatacct cgctctgcta atcctgttac cagtggctgc tgccagtggc    2460
gataagtcgt gtcttaccgg gttggactca agacgatagt taccggataa ggcgcagcgg    2520
tcgggctgaa cgggggttc gtgcacacag cccagcttgg agcgaacgac ctacaccgaa    2580
ctgagatacc tacagcgtga gctatgagaa agcgccacgc ttcccgaagg gagaaaggcg    2640
gacaggtatc cggtaagcgg cagggtcgga acaggagagc gcacgaggga gcttccaggg    2700
ggaaacgcct ggtatcttta tagtcctgtc gggtttcgcc acctctgact tgagcgtcga    2760
tttttgtgat gctcgtcagg ggggcggagc ctatggaaaa acgccagcaa cgcggccttt    2820
ttacggttcc tggccttttg ctggccttttt gctcacatgt tctttcctgc gttatcccct    2880
gattctgtgg ataaccgtat taccgccttt gagtgagctg ataccgctcg ccgcagccga    2940
acgaccgagc gcagcgagtc agtgagcgag gaagcggaag agcgcctgat gcggtatttt    3000
ctccttacgc atctgtgcgg tatttcacac cgcaatggtg cactctcagt acaatctgct    3060
ctgatgccgc atagttaagc cagtatacac tccgctatcg ctacgtgact gggtcatggc    3120 tgcgcccga cacccgccaa cacccgctga cgcgccctga cgggcttgtc tgctcccggc    3180
atccgcttac agacaagctg tgaccgtctc cgggagctgc atgtgtcaga ggttttcacc    3240
gtcatcaccg aaacgcgcga ggcagctgcg gtaaagctca tcagcgtggt cgtgaagcga    3300
ttcacagatg tctgcctgtt catccgcgtc cagctcgttg agtttctcca gaagcgttaa    3360
tgtctggctt ctgataaagc gggccatgtt aagggcggtt ttttcctgtt tggtcactga    3420
tgcctccgtg taagggggat ttctgttcat gggggtaatg ataccgatga aacgagagag    3480
gatgctcacg atacgggtta ctgatgatga acatgcccgg ttactggaac gttgtgaggg    3540
taaacaactg gcggtatgga tgcggcggga ccagagaaaa atcactcagg gtcaatgcca    3600
gcgcttcgtt aatacagatg taggtgttcc acagggtagc cagcagcatc ctgcgatgca    3660
gatccggaac ataatggtgc agggcgctga cttccgcgtt tccagacttt acgaaacacg    3720
gaaaccgaag accattcatg ttgttgctca ggtcgcagac gttttgcagc agcagtcgct    3780
tcacgttcgc tcgcgtatcg gtgattcatt ctgctaacca gtaaggcaac cccgccagcc    3840
tagccgggtc tcaacgaca ggagcacgat catgcgcacc cgtggccagg acccaacgct    3900
gcccgagatg cgccgcgtgc ggctgctgga gatggcggac gcgatggata tgttctgcca    3960
agggttggtt tgcgcattca cagttctccg caagaattga ttggctccaa ttcttggagt    4020
ggtgaatccg ttagcgaggt gccgccggct tccattcagg tcgaggtggc ccggctccat    4080
gcaccgcgac gcaacgcggg gaggcagaca aggtataggg cggcgcctac aatccatgcc    4140
aacccgttcc atgtgctcgc cgaggcggca taaatcgccg tgacgatcag cggtccaatg    4200
atcgaagtta ggctggtaag agccgcgagc gatccttgaa gctgtccctg atggtcgtca    4260
tctacctgcc tggacagcat ggcctgcaac gcgggcatcc cgatgccgcc ggaagcgaga    4320
agaatcataa tggggaaggc catccagcct cgcgtcgcga acgccagcaa gacgtagccc    4380
agcgcgtcgg ccgccatgcc ggcgataatg gcctgcttct cgccgaaacg tttggtggcg    4440
ggaccagtga cgaaggcttg agcgagggcg tgcaagattc cgaataccgc aagcgacagg    4500
ccgatcatcg tcgcgctcca gcgaaagcgg tcctcgccga aaatgaccca gagcgctgcc    4560
ggcacctgtc ctacgagttg catgataaag aagacagtca taagtgcggc gacgatagtc    4620
atgccccgcg cccaccggaa ggagctgact gggttgaagg ctctcaaggg catcggtcga    4680
```

```
gatcccggtg cctaatgagt gagctaactt acattaattg cgttgcgctc actgcccgct    4740
ttccagtcgg gaaacctgtc gtgccagctg cattaatgaa tcggccaacg cgcggggaga    4800
ggcggtttgc gtattgggcg ccagggtggt ttttcttttc accagtgaga cgggcaacag    4860
ctgattgccc ttcaccgcct ggccctgaga gagttgcagc aagcggtcca cgctggtttg    4920
ccccagcagg cgaaaatcct gtttgatggt ggttaacggc gggatataac atgagctgtc    4980
ttcggtatcg tcgtatccca ctaccgagat atccgcacca acgcgcagcc cggactcggt    5040
aatggcgcgc attgcgccca cgccatctg atcgttggca accagcatcg cagtgggaac    5100
gatgccctca ttcagcattt gcatggtttg ttgaaaaccg acatggcac tccagtcgcc    5160 ttcccgttcc gctatcggct gaatttgatt gcgagtgaga tatttatgcc agccagccag    5220
acgcagacgc gccgagacag aacttaatgg gcccgctaac agcgcgattt gctggtgacc    5280
caatgcgacc agatgctcca cgcccagtcg cgtaccgtct tcatgggaga aaataatact    5340
gttgatgggt gtctggtcag agacatcaag aaataacgcc ggaacattag tgcaggcagc    5400
ttccacagca atggcatcct ggtcatccag cggatagtta atgatcagcc cactgacgcg    5460
ttgcgcgaga agattgtgca ccgccgcttt acaggcttcg acgccgcttc gttctaccat    5520
cgacaccacc acgctggcac ccagttgatc ggcgcgagat ttaatcgccg cgacaatttg    5580
cgacggcgcg tgcagggcca gactggaggt ggcaacgcca atcagcaacg actgtttgcc    5640
cgccagttgt tgtgccacgc ggttgggaat gtaattcagc tccgccatcg ccgcttccac    5700 ttttttcccgc gttttcgcag aaacgtggct ggcctggttc accacgcggg aaacggtctg    5760
ataagagaca ccggcatact ctgcgacatc gtataacgtt actggtttca cattcaccac    5820
cctgaattga ctctcttccg ggcgctatca tgccataccg cgaaaggttt tgcgccattc    5880
gatggtgtcc gggatctcga cgctctccct tatgcgactc ctgcattagg aagcagccca    5940
gtagtaggtt gaggccgttg agcaccgccg ccgcaaggaa tggtgcatgc aaggagatgg    6000
cgcccaacag tcccccggcc acggggcctg ccaccatacc cacgccgaaa caagcgctca    6060
tgagcccgaa gtggcgagcc cgatcttccc catcggtgat gtcggcgata taggcgccag    6120
caaccgcacc tgtggcgccg gtgatgccgg ccacgatgcg tccggcgtag aggatcga     6178
```

<210> SEQ ID NO 103
<211> LENGTH: 6511
<212> TYPE: DNA
<213> ORGANISM: Artificial
<220> FEATURE:
<223> OTHER INFORMATION: Vector construct

<400> SEQUENCE: 103

```
gatctcgatc ccgcgaaatt aatacgactc actatagggg aattgtgagc ggataacaat     60
tcccctctag aaataatttt gtttaaactt taagaaggag atatacatat ggcagccaca    120
catgaacact ctgcccaatg ctgaacaac tacaaaaaag ctacggtta tggcccttac    180 cctctgggca ttaacggtgg catgcactac ggcgttgact ttttatgaa catcggcacc    240 cctgtgaaag ccattagctc aggcaaaatc gtggaagccg gttggtcaaa ctatggcggt    300
ggcaaccaga tcggtctgat cgagaacgat ggtgtgcacc gccaatggta catgcacctg    360
tccaaataca cgttaaagt tggtgactac gtgaaagcag gccagattat cggctggtca    420
ggttcaaccg gttattcaac agcccctcat ctgcacttcc aacgcatggt gaatagtttt    480
agtaattcta ccgctcaaga tccgatgcca ttcctgaaat ctgccggtta tggtggcaaa    540
```

-continued

```
ctggaagtta gcaaagcagc aaccattaaa cagtccgatg ttaaacaaga agtgaaaaaa    600
caagaggcca aacaaattgt gaaagcgacc gattggaaac agaacaaaga tggcatttgg    660
tataaagcag aacatgccag ctttaccgtg accgcaccgg aaggcattat tacccgttat    720
aaaggtccgt ggaccggtca tccgcaggca ggcgtgctgc agaaaggtca gaccatcaaa    780
tatgatgagg tgcagaaatt tgatggccat gtttgggtta gctgggaaac ctttgaaggt    840
gaaaccgttt atatgccggt tcgtacctgg gatgcaaaaa ccgtaaagt gggtaaactg     900 tggggtgaaa tcaaagagct ccgccagatc aaaatttggt ttcagaatcg tcgcatgaaa    960
tggaaaaaat aaggatccgg ctgctaacaa agcccgaaag gaagctgagt tggctgctgc   1020
caccgctgag caataactag cataacccct tggggcctct aaacgggtct tgagggtttt   1080
tttgctgaaa ggaggaacta tatccggata tcccgcaaga ggcccggcag taccggcata   1140
accaagccta tgcctacagc atccagggtg acggtgccga ggatgacgat gagcgcattg   1200
ttagatttca tacacggtgc ctgactgcgt tagcaattta actgtgataa actaccgcat   1260
taaagctagc ttatcgatga taagctgtca acatgagaa ttaattcttg aagacgaaag    1320
ggcctcgtga tacgcctatt tttataggtt aatgtcatga taataatggt ttcttagacg   1380
tcaggtggca cttttcgggg aaatgtgcgc ggaaccccta tttgtttatt tttctaaata   1440
cattcaaata tgtatccgct catgagacaa taaccctgat aaatgcttca ataatattga   1500 aaaggaaga gtatgagtat tcaacatttc cgtgtcgccc ttattccctt ttttgcggca    1560
ttttgccttc ctgttttgc tcacccagaa acgctggtga agtaaaaga tgctgaagat     1620 cagttgggtg cacgagtggg ttacatcgaa ctggatctca acagcggtaa gatccttgag   1680
agttttcgcc ccgaagaacg ttttccaatg atgagcactt ttaaagttct gctatgtggc   1740
gcggtattat cccgtgttga cgccgggcaa gagcaactcg gtcgccgcat acactattct   1800
cagaatgact tggttgagta ctcaccagtc acagaaaagc atcttacgga tggcatgaca   1860
gtaagagaat tatgcagtgc tgccataacc atgagtgata acactgcggc caacttactt   1920
ctgacaacga tcggaggacc gaaggagcta accgcttttt tgcacaacat ggggatcat    1980 gtaactcgcc ttgatcgttg ggaaccggag ctgaatgaag ccataccaaa cgacgagcgt   2040
gacaccacga tgcctgcagc aatggcaaca acgttgcgca aactattaac tggcgaacta   2100
cttactctag cttcccggca acaattaata gactggatgg aggcggataa agttgcagga   2160
ccacttctgc gctcggccct tccggctggc tggtttattg ctgataaatc tggagccggt   2220
gagcgtgggt ctcgcggtat cattgcagca ctggggccag atggtaagcc ctcccgtatc   2280
gtagttatct acacgacggg gagtcaggca actatggatg aacgaaatag acagatcgct   2340
gagataggtg cctcactgat taagcattgg taactgtcag accaagttta ctcatatata   2400
ctttagattg atttaaaact tcatttttaa tttaaaagga tctaggtgaa gatcctttt    2460 gataatctca tgaccaaaat cccttaacgt gagttttcgt tccactgagc gtcagacccc   2520
gtagaaaaga tcaaaggatc ttcttgagat cctttttttc tgcgcgtaat ctgctgcttg   2580
caaacaaaaa aaccaccgct accagcggtg gtttgtttgc cggatcaaga gctaccaact   2640 cttttttccga aggtaactgg cttcagcaga gcgcagatac caaatactgt ccttctagtg   2700
tagccgtagt taggccacca cttcaagaac tctgtagcac cgcctacata cctcgctctg   2760
ctaatcctgt taccagtggc tgctgccagt ggcgataagt cgtgtcttac cgggttggac   2820
tcaagacgat agttaccgga taaggcgcag cggtcgggct gaacggggggg ttcgtgcaca   2880 cagcccagct tggagcgaac gacctacacc gaactgagat acctacagcg tgagctatga   2940
```

```
gaaagcgcca cgcttcccga agggagaaag gcggacaggt atccggtaag cggcagggtc   3000
ggaacaggag agcgcacgag ggagcttcca gggggaaacg cctggtatct ttatagtcct   3060
gtcgggtttc gccacctctg acttgagcgt cgattttttgt gatgctcgtc aggggggcgg   3120
agcctatgga aaaacgccag caacgcggcc tttttacggt tcctggcctt ttgctggcct   3180
tttgctcaca tgttctttcc tgcgttatcc cctgattctg tggataaccg tattaccgcc   3240
tttgagtgag ctgataccgc tcgccgcagc cgaacgaccg agcgcagcga gtcagtgagc   3300
gaggaagcgg aagagcgcct gatgcggtat tttctcctta cgcatctgtg cggtatttca   3360
caccgcaatg gtgcactctc agtacaatct gctctgatgc cgcatagtta agccagtata   3420
cactccgcta tcgctacgtg actgggtcat ggctgcgccc cgacaccccgc caacacccgc   3480 tgacgcgccc tgacgggctt gtctgctccc ggcatccgct tacagacaag ctgtgaccgt   3540
ctccgggagc tgcatgtgtc agaggttttc accgtcatca ccgaaacgcg cgaggcagct   3600
gcggtaaagc tcatcagcgt ggtcgtgaag cgattcacag atgtctgcct gttcatccgc   3660
gtccagctcg ttgagtttct ccagaagcgt taatgtctgg cttctgataa agcgggccat   3720
gttaagggcg ttttttttcct gtttggtcac tgatgcctcc gtgtaagggg gatttctgtt   3780
catgggggta atgataccga tgaaacgaga gaggatgctc acgatacggg ttactgatga   3840
tgaacatgcc cggttactgg aacgttgtga gggtaaacaa ctggcggtat ggatgcggcg   3900
ggaccagaga aaatcactc agggtcaatg ccagcgcttc gttaatacag atgtaggtgt   3960
tccacagggt agccagcagc atcctgcgat gcagatccgg aacataatgg tgcagggcgc   4020
tgacttccgc gtttccagac tttacgaaac acggaaaccg aagaccattc atgttgttgc   4080
tcaggtcgca gacgttttgc agcagcagtc gcttcacgtt cgctcgcgta tcggtgattc   4140
attctgctaa ccagtaaggc aaccccgcca gcctagccgg tcctcaacg acaggagcac   4200 gatcatgcgc acccgtggcc aggacccaac gctgcccgag atgcgccgcg tgcggctgct   4260
ggagatggcg gacgcgatgg atatgttctg ccaagggttg gtttgcgcat tcacagttct   4320
ccgcaagaat tgattggctc caattcttgg agtggtgaat ccgttagcga ggtgccgccg   4380
gcttccattc aggtcgaggt ggcccggctc catgcaccgc gacgcaacgc ggggaggcag   4440
acaaggtata gggcggcgcc tacaatccat gccaacccgt tccatgtgct cgccgaggcg   4500
gcataaatcg ccgtgacgat cagcggtcca atgatcgaag ttaggctggt aagagccgcg   4560
agcgatcctt gaagctgtcc ctgatggtcg tcatctacct gcctggacag catggcctgc   4620
aacgcgggca tcccgatgcc gccggaagcg agaagaatca taatggggaa ggccatccag   4680
cctcgcgtcg cgaacgccag caagacgtag cccagcgcgt cggccgccat gccggcgata   4740
atggcctgct tctcgccgaa acgtttggtg cgggaccag tgacgaaggc ttgagcgagg   4800
gcgtgcaaga ttccgaatac cgcaagcgac aggccgatca tcgtcgcgct ccagcgaaag   4860
cggtcctcgc cgaaaatgac ccagagcgct gccggcacct gtcctacgag ttgcatgata   4920
aagaagacag tcataagtgc ggcgacgata gtcatgcccc gcgcccaccg gaaggagctg   4980
actgggttga aggctctcaa ggcatcggt cgagatcccg gtgcctaatg agtgagctaa   5040
cttacattaa ttgcgttgcg ctcactgccc gctttccagt cgggaaacct gtcgtgccag   5100
ctgcattaat gaatcggcca acgcgcgggg agaggcggtt tgcgtattgg gcgccagggt   5160
ggtttttctt ttcaccagtg agacgggcaa cagctgattg cccttcaccg cctggccctg   5220
agagagttgc agcaagcggt ccacgctggt ttgccccagc aggcgaaaat cctgtttgat   5280
```

```
ggtggttaac ggcgggatat aacatgagct gtcttcggta tcgtcgtatc ccactaccga   5340
gatatccgca ccaacgcgca gcccggactc ggtaatggcg cgcattgcgc ccagcgccat   5400
ctgatcgttg gcaaccagca tcgcagtggg aacgatgccc tcattcagca tttgcatggt   5460
ttgttgaaaa ccggacatgg cactccagtc gccttcccgt tccgctatcg gctgaatttg   5520
attgcgagtg agatatttat gccagccagc cagacgcaga cgcgccgaga cagaacttaa   5580
tgggcccgct aacagcgcga tttgctggtg acccaatgcg accagatgct ccacgcccag   5640
tcgcgtaccg tcttcatggg agaaaataat actgttgatg ggtgtctggt cagagacatc   5700
aagaaataac gccggaacat tagtgcaggc agcttccaca gcaatggcat cctggtcatc   5760
cagcggatag ttaatgatca gcccactgac gcgttgcgcg agaagattgt gcaccgccgc   5820
tttacaggct tcgacgccgc ttcgttctac catcgacacc accacgctgg cacccagttg   5880
atcggcgcga gatttaatcg ccgcgacaat ttgcgacggc gcgtgcaggg ccagactgga   5940
ggtggcaacg ccaatcagca acgactgttt gcccgccagt tgttgtgcca cgcggttggg   6000
aatgtaattc agctccgcca tcgccgcttc cactttttcc cgcgttttcg cagaaacgtg   6060
gctggcctgg ttcaccacgc gggaaacggt ctgataagag acaccggcat actctgcgac   6120
atcgtataac gttactggtt tcacattcac cacccctgaat tgactctctt ccgggcgcta   6180
tcatgccata ccgcgaaagg ttttgcgcca ttcgatggtg tccgggatct cgacgctctc   6240
ccttatgcga ctcctgcatt aggaagcagc ccagtagtag gttgaggccg ttgagcaccg   6300
ccgccgcaag gaatggtgca tgcaaggaga tggcgcccaa cagtccccg gccacggggc    6360 ctgccaccat acccacgccg aaacaagcgc tcatgagccc gaagtggcga gcccgatctt   6420
ccccatcggt gatgtcggcg ataggcgc cagcaaccgc acctgtggcg ccggtgatgc     6480
cggccacgat gcgtccggcg tagaggatcg a                                  6511

<210> SEQ ID NO 104
<211> LENGTH: 6490
<212> TYPE: DNA
<213> ORGANISM: Artificial
<220> FEATURE:
<223> OTHER INFORMATION: Vector construct

<400> SEQUENCE: 104
gatctcgatc ccgcgaaatt aatacgactc actataggg aattgtgagc ggataacaat      60
tcccctctag aaataatttt gtttaaactt taagaaggag atatacatat ggcagccaca    120
catgaacact ctgcccaatg ctgaacaac tacaaaaaag ctacggtta tggcccttac      180 cctctgggca ttaacggtgg catgcactac ggcgttgact tttttatgaa catcggcacc    240
cctgtgaaag ccattagctc aggcaaaatc gtggaagccg gttggtcaaa ctatggcggt    300
ggcaaccaga tcggtctgat cgagaacgat ggtgtgcacc gcaatggta catgcacctg    360 tccaaataca acgttaaagt tggtgactac gtgaaagcag gccagattat cggctggtca    420
ggttcaaccg gttattcaac agcccctcat ctgcacttcc aacgcatggt gaatagtttt    480
agtaattcta ccgctcaaga tccgatgcca ttcctgaaat ctgccggtta tggtggcaaa    540
ctggaagtta gcaaagcagc aaccattaaa cagtccgatg ttaaacaaga agtgaaaaaa    600
caagaggcca acaaattgt gaaagcgacc gattggaaac agaacaaaga tggcatttgg    660
tataaagcag aacatgccag ctttaccgtg accgcaccgg aaggcattat tacccgttat    720 aaaggtcgt ggaccggtca tccgcaggca ggcgtgctgc agaaaggtca gaccatcaaa    780
tatgatgagg tgcagaaatt tgatggccat gtttgggtta gctgggaaac ctttgaaggt    840
```

```
gaaaccgttt atatgccggt tcgtacctgg gatgcaaaaa ccggtaaagt gggtaaactg      900
tggggtgaaa tcaaagagct ccgtcgtcgt cgccgtcggc gtcgtcgtta aggatccggc      960
tgctaacaaa gcccgaaagg aagctgagtt ggctgctgcc accgctgagc aataactagc     1020
ataacccctt ggggcctcta acgggtctt gaggggtttt tgctgaaag gaggaactat      1080
atccggatat cccgcaagag gcccggcagt accggcataa ccaagcctat gcctacagca     1140
tccagggtga cggtgccgag gatgacgatg agcgcattgt tagatttcat acacggtgcc     1200
tgactgcgtt agcaatttaa ctgtgataaa ctaccgcatt aaagctagct tatcgatgat     1260
aagctgtcaa acatgagaat taattcttga agacgaaagg gcctcgtgat acgcctattt     1320
ttataggtta atgtcatgat aataatggtt tcttagacgt caggtggcac ttttcgggga     1380
aatgtgcgcg gaaccctat ttgtttattt ttctaaatac attcaaatat gtatccgctc      1440
atgagacaat aaccctgata aatgcttcaa taatattgaa aaaggaagag tatgagtatt     1500
caacatttcc gtgtcgccct tattccctt tttgcggcat tttgccttcc tgttttgct      1560
cacccagaaa cgctggtgaa agtaaaagat gctgaagatc agttgggtgc acgagtgggt     1620
tacatcgaac tggatctcaa cagcggtaag atccttgaga gttttcgccc cgaagaacgt     1680
tttccaatga tgagcacttt taaagttctg ctatgtggcg cggtattatc ccgtgttgac     1740
gccgggcaag agcaactcgg tcgccgcata cactattctc agaatgactt ggttgagtac     1800
tcaccagtca cagaaaagca tcttacggat ggcatgacag taagagaatt atgcagtgct     1860
gccataacca tgagtgataa cactgcggcc aacttacttc tgacaacgat cggaggaccg     1920
aaggagctaa ccgcttttt gcacaacatg ggggatcatg taactcgcct tgatcgttgg      1980
gaaccggagc tgaatgaagc cataccaaac gacgagcgtg acaccacgat gcctgcagca     2040
atggcaacaa cgttgcgcaa actattaact ggcgaactac ttactctagc ttcccggcaa     2100
caattaatag actggatgga ggcggataaa gttgcaggac cacttctgcg ctcggccctt     2160
ccggctggct ggtttattgc tgataaatct ggagccggtg agcgtgggtc tcgcggtatc     2220
attgcagcac tggggccaga tggtaagccc tcccgtatcg tagttatcta cacgacgggg     2280
agtcaggcaa ctatgatga cgaaatagac agatcgctg agataggtgc ctcactgatt      2340
aagcattggt aactgtcaga ccaagtttac tcatatatac tttagattga tttaaaactt     2400
cattttaat ttaaaggat ctaggtgaag atcctttttg ataatctcat gaccaaaatc       2460
ccttaacgtg agttttcgtt ccactgagcg tcagaccccg tagaaaagat caaaggatct     2520
tcttgagatc cttttttct gcgcgtaatc tgctgcttgc aaacaaaaaa accaccgcta      2580
ccagcggtgg tttgtttgcc ggatcaagag ctaccaactc ttttccgaa ggtaactggc      2640
ttcagcagag cgcagatacc aaatactgtc cttctagtgt agccgtagtt aggccaccac     2700
ttcaagaact ctgtagcacc gcctacatac ctcgctctgc taatcctgtt accagtggct     2760
gctgccagtg gcgataagtc gtgtcttacc gggttggact caagacgata gttaccggat     2820
aaggcgcagc ggtcgggctg aacggggggt tcgtgcacac agcccagctt ggagcgaacg     2880
acctacaccg aactgagata cctacagcgt gagctatgag aaagcgccac gcttcccgaa     2940
gggagaaagg cggacaggta tccggtaagc ggcagggtcg aacaggaga gcgcacgagg      3000
gagcttccag ggggaaacgc ctggtatctt tatagtcctg tcgggtttcg ccacctctga     3060
cttgagcgtc gattttgtg atgctcgtca gggggcgga gcctatggaa aaacgccagc      3120
aacgcggcct ttttacggtt cctggccttt tgctggcctt tgctcacat gttctttcct      3180
```

```
gcgttatccc ctgattctgt ggataaccgt attaccgcct ttgagtgagc tgataccgct    3240
cgccgcagcc gaacgaccga gcgcagcgag tcagtgagcg aggaagcgga agagcgcctg    3300
atgcggtatt ttctccttac gcatctgtgc ggtatttcac accgcaatgg tgcactctca    3360
gtacaatctg ctctgatgcc gcatagttaa gccagtatac actccgctat cgctacgtga    3420
ctgggtcatg gctgcgcccc gacacccgcc aacacccgct gacgcgccct gacgggcttg    3480
tctgctcccg gcatccgctt acagacaagc tgtgaccgtc tccgggagct gcatgtgtca    3540
gaggttttca ccgtcatcac cgaaacgcgc gaggcagctg cggtaaagct catcagcgtg    3600
gtcgtgaagc gattcacaga tgtctgcctg ttcatccgcg tccagctcgt tgagtttctc    3660
cagaagcgtt aatgtctggc ttctgataaa gcgggccatg ttaagggcgg ttttttcctg    3720
tttggtcact gatgcctccg tgtaagggg  atttctgttc atgggggtaa tgataccgat    3780
gaaacgagag aggatgctca cgatacgggt tactgatgat gaacatgccc ggttactgga    3840
acgttgtgag ggtaaacaac tggcggtatg gatgcggcgg gaccagagaa aaatcactca    3900
gggtcaatgc cagcgcttcg ttaatacaga tgtaggtgtt ccacagggta gccagcagca    3960
tcctgcgatg cagatccgga acataatggt gcagggcgct gacttccgcg tttccagact    4020
ttacgaaaca cggaaaccga agaccattca tgttgttgct caggtcgcag acgttttgca    4080
gcagcagtcg cttcacgttc gctcgcgtat cggtgattca ttctgctaac cagtaaggca    4140
accccgccag cctagccggg tcctcaacga caggagcacg atcatgcgca cccgtggcca    4200
ggacccaacg ctgcccgaga tgcgccgcgt gcggctgctg gagatggcgg acgcgatgga    4260
tatgttctgc caagggttgg tttgcgcatt cacagttctc cgcaagaatt gattggctcc    4320
aattcttgga gtggtgaatc cgttagcgag gtgccgccgg cttccattca ggtcgaggtg    4380
gcccggctcc atgcaccgcg acgcaacgcg gggaggcaga caaggtatag gcggcgcct    4440
acaatccatg ccaacccgtt ccatgtgctc gccgaggcgg cataaatcgc cgtgacgatc    4500
agcggtccaa tgatcgaagt taggctggta agagccgcga gcgatccttg aagctgtccc    4560
tgatggtcgt catctacctg cctggacagc atggcctgca acgcgggcat cccgatgccg    4620
ccggaagcga aagaatcat  aatggggaag gccatccagc ctcgcgtcgc gaacgccagc    4680
aagacgtagc ccagcgcgtc ggccgccatg ccggcgataa tggcctgctt ctcgccgaaa    4740
cgtttggtgg cgggaccagt gacgaaggct tgagcgaggg cgtgcaagat tccgaatacc    4800
gcaagcgaca ggccgatcat cgtcgcgctc cagcgaaagc ggtcctcgcc gaaaatgacc    4860
cagagcgctg ccggcacctg tcctacgagt tgcatgataa agaagacagt cataagtgcg    4920
gcgacgatag tcatgccccg cgcccaccgg aaggagctga ctgggttgaa ggctctcaag    4980
ggcatcggtc gagatcccgg tgcctaatga gtgagctaac ttacattaat tgcgttgcgc    5040
tcactgcccg ctttccagtc gggaaacctg tcgtgccagc tgcattaatg aatcggccaa    5100
cgcgcgggga gaggcggttt gcgtattggg cgccagggtg ttttttcttt tcaccagtga    5160
gacgggcaac agctgattgc ccttcaccgc ctggccctga gagagttgca gcaagcggtc    5220
cacgctggtt tgccccagca ggcgaaaatc ctgtttgatg gtggttaacg gcgggatata    5280
acatgagctg tcttcggtat cgtcgtatcc cactaccgag atatccgcac caacgcgcag    5340
cccggactcg gtaatggcgc gcattgcgcc cagcgccatc tgatcgttgg caaccagcat    5400
cgcagtggga acgatgccct cattcagcat ttgcatggtt tgttgaaaac cggacatggc    5460
actccagtcg ccttcccgtt ccgctatcgg ctgaatttga ttgcgagtga gatatttatg    5520
ccagccagcc agacgcagac gcgccgagac agaacttaat gggcccgcta acagcgcgat    5580
```

```
ttgctggtga cccaatgcga ccagatgctc cacgcccagt cgcgtaccgt cttcatggga    5640
gaaaataata ctgttgatgg gtgtctggtc agagacatca agaaataacg ccggaacatt    5700
agtgcaggca gcttccacag caatggcatc ctggtcatcc agcggatagt taatgatcag    5760
cccactgacg cgttgcgcga gaagattgtg caccgccgct ttacaggctt cgacgccgct    5820
tcgttctacc atcgacacca ccacgctggc acccagttga tcggcgcgag atttaatcgc    5880
cgcgacaatt tgcgacggcg cgtgcagggc cagactggag gtggcaacgc caatcagcaa    5940
cgactgtttg cccgccagtt gttgtgccac gcggttggga atgtaattca gctccgccat    6000
cgccgcttcc actttttccc gcgttttcgc agaaacgtgg ctggcctggt tcaccacgcg    6060
ggaaacggtc tgataagaga caccggcata ctctgcgaca tcgtataacg ttactggttt    6120
cacattcacc accctgaatt gactctcttc cgggcgctat catgccatac cgcgaaaggt    6180
tttgcgccat cgatggtgt ccgggatctc gacgctctcc cttatgcgac tcctgcatta    6240
ggaagcagcc cagtagtagg ttgaggccgt tgagcaccgc cgccgcaagg aatggtgcat    6300
gcaaggagat ggcgcccaac agtcccccgg ccacggggcc tgccaccata cccacgccga    6360
aacaagcgct catgagcccg aagtggcgag cccgatcttc cccatcggtg atgtcggcga    6420
tataggcgcc agcaaccgca cctgtggcgc cggtgatgcc ggccacgatg cgtccggcgt    6480
agaggatcga                                                          6490
```

<210> SEQ ID NO 105
<211> LENGTH: 6502
<212> TYPE: DNA
<213> ORGANISM: Artificial
<220> FEATURE:
<223> OTHER INFORMATION: Vector construct

<400> SEQUENCE: 105

```
gatctcgatc ccgcgaaatt aatacgactc actatagggg aattgtgagc ggataacaat      60
tcccctctag aaataatttt gtttaaactt taagaaggag atatacatat ggcagccaca     120
catgaacact ctgcccaatg gctgaacaac tacaaaaaag gctacggtta tggcccttac     180
cctctgggca ttaacggtgg catgcactac ggcgttgact ttttatgaa catcggcacc     240 cctgtgaaag ccattagctc aggcaaaatc gtggaagccg gttggtcaaa ctatggcggt     300
ggcaaccaga tcggtctgat cgagaacgat ggtgtgcacc gccaatggta catgcacctg     360
tccaaataca cgttaaagt tggtgactac gtgaaagcag gccagattat cggctggtca     420
ggttcaaccg gttattcaac agcccctcat ctgcacttcc aacgcatggt gaatagtttt     480
agtaattcta ccgctcaaga tccgatgcca ttcctgaaat ctgccggtta tggtggcaaa     540
ctggaagtta gcaaagcagc aaccattaaa cagtccgatg ttaaacaaga agtgaaaaaa     600
caagaggcca acaaattgt gaaagcgacc gattggaaac agaacaaaga tggcatttgg     660
tataaagcag aacatgccag ctttaccgtg accgcaccgg aaggcattat tacccgttat     720
aaaggtccgt ggaccggtca tccgcaggca ggcgtgctgc agaaaggtca gaccatcaaa     780
tatgatgagg tgcagaaatt tgatggccat gtttgggtta gctgggaaac ctttgaaggt     840
gaaaccgttt atatgccggt tcgtacctgg gatgcaaaaa ccggtaaagt gggtaaactg     900
tggggtgaaa tcaaagagct cggtcgtaaa aaacgtcgtc agcgtcgtcg tccgcctcag     960
taaggatccg gctgctaaca aagcccgaaa ggaagctgag ttggctgctg ccaccgctga    1020
gcaataacta gcataacccc ttggggcctc taaacgggtc ttgaggggtt ttttgctgaa    1080
```

-continued

```
aggaggaact atatccggat atcccgcaag aggcccggca gtaccggcat aaccaagcct    1140
atgcctacag catccagggt gacggtgccg aggatgacga tgagcgcatt gttagatttc    1200
atacacggtg cctgactgcg ttagcaattt aactgtgata aactaccgca ttaaagctag    1260
cttatcgatg ataagctgtc aaacatgaga attaattctt gaagacgaaa gggcctcgtg    1320
atacgcctat ttttataggt taatgtcatg ataataatgg tttcttagac gtcaggtggc    1380
acttttcggg gaaatgtgcg cggaacccct atttgtttat ttttctaaat acattcaaat    1440
atgtatccgc tcatgagaca ataaccctga taaatgcttc aataatattg aaaaggaag    1500
agtatgagta ttcaacatt ccgtgtcgcc cttattccct tttttgcggc attttgcctt     1560
cctgtttttg ctcacccaga aacgctggtg aaagtaaaag atgctgaaga tcagttgggt    1620
gcacgagtgg gttacatcga actggatctc aacagcggta agatccttga gttttcgc     1680
cccgaagaac gttttccaat gatgagcact tttaaagttc tgctatgtgg cgcggtatta    1740
tcccgtgttg acgccgggca agagcaactc ggtcgccgca tacactattc tcagaatgac    1800
ttggttgagt actcaccagt cacagaaaag catcttacgg atggcatgac agtaagagaa    1860
ttatgcagtg ctgccataac catgagtgat aacactgcgg ccaacttact tctgacaacg    1920
atcggaggac cgaaggagct aaccgctttt ttgcacaaca tgggggatca tgtaactcgc    1980
cttgatcgtt gggaaccgga gctgaatgaa gccataccaa acgacgagcg tgacaccacg    2040
atgcctgcag caatggcaac aacgttgcgc aaactattaa ctggcgaact acttactcta    2100
gcttcccggc aacaattaat agactggatg gaggcggata agttgcagg accacttctg     2160
cgctcggccc ttccggctgg ctggtttatt gctgataaat ctggagccgg tgagcgtggg    2220
tctcgcggta tcattgcagc actggggcca gatggtaagc cctcccgtat cgtagttatc    2280
tacacgacgg ggagtcaggc aactatggat gaacgaaata gacagatcgc tgagataggt    2340
gcctcactga ttaagcattg gtaactgtca gaccaagttt actcatatat actttagatt    2400
gatttaaaac ttcatttta atttaaaagg atctaggtga agatccttt tgataatctc      2460
atgaccaaaa tcccttaacg tgagttttcg ttccactgag cgtcagaccc cgtagaaaag    2520
atcaaaggat cttcttgaga tccttttttt ctgcgcgtaa tctgctgctt gcaaacaaaa    2580
aaaccaccgc taccagcggt ggtttgtttg ccggatcaag agctaccaac tctttttccg    2640
aaggtaactg gcttcagcag agcgcagata ccaaatactg tccttctagt gtagccgtag    2700
ttaggccacc acttcaagaa ctctgtagca ccgcctacat acctcgctct gctaatcctg    2760
ttaccagtgg ctgctgccag tggcgataag tcgtgtctta ccgggttgga ctcaagacga    2820
tagttaccgg ataaggcgca gcggtcgggc tgaacggggg gttcgtgcac acagcccagc    2880
ttggagcgaa cgacctacac cgaactgaga tacctacagc gtgagctatg agaaagcgcc    2940
acgcttcccg aagggagaaa ggcggacagg tatccggtaa gcggcagggt cggaacagga    3000
gagcgcacga gggagcttcc aggggaaac gcctggtatc tttatagtcc tgtcgggttt    3060
cgccacctct gacttgagcg tcgatttttg tgatgctcgt caggggggcg agcctatgg    3120
aaaaacgcca gcaacgcggc cttttttacgg ttcctggcct tttgctggcc ttttgctcac    3180
atgttctttc ctgcgttatc ccctgattct gtggataacc gtattaccgc ctttgagtga    3240
gctgataccg ctcgccgcag ccgaacgacc gagcgcagcg agtcagtgag cgaggaagcg    3300
gaagagcgcc tgatgcggta ttttctcctt acgcatctgt gcggtatttc acaccgcaat    3360
ggtgcactct cagtacaatc tgctctgatg ccgcatagtt aagccagtat acactccgct    3420
atcgctacgt gactgggtca tggctgcgcc ccgacacccg ccaacacccg ctgacgcgcc    3480
```

```
ctgacgggct tgtctgctcc cggcatccgc ttacagacaa gctgtgaccg tctccgggag    3540
ctgcatgtgt cagaggtttt caccgtcatc accgaaacgc gcgaggcagc tgcggtaaag    3600
ctcatcagcg tggtcgtgaa gcgattcaca gatgtctgcc tgttcatccg cgtccagctc    3660
gttgagtttc tccagaagcg ttaatgtctg gcttctgata aagcgggcca tgttaagggc    3720
ggttttttcc tgtttggtca ctgatgcctc cgtgtaaggg ggatttctgt tcatggggt     3780 aatgataccg atgaaacgag agaggatgct cacgatacgg gttactgatg atgaacatgc    3840
ccggttactg gaacgttgtg agggtaaaca actggcggta tggatgcggc gggaccagag    3900
aaaaatcact cagggtcaat gccagcgctt cgttaataca gatgtaggtg ttccacaggg    3960
tagccagcag catcctgcga tgcagatccg gaacataatg gtgcagggcg ctgacttccg    4020
cgtttccaga ctttacgaaa cacggaaacc gaagaccatt catgttgttg ctcaggtcgc    4080
agacgttttg cagcagcagt cgcttcacgt tcgctcgcgt atcggtgatt cattctgcta    4140
accagtaagg caaccccgcc agcctagccg ggtcctcaac gacaggagca cgatcatgcg    4200
cacccgtggc caggacccaa cgctgcccga gatgcgccgc gtgcggctgc tggagatggc    4260
ggacgcgatg gatatgttct gccaagggtt ggtttgcgca ttcacagttc tccgcaagaa    4320
ttgattggct ccaattcttg gagtggtgaa tccgttagcg aggtgccgcc ggcttccatt    4380
caggtcgagg tggcccggct ccatgcaccg cgacgcaacg cggggaggca gacaaggtat    4440
agggcggcgc ctacaatcca tgccaacccg ttccatgtgc tcgccgaggc ggcataaatc    4500
gccgtgacga tcagcggtcc aatgatcgaa gttaggctgg taagagccgc gagcgatcct    4560
tgaagctgtc cctgatggtc gtcatctacc tgcctggaca gcatggcctg caacgcgggc    4620
atcccgatgc cgccggaagc gagaagaatc ataatgggga aggccatcca gcctcgcgtc    4680
gcgaacgcca gcaagacgta gcccagcgcg tcggccgcca tgccggcgat aatggcctgc    4740
ttctcgccga aacgtttggt ggcgggacca gtgacgaagg cttgagcgag ggcgtgcaag    4800
attccgaata ccgcaagcga caggccgatc atcgtcgcgc tccagcgaaa gcggtcctcg    4860
ccgaaaatga cccagagcgc tgccggcacc tgtcctacga gttgcatgat aaagaagaca    4920
gtcataagtg cggcgacgat agtcatgccc cgcgcccacc ggaaggagct gactgggttg    4980
aaggctctca agggcatcgg tcgagatccc ggtgcctaat gagtgagcta acttacatta    5040
attgcgttgc gctcactgcc cgcttttcag tcgggaaacc tgtcgtgcca gctgcattaa    5100
tgaatcggcc aacgcgcggg gagaggcggt ttgcgtattg ggcgccaggg tggtttttct    5160
tttcaccagt gagacgggca acagctgatt gcccttcacc gcctggccct gagagagttg    5220
cagcaagcgg tccacgctgg tttgccccag caggcgaaaa tcctgtttga tggtggttaa    5280
cggcgggata taacatgagc tgtcttcggt atcgtcgtat cccactaccg agatatccgc    5340
accaacgcgc agcccggact cggtaatggc gcgcattgcg cccagcgcca tctgatcgtt    5400
ggcaaccagc atcgcagtgg gaacgatgcc ctcattcagc atttgcatgg tttgttgaaa    5460
accggacatg gcactccagt cgccttcccg ttccgctatc ggctgaattt gattgcgagt    5520
gagatattta tgccagccag ccagacgcag acgcgccgag acagaactta atgggcccgc    5580
taacagcgcg atttgctggt gacccaatgc gaccagatgc tccacgccca gtcgcgtacc    5640
gtcttcatgg gagaaaataa tactgttgat gggtgtctgg tcagagacat caagaaataa    5700
cgccggaaca ttagtgcagg cagcttccac agcaatggca tcctggtcat ccagcggata    5760
gttaatgatc agcccactga cgcgttgcgc gagaagattg tgcaccgccg ctttacaggc    5820
```

| | |
|---|---|
| ttcgacgccg cttcgttcta ccatcgacac caccacgctg gcacccagtt gatcggcgcg | 5880 |
| agatttaatc gccgcgacaa tttgcgacgg cgcgtgcagg gccagactgg aggtggcaac | 5940 |
| gccaatcagc aacgactgtt tgcccgccag ttgttgtgcc acgcggttgg gaatgtaatt | 6000 |
| cagctccgcc atcgccgctt ccactttttc ccgcgttttc gcagaaacgt ggctggcctg | 6060 |
| gttcaccacg cgggaaacgg tctgataaga gacaccggca tactctgcga catcgtataa | 6120 |
| cgttactggt ttcacattca ccaccctgaa ttgactctct tccgggcgct atcatgccat | 6180 |
| accgcgaaag gttttgcgcc attcgatggt gtccgggatc tcgacgctct cccttatgcg | 6240 |
| actcctgcat taggaagcag cccagtagta ggttgaggcc gttgagcacc gccgccgcaa | 6300 |
| ggaatggtgc atgcaaggag atggcgccca acagtccccc ggccacgggg cctgccacca | 6360 |
| tacccacgcc gaaacaagcg ctcatgagcc cgaagtggcg agcccgatct tccccatcgg | 6420 |
| tgatgtcggc gatataggcg ccagcaaccg cacctgtggc gccggtgatg ccggccacga | 6480 |
| tgcgtccggc gtagaggatc ga | 6502 |

<210> SEQ ID NO 106
<211> LENGTH: 6130
<212> TYPE: DNA
<213> ORGANISM: Artificial
<220> FEATURE:
<223> OTHER INFORMATION: Vector construct

<400> SEQUENCE: 106

| | |
|---|---|
| gatctcgatc ccgcgaaatt aatacgactc actatagggg aattgtgagc ggataacaat | 60 |
| tcccctctag aaataatttt gtttaaactt taagaaggag atatacatat ggcagccaca | 120 |
| catgaacact ctgcccaatg gctgaacaac tacaaaaaag gctacggtta tggcccttac | 180 |
| cctctgggca ttaacggtgg catgcactac ggcgttgact tttttatgaa catcggcacc | 240 |
| cctgtgaaag ccattagctc aggcaaaatc gtggaagccg gttggtcaaa ctatggcggt | 300 |
| ggcaaccaga tcggtctgat cgagaacgat ggtgtgcacc gccaatggta catgcacctg | 360 |
| tccaaataca acgttaaagt tggtgactac gtgaaagcag gccagattat cggctggtca | 420 |
| ggttcaaccg gttattcaac agcccctcat ctgcacttcc aacgcatggt gaatagtttt | 480 |
| agtaattcta ccgctcaaga tccgatgcca ttcctgaaat ctgccggtta tggtgagctc | 540 |
| cgccagatca aaatttggtt tcagaatcgt cgcatgaaat ggaaaaaata aggatccggc | 600 |
| tgctaacaaa gcccgaaagg aagctgagtt ggctgctgcc accgctgagc aataactagc | 660 |
| ataaccccctt ggggcctcta aacgggtctt gaggggtttt ttgctgaaag gaggaactat | 720 |
| atccggatat cccgcaagag gcccggcagt accggcataa ccaagcctat gcctacagca | 780 |
| tccagggtga cggtgccgag gatgacgatg agcgcattgt tagatttcat acacggtgcc | 840 |
| tgactgcgtt agcaatttaa ctgtgataaa ctaccgcatt aaagctagct tatcgatgat | 900 |
| aagctgtcaa acatgagaat taattcttga agacgaaagg gcctcgtgat acgcctattt | 960 |
| ttataggtta atgtcatgat aataatggtt tcttagacgt caggtggcac ttttcgggga | 1020 |
| aatgtgcgcg gaacccctat ttgtttattt ttctaaatac attcaaatat gtatccgctc | 1080 |
| atgagacaat aaccctgata aatgcttcaa taatattgaa aaaggaagag tatgagtatt | 1140 |
| caacatttcc gtgtcgccct tattcccttt tttgcggcat tttgccttcc tgttttttgct | 1200 |
| cacccagaaa cgctggtgaa agtaaaagat gctgaagatc agttgggtgc acgagtgggt | 1260 |
| tacatcgaac tggatctcaa cagcggtaag atccttgaga gttttcgccc cgaagaacgt | 1320 |
| tttccaatga tgagcacttt taaagttctg ctatgtggcg cggtattatc ccgtgttgac | 1380 |

-continued

```
gccgggcaag agcaactcgg tcgccgcata cactattctc agaatgactt ggttgagtac      1440
tcaccagtca cagaaaagca tcttacggat ggcatgacag taagagaatt atgcagtgct      1500
gccataacca tgagtgataa cactgcggcc aacttacttc tgacaacgat cggaggaccg      1560
aaggagctaa ccgctttttt gcacaacatg ggggatcatg taactcgcct tgatcgttgg      1620
gaaccggagc tgaatgaagc cataccaaac gacgagcgtg acaccacgat gcctgcagca      1680
atggcaacaa cgttgcgcaa actattaact ggcgaactac ttactctagc ttcccggcaa      1740
caattaatag actggatgga ggcggataaa gttgcaggac cacttctgcg ctcggccctt      1800
ccggctggct ggtttattgc tgataaatct ggagccggtg agcgtgggtc tcgcggtatc      1860
attgcagcac tggggccaga tggtaagccc tcccgtatcg tagttatcta cacgacgggg      1920
agtcaggcaa ctatggatga acgaaataga cagatcgctg agataggtgc ctcactgatt      1980
aagcattggt aactgtcaga ccaagtttac tcatatatac tttagattga tttaaaactt      2040
catttttaat ttaaaaggat ctaggtgaag atcctttttg ataatctcat gaccaaaatc      2100
ccttaacgtg agttttcgtt ccactgagcg tcagaccccg tagaaaagat caaaggatct      2160
tcttgagatc ctttttttct gcgcgtaatc tgctgcttgc aaacaaaaaa accaccgcta      2220
ccagcggtgg tttgtttgcc ggatcaagag ctaccaactc tttttccgaa ggtaactggc      2280
ttcagcagag cgcagatacc aaatactgtc cttctagtgt agccgtagtt aggccaccac      2340
ttcaagaact ctgtagcacc gcctacatac ctcgctctgc taatcctgtt accagtggct      2400
gctgccagtg gcgataagtc gtgtcttacc gggttggact caagacgata gttaccggat      2460
aaggcgcagc ggtcgggctg aacggggggt tcgtgcacac agcccagctt ggagcgaacg      2520
acctacaccg aactgagata cctacagcgt gagctatgag aaagcgccac gcttcccgaa      2580
gggagaaagg cggacaggta tccggtaagc ggcagggtcg gaacaggaga gcgcacgagg      2640
gagcttccag ggggaaacgc ctggtatctt tatagtcctg tcgggtttcg ccacctctga      2700
cttgagcgtc gatttttgtg atgctcgtca ggggggcgga gcctatggaa aaacgccagc      2760
aacgcggcct ttttacggtt cctggccttt tgctggcctt ttgctcacat gttctttcct      2820
gcgttatccc ctgattctgt ggataaccgt attaccgcct ttgagtgagc tgataccgct      2880
cgccgcagcc gaacgaccga gcgcagcgag tcagtgagcg aggaagcgga agagcgcctg      2940
atgcggtatt ttctccttac gcatctgtgc ggtatttcac accgcaatgg tgcactctca      3000
gtacaatctg ctctgatgcc gcatagttaa gccagtatac actccgctat cgctacgtga      3060
ctgggtcatg gctgcgcccc gacacccgcc aacacccgct gacgcgccct gacgggcttg      3120
tctgctcccg gcatccgctt acagacaagc tgtgaccgtc tccgggagct gcatgtgtca      3180
gaggttttca ccgtcatcac cgaaacgcgc gaggcagctg cggtaaagct catcagcgtg      3240
gtcgtgaagc gattcacaga tgtctgcctg ttcatccgcg tccagctcgt tgagtttctc      3300
cagaagcgtt aatgtctggc ttctgataaa gcgggccatg ttaagggcgg ttttttcctg      3360
tttggtcact gatgcctccg tgtaaggggg atttctgttc atgggggtaa tgataccgat      3420
gaaacgagag aggatgctca cgatacgggt tactgatgat gaacatgccc ggttactgga      3480
acgttgtgag ggtaaacaac tggcggtatg gatgcggcgg gaccagagaa aaatcactca      3540
gggtcaatgc cagcgcttcg ttaatacaga tgtaggtgtt ccacagggta gccagcagca      3600
tcctgcgatg cagatccgga acataatggt gcagggcgct gacttccgcg tttccagact      3660
ttacgaaaca cggaaaccga agaccattca tgttgttgct caggtcgcag acgttttgca      3720
```

```
gcagcagtcg cttcacgttc gctcgcgtat cggtgattca ttctgctaac cagtaaggca   3780
accccgccag cctagccggg tcctcaacga caggagcacg atcatgcgca cccgtggcca   3840
ggacccaacg ctgcccgaga tgcgccgcgt gcggctgctg gagatggcgg acgcgatgga   3900
tatgttctgc caagggttgg tttgcgcatt cacagttctc cgcaagaatt gattggctcc   3960
aattcttgga gtggtgaatc cgttagcgag gtgccgccgg cttccattca ggtcgaggtg   4020
gcccggctcc atgcaccgcg acgcaacgcg gggaggcaga caaggtatag gcggcgcct   4080
acaatccatg ccaacccgtt ccatgtgctc gccgaggcgg cataaatcgc cgtgacgatc   4140
agcggtccaa tgatcgaagt taggctggta agagccgcga gcgatccttg aagctgtccc   4200
tgatggtcgt catctacctg cctggacagc atggcctgca acgcgggcat cccgatgccg   4260
ccggaagcga gaagaatcat aatggggaag gccatccagc ctcgcgtcgc gaacgccagc   4320
aagacgtagc ccagcgcgtc ggccgccatg ccggcgataa tggcctgctt ctcgccgaaa   4380
cgtttggtgg cgggaccagt gacgaaggct tgagcgaggg cgtgcaagat tccgaatacc   4440
gcaagcgaca ggccgatcat cgtcgcgctc cagcgaaagc ggtcctcgcc gaaaatgacc   4500
cagagcgctg ccggcacctg tcctacgagt tgcatgataa agaagacagt cataagtgcg   4560
gcgacgatag tcatgccccg cgcccaccgg aaggagctga ctgggttgaa ggctctcaag   4620
ggcatcggtc gagatcccgg tgcctaatga gtgagctaac ttacattaat tgcgttgcgc   4680
tcactgcccg ctttccagtc gggaaacctg tcgtgccagc tgcattaatg aatcggccaa   4740
cgcgcgggga gaggcggttt gcgtattggg cgccagggtg ttttctttt tcaccagtga   4800
gacgggcaac agctgattgc ccttcaccgc ctggccctga gagagttgca gcaagcggtc   4860
cacgctggtt tgccccagca ggcgaaaatc ctgtttgatg gtggttaacg gcgggatata   4920
acatgagctg tcttcggtat cgtcgtatcc cactaccgag atatccgcac caacgcgcag   4980
cccggactcg gtaatggcgc gcattgcgcc cagcgccatc tgatcgttgg caaccagcat   5040
cgcagtggga acgatgccct cattcagcat ttgcatggtt tgttgaaaac cggacatggc   5100
actccagtcg ccttcccgtt ccgctatcgg ctgaatttga ttgcgagtga gatatttatg   5160
ccagccagcc agacgcagac gcgccgagac agaacttaat gggcccgcta acagcgcgat   5220
ttgctggtga cccaatgcga ccagatgctc cacgcccagt cgcgtaccgt cttcatggga   5280
gaaaataata ctgttgatgg gtgtctggtc agagacatca agaaataacg ccggaacatt   5340
agtgcaggca gcttccacag caatggcatc ctggtcatcc agcggatagt taatgatcag   5400
cccactgacg cgttgcgcga agagattgtg caccgccgct ttacaggctt cgacgccgct   5460
tcgttctacc atcgacacca ccacgctggc acccagttga tcggcgcgag atttaatcgc   5520
cgcgacaatt tgcgacggcg cgtgcagggc cagactggag gtggcaacgc caatcagcaa   5580
cgactgtttg cccgccagtt gttgtgccac gcggttggga atgtaattca gctccgccat   5640
cgccgcttcc acttttttccc gcgttttcgc agaaacgtgg ctggcctggt tcaccacgcg   5700
ggaaacggtc tgataagaga caccggcata ctctgcgaca tcgtataacg ttactggttt   5760
cacattcacc ccctgaatt gactctcttc cgggcgctat catgccatac cgcgaaaggt   5820
tttgcgccat tcgatggtgt ccgggatctc gacgctctcc cttatgcgac tcctgcatta   5880
ggaagcagcc cagtagtagg ttgaggccgt tgagcaccgc cgccgcaagg aatggtgcat   5940
gcaaggagat ggcgcccaac agtccccgg ccacggggcc tgccaccata cccacgccga   6000
aacaagcgct catgagcccg aagtggcgag cccgatcttc cccatcggtg atgtcggcga   6060
tataggcgcc agcaaccgca cctgtggcgc cggtgatgcc ggccacgatg cgtccggcgt   6120
```

-continued

| | |
|---|---:|
| agaggatcga | 6130 |

<210> SEQ ID NO 107
<211> LENGTH: 6114
<212> TYPE: DNA
<213> ORGANISM: Artificial
<220> FEATURE:
<223> OTHER INFORMATION: Vector construct

<400> SEQUENCE: 107

| | |
|---|---:|
| gatctcgatc ccgcgaaatt aatacgactc actatagggg aattgtgagc ggataacaat | 60 |
| tcccctctag aaataatttt gtttaaactt taagaaggag atatacatat ggcagccaca | 120 |
| catgaacact ctgcccaatg gctgaacaac tacaaaaaag ctacggtta tggcccttac | 180 |
| cctctgggca ttaacggtgg catgcactac ggcgttgact ttttatgaa catcggcacc | 240 |
| cctgtgaaag ccattagctc aggcaaaatc gtggaagccg gttggtcaaa ctatggcggt | 300 |
| ggcaaccaga tcggtctgat cgagaacgat ggtgtgcacc gccaatggta catgcacctg | 360 |
| tccaaataca acgttaaagt tggtgactac gtgaaagcag gccagattat cggctggtca | 420 |
| ggttcaaccg gttattcaac agcccctcat ctgcacttcc aacgcatggt gaatagtttt | 480 |
| agtaattcta ccgctcaaga tccgatgcca ttcctgaaat ctgccggtta tggtgagctg | 540 |
| agctccgtcg tcgtcgccgt cggcgtcgtc gttaaggatc cggctgctaa caaagcccga | 600 |
| aaggaagctg agttggctgc tgccaccgct gagcaataac tagcataacc ccttggggcc | 660 |
| tctaaacggg tcttgagggg ttttttgctg aaaggaggaa ctatatccgg atatcccgca | 720 |
| agaggcccgg cagtaccggc ataaccaagc ctatgcctac agcatccagg gtgacggtgc | 780 |
| cgaggatgac gatgagcgca ttgttagatt tcatacacgg tgcctgactg cgttagcaat | 840 |
| ttaactgtga taaactaccg cattaaagct agcttatcga tgataagctg tcaaacatga | 900 |
| gaattaattc ttgaagacga aagggcctcg tgatacgcct atttttatag gttaatgtca | 960 |
| tgataataat ggtttcttag acgtcaggtg gcacttttcg gggaaatgtg cgcggaaccc | 1020 |
| ctatttgttt attttttctaa atacattcaa atatgtatcc gctcatgaga caataaccct | 1080 |
| gataaatgct tcaataatat tgaaaaagga agagtatgag tattcaacat ttccgtgtcg | 1140 |
| cccttattcc cttttttgcg gcattttgcc ttcctgtttt tgctcaccca gaaacgctgg | 1200 |
| tgaaagtaaa agatgctgaa gatcagttgg gtgcacgagt gggttacatc gaactggatc | 1260 |
| tcaacagcgg taagatcctt gagagttttc gccccgaaga acgttttcca atgatgagca | 1320 |
| cttttaaagt tctgctatgt ggcgcggtat tatcccgtgt tgacgccggg caagagcaac | 1380 |
| tcggtcgccg catacactat tctcagaatg acttggttga gtactcacca gtcacagaaa | 1440 |
| agcatcttac ggatggcatg acagtaagag aattatgcag tgctgccata accatgagtg | 1500 |
| ataacactgc ggccaactta cttctgacaa cgatcggagg accgaaggag ctaaccgctt | 1560 |
| ttttgcacaa catgggggat catgtaactc gccttgatcg ttgggaaccg gagctgaatg | 1620 |
| aagccatacc aaacgacgag cgtgacacca cgatgcctgc agcaatggca acaacgttgc | 1680 |
| gcaaactatt aactggcgaa ctacttactc tagcttcccg gcaacaatta atagactgga | 1740 |
| tggaggcgga taaagttgca ggaccacttc tgcgctcgg ccttccggct ggctggttta | 1800 |
| ttgctgataa atctggagcc ggtgagcgtg gtctcgcgg tatcattgca gcactggggc | 1860 |
| cagatggtaa gccctcccgt atcgtagtta tctacacgac ggggagtcag gcaactatgg | 1920 |
| atgaacgaaa tagacagatc gctgagatag gtgcctcact gattaagcat tggtaactgt | 1980 |

```
cagaccaagt ttactcatat atactttaga ttgatttaaa acttcatttt taatttaaaa    2040
ggatctaggt gaagatcctt tttgataatc tcatgaccaa aatcccttaa cgtgagtttt    2100
cgttccactg agcgtcagac cccgtagaaa agatcaaagg atcttcttga gatccttttt    2160
ttctgcgcgt aatctgctgc ttgcaaacaa aaaaaccacc gctaccagcg gtggtttgtt    2220
tgccggatca agagctacca actcttttc cgaaggtaac tggcttcagc agagcgcaga    2280
taccaaatac tgtccttcta gtgtagccgt agttaggcca ccacttcaag aactctgtag    2340
caccgcctac atacctcgct ctgctaatcc tgttaccagt ggctgctgcc agtggcgata    2400
agtcgtgtct taccgggttg gactcaagac gatagttacc ggataaggcg cagcggtcgg    2460
gctgaacggg gggttcgtgc acacagccca gcttggagcg aacgacctac accgaactga    2520
gatacctaca gcgtgagcta tgagaaagcg ccacgcttcc cgaagggaga aaggcggaca    2580
ggtatccggt aagcggcagg gtcggaacag gagagcgcac gagggagctt ccaggggaa    2640
acgcctggta tctttatagt cctgtcgggt ttcgccacct ctgacttgag cgtcgatttt    2700
tgtgatgctc gtcagggggg cggagcctat ggaaaaacgc cagcaacgcg gcctttttac    2760
ggttcctggc cttttgctgg cctttttgctc acatgttctt tcctgcgtta tcccctgatt    2820
ctgtggataa ccgtattacc gcctttgagt gagctgatac cgctcgccgc agccgaacga    2880
ccgagcgcag cgagtcagtg agcgaggaag cggaagagcg cctgatgcgg tattttctcc    2940
ttacgcatct gtgcggtatt tcacaccgca atggtgcact ctcagtacaa tctgctctga    3000
tgccgcatag ttaagccagt atacactccg ctatcgctac gtgactgggt catggctgcg    3060
ccccgacacc cgccaacacc cgctgacgcg ccctgacggg cttgtctgct cccggcatcc    3120
gcttacagac aagctgtgac cgtctccggg agctgcatgt gtcagaggtt ttcaccgtca    3180
tcaccgaaac gcgcgaggca gctgcggtaa agctcatcag cgtggtcgtg aagcgattca    3240
cagatgtctg cctgttcatc cgcgtccagc tcgttgagtt tctccagaag cgttaatgtc    3300
tggcttctga taaagcgggc catgttaagg cggttttttt cctgtttggt cactgatgcc    3360
tccgtgtaag ggggatttct gttcatgggg gtaatgatac cgatgaaacg agagaggatg    3420
ctcacgatac gggttactga tgatgaacat gcccggttac tggaacgttg tgagggtaaa    3480
caactggcgg tatggatgcg gcgggaccag agaaaaatca ctcagggtca atgccagcgc    3540
ttcgttaata cagatgtagg tgttccacag ggtagccagc agcatcctgc gatgcagatc    3600
cggaacataa tggtgcaggg cgctgacttc cgcgtttcca gactttacga aacacggaaa    3660
ccgaagacca ttcatgttgt tgctcaggtc gcagacgttt tgcagcagca gtcgcttcac    3720
gttcgctcgc gtatcggtga ttcattctgc taaccagtaa ggcaaccccg ccagcctagc    3780
cgggtcctca acgacaggag cacgatcatg cgcacccgtg gccaggaccc aacgctgccc    3840
gagatgcgcc gcgtgcggct gctggagatg gcggacgcga tggatatgtt ctgccaaggg    3900
ttggtttgcg cattcacagt tctccgcaag aattgattgg ctccaattct tggagtggtg    3960
aatccgttag cgaggtgccg ccggcttcca ttcaggtcga ggtggcccgg ctccatgcac    4020
cgcgacgcaa cgcggggagg cagacaaggt atagggcggc gcctacaatc catgccaacc    4080
cgttccatgt gctcgccgag gcggcataaa tcgccgtgac gatcagcggt ccaatgatcg    4140
aagttaggct ggtaagagcc gcgagcgatc cttgaagctg tccctgatgg tcgtcatcta    4200
cctgcctgga cagcatggcc tgcaacgcgg gcatcccgat gccgccggaa gcgagaagaa    4260
tcataatggg gaaggccatc cagcctcgcg tcgcgaacgc cagcaagacg tagcccagcg    4320
cgtcggccgc catgccggcg ataatggcct gcttctcgcc gaaacgtttg gtggcgggac    4380
```

```
cagtgacgaa ggcttgagcg agggcgtgca agattccgaa taccgcaagc gacaggccga    4440
tcatcgtcgc gctccagcga aagcggtcct cgccgaaaat gacccagagc gctgccggca    4500
cctgtcctac gagttgcatg ataaagaaga cagtcataag tgcggcgacg atagtcatgc    4560
cccgcgccca ccggaaggag ctgactgggt tgaaggctct caagggcatc ggtcgagatc    4620
ccggtgccta atgagtgagc taacttacat taattgcgtt gcgctcactg cccgctttcc    4680
agtcgggaaa cctgtcgtgc cagctgcatt aatgaatcgg ccaacgcgcg gggagaggcg    4740
gtttgcgtat tgggcgccag ggtggttttt cttttcacca gtgagacggg caacagctga    4800
ttgcccttca ccgcctggcc ctgagagagt gcagcaagc ggtccacgct ggtttgcccc     4860
agcaggcgaa aatcctgttt gatggtggtt aacgcgggga tataacatga gctgtcttcg    4920
gtatcgtcgt atcccactac cgagatatcc gcaccaacgc gcagcccgga ctcggtaatg    4980
gcgcgcattg cgcccagcgc catctgatcg ttggcaacca gcatcgcagt gggaacgatg    5040
ccctcattca gcatttgcat ggtttgttga aaaccggaca tggcactcca gtcgccttcc    5100
cgttccgcta tcggctgaat ttgattgcga gtgagatatt tatgccagcc agccagacgc    5160
agacgcgccg agacagaact taatgggccc gctaacagcg cgatttgctg gtgacccaat    5220
gcgaccagat gctccacgcc cagtcgcgta ccgtcttcat gggagaaaat aatactgttg    5280
atgggtgtct ggtcagagac atcaagaaat aacgccggaa cattagtgca ggcagcttcc    5340
acagcaatgg catcctggtc atccagcgga tagttaatga tcagcccact gacgcgttgc    5400
gcgagaagat tgtgcaccgc cgctttacag gcttcgacgc cgcttcgttc taccatcgac    5460
accaccacgc tggcacccag ttgatcggcg cgagattaa tcgccgcgac aatttgcgac     5520
ggcgcgtgca gggccagact ggaggtggca acgccaatca gcaacgactg tttgcccgcc    5580
agttgttgtg ccacgcggtt gggaatgtaa ttcagctccg ccatcgccgc ttccactttt    5640
tcccgcgttt tcgcagaaac gtggctggcc tggttcacca cgcgggaaac ggtctgataa    5700
gagacaccgg catactctgc gacatcgtat aacgttactg gtttcacatt caccaccctg    5760
aattgactct cttccgggcg ctatcatgcc ataccgcgaa aggttttgcg ccattcgatg    5820
gtgtccggga tctcgacgct ctcccttatg cgactcctgc attaggaagc agcccagtag    5880
taggttgagg ccgttgagca ccgccgccgc aaggaatggt gcatgcaagg agatggcgcc    5940
caacagtccc ccggccacgg ggcctgccac catacccacg ccgaaacaag cgctcatgag    6000
cccgaagtgg cgagcccgat cttccccatc ggtgatgtcg gcgatatagg cgccagcaac    6060
cgcacctgtg gcgccggtga tgccggccac gatgcgtccg gcgtagagga tcga          6114
```

<210> SEQ ID NO 108
<211> LENGTH: 6126
<212> TYPE: DNA
<213> ORGANISM: Artificial
<220> FEATURE:
<223> OTHER INFORMATION: Vector construct

<400> SEQUENCE: 108

```
gatctcgatc ccgcgaaatt aatacgactc actatagggg aattgtgagc ggataacaat      60
tcccctctag aaataatttt gtttaaactt taagaaggag atatacatat ggcagccaca     120
catgaacact ctgcccaatg gctgaacaac tacaaaaaag gctacggtta tggcccttac    180
cctctgggca ttaacggtgg catgcactac ggcgttgact tttttatgaa catcggcacc    240
cctgtgaaag ccattagctc aggcaaaatc gtggaagccg gttggtcaaa ctatggcggt    300
```

-continued

| | | | | |
|---|---|---|---|---|
| ggcaaccaga | tcggtctgat | cgagaacgat | ggtgtgcacc | gccaatggta catgcacctg | 360 |
| tccaaataca | acgttaaagt | tggtgactac | gtgaaagcag | gccagattat cggctggtca | 420 |
| ggttcaaccg | gttattcaac | agcccctcat | ctgcacttcc | aacgcatggt gaatagtttt | 480 |
| agtaattcta | ccgctcaaga | tccgatgcca | ttcctgaaat | ctgccggtta tggtgagctg | 540 |
| agctcggtcg | taaaaaacgt | cgtcagcgtc | gtcgtccgcc | tcagtaagga tccggctgct | 600 |
| aacaaagccc | gaaaggaagc | tgagttggct | gctgccaccg | ctgagcaata actagcataa | 660 |
| cccccttgggg | cctctaaacg | ggtcttgagg | ggttttttgc | tgaaaggagg aactatatcc | 720 |
| ggatatcccg | caagaggccc | ggcagtaccg | gcataaccaa | gcctatgcct acagcatcca | 780 |
| gggtgacggt | gccgaggatg | acgatgagcg | cattgttaga | tttcatacac ggtgcctgac | 840 |
| tgcgttagca | atttaactgt | gataaactac | cgcattaaag | ctagcttatc gatgataagc | 900 |
| tgtcaaacat | gagaattaat | tcttgaagac | gaaagggcct | cgtgatacgc ctatttttat | 960 |
| aggttaatgt | catgataata | atggtttctt | agacgtcagg | tggcactttt cggggaaatg | 1020 |
| tgcgcggaac | ccctatttgt | ttattttttct | aaatacattc | aaatatgtat ccgctcatga | 1080 |
| gacaataacc | ctgataaatg | cttcaataat | attgaaaaag | gaagagtatg agtattcaac | 1140 |
| atttccgtgt | cgcccttatt | cccttttttg | cggcattttg | ccttcctgtt tttgctcacc | 1200 |
| cagaaacgct | ggtgaaagta | aaagatgctg | aagatcagtt | gggtgcacga gtgggttaca | 1260 |
| tcgaactgga | tctcaacagc | ggtaagatcc | ttgagagttt | tcgccccgaa gaacgttttc | 1320 |
| caatgatgag | cacttttaaa | gttctgctat | gtggcgcggt | attatcccgt gttgacgccg | 1380 |
| ggcaagagca | actcggtcgc | cgcatacact | attctcagaa | tgacttggtt gagtactcac | 1440 |
| cagtcacaga | aaagcatctt | acggatggca | tgacagtaag | agaattatgc agtgctgcca | 1500 |
| taaccatgag | tgataacact | gcggccaact | tacttctgac | aacgatcgga ggaccgaagg | 1560 |
| agctaaccgc | ttttttgcac | aacatggggg | atcatgtaac | tcgccttgat cgttgggaac | 1620 |
| cggagctgaa | tgaagccata | ccaaacgacg | agcgtgacac | cacgatgcct gcagcaatgg | 1680 |
| caacaacgtt | gcgcaaacta | ttaactggcg | aactacttac | tctagcttcc cggcaacaat | 1740 |
| taatagactg | gatggaggcg | gataaagttg | caggaccact | tctgcgctcg gcccttccgg | 1800 |
| ctggctggtt | tattgctgat | aaatctggag | ccggtgagcg | tgggtctcgc ggtatcattg | 1860 |
| cagcactggg | gccagatggt | aagccctccc | gtatcgtagt | tatctacacg acggggagtc | 1920 |
| aggcaactat | ggatgaacga | aatagacaga | tcgctgagat | aggtgcctca ctgattaagc | 1980 |
| attggtaact | gtcagaccaa | gtttactcat | atatacttta | gattgattta aaacttcatt | 2040 |
| tttaatttaa | aaggatctag | gtgaagatcc | tttttgataa | tctcatgacc aaaatccctt | 2100 |
| aacgtgagtt | ttcgttccac | tgagcgtcag | accccgtaga | aaagatcaaa ggatcttctt | 2160 |
| gagatccttt | ttttctgcgc | gtaatctgct | gcttgcaaac | aaaaaaacca ccgctaccag | 2220 |
| cggtggtttg | tttgccggat | caagagctac | caactctttt | tccgaaggta actggcttca | 2280 |
| gcagagcgca | gataccaaat | actgtccttc | tagtgtagcc | gtagttaggc caccacttca | 2340 |
| agaactctgt | agcaccgcct | acatacctcg | ctctgctaat | cctgttacca gtggctgctg | 2400 |
| ccagtggcga | taagtcgtgt | cttaccgggt | tggactcaag | acgatagtta ccggataagg | 2460 |
| cgcagcggtc | gggctgaacg | gggggttcgt | gcacacagcc | cagcttggag cgaacgacct | 2520 |
| acaccgaact | gagataccta | cagcgtgagc | tatgagaaag | cgccacgctt cccgaaggga | 2580 |
| gaaaggcgga | caggtatccg | gtaagcggca | gggtcggaac | aggagagcgc acgagggagc | 2640 |
| ttccaggggg | aaacgcctgg | tatctttata | gtcctgtcgg | gtttcgccac ctctgacttg | 2700 |

```
agcgtcgatt tttgtgatgc tcgtcagggg ggcggagcct atggaaaaac gccagcaacg    2760
cggccttttt acggttcctg gccttttgct ggccttttgc tcacatgttc tttcctgcgt    2820
tatcccctga ttctgtggat aaccgtatta ccgcctttga gtgagctgat accgctcgcc    2880
gcagccgaac gaccgagcgc agcgagtcag tgagcgagga agcggaagag cgcctgatgc    2940
ggtattttct ccttacgcat ctgtgcggta tttcacaccg caatggtgca ctctcagtac    3000
aatctgctct gatgccgcat agttaagcca gtatacactc cgctatcgct acgtgactgg    3060
gtcatggctg cgccccgaca cccgccaaca cccgctgacg cgccctgacg ggcttgtctg    3120
ctcccggcat ccgcttacag acaagctgtg accgtctccg ggagctgcat gtgtcagagg    3180
ttttcaccgt catcaccgaa acgcgcgagg cagctgcggt aaagctcatc agcgtggtcg    3240
tgaagcgatt cacagatgtc tgcctgttca tccgcgtcca gctcgttgag tttctccaga    3300
agcgttaatg tctggcttct gataaagcgg gccatgttaa gggcggtttt tcctgtttg    3360 gtcactgatg cctccgtgta agggggattt ctgttcatgg ggtaatgat accgatgaaa    3420 cgagagagga tgctcacgat acgggttact gatgatgaac atgcccggtt actggaacgt    3480
tgtgagggta aacaactggc ggtatggatg cggcgggacc agagaaaaat cactcagggt    3540
caatgccagc gcttcgttaa tacagatgta ggtgttccac agggtagcca gcagcatcct    3600
gcgatgcaga tccggaacat aatggtgcag ggcgctgact ccgcgtttc cagactttac    3660 gaaacacgga aaccgaagac cattcatgtt gttgctcagg tcgcagacgt tttgcagcag    3720
cagtcgcttc acgttcgctc gcgtatcggt gattcattct gctaaccagt aaggcaaccc    3780
cgccagccta gccgggtcct caacgacagg agcacgatca tgcgcacccg tggccaggac    3840
ccaacgctgc ccgagatgcg ccgcgtgcgg ctgctggaga tggcggacgc gatggatatg    3900
ttctgccaag ggttggtttg cgcattcaca gttctccgca agaattgatt ggctccaatt    3960
cttggagtgg tgaatccgtt agcgaggtgc cgccggcttc cattcaggtc gaggtggccc    4020
ggctccatgc accgcgacgc aacgcgggga ggcagacaag gtatagggcg cgcctacaa    4080 tccatgccaa cccgttccat gtgctcgccg aggcggcata atcgccgtg acgatcagcg    4140 gtccaatgat cgaagttagg ctggtaagag ccgcgagcga tccttgaagc tgtccctgat    4200
ggtcgtcatc tacctgcctg gacagcatgg cctgcaacgc gggcatcccg atgccgccgg    4260
aagcgagaag aatcataatg gggaaggcca tccagcctcg cgtcgcgaac gccagcaaga    4320
cgtagcccag cgcgtcggcc gccatgccgg cgataatggc ctgcttctcg ccgaaacgtt    4380 tggtggcgg accagtgacg aaggcttgag cgagggcgtg caagattccg aataccgcaa    4440
gcgacaggcc gatcatcgtc gcgctccagc gaaagcggtc ctcgccgaaa atgacccaga    4500
gcgctgccgg cacctgtcct acgagttgca tgataaagaa gacagtcata agtgcggcga    4560
cgatagtcat gccccgcgcc caccggaagg agctgactgg gttgaaggct ctcaagggca    4620
tcggtcgaga tcccggtgcc taatgagtga gctaacttac attaattgcg ttgcgctcac    4680
tgcccgcttt ccagtcggga aacctgtcgt gccagctgca ttaatgaatc ggccaacgcg    4740
cggggagagg cggtttgcgt attgggcgcc agggtggttt tcttttcac cagtgagacg    4800 ggcaacagct gattgccctt caccgcctgg ccctgagaga gttgcagcaa gcggtccacg    4860
ctggtttgcc ccagcaggcg aaaatcctgt ttgatggtgg ttaacggcgg gatataacat    4920
gagctgtctt cggtatcgtc gtatcccact accgagatat ccgcaccaac gcgcagcccg    4980
gactcggtaa tggcgcgcat tgcgcccagc gccatctgat cgttggcaac cagcatcgca    5040
```

-continued

```
gtgggaacga tgccctcatt cagcatttgc atggtttgtt gaaaaccgga catggcactc   5100
cagtcgcctt cccgttccgc tatcggctga atttgattgc gagtgagata tttatgccag   5160
ccagccagac gcagacgcgc cgagacagaa cttaatgggc ccgctaacag cgcgatttgc   5220
tggtgaccca atgcgaccag atgctccacg cccagtcgcg taccgtcttc atgggagaaa   5280
ataatactgt tgatgggtgt ctggtcagag acatcaagaa ataacgccgg aacattagtg   5340
caggcagctt ccacagcaat ggcatcctgg tcatccagcg gatagttaat gatcagccca   5400
ctgacgcgtt gcgcgagaag attgtgcacc gccgctttac aggcttcgac gccgcttcgt   5460
tctaccatcg acaccaccac gctggcaccc agttgatcgg cgcgagattt aatcgccgcg   5520
acaatttgcg acggcgcgtg cagggccaga ctggaggtgg caacgccaat cagcaacgac   5580
tgtttgcccg ccagttgttg tgccacgcgg ttgggaatgt aattcagctc cgccatcgcc   5640
gcttccactt tttcccgcgt tttcgcagaa acgtggctgg cctggttcac cacgcgggaa   5700
acggtctgat aagagacacc ggcatactct gcgacatcgt ataacgttac tggtttcaca   5760
ttcaccaccc tgaattgact ctcttccggg cgctatcatg ccataccgcg aaaggttttg   5820
cgccattcga tggtgtccgg gatctcgacg ctctccctta tgcgactcct gcattaggaa   5880
gcagcccagt agtaggttga ggccgttgag caccgccgcc gcaaggaatg gtgcatgcaa   5940
ggagatggcg cccaacagtc ccccggccac ggggcctgcc accataccca cgccgaaaca   6000
agcgctcatg agcccgaagt ggcgagcccg atcttcccca tcggtgatgt cggcgatata   6060
ggcgccagca accgcacctg tggcgccggt gatgccggcc acgatgcgtc cggcgtagag   6120
gatcga                                                             6126
```

COMBINATION OF BACTERICIDAL AGENT WITH A LYSOSOMOTROPIC ALKALINISING AGENT FOR THE TREATMENT OF A BACTERIAL INFECTION

CROSS REFERENCE TO RELATED APPLICATIONS

This application is a national stage application under 35 U.S.C. § 371 of International Application No. PCT/EP2016/055076, filed on Mar. 10, 2016. This invention relates to and claims the benefit of priority to European Patent Application No. 15158880.3, filed on Mar. 12, 2015, the disclosures of each of which are explicitly herein incorporated by reference in their entirety.

FIELD OF THE INVENTION

The present invention relates to the field of medicine, specifically the field of bacterial infection and treatment thereof.

BACKGROUND OF THE INVENTION

The human pathogen *Staphylococcus aureus* colonizes approximately a third of all humans and is one of the leading causes of bacteremia and infective endocarditis in the industrialized world (1). In addition to emerging antibiotic resistance, persisting and recurrent infections substantially add to morbidity and mortality (2,3). Recurrence rates, in particular after osteomyelitis or endocarditis, are high and infections may relapse even years after apparent cure (4). Infection recurrence is associated with SCVs (small colony variants) and/or non-replicating persisters for several reasons (5-8). Their arrested or slow growth and reduced metabolism renders antibiotics inefficient (9-13). Moreover, they preferentially hide in privileged locations such as in abscesses and within host cells (14-16). These privileged locations shield them from the host's innate immune system and from extracellularly active antibiotics. In addition, antibiotics do not penetrate abscesses efficiently and are less active due to the low pH (17-21). Therefore the 'ubi pus ibi evacua'—the necessity of surgical removal of abscesses formulated in the antiquity still applies nowadays despite highly active antibiotics. In contrast to abscesses, intracellular bacteria cannot be mechanically removed and often resist eradication by currently available antibiotics. Most SCVs isolated in clinics revert to the large colony phenotype upon sub-cultivation. Due to these unstable properties, stable genetically-modified SCV mutants with defects in the electron transport system have been used to find new strategies to target SCVs and have been found to localize in host cell lysosomes (22). However, stable SCVs only partially reflect the clinical SCVs. They are less virulent (23) and do not revert to the highly virulent and fast-growing phenotype. Consequently, there is an urgent need for means to study clinical SCVs and persisters and ultimately an effective method of treatment of SCVs and persisters.

DETAILED DESCRIPTION OF THE INVENTION

Surprisingly, the inventors have established that reversible persisters and reversible SCV's can be induced by low pH and that low pH adapted bacteria persisted intracellularly, specifically within lysosomes (low pH organelles). Low pH induced SCVs and persisters reverted to the highly virulent phenotype upon raising the pH.

Raising the pH intracellularly reverted the low pH adapted bacteria in vitro and in vivo and rendered the SCV's and persisters susceptible to antibacterial agents that are usually not effective intracellularly. This provide a completely new way of preventing and/or treating infections that persist primarily or at least partly intracellularly in intracellular compartments, such as but not limited to infections of the skin, of the respiratory or tonsillar epithelium (pharyngotonsillitis), (bovine) mastitis, or eradicating vaginal *S. agalactiae* infection (in macrophages) in pregnant women to prevent neonatal sepsis or preventing/treating *S. pneumoniae*-induced monocyte-derived macrophage apoptosis, or treating tuberculosis, leprosy, listeriosis, typhoid fever, bacillary dysenteria, plague, brucellosis, typhus, Rocky Mountains spotted fever, *chlamydia*, trachoma.

Accordingly, in a first aspect the invention provides for a method of treatment of a bacterial infection in a subject in need thereof, comprising:
   administration of an effective amount of an agent that increases the intracellular pH of a host cell and/or of an intracellular compartment of a host cell, and
   administration of an effective amount of a bactericidal agent. Said method is herein referred to as a method according to the invention.

Preferably, in the embodiments of the invention, the increase in pH activates a non-replicating intracellular bacterium and the bactericidal agent kills the activated intracellular bacterium.

In the embodiments of the invention, the bacterial infection is preferably a persistent bacterial infection and may be related to a persistent *S. aureus* infection of various tissues such as but not limited to skin, respiratory epithelium, tonsillar tissue, mastitis. In the embodiments of the invention, the bacterial infection is preferably an infection by a species selected from the group bacteria consisting of *Staphylococcus*, *Streptococcus* (such as *S. pyogenes*, *S. agalactiae* and *S.pneumonia*), *Actinomyces*, *Nocardia*, *Bacillus* (such as *B. anthracis*), *Coxiella* (such as *Coxiella burnetii*), *Rickettsia*, Mycobacteria (such as *M. tuberculosis* and *M. leprae*), *Legionella* (such as *L. pneumophila*), *Mycoplasma*, *Salmonella* (such as *S. typhimurium*), *Shigella* (such as *S. dysenteriae*), *Yersinia* (such as *Y. pestis*), *Brucella*, *Listeria* (such as *L. monocytogenesis*), *Actinobacillus* (such as *A. actinomycetemcomitans*), *Gardnerella* (such as *G. vaginalis*), *Chlamydia* (such as *C. trachomatis*), and Chlamidophila; a more preferred bacterium is a species of *Staphylococcus*; a preferred species of *Staphylococcus* is *S. aureus*. In the embodiments of the invention, a bacterium causing the bacterial infection is preferably present intracellularly in a host cell, such as in the cytosol; more preferably a bacterium causing the bacterial infection is preferably present within an intracellular compartment *S. aureus* Preferably, the bacterial infection comprises a population of bacteria comprising at least one subpopulation of bacteria that is resistant to a bactericidal agent (e.g. an antibiotic), such as, but not limited to MRSA. In the embodiments of the invention, the intracellular compartment may be any intracellular compartment wherein a bacterium can be persistently present and/or persistently present; preferably the intracellular compartment is a compartment with low pH. A preferred intracellular compartment is a compartment selected from the group consisting of an endosome, a lysozome, a phagosome, a phagolysosome, an autophagosome and an autolysosome' a more preferred intracellular compartment is a phagosome, lysozome of phagolysosome; an even more preferred intracellular compartment is a phagolysosome.

In the embodiments of the invention within a subject in need of treatment, the infected host cell is preferably a eukaryotic host cell; the eukaryotic host cell is preferably selected from the group consisting of professional and non-professional phagocytes, a lymphoid cell, a tonsillar tissue cell, a respiratory epithelial cell, a buccal epithelial cell, a bone marrow cell, an osteoblast, a keratinocyte, a muscle cell, a monocyte, a macrophage, a dendritic cell, an endothelial cell, an epithelial cell, a fibroblasts, an astrocyte, and an microglial cell; a more preferred eukaryotic host cell is a professional or a non-professional phagocyte. The subject may be any subject susceptible to or suffering from a persistent bacterial infection, such as, but not limited to, a human being or an animal. The animal may be a domestic animal or may be a breeding animal, pet, cattle, poultry or the like. A preferred subject is a human being and may be a newborn, a juvenile, an adult or an aged subject.

In the embodiments of the invention, the agent that increases the intracellular pH and/or the pH of the intracellular compartment may be any agent known to the person skilled in the art that effectively increases the intracellular pH and/or the pH of the intracellular compartment.

Preferably, in the embodiments of the invention, the agent that increases the intracellular pH and/or the pH of the intracellular compartment is an alkalizing agent, preferably an lysosomotropic alkalizing agent, preferably selected from the group of chloroquine, bafilomycin A1, ammonium chloride; a more preferred alkalizing agent is chloroquine. A preferred alkalyzing agent is one that is capable of entering the host cell and more preferably is targeted to the intracellular compartment wherein the infecting bacterium is present. The alkalizing agent may passively enter the cell or a vehicle may be used. The vehicle may be any vehicle known to a person skilled in the art that enables delivery into a host cell.

The term "low pH" in the embodiments of the invention is defined as a pH that is lower than pH 7.4; preferably low pH is about pH 7.0, 6.8, 6.6, 6.4, 6.2, 6.0, 5.8, 5.6, 5.4, 5.2, 5.0, 4.8, 4.6, 4.4, 4.2, 4.0, 3.8, 3.6, 3.4, 3.2, 3.0 or about 2.8. A low pH is preferably a pH lower than about 6.5 A more preferred low pH is about 5.0.

In the embodiments of the present invention, the term raising the pH and increasing the pH are used interchangeably and are defined as raising the pH about 0.2, 0.4, 0.6, 0.8, 1.0, 1.2, 1.4, 1.6, 1.8, 2.0, 2.2, 2.4, 2.6, 2.8, 3.0, 3.2, 3.4, 3.6, 3.8, 4.0, 4.2, 4.4, 4.6 or about 4.8. Preferably, the pH is raised to within the range of about pH 6 to about 7; preferably to within the range of about 6.5 to about 7 The term "an effective amount" in the embodiments of the invention in the context of an agent that increases the intracellular pH and/or the pH of an intracellular compartment is defined as any amount that is sufficient to raise the intracellular pH and/or the pH of an intracellular compartment at least about 0.2, 0.4, 0.6, 0.8, 1.0, 1.2, 1.4, 1.6, 1.8, 2.0, 2.2, 2.4, 2.6, 2.8, 3.0 to reach the range as depicted here above. The exact amount used will inter alia depend on the agent used and on the bodyweight of the subject.

The term "an effective amount" in the embodiments of the invention in the context of a bactericidal agent is defined as any amount that is sufficient to have a bactericidal affect intracellularly and/or within the intracellular compartment. The exact amount used will inter alia depend on the agent used and on the bodyweight of the subject.

Intracellular pH and the pH of an intracellular compartment can be assessed by any means known to the person skilled in the art. In the embodiments of the invention, the bactericidal agent may be any bactericidal agent known to the person skilled in the art and preferably is a bactericidal agent capable of entering the host cell and/or the intracellular compartment of the host cell. A preferred bactericidal agent is a chimeric bactericidal agent. A preferred bactericidal agent is selected from the group consisting of a bacteriocin or a functional part thereof, a bacterial lysin or autolysin or a functional part thereof, a bacteriophage lysin or a functional part thereof, a viral lysin or a part thereof, an antimicrobial peptide and an antibiotic. A further preferred bactericidal agent is a bacteriophage derived lytic structural protein (such as a tail lysin and a virion associated lytic protein) or an isolated lytic domain from such lytic structural protein or bacteriophage lysin. The bactericidal agents of the invention may be used alone or may be used in combinations of two or three or more bactericidal agents of the invention. A preferred bactericidal agent is one that is capable of entering the host cell and more preferably is targeted to the intracellular compartment wherein the infecting bacterium is present. The bactericidal agent may passively enter the cell or a vehicle may be used. The vehicle may be any vehicle known to a person skilled in the art that enables delivery into a host cell.

The antibiotic may be any antibiotic known to the person skilled in the art. A preferred antibiotic is selected from the group consisting of beta-lactam antibiotics such as penicillin derivatives, cephalosporins, monobactams, carbapenems, vancomycins, daptomycin, fluoroquinolones, metronidazole, nitrofurantoin, co-trimoxazole, telithromycin, aminoglycosidic antibiotics; a more preferred antibiotic is flucloxacillin. The bacteriocin may be any bacteriocin known to the person skilled in the art, preferably a bacteriocin of any Class I-IV.

Class I bacteriocins herein are small peptide inhibitors and include nisin and other lantibiotics.

Class II bacteriocins herein are small (<10 kDa) heat-stable proteins. This class is subdivided into five subclassses. The class IIa bacteriocins (pediocin-like bacteriocins) are the largest subgroup and contain an N-terminal consensus sequence -Tyr-Gly-Asn-Gly-Val-Xaa-Cys across this group. The C-terminal is responsible for species-specific activity, causing cell-leakage by permeabilizing the target cell wall. The class IIb bacteriocins (two-peptide bacteriocins) require two different peptides for activity. One such an example is lactococcin G, which permeabilizes cell membranes for monovalent ions such as Na and K, but not for divalents ones. Almost all of these bacteriocins have a GxxxG motif. This motif is also found in transmembrane proteins where they are involved in helix-helix interactions. The bacteriocin's GxxxG motif can interact with the motifs in the membranes of the bacterial cells and kill the bacteria by doing so. Class IIc encompasses cyclic peptides, which possesses the N-terminal and C-terminal regions covalentely linked. Enterocin AS-48 is the prototype of this group. Class IId cover single-peptide bacteriocins, which are not post-translated modified and do not show the pediocin-like signature. The best example of this group is the highly stable aureocin A53. This bacteriocin is stable under highly acidic environment (HCl 6 N), not affected by proteases and thermoresistant. The most recently proposed subclass is the Class IIe, which encompasses those bacteriocins composed by three or four non-pediocin like peptides. The best example is aureocin A70, a four-peptides bacteriocin, highly active against *L. monocytogenes*, with potential biotechnological applications.

Class III bacteriocins are large, heat-labile (>10 kDa) protein bacteriocins. This class is subdivided in two subclasses: subclass IIIa or bacteriolysins and subclass Mb. Subclass IIIa comprises those peptides that kill bacterial cells by cell-wall degradation, thus causing cell lysis. The best studied bacteriolysin is lysostaphin, a 27 kDa peptide that hydrolises several *Staphylococcus* spp. cell walls, principally *S. aureus*. Subclass Mb, in contrast, comprises those peptides that do not cause cell lysis, killing the target cells by disrupting the membrane potential, which causes ATP efflux.

Class IV bacteriocins are defined as complex bacteriocins containing lipid or carbohydrate moieties. Confirmatory experimental data was only recently established with the characterisation of Sublancin and Glycocin F (GccF) by two independent groups.

A preferred bacteriocin is selected from the group consisting of an acidocin, actagardine, agrocin, alveicin, aureocin, aureocin A53, aureocin A70, carnocin, carnocyclin circularin A, colicin, Curvaticin, divercin, duramycin, Enterocin, enterolysin, epidermin/gallidermin, erwiniocin, gassericin A, glycinecin, halocin, haloduracin, lactocin S, lactococin, lacticin, leucoccin, lysostaphin macedocin, mersacidin, mesentericin, microbisporicin, microcin S, mutacin, nisin, paenibacillin, planosporicin, pediocin, pentocin, plantaricin, pyocin, reutericin 6, sakacin, salivaricin, subtilin, sulfolobicin, thuricin 17, trifolitoxin, variacin, vibriocin, warnericin and a warnerin. The bacteriocin may be from a bacterium itself (24), such as, but not limited to a pyocin from *Pseudomonas aeruginosa*, preferably pyocin SA189 (25).

The antimicrobial peptide may be any antimicrobial peptide known to the person skilled in the art. Sometimes in the art, antimicrobial peptides are considered bacteriocins as listed here above. A preferred antimicrobial peptide is selected from the group consisting of a cationic or polycationic peptide, an amphipatic peptide, a sushi peptide, a defensin and a hydrophobic peptide.

The bacterial autolysin may be any a bacterial autolysin known to the persons killed in the art. A preferred bacterial autolysin is LytM.

The bacteriophage lysin may be any bacteriophage lysin known to the persons skilled in the art. Herein, the terms bacteriophage lysin, bacteriophage endolysin and endolysin are used interchangeably. A preferred endolysin is selected from the group defined in WO2012/150858, in WO2013/169104, in WO2011/023702, and in WO2012146738, which are herein incorporated by reference with their entire content.

The bactericidal agent may be any agent described here above or be a functional fragment thereof. Herein, the term functional fragment is interchangeably used with the term functional domain. A functional fragment is herein defined as a fragment that still has at least 20, 30, 40, 50, 60, 70, 80, 90, 95, or 99, or at least or 99.9% bactericidal activity as compared to the parent wherefrom the functional fragment is derived when assayed in identical conditions. Preferred functional fragments of bactericidal agents are described in WO2012/150858 and in WO2013/169104.

The bactericidal agent may be a fusion of a bactericidal agent and a functional fragment of bactericidal agents or may be a fusion of different, similar or identical bactericidal agents or of functional fragments of bactericidal agents.

The inventors have come to the surprising finding that the efficiency of a method of treatment according to the invention is greatly enhance when the bactericidal agent is targeted into the host cell. Such targeting may be achieved any means known to the person skilled in the art, as already depicted here above. A preferred means is a protein transduction domain that is operably linked to the bactericidal agent; further referred to herein as a protein transduction domain according to the invention. The term "protein transduction domain" is herein interchangeably used with the term "cell permeable protein (CPP)" and with the term "membrane translocating sequence". Operably linked is defined herein as such association of the protein transduction domain with the bactericidal agent that the bactericidal agent is targeted into the cell. A preferred operable linkage is fusion by means of covalent binding of the protein transduction domain to the bactericidal agent.

In the embodiments of the invention, the bactericidal agent preferably comprises a functional enzymatic domain of a cell wall lytic enzyme. A cell wall lytic enzyme is herein defined as any bactericidal agent that acts upon the cell wall of the bacterium it is effective against.

Preferably in the embodiments of the present invention, the bactericidal agent comprises a functional domain from a cell wall lytic enzyme and further comprises a protein transduction domain according to the invention. Preferably in the embodiments according to the invention, the bactericidal agent may further comprise an antimicrobial peptide. Such fusion bactericidal agent preferably is a cell wall lytic enzyme fused to an antimicrobial peptide selected from the group consisting of a cationic or polycationic peptide, an amphipatic peptide, a sushi peptide, a defensin and a hydrophobic peptide, more preferably a fusion protein as defined in U.S. Pat. No. 8,383,102 which is herein incorporated by reference in its entirety. Such bactericidal agent fused to an antimicrobial peptide may further comprise a protein transduction domain according to the invention.

In the embodiments of the invention, the bactericidal agent as described here above comprising a functional enzymatic domain of a cell wall lytic enzyme and/or comprising a protein transduction domain and/or comprising an antimicrobial peptide, may further preferably further comprises a cell wall binding domain. Said cell wall binding domain preferably is a cell wall binding domain that binds the peptidoglycan cell wall of the bacteria causing the bacterial infection to be treated.

In the embodiments of the invention, the protein transduction domain may be any such domain known to the person skilled in the art. Preferably, in the bactericidal agent according to the invention, the protein transduction domain is selected from the group consisting of SEQ ID NO: 12-25, or a variant thereof, wherein the variant is a functional protein transduction domain and has at least 40%, 45%, 50%, 60%, 65%, 70%, 75%, 80%, 85%, 90%, 95%, 96%, 97%, 98%, 99% or 100% sequence identity with a sequence selected from the group consisting of SEQ ID NO: 12-25, respectively.

Preferably, in the bactericidal agent according to the invention, the functional enzymatic domain from a cell wall lytic enzyme is selected from the group consisting of SEQ ID NO: 1-7, or a variant thereof, wherein the variant is a functional enzymatic domain from a cell wall lytic enzyme and has at least 40%, 45%, 50%, 60%, 65%, 70%, 75%, 80%, 85%, 90%, 95%, 96%, 97%, 98%, 99% or 100% sequence identity with a sequence selected from the group consisting of SEQ ID NO: 1-7, respectively.

Preferably, in the bactericidal agent according to the invention, the cell wall binding domain is selected from the group consisting of SEQ ID NO: 8-11, or a variant thereof, wherein the variant is a functional cell wall binding domain and has at least 40%, 45%, 50%, 60%, 65%, 70%, 75%, 80%, 85%, 90%, 95%, 96%, 97%, 98%, 99% or 100% sequence identity with a sequence selected from the group consisting of SEQ ID NO: 8-11, respectively.

Preferably, in the bactericidal agent according to the invention, the antimicrobial peptide is selected from the group consisting of SEQ ID NO: 70-90, or a variant thereof, wherein the variant is a functional cell wall binding domain and has at least 40%, 45%, 50%, 60%, 65%, 70%, 75%, 80%, 85%, 90%, 95%, 96%, 97%, 98%, 99% or 100% sequence identity with a sequence selected from the group consisting of SEQ ID NO: 70-90, respectively.

A preferred bactericidal agent according to the invention is a bactericidal agent with at least 40%, 45%, 50%, 60%, 65%, 70%, 75%, 80%, 85%, 90%, 95%, 96%, 97%, 98%, 99% or 100% sequence identity with a sequence selected from the group consisting of SEQ ID NO: 27, 28, 29, 30-47, or is a bactericidal agent encoded by polynucleotide sequence with at least 40%, 45%, 50%, 60%, 65%, 70%, 75%, 80%, 85%, 90%, 95%, 96%, 97%, 98%, 99% or 100% sequence identity with a sequence selected from the group consisting of SEQ ID NO: 50-67.

A preferred bactericidal agent according to the invention is an expression product from a vector with a sequence of at least 40%, 45%, 50%, 60%, 65%, 70%, 75%, 80%, 85%, 90%, 95%, 96%, 97%, 98%, 99% or 100% sequence identity with a sequence selected from the group consisting of SEQ ID NO: 91-108.

A further preferred bactericidal agent according to the invention is one selected from the group consisting of a bactericidal agent comprising a protein transduction domain selected from the group consisting of SEQ ID NO: 12-25, or a variant thereof, a functional enzymatic domain from a cell wall lytic enzyme selected from the group consisting of SEQ ID NO: 1-7, or a variant thereof and, optionally, a cell wall binding domain selected from the group consisting of SEQ ID NO: 8-11, or a variant thereof and/or an antimicrobial peptide selected from the group consisting of SEQ ID NO: 70-90, or a variant thereof; wherein a variant has at least 40%, 45%, 50%, 60%, 65%, 70%, 75%, 80%, 85%, 90%, 95%, 96%, 97%, 98%, 99% or 100% sequence identity with the respective original sequence.

Further to a method of treatment, this aspect relates to the embodiments of this aspect for the manufacture of a medicament for the treatment of a bacterial infection in a subject in need thereof. Further to a method of treatment, this aspect relates to the embodiments of this aspect for use in the treatment of a bacterial infection in a subject in need thereof.

In a second aspect, the invention provides for a chimeric bactericidal polypeptide comprising a functional enzymatic domain from a cell wall lytic enzyme selected from the group consisting of SEQ ID NO: 1-7, or a variant thereof, wherein the variant is a functional enzymatic domain from a cell wall lytic enzyme and has at least 40%, 45%, 50%, 60%, 65%, 70%, 75%, 80%, 85%, 90%, 95%, 96%, 97%, 98%, 99% or 100% sequence identity with a sequence selected from the group consisting of SEQ ID NO: 1-7, respectively; and a protein transduction domain selected from the group consisting of SEQ ID NO: 12-25, or a variant thereof, wherein the variant is a functional protein transduction domain and has at least 40%, 45%, 50%, 60%, 65%, 70%, 75%, 80%, 85%, 90%, 95%, 96%, 97%, 98%, or 99% or 100% sequence identity with a sequence selected from the group consisting of SEQ ID NO: 12-25, respectively; and optionally comprising a cell wall binding domain selected from the group consisting of SEQ ID NO: 8-11, or a variant thereof, wherein the variant is a functional cell wall binding domain and has at least 40%, 45%, 50%, 60%, 65%, 70%, 75%, 80%, 85%, 90%, 95%, 96%, 97%, 98%, 99% or 100% sequence identity with a sequence selected from the group consisting of SEQ ID NO: 8-11, respectively; and/or an antimicrobial peptide selected from the group consisting of SEQ ID NO: 70-90, or a variant thereof, wherein the variant is a functional cell wall binding domain and has at least 40%, 45%, 50%, 60%, 65%, 70%, 75%, 80%, 85%, 90%, 95%, 96%, 97%, 98%, 99% or 100% sequence identity with a sequence selected from the group consisting of SEQ ID NO: 70-90, respectively.

The invention further provides for a chimeric bactericidal polypeptide having at least 40%, 45%, 50%, 60%, 65%, 70%, 75%, 80%, 85%, 90%, 95%, 96%, 97%, 98%, or 99% or 100% sequence identity with a sequence selected from the group consisting of SEQ ID NO: 27, 28, 29, 30-47, or a chimeric bactericidal agent encoded by polynucleotide sequence with at least 40%, 45%, 50%, 60%, 65%, 70%, 75%, 80%, 85%, 90%, 95%, 96%, 97%, 98%, 99% or 100% sequence identity with a sequence selected from the group consisting of SEQ ID NO: 50-67.

The invention further provides for a chimeric bactericidal polypeptide selected from the group consisting of a bactericidal agent comprising a protein transduction domain selected from the group consisting of SEQ ID NO: 12-25, or a variant thereof, a functional enzymatic domain from a cell wall lytic enzyme selected from the group consisting of SEQ ID NO: 1-7, or a variant thereof and, optionally, a cell wall binding domain selected from the group consisting of SEQ ID NO: 8-11, or a variant thereof and/or an antimicrobial peptide selected from the group consisting of SEQ ID NO: 70-90, or a variant thereof; wherein a variant has at least 40%, 45%, 50%, 60%, 65%, 70%, 75%, 80%, 85%, 90%, 95%, 96%, 97%, 98%, 99% or 100% sequence identity with the respective original sequence.

The invention further provides for a polynucleotide encoding a chimeric bactericidal polypeptide according to this aspect of the invention.

The invention further provides for a polynucleotide construct comprising a polynucleotide encoding a chimeric bactericidal polypeptide according to the invention.

The invention further provides for a vector for expression and production of a chimeric bactericidal polypeptide according to the invention. A vector according to the invention preferably comprises a polynucleotide construct according to the invention comprising a polynucleotide encoding a chimeric bactericidal polypeptide according to the invention. A preferred vector according to the invention is a vector with a sequence of at least 40%, 45%, 50%, 60%, 65%, 70%, 75%, 80%, 85%, 90%, 95%, 96%, 97%, 98%, 99% or 100% sequence identity with a sequence selected from the group consisting of SEQ ID NO: 91-108.

The invention further provides for a host cell for the production of a chimeric bactericidal polypeptide according to the invention, comprising a polynucleotide construct or a vector according to the invention. The host cell may be any host cell suitable for the production of a chimeric bactericidal polypeptide according to the invention such a prokaryotic and a eukaryotic host cell.

The invention further provides for the production of a chimeric bactericidal polypeptide according to the invention, comprising culturing a host cell according to the invention, comprising a polynucleotide construct or a vector according to the invention under conditions conducive to the production of the a chimeric bactericidal polypeptide according to the invention and, optionally, isolating and/or purifying the chimeric bactericidal polypeptide produced.

Any suitable route of administration can be used to administer the alkalizing agent according to the invention and the bactericidal agent according to the invention including but not limited to: oral, aerosol or other device for delivery to the lungs, nasal spray, intravenous, intramuscular, intraperitoneal, intrathecal, vaginal, rectal, topical, lumbar puncture, intrathecal, and direct application to the brain and/or meninges. The alkalizing agent according to the invention and the bactericidal agent the invention may be administered to a subject in need thereof or to a cell, tissue or organ of said subject at least once a day, once a week, once a month, once every six months, once a year or whatever regime is suitable for the treatment.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one". The word "about" or "approximately" when used in association with a numerical value (e.g. about 10) preferably means that the value may be the given value (of 10) more or less 0.1% of the value.

All patent and literature references cited in the present specification are hereby incorporated by reference in their entirety.

Herein, sequence identity with a particular sequence preferably means sequence identity over the entire length of said particular polypeptide or polynucleotide sequence. The sequence information as provided herein should not be so narrowly construed as to require inclusion of erroneously identified bases. The skilled person is capable of identifying such erroneously identified bases and knows how to correct for such errors. "Similarity" between two amino acid sequences is determined by comparing the amino acid sequence and its conserved amino acid substitutes of one peptide or polypeptide to the sequence of a second peptide or polypeptide. Preferably, identity or similarity is calculated over the whole SEQ ID NO as identified herein. "Identity" and "similarity" can be readily calculated by known methods, including but not limited to those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heine, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48:1073 (1988).

Preferred methods to determine identity are designed to give the largest match between the sequences tested. Methods to determine identity and similarity are codified in publicly available computer programs. Preferred computer program methods to determine identity and similarity between two sequences include e.g. the GCG program package (Devereux, J., et al., Nucleic Acids Research 12 (1): 387 (1984)), BestFit, BLASTP, BLASTN, and FASTA (Altschul, S. F. et al., J. Mol. Biol. 215:403-410 (1990). The BLAST X program is publicly available from NCBI and other sources (BLAST Manual, Altschul, S., et al., NCBI NLM NIH Bethesda, Md. 20894; Altschul, S., et al., J. Mol. Biol. 215:403-410 (1990). The well-known Smith Waterman algorithm may also be used to determine identity.

Preferred parameters for polypeptide sequence comparison include the following: Algorithm: Needleman and Wunsch, J. Mol. Biol. 48:443-453 (1970); Comparison matrix: BLOSSUM62 from Hentikoff and Hentikoff, Proc. Natl. Acad. Sci. USA. 89:10915-10919 (1992); Gap Penalty: 12; and Gap Length Penalty: 4. A program useful with these parameters is publicly available as the "Ogap" program from Genetics Computer Group, located in Madison, Wis. The aforementioned parameters are the default parameters for amino acid comparisons (along with no penalty for end gaps).

Preferred parameters for nucleic acid comparison include the following: Algorithm: Needleman and Wunsch, J. Mol. Biol. 48:443-453 (1970); Comparison matrix: matches=+10, mismatch=0; Gap Penalty: 50; Gap Length Penalty: 3. Available as the Gap program from Genetics Computer Group, located in Madison, Wis. Given above are the default parameters for nucleic acid comparisons.

Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to ser; Arg to lys; Asn to gln or his; Asp to glu; Cys to ser or ala; Gln to asn; Glu to asp; Gly to pro; His to asn or gln; Ile to leu or val; Leu to ile or val; Lys to arg; gln or glu; Met to leu or ile; Phe to met, leu or tyr; Ser to thr; Thr to ser; Trp to tyr; Tyr to trp or phe; and, Val to ile or leu.

A polynucleotide is represented by a nucleotide sequence. A polypeptide is represented by an amino acid sequence.

TABLE 1

Sequences

| SEQ ID NO | Gene/Polypeptide | Sequence |
|---|---|---|
| 1 | EAD Ami2638 | MLKHIYSNHIKGNKITAPKPSIQGVVIHNDYGSMTPSQYLPWLYARE NNGTHVNGWASVYANRNEVLWYHPTDYVEWHCGNQWANANLIGFEVC ESYPGRISDKLFLENEEATLKVAADVMKSYGLPVNRNTVRLHNEFFG TSCPHRSWDLHVGKGEPYTTTNINKMKDYFIKRIKHYYD |
| 2 | EAD M23-LST | AATHEHSAQWLNNYKKGYGYGPYPLGINGGMHYGVDFFMNIGTPVKA ISSGKIVEAGWSNYGGGNQIGLIENDGVHRQWYMHLSKYNVKVGDYV KAGQIIGWSGSTGYSTAPHLHFQRMVNSFSNSTAQDPMPFLKSAGYG |
| 3 | EAD CHAP11 | MSIIMEVATMQAKLTKNEFIEWLKTSEGKQFNVDLWYGFQCFDYANA GWKVLFGLLLKGLGAKDIPFANNFDGLATVYQNTPDFLAQPGDMVVF GSNYGAGYGHVAWVIEATLDYIIVYEQNWLGGGWTDGIEQPGWGWEK VTRRQHAYDFPMWFIRPNFK |
| 4 | EAD CHAPTw | MKTLKQAESYIKSKVNTGTDFDGLYGYQCMDLAVDYIYHVTDGKIRM WGNAKDAINNSFGGTATVYKNYPAFRPKYGDVVVWTTGNFATYGHIA IVTNPDPYGDLQYVTVLEQNWNGNGIYKTELATIRTHDYTGITHFIR PNFA |
| 5 | EAD C11811 | MGLPSPKKRKPTASEVAAWAKRMIGRRVDVDGYHGAQCWDLPNYIFN RYWHFKTTGNAIAMAWYRYPKGFKFYRNTRNFVPKPGDMAVWGKGSF NNGVGHTAVVIGPSTKSYFTSVDQNWIGANSYTGSPGAKIKHSYNGI SGFVRPPYHA |
| 6 | EAD TC187 | MALPKTGKPTAKQVVDWAINLIGSGVDVDGYYGRQCWDLPNYIFNRY WNFKTPGNARDMAWYRYPEGFKVFRNTSDFVPKPGDIAVWTGGNYNW NTWGHTGIVVGPSTKSYFYSVDQNWNNSNSYVGSPAAKIKHSYFGVT HFVRPA |
| 7 | EAD CHAPK/GH15 | MAKTQAEINKRLDAYAKGTVDSPYRIKKATSYDPSFGVMEAGAIDAD GYYHAQCQDLITDYVLWLTDNKVRTWGNAKDQIKQSYGTGFKIHENK PSTVPKKGWIAVFTSGSYQQWGHIGIVYDGGNTSTFTILEQNWNGYA NKKPTKRVDNYYGLTHFIEIPVKA |
| 8 | CBD CBD2638 | GGKLEVSKAATIKQSDVKQEVKKQEAKQIVKATDWKQNKDGIWYKAE HASFTVTAPEGIITRYKGPWTGHPQAGVLQKGQTIKYDEVQKFDGHV WVSWETFEGETVYMPVRTWDAKTGKVGKLWGEIK |
| 9 | CBD CBD118II | APKSKPSKIKTTWNWGGKFTANSTIKVRKSPGLKGIVVESGSWLYKG NYVPFDQVIKKDGYWWIRFKYVQPGSSNKHF |
| 10 | CBD CWT-LST | WKTNKYGTLYKSESASFTPNTDIITRTTGPFRSMPQSGVLKAGQTIH YDEVMKQDGHVWVGYTGNSGQRIYLPVRTWNKSTNTLGVLWGTIK |
| 11 | CBD CWT-Ale-1 | YKTNKYGTLYKSESASFTANTDIITRLTGPFRSMPQSGVLRKGLTIK YDEVMKQDGHVWVGYNTNSGKRVYLPVRTWNESTGELGPLWGTIK |
| 12 | CPP 1: Kala Syn | WEAKLAKALAKALAKALAKHLAKALAKALKACEA |
| 13 | CPP 2: M918 | MVTVLFRRLRIRRASGPPRVRV |
| 14 | CPP 3: MAP | KLALKLALKALKAALKLA |
| 15 | CPP 4: MPG | GALFLGFLGAAGSTMGAWSQPKKKRKV |
| 16 | CPP 5: Penetratin | RQIKIWFQNRRMKWKK |
| 17 | CPP 6: Pep-1 | KETWWETWWTEWSQPKKKRKV |
| 18 | CPP 7: PTD5-Syn | RRQRRTSKLMKR |
| 19 | CPP 8: pVEC | LLIILRRRIRKQAHAHSK |
| 20 | CPP 9: R6W3 | RRWWRRWRR |
| 21 | CPP10: Polyarginines | (R)n: 6 < n < 15 |
| 22 | CPP 11: TAT | GRKKRRQRRRPPQ |
| 23 | CPP 12: TAT | RKKRRQRRR |

TABLE 1-continued

Sequences

| SEQ ID NO | Gene/Polypeptide | Sequence |
|---|---|---|
| 24 | CPP 13: Transportan | GWTLNSAGYLLGKINLKALAALAKKIL |
| 25 | CPP 14: Transportan 10 | AGYLLGKINLKALAALAKKIL |
| 26 | — | |
| 27 | M23-CBD | MAATHEHSAQWLNNYKKGYGYGPYPLGINGGMHYGVDFFMNIGTPVK AISSGKIVEAGWSNYGGGNQIGLIENDGVHRQWYMHLSKYNVKVGDY VKAGQIIGWSGSTGYSTAPHLHFQRMVNSFSNSTAQDPMPFLKSAGY GGKLEVSKAATIKQSDVKQEVKKQEAKQIVKATDWKQNKDGIWYKAE HASFTVTAPEGIITRYKGPWTGHPQAGVLQKGQTIKYDEVQKFDGHV WVSWETFEGETVYMPVRTWDAKTGKVGKLWGEIK |
| 28 | CHAP-CBD | MSIIMEVATMQAKLTKNEFIEWLKTSEGKQFNVDLWYGFQCFDYANA GWKVLFGLLLKGLGAKDIPFANNFDGLATVYQNTPDFLAQPGDMVVF GSNYGAGYGHVAWVIEATLDYIIVYEQNWLGGGWTDGIEQPGWGWEK VTRRQHAYDFPMWFIRPNFKGGKLEVSKAATIKQSDVKQEVKKQEAK QIVKATDWKQNKDGIWYKAEHASFTVTAPEGIITRYKGPWTGHPQAG VLQKGQTIKYDEVQKFDGHVWVSWETFEGETVYMPVRTWDAKTGKVG KLWGEIK |
| 29 | Ami-CBD | MLKHIYSNHIKGNKITAPKPSIQGVVIHNDYGSMTPSQYLPWLYARE NNGTHVNGWASVYANRNEVLWYHPTDYVEWHCGNQWANANLIGFEVC ESYPGRISDKLFLENEEATLKVAADVMKSYGLPVNRNTVRLHNEFFG TSCPHRSWDLHVGKGEPYTTTNINKMKDYFIKRIKHYYDGGKLEVSK AATIKQSDVKQEVKKQEAKQIVKATDWKQNKDGIWYKAEHASFTVTA PEGIITRYKGPWTGHPQAGVLQKGQTIKYDEVQKFDGHVWVSWETFE GETVYMPVRTWDAKTGKVGKLWGEIK |
| 30 | Ami-CBD-Penetratin | MLKHIYSNHIKGNKITAPKPSIQGVVIHNDYGSMTPSQYLPWLYARE NNGTHVNGWASVYANRNEVLWYHPTDYVEWHCGNQWANANLIGFEVC ESYPGRISDKLFLENEEATLKVAADVMKSYGLPVNRNTVRLHNEFFG TSCPHRSWDLHVGKGEPYTTTNINKMKDYFIKRIKHYYDGGKLEVSK AATIKQSDVKQEVKKQEAKQIVKATDWKQNKDGIWYKAEHASFTVTA PEGIITRYKGPWTGHPQAGVLQKGQTIKYDEVQKFDGHVWVSWETFE GETVYMPVRTWDAKTGKVGKLWGEIKELRQIKIWFQNRRMKWKK |
| 31 | Ami-CBD-R9 | MLKHIYSNHIKGNKITAPKPSIQGVVIHNDYGSMTPSQYLPWLYARE NNGTHVNGWASVYANRNEVLWYHPTDYVEWHCGNQWANANLIGFEVC ESYPGRISDKLFLENEEATLKVAADVMKSYGLPVNRNTVRLHNEFFG TSCPHRSWDLHVGKGEPYTTTNINKMKDYFIKRIKHYYDGGKLEVSK AATIKQSDVKQEVKKQEAKQIVKATDWKQNKDGIWYKAEHASFTVTA PEGIITRYKGPWTGHPQAGVLQKGQTIKYDEVQKFDGHVWVSWETFE GETVYMPVRTWDAKTGKVGKLWGEIKELRRRRRRRRR |
| 32 | Ami-CBD-TAT | MLKHIYSNHIKGNKITAPKPSIQGVVIHNDYGSMTPSQYLPWLYARE NNGTHVNGWASVYANRNEVLWYHPTDYVEWHCGNQWANANLIGFEVC ESYPGRISDKLFLENEEATLKVAADVMKSYGLPVNRNTVRLHNEFFG TSCPHRSWDLHVGKGEPYTTTNINKMKDYFIKRIKHYYDGGKLEVSK AATIKQSDVKQEVKKQEAKQIVKATDWKQNKDGIWYKAEHASFTVTA PEGIITRYKGPWTGHPQAGVLQKGQTIKYDEVQKFDGHVWVSWETFE GETVYMPVRTWDAKTGKVGKLWGEIKELGRKKRRQRRRPPQ |
| 33 | Ami-Penetratin | MLKHIYSNHIKGNKITAPKPSIQGVVIHNDYGSMTPSQYLPWLYARE NNGTHVNGWASVYANRNEVLWYHPTDYVEWHCGNQWANANLIGFEVC ESYPGRISDKLFLENEEATLKVAADVMKSYGLPVNRNTVRLHNEFFG TSCPHRSWDLHVGKGEPYTTTNINKMKDYFIKRIKHYYDGELRQIKI WFQNRRMKWKK |
| 34 | Ami-R9 | MLKHIYSNHIKGNKITAPKPSIQGVVIHNDYGSMTPSQYLPWLYARE NNGTHVNGWASVYANRNEVLWYHPTDYVEWHCGNQWANANLIGFEVC ESYPGRISDKLFLENEEATLKVAADVMKSYGLPVNRNTVRLHNEFFG TSCPHRSWDLHVGKGEPYTTTNINKMKDYFIKRIKHYYDGELRRRRR RRRR |
| 35 | Ami-TAT | MLKHIYSNHIKGNKITAPKPSIQGVVIHNDYGSMTPSQYLPWLYARE NNGTHVNGWASVYANRNEVLWYHPTDYVEWHCGNQWANANLIGFEVC ESYPGRISDKLFLENEEATLKVAADVMKSYGLPVNRNTVRLHNEFFG TSCPHRSWDLHVGKGEPYTTTNINKMKDYFIKRIKHYYDGELGRKKR RQRRRPPQ |

TABLE 1-continued

Sequences

| SEQ ID NO | Gene/Polypeptide | Sequence |
|---|---|---|
| 36 | CHAP11-CBD-Penetratin | MSIIMEVATMQAKLTKNEFIEWLKTSEGKQFNVDLWYGFQCFDYANA GWKVLFGLLLKGLGAKDIPFANNFDGLATVYQNTPDFLAQPGDMVVF GSNYGAGYGHVAWVIEATLDYIIVYEQNWLGGGWTDGIEQPGWGWEK VTRRQHAYDFPMWFIRPNFKGGKLEVSKAATIKQSDVKQEVKKQEAK QIVKATDWKQNKDGIWYKAEHASFTVTAPEGIITRYKGPWTGHPQAG VLQKGQTIKYDEVQKFDGHVWVSWETFEGETVYMPVRTWDAKTGKVG KLWGEIKELRQIKIWFQNRRMKWKK |
| 37 | CHAP11-CBD-R9 | MSIIMEVATMQAKLTKNEFIEWLKTSEGKQFNVDLWYGFQCFDYANA GWKVLFGLLLKGLGAKDIPFANNFDGLATVYQNTPDFLAQPGDMVVF GSNYGAGYGHVAWVIEATLDYIIVYEQNWLGGGWTDGIEQPGWGWEK VTRRQHAYDFPMWFIRPNFKGGKLEVSKAATIKQSDVKQEVKKQEAK QIVKATDWKQNKDGIWYKAEHASFTVTAPEGIITRYKGPWTGHPQAG VLQKGQTIKYDEVQKFDGHVWVSWETFEGETVYMPVRTWDAKTGKVG KLWGEIKELRRRRRRRRR |
| 38 | CHAP11-CBD-TAT | MSIIMEVATMQAKLTKNEFIEWLKTSEGKQFNVDLWYGFQCFDYANA GWKVLFGLLLKGLGAKDIPFANNFDGLATVYQNTPDFLAQPGDMVVF GSNYGAGYGHVAWVIEATLDYIIVYEQNWLGGGWTDGIEQPGWGWEK VTRRQHAYDFPMWFIRPNFKGGKLEVSKAATIKQSDVKQEVKKQEAK QIVKATDWKQNKDGIWYKAEHASFTVTAPEGIITRYKGPWTGHPQAG VLQKGQTIKYDEVQKFDGHVWVSWETFEGETVYMPVRTWDAKTGKVG KLWGEIKELGRKKRRQRRRPPQ |
| 39 | CHAP11-Penetratin | MSIIMEVATMQAKLTKNEFIEWLKTSEGKQFNVDLWYGFQCFDYANA GWKVLFGLLLKGLGAKDIPFANNFDGLATVYQNTPDFLAQPGDMVVF GSNYGAGYGHVAWVIEATLDYIIVYEQNWLGGGWTDGIEQPGWGWEK VTRRQHAYDFPMWFIRPNFKELRQIKIWFQNRRMKWKK |
| 40 | CHAP11-R9 | MSIIMEVATMQAKLTKNEFIEWLKTSEGKQFNVDLWYGFQCFDYANA GWKVLFGLLLKGLGAKDIPFANNFDGLATVYQNTPDFLAQPGDMVVF GSNYGAGYGHVAWVIEATLDYIIVYEQNWLGGGWTDGIEQPGWGWEK VTRRQHAYDFPMWFIRPNFKELRRRRRRRRR |
| 41 | CHAP11-TAT | MSIIMEVATMQAKLTKNEFIEWLKTSEGKQFNVDLWYGFQCFDYANA GWKVLFGLLLKGLGAKDIPFANNFDGLATVYQNTPDFLAQPGDMVVF GSNYGAGYGHVAWVIEATLDYIIVYEQNWLGGGWTDGIEQPGWGWEK VTRRQHAYDFPMWFIRPNFKELGRKKRRQRRRPPQ |
| 42 | M23-CBD-Penetratin | MAATHEHSAQWLNNYKKGYGYGPYPLGINGGMHYGVDFFMNIGTPVK AISSGKIVEAGWSNYGGGNQIGLIENDGVHRQWYMHLSKYNVKVGDY VKAGQIIGWSGSTGYSTAPHLHFQRMVNSFSNSTAQDPMPFLKSAGY GGKLEVSKAATIKQSDVKQEVKKQEAKQIVKATDWKQNKDGIWYKAE HASFTVTAPEGIITRYKGPWTGHPQAGVLQKGQTIKYDEVQKFDGHV WVSWETFEGETVYMPVRTWDAKTGKVGKLWGEIKELRQIKIWFQNRR MKWKK |
| 43 | M23-CBD-R9 | MAATHEHSAQWLNNYKKGYGYGPYPLGINGGMHYGVDFFMNIGTPVK AISSGKIVEAGWSNYGGGNQIGLIENDGVHRQWYMHLSKYNVKVGDY VKAGQIIGWSGSTGYSTAPHLHFQRMVNSFSNSTAQDPMPFLKSAGY GGKLEVSKAATIKQSDVKQEVKKQEAKQIVKATDWKQNKDGIWYKAE HASFTVTAPEGIITRYKGPWTGHPQAGVLQKGQTIKYDEVQKFDGHV WVSWETFEGETVYMPVRTWDAKTGKVGKLWGEIKELRRRRRRRRR |
| 44 | M23-CBD-TAT | MAATHEHSAQWLNNYKKGYGYGPYPLGINGGMHYGVDFFMNIGTPVK AISSGKIVEAGWSNYGGGNQIGLIENDGVHRQWYMHLSKYNVKVGDY VKAGQIIGWSGSTGYSTAPHLHFQRMVNSFSNSTAQDPMPFLKSAGY GGKLEVSKAATIKQSDVKQEVKKQEAKQIVKATDWKQNKDGIWYKAE HASFTVTAPEGIITRYKGPWTGHPQAGVLQKGQTIKYDEVQKFDGHV WVSWETFEGETVYMPVRTWDAKTGKVGKLWGEIKELGRKKRRQRRRP PQ |
| 45 | M23-Penetratin | MAATHEHSAQWLNNYKKGYGYGPYPLGINGGMHYGVDFFMNIGTPVK AISSGKIVEAGWSNYGGGNQIGLIENDGVHRQWYMHLSKYNVKVGDY VKAGQIIGWSGSTGYSTAPHLHFQRMVNSFSNSTAQDPMPFLKSAGY GELRQIKIWFQNRRMKWKK |
| 46 | M23-R9 | MAATHEHSAQWLNNYKKGYGYGPYPLGINGGMHYGVDFFMNIGTPVK AISSGKIVEAGWSNYGGGNQIGLIENDGVHRQWYMHLSKYNVKVGDY VKAGQIIGWSGSTGYSTAPHLHFQRMVNSFSNSTAQDPMPFLKSAGY GELRRRRRRRRR |

TABLE 1-continued

Sequences

| SEQ ID NO | Gene/ Polypeptide | Sequence |
|---|---|---|
| 47 | M23-TAT | MAATHEHSAQWLNNYKKGYGYGPYPLGINGGMHYGVDFFMNIGTPVK AISSGKIVEAGWSNYGGGNQIGLIENDGVHRQWYMHLSKYNVKVGDY VKAGQIIGWSGSTGYSTAPHLHFQRMVNSFSNSTAQDPMPFLKSAGY GELGRKKRRQRRRPPQ |
| 48 | — | |
| 49 | — | |
| 50 | Ami-CBD-Penetratin | Polynucleotide sequence; see sequence listing |
| 51 | Ami-CBD-R9 | Polynucleotide sequence; see sequence listing |
| 52 | Ami-CBD-TAT | Polynucleotide sequence; see sequence listing |
| 53 | Ami-Penetratin | Polynucleotide sequence; see sequence listing |
| 54 | Ami-R9 | Polynucleotide sequence; see sequence listing |
| 55 | Ami-TAT | Polynucleotide sequence; see sequence listing |
| 56 | CHAP11-CBD-Penetratin | Polynucleotide sequence; see sequence listing |
| 57 | CHAP11-CBD-R9 | Polynucleotide sequence; see sequence listing |
| 58 | CHAP11-CBD-TAT | Polynucleotide sequence; see sequence listing |
| 59 | CHAP11-Penetratin | Polynucleotide sequence; see sequence listing |
| 60 | CHAP11-R9 | Polynucleotide sequence; see sequence listing |
| 61 | CHAP11-TAT | Polynucleotide sequence; see sequence listing |
| 62 | M23-CBD-Penetratin | Polynucleotide sequence; see sequence listing |
| 63 | M23-CBD-R9 | Polynucleotide sequence; see sequence listing |
| 64 | M23-CBD-TAT | Polynucleotide sequence; see sequence listing |
| 65 | M23-Penetratin | Polynucleotide sequence; see sequence listing |
| 66 | M23-R9 | Polynucleotide sequence; see sequence listing |
| 67 | M23-TAT | Polynucleotide sequence; see sequence listing |
| 68 | — | |
| 69 | — | |
| 70 | LL-37 | LLGDFFRKSKEKIGKEFKRIVQRIKDFLRNLVPRTES |
| 71 | SMAP-29 | RGLRRLGRKIAHGVKKYGPTVLRIIRIAG |
| 72 | Indolicidin | ILPWKWPWWPWRR |
| 73 | Protegrin | RGGRLCYCRRRFCVCVGR |
| 74 | Cecropin P1 | SWLSKTAKKLENSAKKRISEGIAIAIQGGPR |
| 75 | Magainin | GIGKFLHSAKKFGKAFVGEIMNS |
| 76 | Pleurocidin | GWGSFFKKAAHVGKHVGKAALTHYL |
| 77 | Cecropin A A. aegyptae | GGLKKLGKKLEGAGKRVFNAAEKALPVVAGAKALRK |

TABLE 1-continued

Sequences

| SEQ ID NO | Gene/Polypeptide | Sequence |
|---|---|---|
| 78 | Cecroptin A D. melanogaster | GWLKKIGKKIERVGQHTRDATIQGLGIPQQAANVAATARG |
| 79 | Buforin II | TRSSRAGLQFPVGRVHRLLRK |
| 80 | Sarcotoxin IA | GWLKKIGKKIERVGQHTRDATIQGLGIAQQAANVAATAR |
| 81 | Ascaphine | GIKDWIKGAAKKLIKTVASHIANQ |
| 82 | Apidaecine | ANRPVYIPPPRPPHPRL |
| 83 | Nigrocine | GLLSKVLGVGKKVLCGVSGLVC |
| 84 | Pseudin 1 | GLNTLKKVFQGLHEAIKLINNHVQ |
| 85 | Parasin 1 | KGRGKQGGKVRAKAKTRSS |
| 86 | Lycotoxin | IWLTALKFLGKHAAKKLAKQQLSKL |
| 87 | Ranalexin | FLGGLIVPAMICAVTKKC |
| 88 | Melittin | GIGAVLKVLTTGLPALISWIKRKRQQ |
| 89 | OR-7 | KTYYGTNGVHCTKNSLWGKVRLKNMKYDQNTTYMGRLQDILLGWATG AFGKTFH |
| 90 | Buforin I | AGRGKQGGKVRAKAKTRSSRAGLQFPVGRVHRLLRKGNY |
| 91 | Ami-CBD-Penetratin | Vector construct: see sequence listing |
| 92 | Ami-CBD-R9 | Vector construct: see sequence listing |
| 93 | Ami-CBD-TAT | Vector construct: see sequence listing |
| 94 | Ami-Penetratin | Vector construct: see sequence listing |
| 95 | Ami-R9 | Vector construct: see sequence listing |
| 96 | Ami-TAT | Vector construct: see sequence listing |
| 97 | CHAP11-CBD-Penetratin | Vector construct: see sequence listing |
| 98 | CHAP11-CBD-R9 | Vector construct: see sequence listing |
| 99 | CHAP11-CBD-TAT | Vector construct: see sequence listing |
| 100 | CHAP11-Penetratin | Vector construct: see sequence listing |
| 101 | CHAP11-R9 | Vector construct: see sequence listing |
| 102 | CHAP11-TAT | Vector construct: see sequence listing |
| 103 | M23-CBD-Penetratin | Vector construct: see sequence listing |
| 104 | M23-CBD-R9 | Vector construct: see sequence listing |
| 105 | M23-CBD-TAT | Vector construct: see sequence listing |
| 106 | M23-Penetratin | Vector construct: see sequence listing |
| 107 | M23-R9 | Vector construct: see sequence listing |
| 108 | M23-TAT | Vector construct: see sequence listing |

FIGURE LEGENDS

FIG. 1.

Induction of S. aureus SCVs and non-replicating persisters by low pH and bacterial regrowth through pH increase.

MRSA S. aureus strains 6850 (a), JE2 (b) and Cowan (c) were inoculated in media buffered at different pH as indicated. Colony phenotypes of viable bacteria were determined and the percentage of SCVs plotted over time. Three independent experiments done in triplicates are presented as mean±SEM.

Low pH-induced MRSA S. aureus strains 6850 (d), JE2 (e) and Cowan (f) persisters were re-inoculated in various buffered pH media as indicated and growth was followed over time. Three independent experiments done in triplicates presented as mean±SEM.

FIG. 2

Intracellular Persistence of S. aureus within Phagolysosomes.

A549 cells were infected with S. aureus Cowan and extracellular bacteria were killed by addition of flucloxacillin. The number (a) and phenotype (b) of viable intracellular persisting bacteria were determined at indicated time points. Data are pooled from two experiments performed in triplicates, mean±SEM.

FIG. 3

Reduction of S. aureus persisters through phagolysosome alkalinization. S. aureus Cowan-infected A549 cells were treated with flucloxacillin alone (control) or supplemented with lysosomotropic alkalinizing agents (chloroquine (a), bafilomycin A1 (b) and ammonium chloride (c)). Colony phenotypes of viable intracellular persisting bacteria were determined and enumerated at indicated time points. Data were pooled from three independent experiments done in triplicates, mean±SEM. Two-way ANOVA found the factors time and treatment to be significant (p-value<0.01).

FIG. 4

Reduction of S. aureus Persisters by Chloroquine in an In Vivo Infection Model.

Mice were infected with S. aureus Cowan intraperitoneally. Six hours and two days post-infection mice were treated with 1 mg flucloxacillin and 0.2 mg chloroquine (+CQ). Mice treated with flucloxacillin only served as control (−CQ). †, sacrifice (a). Colony phenotypes of bacteria recovered from target tissues (b), peripheral blood and peritoneal lavage (c) were determined and enumerated. Each point represents one mouse. Horizontal bars indicate mean±SEM, n=11 mice per group. PL, peritoneal lavage. Two-way ANOVA found the factor treatment to be significant (p-value<0.01).

FIG. 5

Intracellular targeting of S. aureus in osteosarcoma cells by mixtures of engineered endolysins. (A) Cells infected for 3 h with S. aureus Newman (MOI 0.1) treated by endolysin mixtures for 1 h and 4 h. (B) Cells infected for 3 h with S. aureus Newman (MOI 0.1) treated by endolysin mixtures for 1 h and 4 h in the presence of 20 µM chloroquine. (C) Cells infected for 3 h with S. aureus Cowan (MOI 0.01) treated by endolysin mixtures for 1 h and 4 h. (D) Cells infected for 3 h with S. aureus Cowan (MOI 0.01) treated by endolysin mixtures for 1 h and 4 h in the presence of 20 µM chloroquine.

FIG. 6

Intracellular targeting of S. aureus in osteosarcoma cells (MOI 1.0) by mixtures of engineered endolysins. (A) Cells infected for 24 h with S. aureus Newman treated by endolysin mixtures for 4 h. (B) Cells infected for 24 h with S. aureus Newman treated by endolysin mixtures for 4 h in the presence of 20 µM chloroquine. (C) Cells infected for 72 h with S. aureus Cowan treated by endolysin mixtures for 4 h. (D) Cells infected for 72 h with S. aureus Cowan treated by endolysin mixtures for 4 h in the presence of 20 µM chloroquine.

FIG. 7

Activity of bactericidal agents according to the invention comprising a functional enzymatic domain from a cell wall lytic enzyme and further comprising a protein transduction domain on the N-terminal side of the molecule: (A) R9-CHAP-CBD, (B) R9-M23-CBD, (C) TAT-Ami-CBD, (D) TAT-CHAP-CBD, and (E) TAT-M23-CBD.

EXAMPLES

The present invention is further described by the following examples which should not be construed as limiting the scope of the invention.

Unless stated otherwise, the practice of the invention will employ standard conventional methods of molecular biology, virology, microbiology or biochemistry. Such techniques are described in Sambrook et al. (1989) Molecular Cloning, A Laboratory Manual (2$^{nd}$ edition), Cold Spring Harbor Laboratory, Cold Spring Harbor Laboratory Press; in Sambrook and Russell (2001) Molecular Cloning: A Laboratory Manual, Third Edition, Cold Spring Harbor Laboratory Press, NY; in Volumes 1 and 2 of Ausubel et al. (1994) Current Protocols in Molecular Biology, Current Protocols, USA; and in Volumes I and II of Brown (1998) Molecular Biology LabFax, Second Edition, Academic Press (UK); Oligonucleotide Synthesis (N. Gait editor); *Nucleic Acid Hybridization* (Hames and Higgins, eds.).

Example 1

Induction of *Staphylococcus aureus* persisters by low pH, awakening by phagolysosomal alkalinization and effective treatment by phagolysosomal alkalinization combined with a bactericidal agent.

1.1 pH-Dependent Induction of S. aureus Small Colony Variants (SCVs)

Figure 1B:
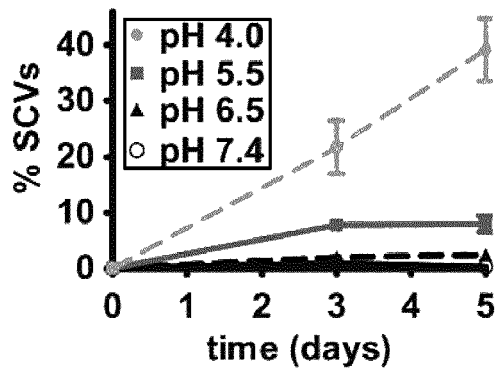
Figure 1C:
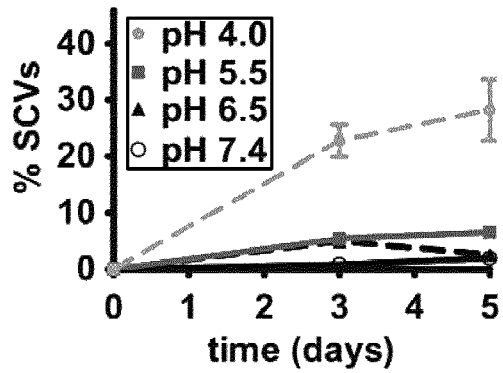

The well-defined MSSA strains 6850 and Cowan and MRSA strain JE2 were grown in 4.0, 5.5, 6.5 and 7.4 pH media, mimicking the pH found in physiologic sites such as lysosomes, abscesses and blood. Directly after inoculation S. aureus showed a large colony phenotype, independent of the pH. The frequency of SCVs significantly increased over time in pH 4.0 growth medium and reached 39% (JE2 and 6850) and 28% (Cowan) after five days. In contrast pH 7.4 growth medium sustained SCVs below 2% in all strains tested (FIG. 1a-c). An intermediate percentage of SCVs was found at pH 5.5 and 6.5. Thus, we showed a clear correlation between low pH and SCV formation. This method permitted easy and controlled formation of unstable, non-genetically modified SCVs in various S. aureus strains.

1.2 Induction of Non-Replicating S. aureus by Low pH

The pH-dependent growth of S. aureus Cowan was followed over time by labeling the bacterial cell wall with fluorescent cell wall binding domains (CBDs). Immediately after staining, bacterial cell walls were fully labeled. After three days in pH 4.0 growth medium, the majority of bacteria still exhibited fluorescent cell walls, consistent with absent bacterial replication. In contrast, bacteria grown at pH 7.4 proliferated extensively, demonstrated by highly fragmented and 89 reduced fluorescent cell wall labeling. Scanning electron microscopy (SEM) of bacteria originating from a small colony, obtained under low-pH conditions, showed impaired cell division resulting in rod-shaped *S. aureus*, in contrast to large colony bacteria showing normal cell division.

1.3 Growth Resumption of Low pH-Adapted *S. aureus* Persisters

Figure 1D:
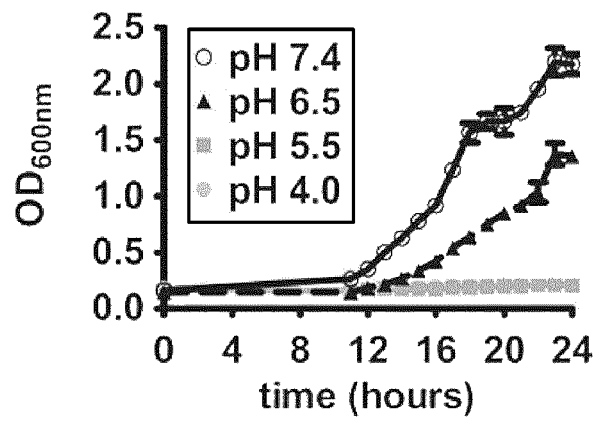
Figure 1E:
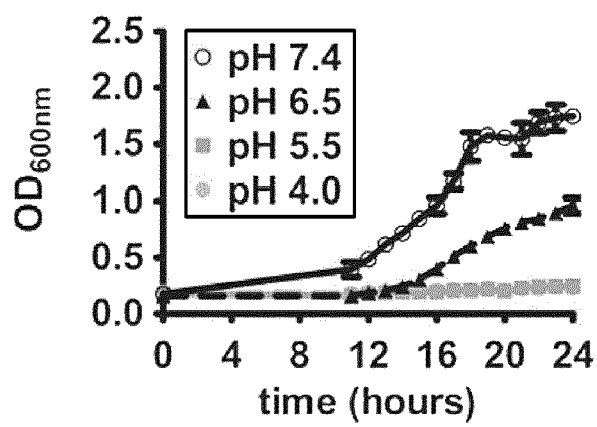
Figure 1F:
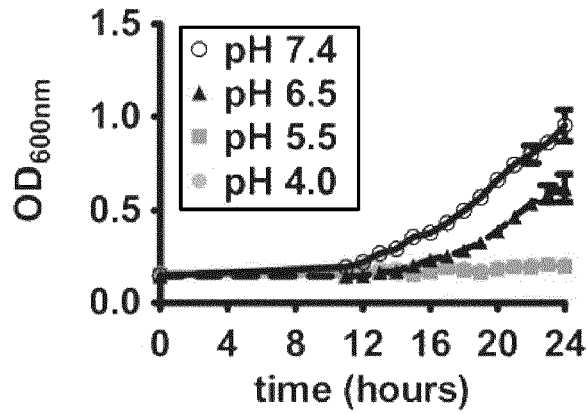

Our findings indicated that both, SCVs and non-replicating persisters, are induced by low pH. In clinics, the presence of these persisting bacteria correlates with increased recurrence of infection which implies that bacteria revert to a highly virulent and fast-growing form 14. We therefore tested in vitro whether low pH-induced SCVs and/or non-replicating persisters can restore normal growth in neutral pH. Non-replicating *S. aureus* persisters were induced and kept at pH 4.0 for three days and then transferred to pH 4.0, 5.5, 6.5 or 7.4 growth media. Bacteria in pH 7.4 and 6.5 resumed growth after approximately 12 hours (FIG. 1*d-f*) whereas bacteria kept at low pHs (<6.5) remained in a nonproliferating state (FIG. 1*d-f*). These data suggest that both persisting phenotypes were reversible adaptions to low pH as supported by the capability of regrowth upon neutralization of pH.

1.4 Intracellular Induction of *S. aureus* SCVs

Figure 2A:
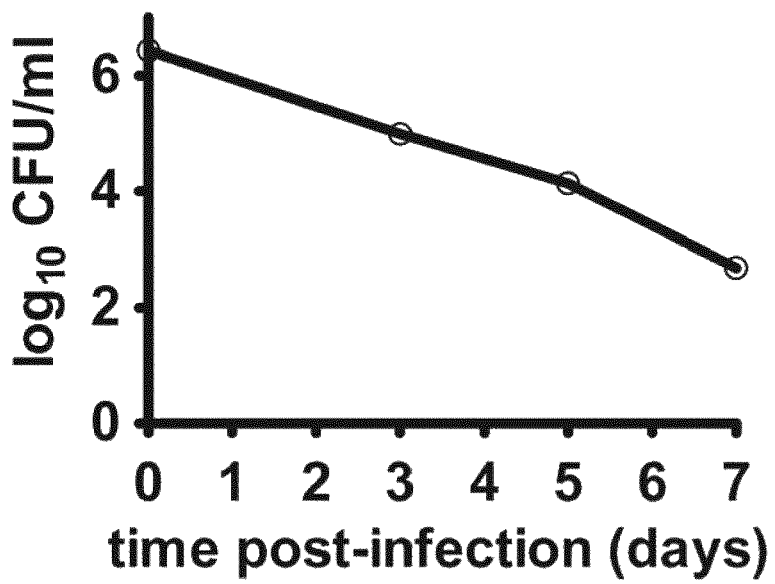
Figure 2B:
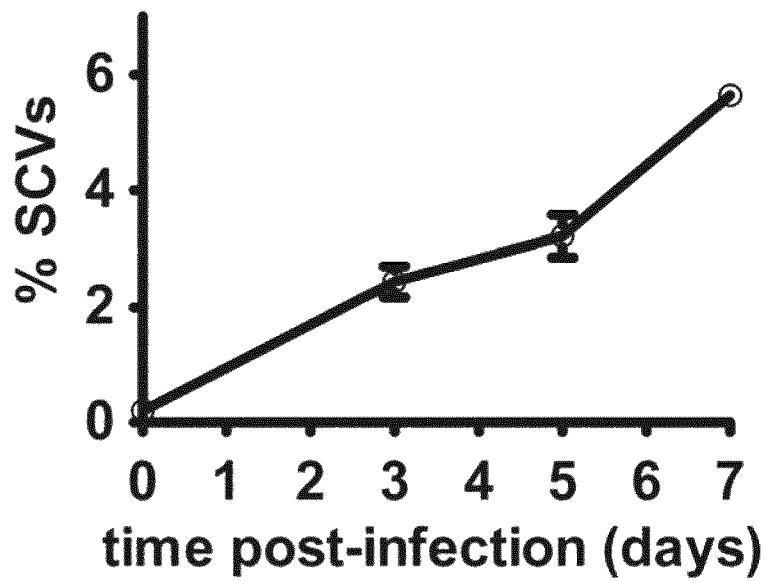

We investigated whether internalized *S. aureus* exhibited a SCV phenotype. MSSA strain Cowan is highly invasive, but not cytotoxic which allowed maintaining this strain intracellularly over several days in the lung epithelial cell line A549. Extracellular bacteria were killed by adding a high dose of flucloxacillin to the infected host cells. Flucloxacillin is typically used to treat *S. aureus* endocarditis in patients. Absence of extracellular bacteria was confirmed by sterility of culture supernatants. Host cells were lysed to release intracellular bacteria and colony counts, as well as colony phenotypes, were determined at various time points. Five hours after infection, 0.2% of all viable intracellular bacteria had a SCV phenotype (FIG. 2*a-b*). The number of viable intracellular persisting bacteria decreased during the course of infection while the frequency of SCVs increased and reached 5.6% after seven days.

1.5 Phagolysosomal Localization of Persisting *S. aureus*

Our data indicated that acidity favored SCV formation, suggesting that the acidic phagolysosomal milieu may have the same effect. A549 cells were infected with *S. aureus* Cowan. Intracellular bacteria were localized within LAMP-2 antibody positive vesicles, visualized by fluorescence microscopy. LAMP-2 (CD 107b) is highly expressed in phagolysosomes, suggesting that intracellular persisting *S. aureus* predominantly resided within phagolysosomes.

1.6 Reduction of *S. aureus* SCVs Through Phagolysosomal Alkinization

Figure 3A:
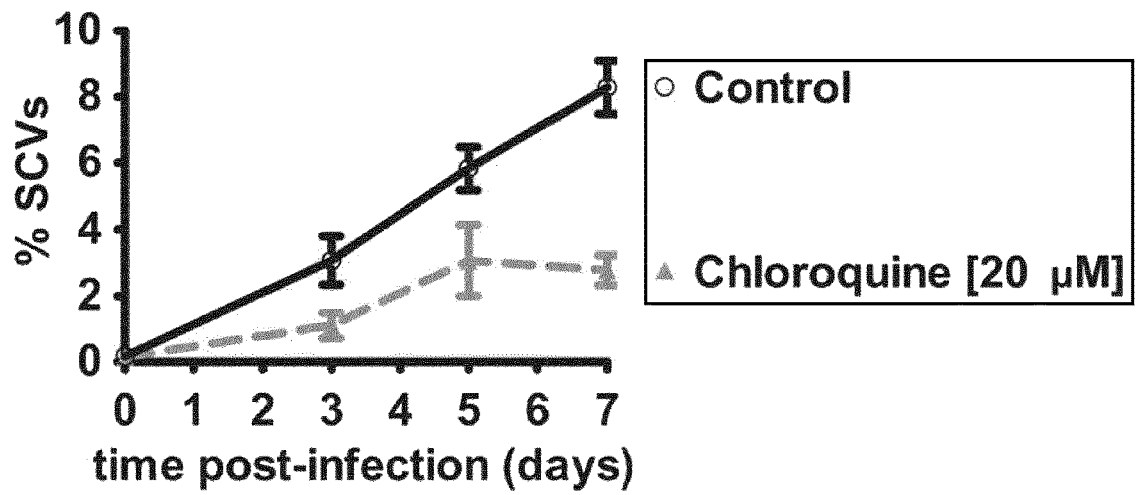
Figure 3B:
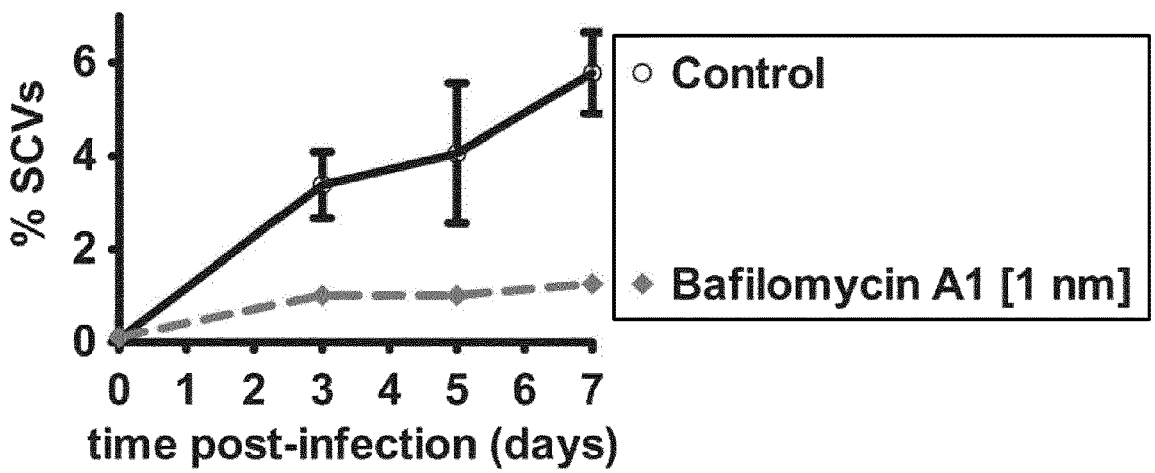
Figure 3C:
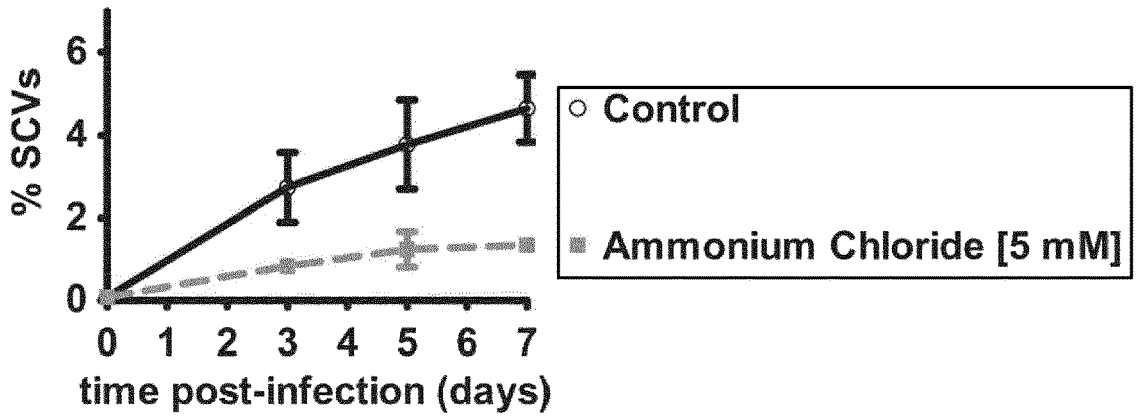
Figure 4A:
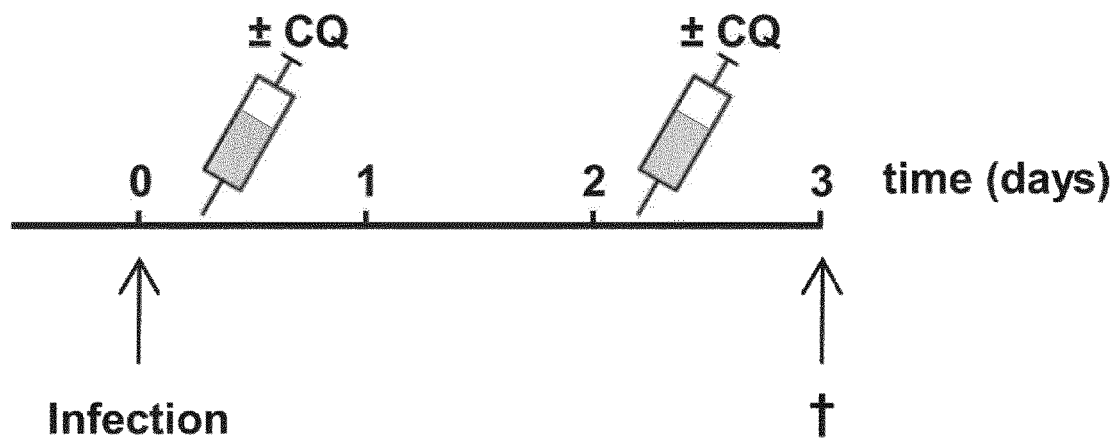
Figure 4B:
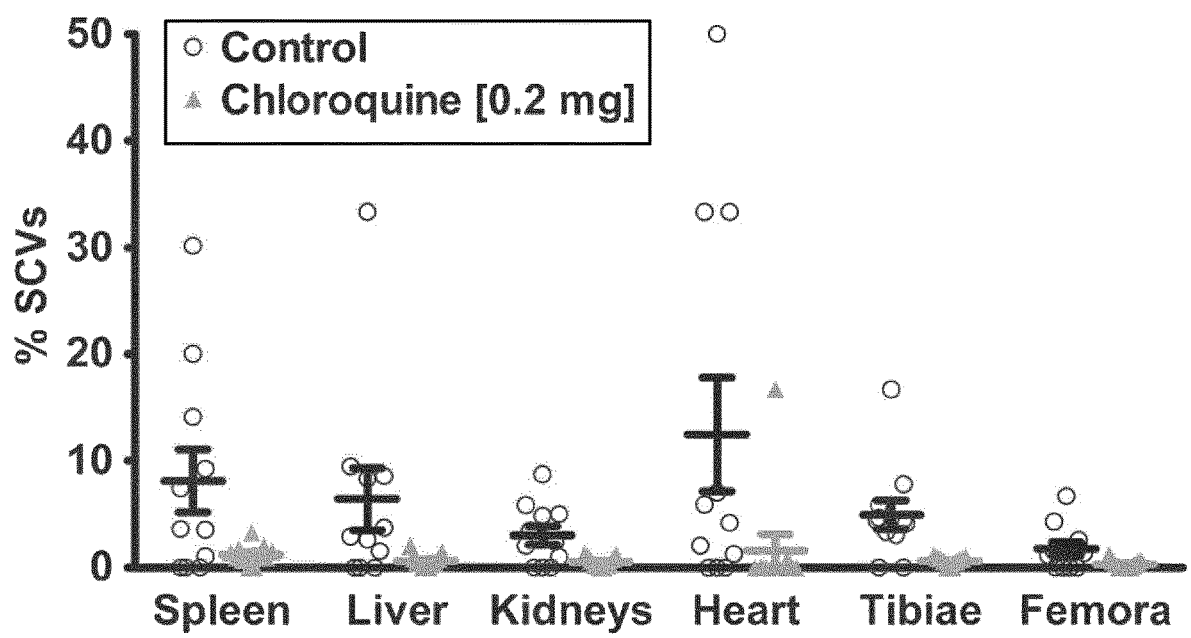
Figure 4C:
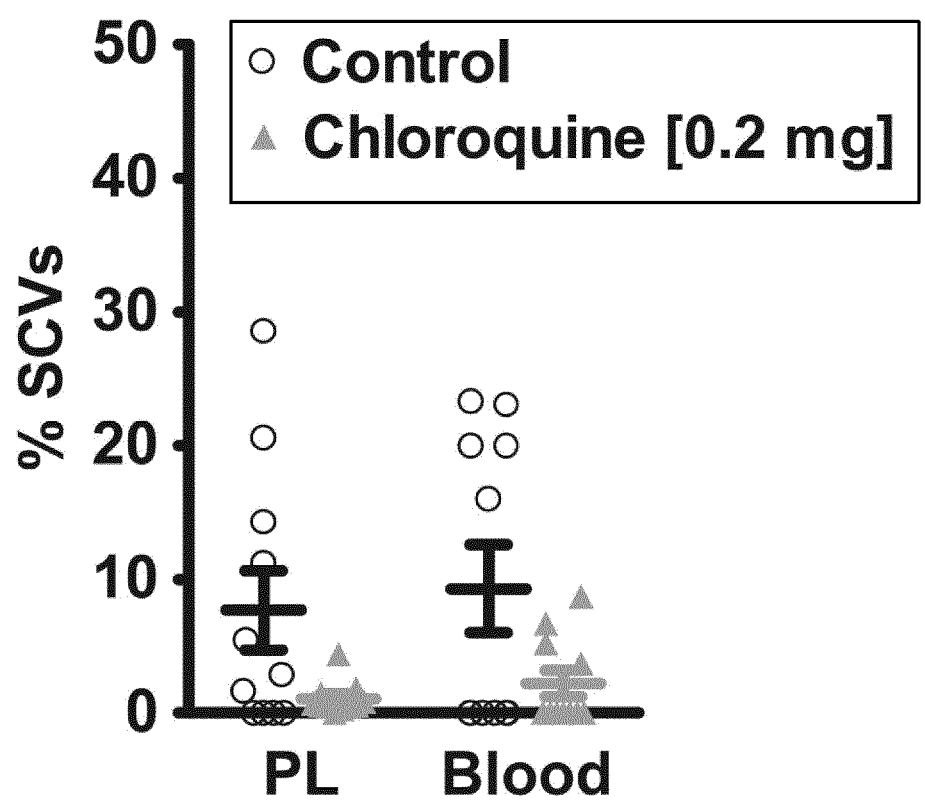

Since low pH induced SCVs and/or non-replicating *S. aureus* and medium pH neutralization resulted in bacterial regrowth, we treated infected host cells with lysosomotropic alkalinizing agents. Chloroquine, bafilomycin A1 or ammonium chloride all neutralized the phagolysosomal pH. Host cells treated with lysosomotropic alkalinizing agents exhibited significantly lower percentages of SCVs seven days after infection (FIG. 3). No differences in total colony counts between control and treated cells were observed. Lysosomotropic alkalinizing agents did not inhibit bacterial growth at the concentrations used. No significant differences in host cell viability were observed after treatment with the alkalinizing agents.

1.7 Growth Resumption of Intra-Phagolysosomal Persisting *S. aureus* by Chloroquine Treatment Resulting in Reduction of SCV Percentages in Cells and in Mice Growth resumption of *S. aureus* persisters through treatment of host cells with chloroquine was assessed. Fluorescence microscopy revealed that *S. aureus* localized within phagolysosomes in both, control and chloroquine-treated host cells, three days post-infection. We observed no dividing bacteria in infected host cells without chloroquine treatment. However, chloroquine facilitated bacterial cell division as assessed by transmission electron microscopy (TEM).

Figure 5A:
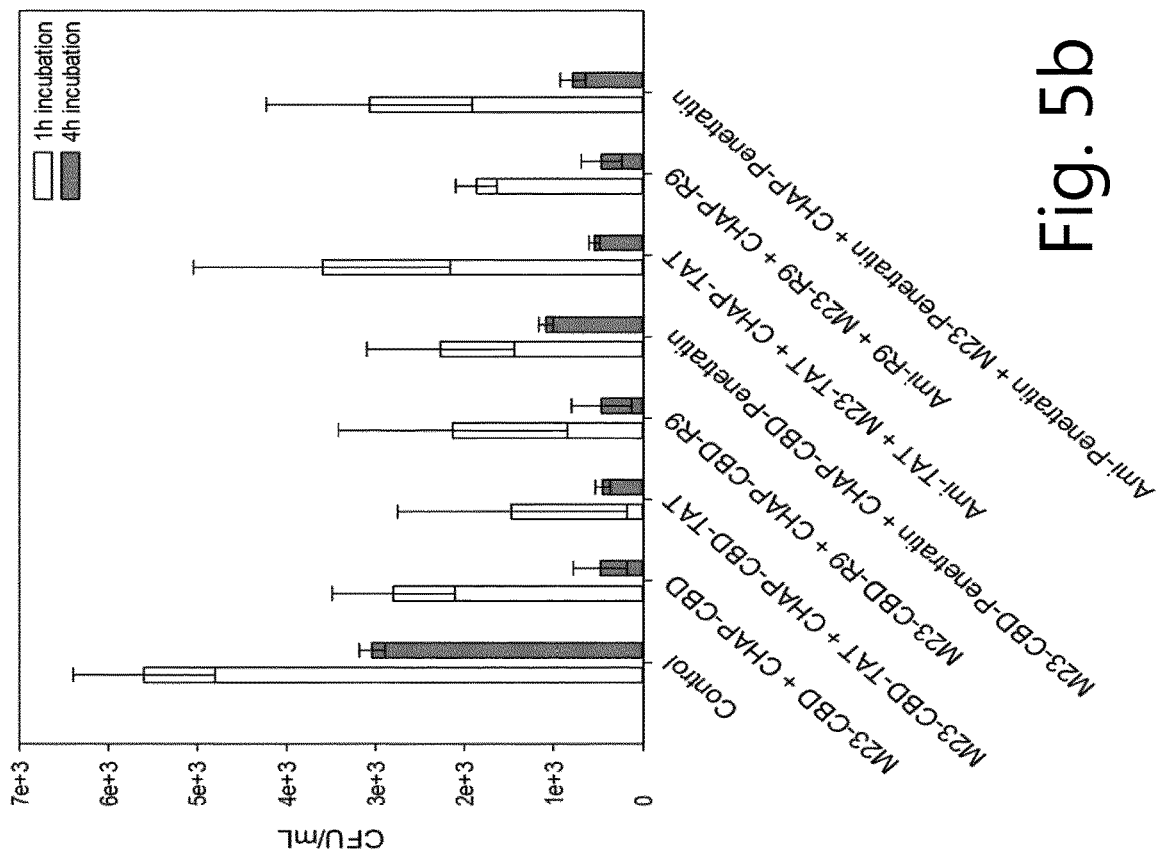

Mice infected with *S. aureus* Cowan were treated with flucloxacillin alone (control), or in combination with chloroquine (FIG. 5*a*). Chloroquine treatment significantly reduced the frequency of SCVs in mice in various organs (FIG. 5*b*) and compartments (FIG. 5*c*). Absolute bacterial numbers were comparable, independent of chloroquine treatment

1.8 Discussion

This study showed that low pH, as found in abscesses and within lysosomes, induced the persisting *S. aureus* subpopulations SCVs and non-replicating persisters. Raising pH in the culture medium or within the phagolysosomes using alkalinizing agents reverted *S. aureus* to normal growth. SCV formation was shown to be triggered by antibiotic pressure. In addition, extreme environmental stresses such as prolonged exposure to low temperature, very acidic or alkaline environments, or osmotic stress may trigger SCV and/or persister formation in *S. aureus* and coagulase-negative staphylococci. These observations, together with our new findings, show how multiple stimuli lead to *S. aureus* persister formation. Localization within the host cell shields *S. aureus* from commonly used antibiotics such as the extracellularly active beta-lactams with poor cell penetration In addition, the low intraphagolysosomal pH renders antibiotics with intracellular activity such as clindamycin and fluoroquinolones less active. We found that the addition of lysosomotropic alkalinizing agents to the usually prescribed antibiotics such as flucloxacillin reduced the frequency of *S. aureus* SCVs in vitro as well as in vivo. We thus identified a simple strategy to circumvent the host dependent component of *S. aureus* persister formation. In clinical settings, the presence of SCVs in osteomyelitis and device-related infections has been associated with increased relapse rates, despite administration of antibiotics. Bacteria adapt to antibiotic stress by SCV and/or persister formation. We now showed that *S. aureus* SCVs and non-replicating persisters retained the ability to revert to a highly virulent and fast-growing form. The capacity to revert to fast growth (phenotype switching) results in relapsing infection. In addition, it renders identification of SCVs difficult. Further aggravating the SCV problem in clinics is underestimation of SCVs in clinical microbiology laboratories, since they form tiny and thus difficult to detect colonies which are easily overgrown by their fast growing counterparts. We postulate that the addition of alkalinizing agents to the usually prescribed antibiotics will reduce the frequency of SCVs and could therefore reduce recurrence rates in the future. Persisting bacteria are not unique to *S. aureus* but have also been described to occur in various other human pathogens, such as *Salmonella* spp., *Pseudomonas aeruginosa, Escherichia coli* and *Mycobacterium tuberculosis*. In addition to low pH, bacterial persisters can arise due to mechanisms that include the toxin-antitoxin systems. Accordingly, activation of a SOS response (ppGpp) in response to DNA damage due to oxidative stress results in decreased ATP levels. This leads to the shutdown of metabolism resulting in reduced growth. Various toxin-antitoxin modules are activated by acidification and/or nutrient starvation in *Salmonella*, causing formation of persisters. In accordance with our findings, *Salmonella* persister formation has been reported in macrophages triggered by the acidic and nutritionally poor environment of the *Salmonella*-containing vacuole that was reversible by addition of bafilomycin A1 44. In contrast to bafilomycin A1, chloroquine is routinely used in patients to treat malaria as well as some rheumatic diseases. Phagolysosomal pH neutralization with chloroquine may therefore provide a novel therapeutic eradication strategy against intracellular persisting staphylococcal reservoirs.

Example 2

Effective treatment of Staphylococcus Aureus Persisters by Phagolysosomal Alkalinization Combined with a Bactericidal Agent Comprising a Protein Transduction Domain.

The bactericidal agents according to the invention with a protein transduction domain for efficient delivery into the infected host cell with a sequence selected from the group consisting of SEQ ID NO: 30-47 are used for combination with phagolysosomal pH neutralization for treatment of intracellular *S. aureus* infection in vitro and in vivo. The treatment results in effective treatment of the intracellular *S. aureus* infection, with some variety in the efficiency depending on the specific bactericidal agent according to the invention used.

Example 3

Effective Treatment of Intracellular Infection with *Staphylococcus aureus*.

The bactericidal agents according to the invention with a protein transduction domain for efficient delivery into the infected host cell with a sequence selected from the group consisting of SEQ ID NO: 27-47 were used for treatment of intracellular *S. aureus* infection, either combined or not with phagolysosomal pH neutralization.

Method Intracellular *S. aureus* Killing Assay.

*S. aureus* was grown in LB broth at 37° C., shaking at 220 rpm, overnight. The overnight culture was diluted in fresh LB (1:10) and grown further for 2 h. Then, the bacteria were centrifuged, the pellet was washed with PBS and the culture was re-suspended in PBS with the OD600 adjusted to 0.4 (c.a. $2 \times 10^8$ CFU/mL). Bacterial cells were sonicated prior to infection (SONOPULS HD 2070) for 1 minute with 1 second pulses at 40% of the power. MG-63 osteosarcoma cells were grown in 12-well dishes with the amount of $5 \times 10^5$ cells/well in 1 mL EMEM culture media with 10% fetal bovine serum (FBS) for 24 h prior infection. Then, the cells were infected with *S. aureus* Newman and Cowan at the following conditions: (A) *S. aureus* Newman at MOI of 0.1 for 3 h, (B) *S. aureus* Newman at MOI of 1.0 for 24 h, and (C) *S. aureus* Cowan at MOI of 1.0 for 72 h. The plates were centrifuged at 1200 rpm for 5 min and incubated at 37° C. with the flush of CO2. After invasion, eukaryotic cells were washed 3× with PBS to remove remaining extracellular *S. aureus* and exposed to floxacillin (1 mg/mL) for 2 h to kill any left non-internalized bacteria. For each experiment (A, B, and C) one part of the samples was exposed to chloroquine treatment (20 µM) to increase lysosomal pH and evaluate its effect on further treatment with endolysins. The supernatant from the antibiotic-treated cells was plated to check for floxacillin treatment efficiency. Then, the eukaryotic cells were again washed with PBS (3×) to remove dead bacteria and subjected to endolysin treatment. The composition of applied endolysin preparations is summarized in Table 2. Eukaryotic cells were treated with 1 mL of 1 µM endolysin preparation (diluted in EMEM supplemented with 1 mg/mL floxacillin and +/−20 µM chloroquine) for (A) 1 h and 4 h, (B and C) 4 h. The control was treated with 1 mL of 1 mg/mL floxacillin, +/−20 µM chloroquine in EMEM. The cultures were then washed 3× with PBS and examined under microscope to determine if there had been osteoblast cell lysis. Next, they were trypsinized (Trypsin-EDTA 0.25%, Gibco®) and lysed with 800 µL 0.1% Triton X-100. The cell lysate was subjected to serial dilution plating on LB and overnight incubation at 37° C.

TABLE 2

Composition of the endolysin mixtures used for intracellular eradication of *S. aureus*.

| Components of the endolysin mixture | Ratio | Concentration of each component |
|---|---|---|
| CHAP-CBD + M23-CBD | 1:1 | 500 nM:500 nM |
| CHAP-CBD-TAT + M23-CBD-TAT | 1:1 | 500 nM:500 nM |
| CHAP-CBD-R9 + M23-CBD-R9 | 1:1 | 500 nM:500 nM |
| CHAP-CBD-Penetratin + M23-CBD-Penetratin | 1:1 | 500 nM:500 nM |
| CHAP-TAT + M23-TAT + Ami-TAT | 1:1:1 | 333 nM:333 nM:333 nM |
| CHAP-R9 + M23-R9 + Ami-R9 | 1:1:1 | 333 nM:333 nM:333 nM |
| CHAP-Penetratin + M23-Penetratin + Ami-Penetratin | 1:1:1 | 333 nM:333 nM:333 nM |

Results

Successful expression and purification of all protein constructs was achieved. The summary of all expressed endolysin constructs with the corresponding molecular weights and concentrations is shown in Table 3. Relatively high concentrations were obtained for most of the endolysin constructs, implying that a correct protein expression and purification strategy was used.

TABLE 3

Summary of all expressed endolysin constructs with the corresponding molecular weight and concentration

| SEQ ID NO: | Protein | Mol. Weight (KDa) | Concentration (mg/ml) | Concentration (µM) |
|---|---|---|---|---|
| 27 | M23-CBD | 29.973 | 3.82 | 127.4 |
| 28 | CHAP-CBD | 33.088 | 2.36 | 71.33 |
| 29 | Ami-CBD | 35.385 | 3.30 | 93.26 |
| 44 | M23-CBD-TAT | 31.916 | 1.13 | 34.30 |
| 38 | CHAP-CBD-TAT | 35.031 | 1.85 | 52.81 |
| 32 | Ami-CBD-TAT | 37.328 | 0.40 | 10.71 |
| 43 | M23-CBD-R9 | 31.620 | 0.45 | 14.23 |
| 37 | CHAP-CBD-R9 | 34.736 | 1.05 | 30.20 |
| 31 | Ami-CBD-R9 | 37.033 | 0.30 | 8.10 |
| 42 | M23-CBD-Penetratin | 32.444 | 0.56 | 17.26 |
| 36 | CHAP-CBD-Penetratin | 35.559 | 2.03 | 57.08 |
| 30 | Ami-CBD-Penetratin | 37.856 | 0.41 | 10.82 |
| 47 | M23-TAT | 17.485 | 1.26 | 72.00 |
| 41 | CHAP-TAT | 20.600 | 1.44 | 69.90 |
| 35 | Ami-TAT | 22.897 | 0.83 | 36.25 |
| 46 | M23-R9 | 17.189 | 2.51 | 146.00 |
| 40 | CHAP-R9 | 20.305 | 0.83 | 40.88 |
| 34 | Ami-R9 | 22.601 | 0.76 | 33.63 |
| 45 | M23-Penetratin | 18.012 | 0.80 | 44.41 |
| 39 | CHAP-Penetratin | 21.128 | 0.73 | 34.55 |
| 33 | Ami-Penetratin | 23.424 | 0.96 | 41.00 |

All expressed endolysins were effective in killing *S. aureus* Cowan in plate assay and in time-killing assay.

Intracellular *S. aureus* Killing Assay

The mixtures of endolysin constructs as listed in Table 2 were further tested for their bacterial killing efficacy in cell tissue cultures.

In our model MG-63 osteosarcoma cells were used to mimic the condition of osteomyelitis. Cells were first infected for a certain time with the pathogen *S. aureus* Newman or Cowan and then treated with the endolysin mixture in presence or absence of chloroquine. We expected that increasing intracellular pH by application of chloroquine would create more favorable conditions for endolysin activity.

Figure 5B:
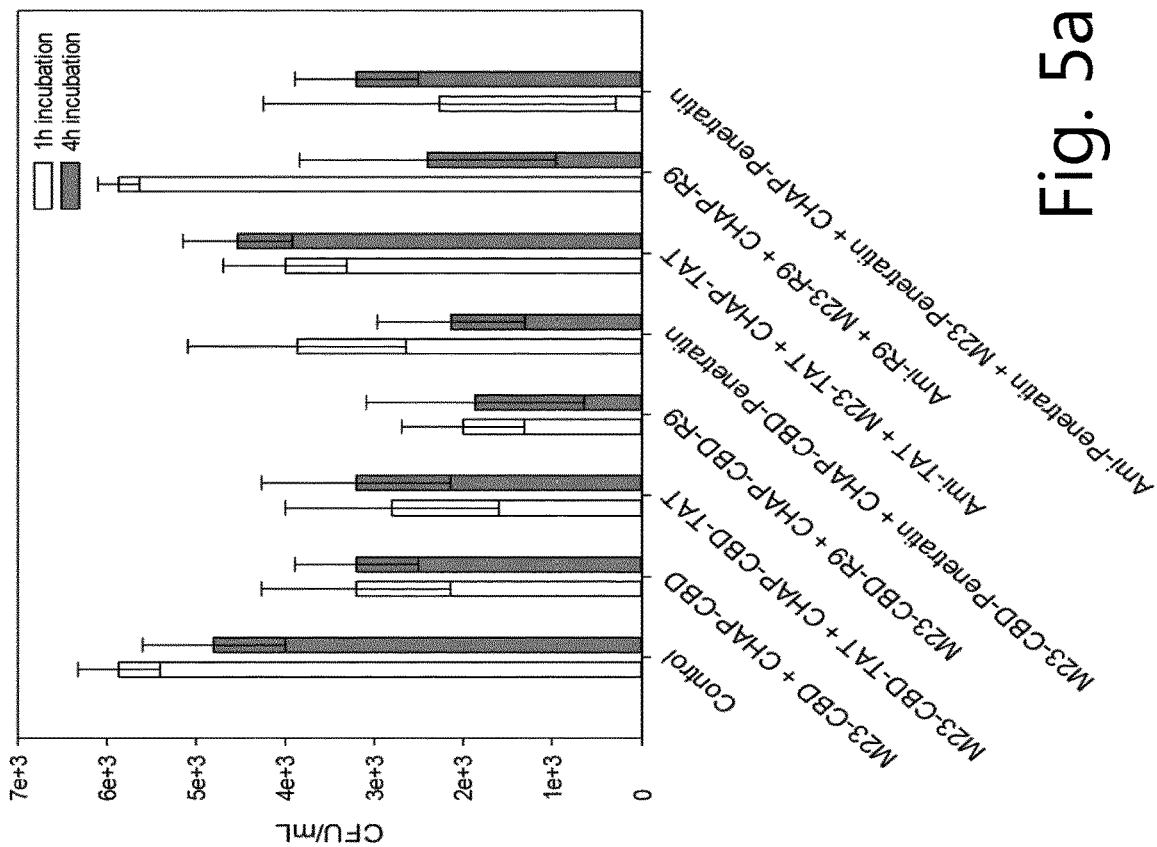

Osteosarcoma cells were exposed to *S. aureus* Newman and Cowan for 3 h followed by 2 h floxacillin treatment to inactivate any non-internalized bacteria. Then, the tissue cells were treated for 1 h and 4 h with 1 µM of endolysin mixture with and without chloroquine. The results are shown in FIG. 5. FIG. 5A shows the result of treatment of *S. aureus* Newman by endolysin mixtures exclusively and FIG. 5B shows the result of a combination treatment with chloroquine. Clearly, 4 h treatment was more effective in both experimental settings. Moreover, endolysin treatment in the presence of chloroquine resulted in greater decrease in bacterial counts. Interestingly, mixture of the CPP-free endolysins showed a very good killing efficacy, which was not expected. It is, however, possible that the vast amount of positive charge associated with CBD attracts the enzyme to the negatively charged cell membrane and induces its intracellular translocation. Such a putative mechanism for CPP-free endolysin translocation is the key of the translocation of CPPs. All endolysin mixtures displayed similar killing properties in this assay, even though their activity differed substantially depending on the presence of CBD and type of CPP tag. It is likely that different constructs have different penetrating properties, depending on the CPP, EAD and CBD presence. For instance, EAD-CBD mixture has very high activity but might not be transported via the cell membrane as efficient as any CPP-containing variants. Whereas, EAD-CPP constructs do not have as high activity but are smaller and contain the transduction domain, which make their intracellular transport more efficient and their diffusivity better due to the lack of immobilization of the enzyme on the cell surface mediated by CBD binding. As a result, enzymes with different properties might have given similar results eventually. FIG. 5C and FIG. 5D show the results of the same experiment performed with a different strain of the pathogen: *S. aureus* Cowan. In this case, the treatment did not seem to be effective. For both samples, without chloroquine (FIG. 5C) and with chloroquine (FIG. 5D), the decrease in the viable counts is negligible. Only treatment with the mixture of CHAP-CBD-R9+M23-CBD-R9 in presence of chloroquine resulted in a significant eradication of the pathogen. It is known that *S. aureus* Cowan resides intracellularly in the lysosomes. It is very likely that intracellular localization of *S. aureus* Newman is different—it may just reside in the cytoplasm, hence the results of the two experiments are different. Moreover, the intracellular fate of CPP-tagged endolysin constructs is unknown at this point, therefore one may only speculate that endolysin constructs fused with the R9 tag are the only ones that accumulate in the lysosomes, hence they showed good killing properties against *S. aureus* Cowan.

Figure 6B:
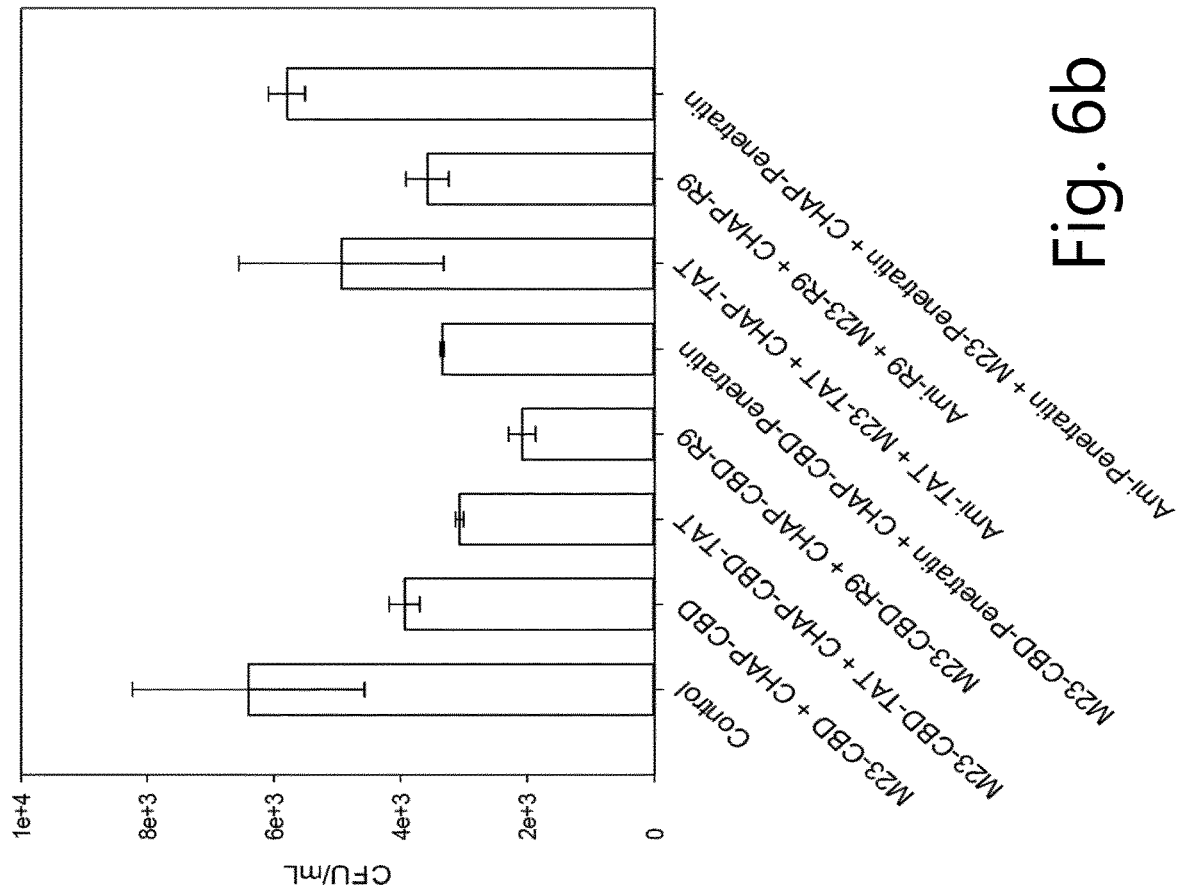
Figure 6A:
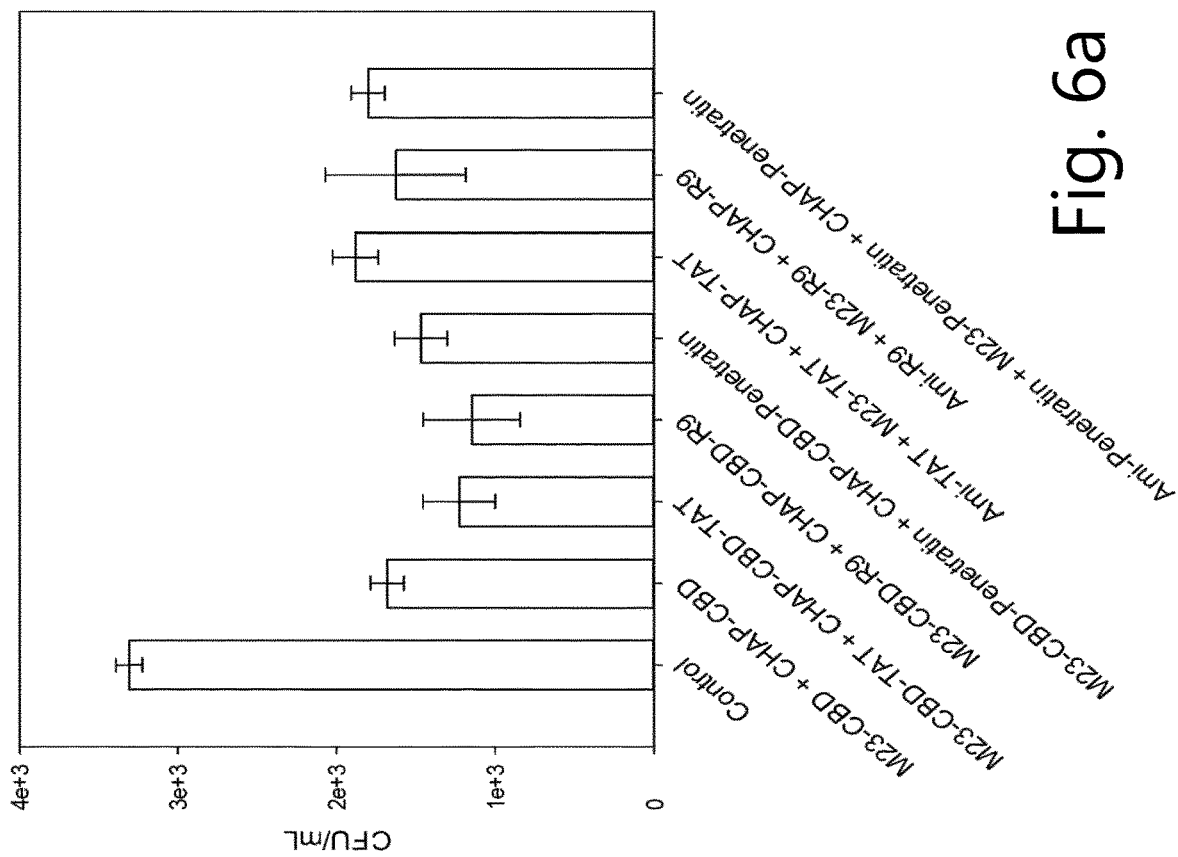
Figure 6D:
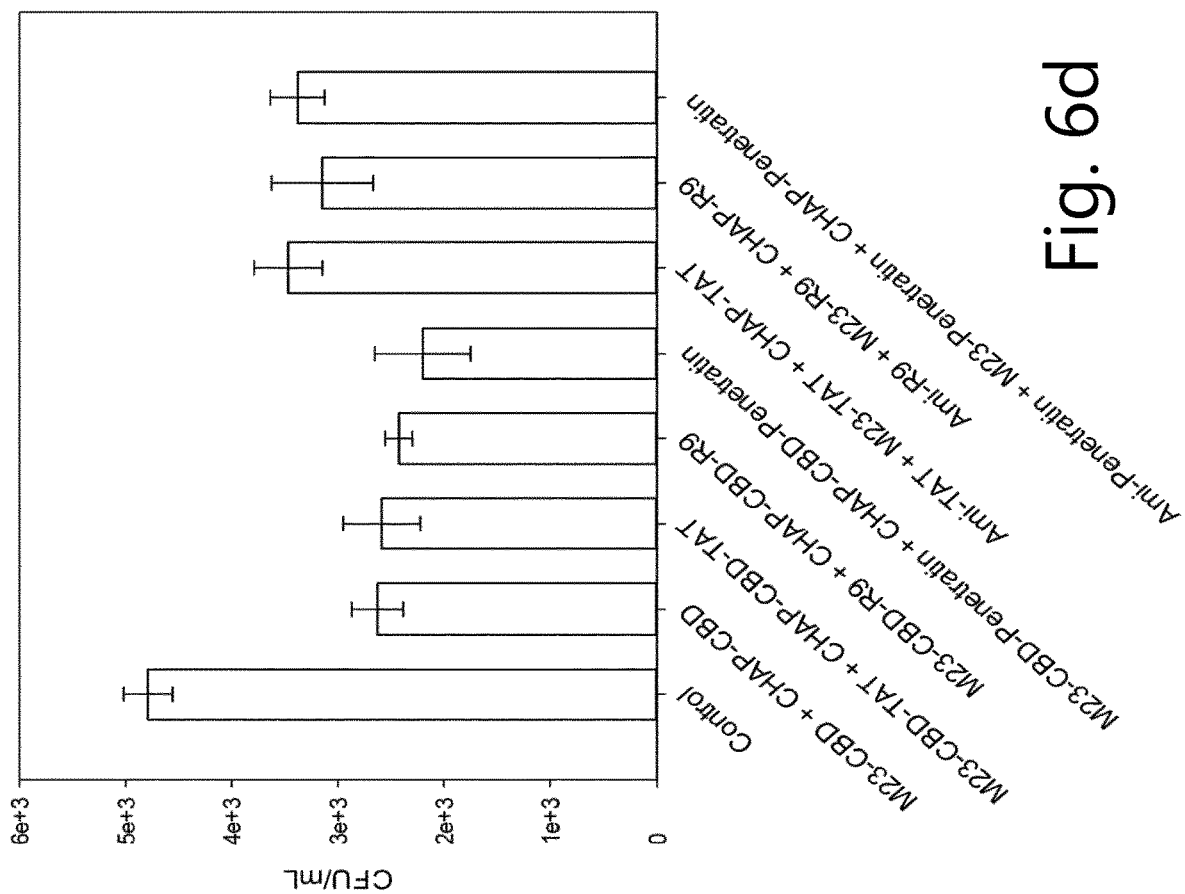
Figure 6C:
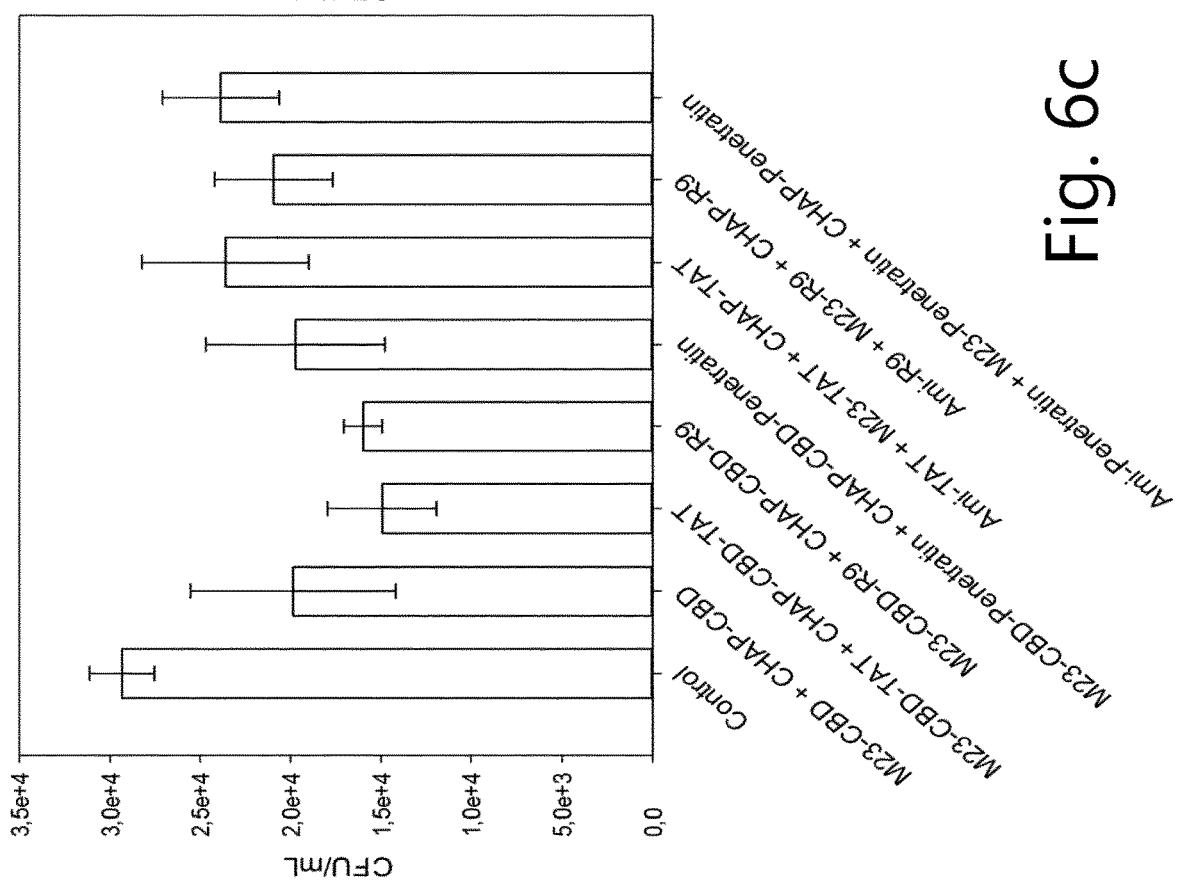
Figure 7A:
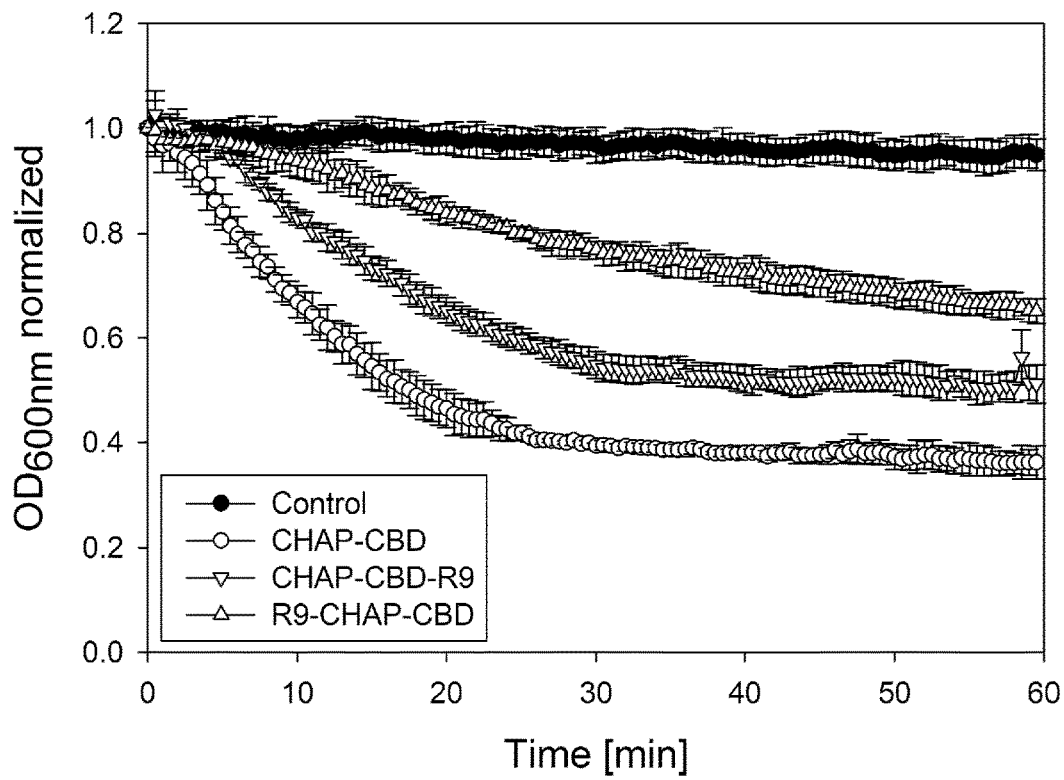
Figure 7B:
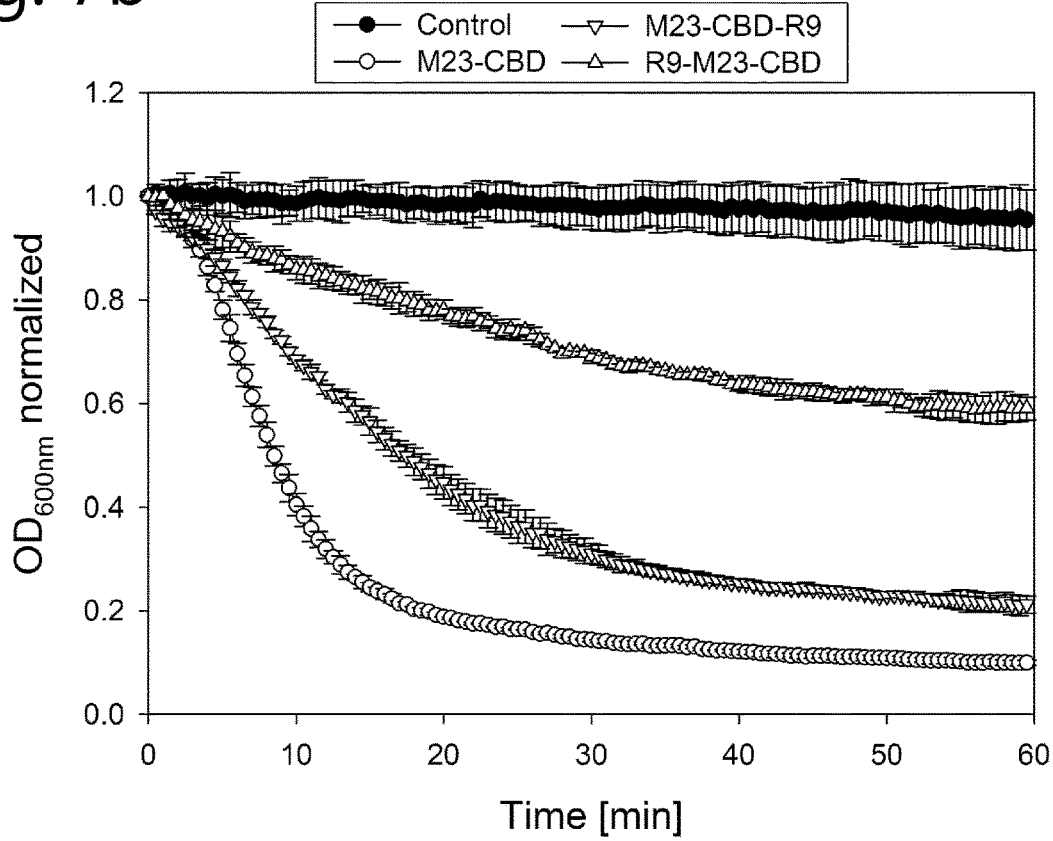
Figure 7C:
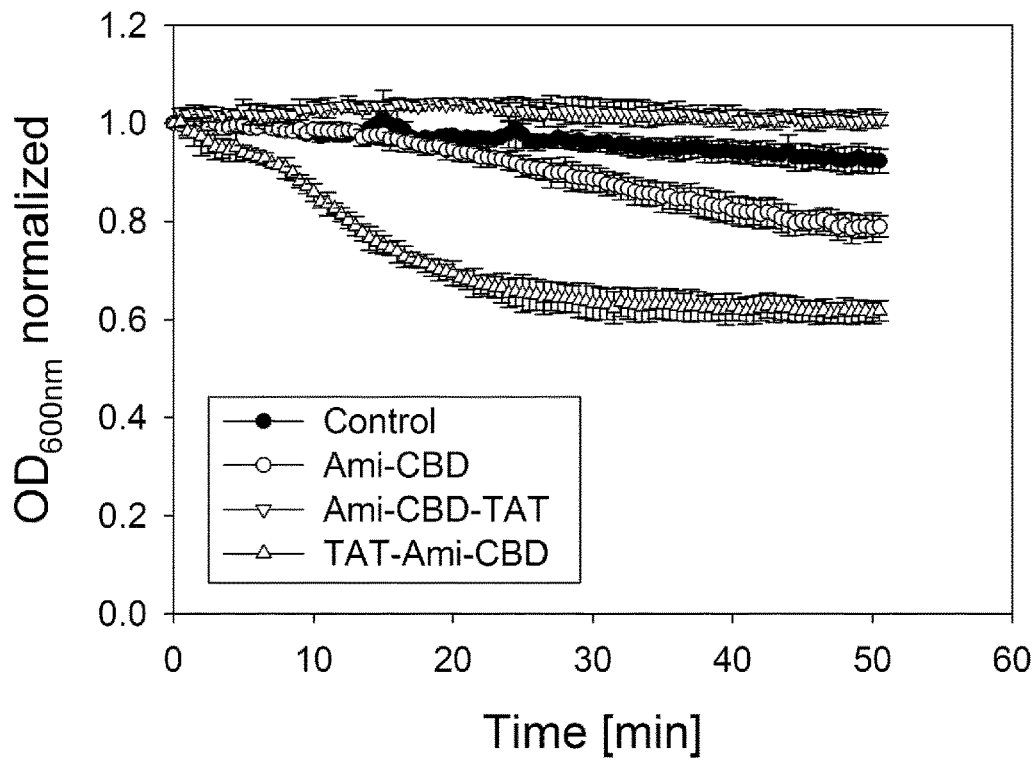
Figure 7D:
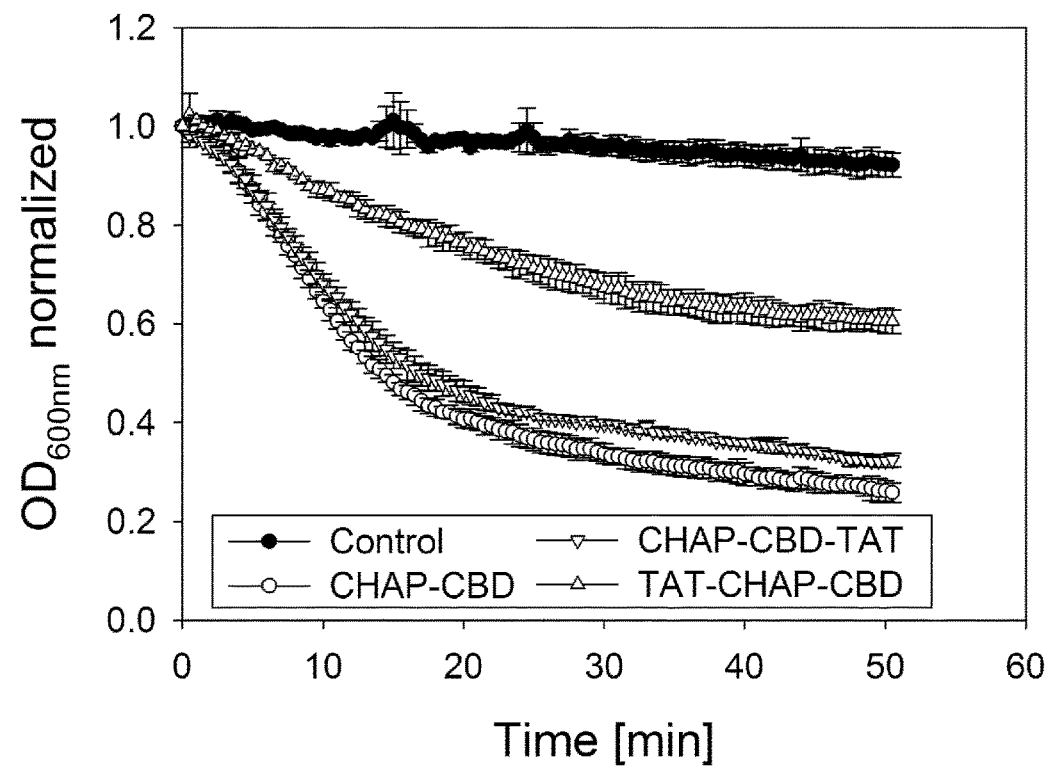
Figure 7E:
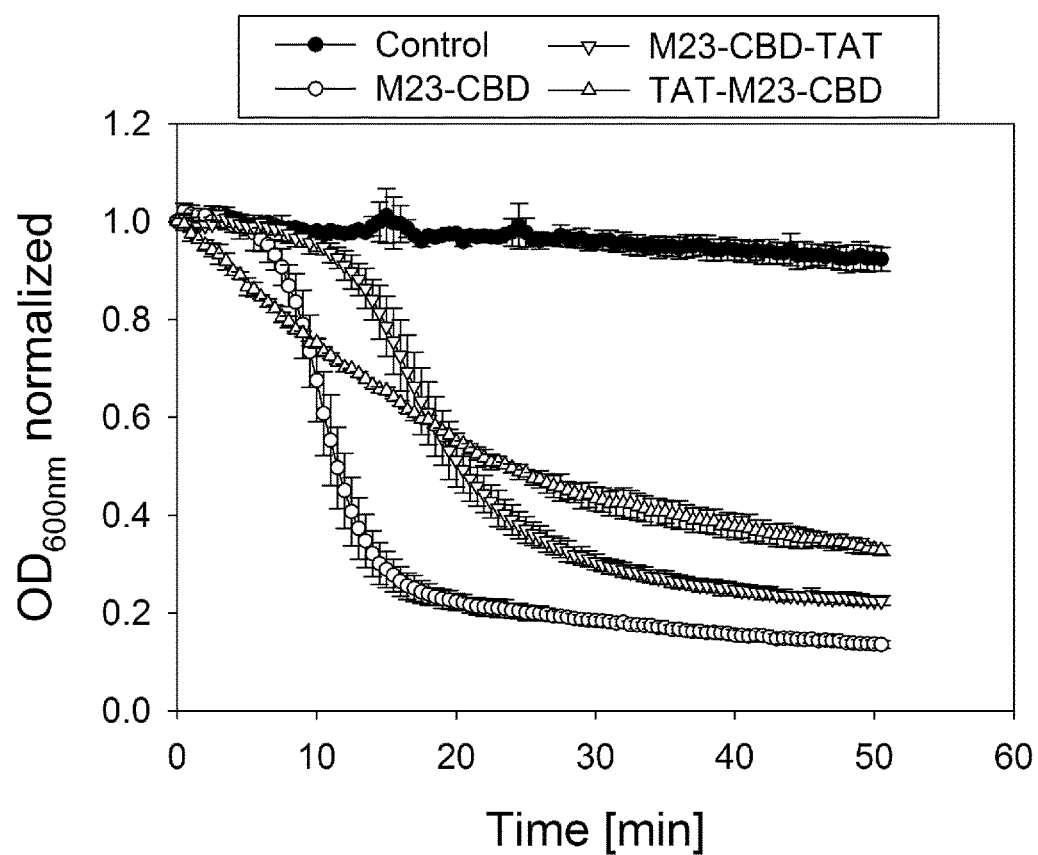

To simulate a real-life infection osteosarcoma tissue cells were infected with *S. aureus* for 24 h and 72 h before the treatment. Such a long infection time allowed the bacteria to settle intracellularly in their final destinations. Again, the cells were treated with the mixtures of endolysin constructs in presence and in absence of chloroquine. FIG. 6A and FIG. 6B show the results of the treatment of osteosarcoma cells infected for 24 h with *S. aureus* Newman in absence and in presence of chloroquine, respectively. FIG. 6C and FIG. 6D correspond to the results of treated cells infected for 72 h with *S. aureus* Cowan. In both cases treatment with endolysin mixtures seems effective, especially with the addition of chloroquine. The best result was obtained for the treatment of *S. aureus* Newman with EAD-CBD-R9 mixture in the presence of chloroquine, where ca. 60% of the pathogen was eradicated (FIG. 6B). Equally good results were achieved for *S. aureus* Cowan treated with the mixtures of EAD-CBD, EAD-CBD-TAT, EAD-CBD-R9 and EAD-CBD-Penetratin, where around 50% of the pathogen was killed. In general, CBD-containing endolysin constructs displayed better killing efficacy, including EAD-CBD mixture, not fused with the transduction domain.

Altogether it was demonstrated that treatment of intracellular *S. aureus* by engineered endolysins together with chloroquine was more effective that without chloroquine. Application of such alkalizing agents likely enhances the activity of lytic enzymes intracellularly and the combinatorial treatment of endolysins with chloroquine could be a good alternative to conventional antibiotic therapy.

In conclusion, this study showed the potential of CPP-fused endolysins in treatment of intracellular and extracellular *S. aureus*. Such a method of therapy could be used to treat patients with conditions like e.g. osteomyelitis, endocarditis, bacteremia or sepsis, as well as bovine mastitis in dairy cattle.

Example 4

Several bactericidal agents according to the invention comprising a functional enzymatic domain from a cell wall lytic enzyme and further comprising a protein transduction domain on the N-terminal side of the molecule were prepared and analyzed according to methods as described elsewhere herein (R9-CHAP-CBD, R9-M23-CBD, TAT-Ami-CBD, TAT-CHAP-CBD, and TAT-M23-CBD). All data were collected in turbidity reduction assays on *S. aureus* SA113 substrate cells and at 100 nM protein concentrations (except Ami-CBD constructs where 1 µM was used) according as described previously in WO2013/169104. FIG. 7 depicts the performance of the constructs. As can be observed from FIG. 7, in general, the N-terminal CPP tagged proteins are active, but perform less compared to un-tagged or C-terminal tagged variants when analyzed on *S. aureus* cells. To analyze the efficiency of intracellular killing, the constructs should be tested in an intracellular *S. aureus* killing assay as in example 3.

REFERENCE LIST

1. Dantes, R., et al. National burden of invasive methicillin-resistant *Staphylococcus aureus* infections, United States, 2011. JAMA internal medicine 173, 1970-1978 (2013).
2. Fowler, V. G., Jr., et al. Persistent bacteremia due to methicillin-resistant *Staphylococcus aureus* infection is associated with agr dysfunction and low-level in vitro resistance to thrombin-induced platelet microbicidal protein. The Journal of infectious diseases 190, 1140-1149 (2004).
3. Welsh, K. J., et al. Predictors of relapse of methicillin-resistant *Staphylococcus aureus* bacteremia after treatment with vancomycin. Journal of clinical microbiology 49, 3669-3672 (2011).

4. Libraty, D. H., Patkar, C. & Torres, B. *Staphylococcus aureus* reactivation osteomyelitis after 75 years. The New England journal of medicine 366, 481-482 (2012).
5. Proctor, R. A., et al. Small colony variants: a pathogenic form of bacteria that facilitates persistent and recurrent infections. Nat Rev Microbiol 4, 295-305 (2006).
6. Proctor, R. A., van Langevelde, P., Kristjansson, M., Maslow, J. N. & Arbeit, R. D. Persistent and relapsing infections associated with small-colony variants of *Staphylococcus aureus*. Clinical infectious diseases: an official publication of the Infectious Diseases Society of America 20, 95-102 (1995).
7. Conlon, B. P. *Staphylococcus aureus* chronic and relapsing infections: Evidence of a role for persister cells: An investigation of persister cells, their formation and their role in *S. aureus* disease. BioEssays: news and reviews in molecular, cellular and developmental biology 36, 991-996 (2014).
8. Fauvart, M., De Groote, V. N. & Michiels, J. Role of persister cells in chronic infections: clinical relevance and perspectives on anti-persister therapies. Journal of medical microbiology 60, 699-709 (2011).
9. Conlon, B. P., et al. Activated ClpP kills persisters and eradicates a chronic biofilm infection. Nature 503, 365-370 (2013).
10. Lechner, S., Lewis, K. & Bertram, R. *Staphylococcus aureus* persisters tolerant to bactericidal antibiotics. Journal of molecular microbiology and biotechnology 22, 235-244 (2012).
11. Kaiser, P., et al. Cecum lymph node dendritic cells harbor slow-growing bacteria phenotypically tolerant to antibiotic treatment. PLoS biology 12, e1001793 (2014).
12. Singh, R., Ray, P., Das, A. & Sharma, M. Role of persisters and small-colony variants in antibiotic resistance of planktonic and bio film-associated *Staphylococcus aureus*: an in vitro study. Journal of medical microbiology 58, 1067-1073 (2009).
13. Garcia, L. G., et al. Antibiotic activity against small-colony variants of *Staphylococcus aureus*: review of in vitro, animal and clinical data. The Journal of antimicrobial chemotherapy 68, 1455-1464 (2013).
14. Tuchscherr, L., et al. *Staphylococcus aureus* phenotype switching: an effective bacterial strategy to escape host immune response and establish a chronic infection. Embo Molecular Medicine 3, 129-141 (2011).
15. Vesga, O., et al. *Staphylococcus aureus* small colony variants are induced by the endothelial cell intracellular milieu. J Infect Dis 173, 739-742 (1996).
16. Tuchscherr, L., et al. *Staphylococcus aureus* small-colony variants are adapted phenotypes for intracellular persistence. The Journal of infectious diseases 202, 1031-1040 (2010).
17. Baudoux, P., et al. Combined effect of pH and concentration on the activities of gentamicin 326 and oxacillin against *Staphylococcus aureus* in pharmacodynamic models of extracellular and intracellular infections. The Journal of antimicrobial chemotherapy 59, 246-253 (2007).
18. Lam, C. & Mathison, G. E. Effect of low intraphagolysosomal pH on antimicrobial activity of antibiotics against ingested staphylococci. Journal of medical microbiology 16, 309-316 (1983).
19. Nguyen, H. A., et al. Factors influencing the intracellular activity of fluoroquinolones: a study using levofloxacin in a *Staphylococcus aureus* THP-1 monocyte model. The Journal of antimicrobial chemotherapy 57, 883-890 (2006).
20. Barcia-Macay, M., Seral, C., Mingeot-Leclercq, M. P., Tulkens, P. M. & Van Bambeke, F. Pharmacodynamic evaluation of the intracellular activities of antibiotics against *Staphylococcus aureus* in a model of THP-1 macrophages. Antimicrobial agents and chemotherapy 50, 841-851 (2006).
21. Lebeaux, D., et al. pH-mediated potentiation of aminoglycosides kills bacterial persisters and eradicates in vivo biofilms. The Journal of infectious diseases 210, 1357-1366 (2014).
22. Schroeder, A., Kland, R., Peschel, A., von 340 Eiff, C. & Aepfelbacher, M. Live cell imaging of phagosome maturation in *Staphylococcus aureus* infected human endothelial cells: small colony variants are able to survive in lysosomes. Medical Microbiology and Immunology 195, 185-194 (2006).
23. Kahl, B. C., et al. Thymidine-dependent *Staphylococcus aureus* small-colony variants are associated with extensive alterations in regulator and virulence gene expression profiles. Infect Immun 73, 4119-4126 (2005).
24. Parret, A. H. et al. Bacteria killing their own kind: novel bacteriocins of *Pseudomonas* and other γ-proteobacteria. Trends in Microbiology 10, 107-112 (2002)
25. Naz S. A. et al. Biophysicochemical characterization of Pyocin SA189 produced by *Pseudomonas aeruginosa* SA189. Brazilian Journal of Microbiology 46, 1147-1154 (2015).

The invention claimed is:

1. A method of treatment of an intracellular and/or persistent Staphylococcus infection in a subject in need thereof, comprising:
    a) administration of an effective amount of a first agent, wherein said first agent increases the intracellular pH of a host cell and/or of an intracellular compartment of a host cell; and
    b) administration of an effective amount of a second agent, wherein said second agent is a bactericidal agent, wherein the first agent is a lysosomotropic alkalinizing agent and enhances the activity of the second agent, and wherein the second agent is a bacterial lysin or autolysin, or a bacteriophage lysin.

2. The method of treatment according to claim 1, wherein the Staphylococcus infection is an S. aureus infection.

3. The method of treatment according to claim 1, wherein the host cell is a eukaryotic host cell within the subject in need of treatment and/or wherein the intracellular compartment is a phagolysosome.

4. The method of treatment according to claim 1, wherein the first agent is selected from the group consisting of chloroquine, bafilomycin A1 and ammonium chloride.

5. The method of treatment according claim 1, wherein the second agent is a bactericidal agent capable of entering the host cell and/or the intracellular compartment of the host cell.

6. The method of treatment according to claim 1, wherein the second agent further comprises a protein transduction domain.

7. The method of treatment according to claim 1, wherein the second agent further comprises an antimicrobial peptide.

8. The method of treatment according to claim 6, wherein the protein transduction domain is selected from the group consisting of SEQ ID NO: 12-25.

9. The method of treatment according to claim 7, wherein the antimicrobial peptide is selected from the group consisting of SEQ ID NO: 70-90.

10. The method of treatment according to claim 1, wherein the second agent comprises a chimeric bactericidal polypeptide having at least 80% sequence identity with a sequence selected from the group consisting of SEQ ID NO: 27-47.

* * * * *